(12) United States Patent
Selnick et al.

(10) Patent No.: US 6,306,891 B1
(45) Date of Patent: Oct. 23, 2001

(54) HIV INTEGRASE INHIBITORS

(75) Inventors: Harold G. Selnick; Melissa Egbertson, both of Ambler; Daria Jean Hazuda, Doylestown; James P. Guare, Jr., Quakertown; John S. Wai, Harleysville; Steven D. Young, Lansdale, all of PA (US); David L. Clark, Albany; Julio C. Medina, Belmont, both of CA (US)

(73) Assignees: Merck & Co., Inc., Rahway, NJ (US); Tularik Inc., S. San Francisco, CA (US)

( * ) Notice: Subject to any disclaimer, the term of this patent is extended or adjusted under 35 U.S.C. 154(b) by 89 days.

(21) Appl. No.: 09/323,519

(22) Filed: Jun. 1, 1999

Related U.S. Application Data
(60) Provisional application No. 60/087,845, filed on Jun. 3, 1998.

(51) Int. Cl.$^7$ .................. A61K 31/40; A61K 31/445; C07D 207/00; C07D 401/00; C07D 209/04

(52) U.S. Cl. .................. 514/423; 514/406; 514/396; 514/326; 514/417; 548/540; 548/469; 548/374.1; 548/333.5; 546/208

(58) Field of Search .................. 514/423, 406, 514/396, 326, 419; 548/540, 469, 374.1, 333.5; 546/208

(56) References Cited

U.S. PATENT DOCUMENTS

| | | |
|---|---|---|
| 3,772,336 | 11/1973 | Wright et al. . |
| 3,899,508 | 8/1975 | Wikel . |
| 4,336,397 | 6/1982 | Cragoe, Jr. et al. . |
| 4,377,258 | 3/1983 | Kipp, Jr. . |
| 4,386,092 | * 5/1983 | Oe et al. .................. 424/256 |
| 4,423,063 | 12/1983 | Rooney et al. . |
| 5,134,142 | 7/1992 | Matsuo et al. . |
| 5,516,797 | 5/1996 | Armistead et al. .................. 514/548 |
| 5,618,830 | 4/1997 | Selnick et al. . |

FOREIGN PATENT DOCUMENTS

| | | |
|---|---|---|
| 418 845 | 3/1991 | (EP) . |
| 61-134346 | 3/1984 | (JP) . |
| WO 97/17316 | 5/1997 | (WO) . |
| WO 97/17317 | 5/1997 | (WO) . |
| WO 99/30699 | 6/1999 | (WO) . |
| WO 00/06529 | 2/2000 | (WO) . |
| WO 00/39086 | 7/2000 | (WO) . |

OTHER PUBLICATIONS

Munakata et al, " Pyrazole derivatives ", CA93:150250, 1980.*

Howarth et al., J.C.S. Perkin Trans, I, vol. 4, pp. 490–501 (1974), "Pyrroles and Related Compounds . . . ".

Derwent Abstract No. 1999–580735/49, "New indole derivatives are integrase inhibitors useful as antiviral and anit–HIV agents", abstract of WO 99/50245 (Shionogi & Co., Ltd.).

Derwent Abstract No. 2000–465713, "New and known di–heterocyclyl hydroxypropenone derivatives are integrase inhibitors for treating retroviral infections, including HIV and AIDS", abstract of WO 00/39086 (Shionogi & Co., Ltd.).

Y. Goldgur et al., "Structure of athe HIV–1 integrase catalytic domain complexed with an inhibitor: A platform for antiviral drug design", Proc. Nat'l Acad. Science USA, vol. 96, No. 23, pp. 13040–13043 (Nov. 9, 1999).

F. Jonas, M.D., "Topical Treatment of Burns, Acid Burns and Other Skin Damage with a Film Forming Powder", Med. Klin., No. 7, (1962), pp. 272–274.

Tanaka et al., Bull. Chem. Soc. JPN., Studies on Aromatic Sesquiterpenes . . . (1989), vol. 62, No. 6, pp. 2102–2104.

Freri, Variations in the Claisen condensation reaction, 1938, Chemical Abstracts No. 33:2488.

Schummer, et al., Tetrahedron, Polyfunctional (R)–2–Hydroxycarboxylic . . . , (1991), 47 (43), pp. 9019–9034.

Lin et al., Substituted pyrazolyl compounds and methods employing these compounds, 1996, Chemical Abstracts No. 124: 202242 (HCAPLUS).

R.M. Saleh, Use of ethyl 2–thenoylpyruvate in the synthesis of heterocycles and their derivatives, 1991, Chemical Abstracts No. 114: No. 228839 (HCAPLUS).

Yanborisov, et al., Synthesis and pharmacological activity of heteroylpyruvic acids and their derivatives, 1998, Chemical Abstracts No. 130:153601 (HCAPLUS).

Murray, et al., J. Heterocyclic Chem., A Simple Regioselective Synthesis of Ethyl 1,5 Diarylpyrazole–3–carboxylates, (1989), vol. 26, pp. 1389–1392.

Witiak, et al., Journal of Med. Chem., Synthesis of Ethyl 6–substituted–Chroman–and–Chromone–2–carboxylates, (1975), vol. 18, No. 9, pp. 934–942.

Andreichekov, et al., Synthesis of 4–Aroyltetrahydro–1, 5–diphenyl–2,3–pyrrolediones . . . 1986, Chemical Abstracts No. 107:39766.

(List continued on next page.)

*Primary Examiner*—Deborah C. Lambkin
(74) *Attorney, Agent, or Firm*—Kenneth R. Walton; Catherine D. Fitch; Melvin Winokur

(57) ABSTRACT

Nitrogen-containing heteroaryl dioxo-butyric acid derivatives are described as inhibitors of HIV integrase and inhibitors of HIV replication. These compounds are useful in the prevention or treatment of infection by HIV and the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described.

31 Claims, No Drawings

OTHER PUBLICATIONS

Oka, et al., Chem. Pharm. Bull., Studies on the Sytheses of N–Heterocyclic Compounds. XXVI . . . . (1975), 23 (10), pp. 2306–2317.

Oka, et al., Chem. Pharm. Bull. , Studies on the Sytheses of N–Heterocyclic Compounds XXV . . . (1975), 23, (10), pp. 2239–2250.

Cooke et al., Aust. J. Chem., Colouring Matters of Australian Plants. XXIII . . . , (1980), 33, pp. 2317–2324.

Seki, et al., J. Heterocyclic Chem., 3–Phenacylidene–3, 4–dihydro–1H–pyrido[2,3–b]pyrazin–2–ones . . . (1995), 32, pp. 347–348.

Sweeny, et al., Tetrahedron, Synthesis of Anthocycandins–III . . . , (1981) 37, pp. 1481–1483.

Burch, et al., "Acylpyruvates as potential antifungal agents", 1972, Chemical Abstracts No. 77:14833 (HCAPLUS).

Zhao, et al., Hydrazide–Containing Inhibitors of HIV–1 Integrase, J. Med. Chem., (1997), vol. 40, No. 8, pp. 937–941.

Zhao, et al., Arylamide Inhibitors of HIV–1 Integrase, J. Med. Chem., (1997), vol. 40, No. 8, pp. 1186–1194.

Williams, et al., Inhibitors of Glycolic Acid Oxidase. 4–Substituted 2,4–Dioxobutanoic Acid Derivatives, J. Med. Chem., (1983), vol. 26, pp. 1196–1200.

Tomassini, et al., Inhibition of Cap (m7 GpppXm)–Dependent Endonuclease of Influenza Virus by 4–Substituted 2,4–Dioxobutanoic Acid Compounds, Antimicrobial Agents & Chemotherapy. (1994). vol. 38. No. 12. pp. 2827–2837.

Ratner, et al., Complete nucleotide sequence of the AIDS virus, HTLV–III, Nature, (1985) vol. 313, pp. 277–284.

Toh, et al., Close structural resemblance between putative polymerase of a *Drosophila* transposable genetic element 17.6 and pol gene product of Moloney murine leukaemia virus. The EMBO Journal. (1985). vol. 4. No. 5. pp. 1267–1272.

Power, et al., Nucleotide Sequence of SRV–1, a Type D Simian Acquired Immune Deficiency Syndrome Retrovirus, Science, (1986) , vol. 231, pp. 1567–1572.

Pearl, et al., A structural model for the retroviral proteases, Nature, (1987), vol. 329, pp. 351–354.

LaFemina, et al., Inhibition of Human Immunodeficiency Virus Integrase by Bis–Catechols, Antimicrobial Agents & Chemotherapy, (1995), vol. 39, No. 2, pp. 320–324.

Giordani, et al., 4–Phenyl–4–oxo–butanoic Acid Derivative Inhibitors of Kynurenine 3–Hydroxylase, Bioorganic & Medicinal Chemistry Letters , (1998), vol. 8, pp. 2907–2912.

Hastings, et al., Anti–Influenza Virus Activities of 4–Substituted 2,4–Dioxobutanoic Acid Inhibitors, Antimicrobial Agents and Chemotherapy, (May 1996) vol. 40, No. 5, pp. 1304–1307.

\* cited by examiner

HIV INTEGRASE INHIBITORS

CROSS-REFERENCE TO RELATED APPLICATIONS

The present application claims priority of U.S. provisional application Serial No. 60/087,845, filed Jun. 3, 1998.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HTV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, e.g., azidothymidine or AZT. Applicants demonstrate that the compounds of this invention are inhibitors of HIV integrase and inhibitors of HIV replication. The applicants additionally demonstrate that inhibition of integrase in vitro and HIV replication in cells is a direct result of inhibiting the strand transfer reaction catalyzed by the recombinant integrase in vitro and integrase as a component of the preintegration complex in HIV infected cells. The particular advantage of the present invention is highly specific inhibition of HIV integrase and HIV replication. The compounds of the present invention inhibit integrases of closely related lentiviruses such as HIV 2 and SIV, but not integrases from more distantly related retroviruses, for example RSV. These compounds do not inhibit binding or catalysis of other nucleic acid binding proteins, including enzymatic reactions such as those catalyzed by HIV reverse transcriptase, HIV Rnase H, Influenza transcriptase, Hepatitis C polymerase, Yeast DNA polymerase, DNase I, Eco RI endonuclease, or mammalian polymerase II.

Zhao et al., (J. Med Chem. vol. 40, pp. 937–941 and 1186–1194 (1997)) describe hydrazide and arylamide HIV integrase inhibitors. Bis-catechols useful for inhibiting HIV integrase are described in LaFemina et al. (Antimicrobial Agents & Chemotherapy, vol. 39, no. 2, pp. 320–324, February 1995).

U.S. Pat. Nos. 4,377,258; 4,336,397; and 4,423,063 as well as Williams and Rooney (J. Med. Chem. vol 26, pp. 1196–1200, 1983) disclose 2,4-dioxo-4-substituted-1-butanoic acid derivatives useful intreating urinary tract calcium oxalate lithiasis. 4-substituted 2,4-dioxobutanoic acid compounds useful for inhibiting an influenza virus endonuclease are described in Tomassini et al. (Antimicrobial Agents & Chemotherapy, vol. 38, no. 12, pp. 2827–2837, December, 1994).

Applicants have discovered that certain 5-membered nitrogen containing heteroaromatic diketo acid derivatives are potent inhibitors of HIV integrase. These compounds are useful in the treatment of AIDS or HIV infection.

SUMMARY OF THE INVENTION

Compounds of formula I, as herein defined, are disclosed. These compounds are useful in the inhibition of HIV integrase, the prevention of infection by HIV, the treatment of infection by HIV and in the treatment of AIDS and/or ARC, either as compounds, pharmaceutically acceptable salts or hydrates (when appropriate), pharmaceutical composition ingredients, whether or not in combination with other antivirals, anti-infectives, immunomodulators, antibiotics or vaccines. Methods of treating AIDS, methods of preventing infection by HIV, and methods of treating infection by HIV are also disclosed.

DETAILED DESCRIPTION OF THE INVENTION

This invention is concerned with compounds of formula I, combinations thereof, or pharmaceutically acceptable salts thereof, in the inhibition of HIV integrase, the prevention or treatment of infection by HIV and in the treatment of the resulting acquired immune deficiency syndrome (AIDS). Compounds of formula I are defined as follows:

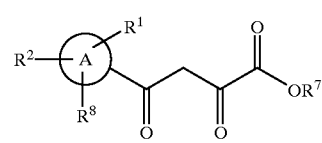

(I)

and tautomers and pharmaceutically acceptable salts thereof, wherein:

A is a five-membered heteroaromatic ring containing 1 or 2 nitrogen atoms and substituted on carbon or nitrogen by $R^1$, $R^2$ and $R^8$; the heteroaromatic ring may optionally be fused with a phenyl ring to form a fused ring system, provided that when A is a fused ring system, the nitrogen-containing heteroaromatic ring is substituted by the dioxobutyric acid/ester moiety;

$R^1$ is selected from:
(1) —H,
(2) —$C_{1-5}$ alkyl,
(3) —$CF_3$,
(4) —halo,
(5) —$NO_2$,
(6) —$N(R^4)(R^5)$,
(7) —$R^6$,
(8) —$C_{2-5}$ alkenyl-$R^3$,
(9) —$C_{2-5}$ alkynyl-$R^3$,
(10) —O—$R^6$,
(11) —O—$C_{1-6}$ alkyl, and
(12) —C(O)$CH_2$C(O)C(O)$OR_7$;

$R^2$ is selected from:
(1) —H,
(2) —$R^3$,
(3) —$C_{1-6}$ alkyl, (4) —$C_{1-6}$ alkyl substituted with $R^3$,
(5) —O—$R^6$,
(6) —O—$C_{1-6}$ alkyl-$OR^6$,
(7) —S(O)n-$R^6$,
(8) —$C_{1-6}$ alkyl($OR^6$)($R^4$),
(9) —$C_{1-6}$ alkyl-N($R^4$)($R^6$),
(10) —$C_{1-6}$ alkyl S(O)n-$R^6$,
(11) —$C_{1-6}$ alkyl C(O)—$R^6$,
(12) —$C_{1-6}$ alkyl C(S)—$R^6$,
(13) —$C_{1-6}$ alkyl $NR^4$C(O)—$R^6$, and
(14) —$C_{1-6}$ alkyl-C(O)N($R^4$)($R^5$);

each $R^3$ is independently selected from:
  (1) a 5 or 6 membered aromatic or heteroaromatic ring, containing 0, 1, 2, 3, or 4 heteroatoms selected from oxygen, nitrogen and sulfur, unsubstituted or substituted on a nitrogen or carbon atom by 1 to 5 substituents selected from:
    (a) halogen,
    (b) $C_{1-6}$ alkyl,
    (c) $C_{1-6}$ alkyloxy-,
    (d) phenyl,
    (e) —$CF_3$,
    (f) —$OCF_3$,
    (g) —CN,
    (h) hydroxy,
    (i) phenyloxy, and
    (j) substituted phenyloxy with 1, 2, or 3 substituents selected from:
      (i) halogen,
      (ii) $C_{1-6}$ alkyl,
      (iii) —$CF_3$, and
      (iv) hydroxy;
  (2) a 3 to 6 membered saturated ring containing 0 or 1 heteroatoms selected from oxygen, nitrogen or sulfur, unsubstituted or substituted with 1 to 5 substituents selected from:
    (a) halogen,
    (b) $C_{1-6}$ alkyl,
    (c) $C_{1-6}$ alkyloxy-,
    (d) —$CF_3$,
    (e) —$OCF_3$,
    (f) —CN,
    (g) =O,
    (h) hydroxy;
  (3) unsubstituted or substituted hexahydrothieno[3,4-d]imidazolyl with one or two substituents selected from:
    (a) oxo,
    (b) halogen,
    (c) $C_{1-6}$ alkyl,
    (d) $C_{1-6}$ alkyloxy-,
    (e) —$CF_3$,
    (f) —$OCF_3$,
    (g) —CN, and
    (h) hydroxy;
  (4) a 5 or 6 membered aromatic or heteroaromatic ring, containing 0, 1, or 2 heteroatoms selected from oxygen, nitrogen and sulfur, fused with a phenyl ring; wherein the ring system is unsubstituted or substituted on a nitrogen or carbon atom by 1 to 3 substituents selected from:
    (a) -halogen,
    (b) —$C_{1-6}$ alkyl,
    (c) —$C_{1-6}$ alkyloxy-,
    (d) —$CF_3$,
    (e) —$OCF_3$,
    (f) —CN, and
    (g) -hydroxy;
  (5) a 3 to 6 membered saturated ring containing 0 or 1 heteroatoms selected from oxygen, nitrogen or sulfur, fused with a phenyl ring, unsubstituted or substituted with 1 or 2 substituents selected from:
    (a) halogen,
    (b) $C_{1-6}$ alkyl,
    (c) $C_{1-6}$ alkyloxy-,
    (d) —$CF_3$,
    (e) —$OCF_3$,
    (f) —CN,
    (g) =O,
    (h) hydroxy; and
  (6) a 5 to 6 membered ring containing 0, 1 or 2 heteroatoms selected from oxygen, nitrogen or sulfur, containing 2 or 3 double bonds, unsubstituted or substituted with 1 or 2 substituents selected from:
    (a) halogen,
    (b) $C_{1-6}$ alkyl,
    (c) $C_{1-6}$ alkyloxy-,
    (d) —$CF_3$,
    (e) —$OCF_3$,
    (f) —CN,
    (g) =O,
    (h) hydroxy;

each $R^4$ is independently selected from:
  (1) —H,
  (2) —$C_{1-3}$ alkyl,
  (3) —$CF_3$,
  (4) —$R^3$,
  (5) —$C_{2-3}$ alkenyl,
  (6) —$C_{1-3}$ alkyl-$R^3$,
  (7) —$C_{2-3}$ alkenyl-$R^3$,
  (8) —$S(O)_n$—$R^3$, and
  (9) —C(O)—$R^3$;

each $R^5$ is independently selected from:
  (1) —H,
  (2) —$C_{1-3}$ alkyl,
  (3) —$CF_3$,
  (4) —$R^3$,
  (5) —$C_{2-3}$ alkenyl,
  (6) —$C_{1-3}$ alkyl-$R^3$,
  (7) —$C_{2-3}$ alkenyl-$R^3$,
  (8) —$S(O)_n$—$R^3$, and
  (9) —C(O)—$R^3$;

each $R^6$ is independently selected from:
  (1) —$C_{1-3}$ alkyl-$R^3$, and
  (2) —$R^3$;

$R^7$ is selected from:
  (1) —H, and
  (2) $C_{1-6}$ alkyl;

$R^8$ is selected from:
  (1) —H,
  (2) $C_{1-6}$ alkyl-oxy, and
  (3) $C_{1-6}$ alkyl; and each n is independently selected from 0, 1 and 2.

Particular compounds of structural formula I include:
  (1) 4-[1-(4-fluorobenzyl)-1H-pyrrol-2-yl]-2,4-dioxobutyric acid methyl ester,
  (2) 4-[1-(4-fluorobenzyl)-1H-pyrrol-2-yl]-2,4-dioxobutyric acid,
  (3) 4-[1-(4-methylbenzyl)-1-H-pyrrol-2-yl]-2,4-dioxobutyric acid ethyl ester,
  (4) 4-[1-(4-methylbenzyl)-1-H-pyrrol-2-yl]-2,4-dioxobutyric acid, (5) 4-[1-(4-fluorobenzyl)-1-H-pyrrol-2-yl]-2,4-dioxobutyric acid ethyl ester, (6) 4-[1-(4-fluorobenzyl)-1H-pyrrol-2-yl]-2,4-dioxobutyric acid isopropyl ester, (7) 4-[1-(4-fluorobenzyl)-1H-pyrrol-2-yl]-2,4-dioxobutyric acid n-butyl ester, (8) 4-(1-benzyl-1H-pyrrol-2-yl)-2,4-dioxobutyric acid, (9) 4-(1-naphthalen-2-ylmethyl-1H-pyrrol-2-yl)-2,4-dioxobutyric acid, (10) 4-(1-biphenyl-4-ylmethyl-1H-pyrrol-2-yl)-2,4-dioxobutyric acid,

(11) 4-(1-naphthalen-1-ylmethyl-1H-pyrrol-2-yl)-2,4-dioxobutyric acid, (12) 2,4-dioxo-4-[1-(4-phenylbutyl)-1H-pyrrol-2-yl]-butyric acid, (13) 4-[1-(4-chlorobenzyl)-1H-pyrrol-2-yl]-2,4-dioxobutyric acid, (14) 2,4-dioxo-4-(1-phenethyl-1H-pyrrol-2-yl)-butyric acid,

(15) 4-[1-(2-methylbenzyl)-1H-pyrrol-2-yl]-2,4-dioxobutyric acid,

(16) 4-[1-(3,4-difluorobenzyl)-1H-pyrrol-2-yl]-2,4-dioxobutyric acid, (17) 4-[1-(4-bromobenzyl)-1H-pyrrol-2-yl]-2,4-dioxobutyric acid, (18) 4-[1-(2-bromobenzyl)-1H-pyrrol-2-yl]-2,4-dioxobutyric acid, (19) 4-[1-(3-bromobenzyl)-1H-pyrrol-2-yl]-2,4-dioxobutyric acid, (20) 4-[1-(3-chlorobenzyl)-1H-pyrrol-2-yl]-2,4-dioxobutyric acid,

(21) 4-[1-(3-methylbenzyl)-1H-pyrrol-2-yl]-2,4-dioxobutyric acid,

(22) 4-[1-(2-fluorobenzyl)-1H-pyrrol-2-yl]-2,4-dioxobutyric acid,

(23) 2,4-dioxo-4-(1-hexyl-1H-pyrrol-2-yl)-butyric acid, (24) 4-(1-biphenyl-2-ylmethyl-1H-pyrrol-2-yl)-2,4-dioxobutyric acid,

(25) 2,4-dioxo-4-[1-(4-phenoxybutyl)-1H-pyrrol-2-yl]-butyric acid,

(26) 4-[1-(3-fluorobenzyl)-1H-pyrrol-2-yl]-2,4-dioxobutyric acid,

(27) 4-[1-(2-chlorobenzyl)-1H-pyrrol-2-yl]-2,4-dioxobutyric acid, (28) 4-[1-(4-fluorobenzyl)-4-iodo-1H-pyrrol-2-yl]-2,4-dioxobutyric acid (29) 4-[1-(4-methoxybenzyl)-1H-pyrrol-2-yl]-2,4-dioxobutyric acid, (30) 4-[1-(2,4,5-trifluorobenzyl)-1H-pyrrol-2-yl]-2,4-dioxobutyric acid, (31) 4-[1-(2,3-difluorobenzyl)-1H-pyrrol-2-yl]-2,4-dioxobutyric acid, (32) 4-[1-(3,5-difluorobenzyl)-1H-pyrrol-2-yl]-2,4-dioxobutyric acid,

(33) 4-[1-(2,5-difluorobenzyl)-1H-pyrrol-2-yl]-2,4-dioxobutyric acid,

(34) 4-[1-(2,5,6-difluorobenzyl)-1H-pyrrol-2-yl]-2,4-dioxobutyric acid, (35) 4-[1-(2-fluorobenzyl)-1H-pyrrol-2-yl]-2,4-dioxobutyric acid,

(36) 4-[1-(4-trifluoromethylbenzyl)-1H-pyrrol-2-yl]-2,4-dioxobutyric acid,

(37) 4-[1-(4-cyanobenzyl)-1H-pyrrol-2-yl]-2,4-dioxobutyric acid,

(38) 4-[1-(3-methoxybenzyl)-1H-pyrrol-2-yl]-2,4-dioxobutyric acid,

(39) 2-hydroxy-4-[1-(4-hydroxybenzyl)-1H-pyrrol-2-yl]-2,4-dioxobutyric acid, (40) 4-(1-cyclopentylmethyl-1H-pyrrol-2-yl)-2,4-dioxobutyric acid,

(41) 4-{1-[3-(4-fluorophenyl)propyl]-1H-pyrrol-2-y}-2,4-dioxobutyric acid,

(42) 4-{1-[2-(4-fluorophenyl)ethyl]-1H-pyrrol-2-yl}-2,4-dioxobutyric acid,

(43) 4-[1-(3-phenylpropyl)-1H-pyrrol-2-yl]-2,4-dioxobutyric acid,

(44) 4-(1-ethyl-1H-pyrrol-2-yl)-2,4-dioxobutyric acid,

(45) 4-[1-(3-fluoro-benzyl)-1-H-pyrrol-2-yl]-2,4-dioxobutyric acid,

(46) 4-[1-(2-chloro-benzyl)-1-H-pyrrol-2-yl]-2,4-dioxobutyric acid,

(47) 4-[1-(3-benzoylaminopropyl)-1H-pyrrol-3-yl]-2,4-dioxobutyric acid,

(48) 4-{1-[3-(4-fluorophenoxy)benzyl]-1H-pyrrol-2-yl}-2,4-dioxobutyric acid,

(49) 4-(1-cyclohexylmethyl-1-H-pyrrol-2-yl)-2,4-dioxobutyric acid methyl ester

(50) 4-(1-cyclohexylmethyl-1-H-pyrrol-2-yl)-2,4-dioxobutyric acid,

(51) 4-[1-(4-fluorobenzyl)-4-phenylethynyl-1H-pyrrol-2-yl]-2,4-dioxobutyric acid ethyl ester,

(52) 4-[1-(4-fluorobenzyl)-4-phenylethynyl-1H-pyrrol-2-yl]-2,4-dioxobutyric acid,

(53) 4-[1-(4-fluorobenzyl)-4-phenethyl-1H-pyrrol-2-yl]-2,4-dioxobutyric acid ethyl ester,

(54) 4-[1-(4-fluorobenzyl)-4-phenethyl-1H-pyrrol-2-yl]-2,4-dioxobutyric acid,

(55) 4-[5-(4-fluorobenzyl)-1-methyl-1H-pyrrol-2-yl]-2,4-dioxobutyric acid methyl ester,

(56) 4-[5-(4-fluorobenzyl)-1-methyl-1H-pyrrol-2-yl]-2,4-dioxobutyric acid,

(57) 4-[5-(3-chlorobenzyl)-1-methyl-1H-pyrrol-2-yl]-2,4-dioxobutyric acid,

(58) 4-[5-(4-fluorobenzyl)-1H-pyrrol-2-yl]-2,4-dioxobutyric acid,

(59) 4-[5-(3-chlorobenzyl)-1H-pyrrol-2-yl]-2,4-dioxobutyric acid,

(60) 4-[5-(benzyl)-1H-pyrrol-2-yl]-2,4-dioxobutyric acid,

(61) 4-[5-(3-fluorobenzyl)-1H-pyrrol-2-yl]-2,4-dioxobutyric acid,

(62) 4-[5-(4-fluorobenzyl)-1-(4-fluorobenzyl)-1H-pyrrol-2-yl]-2,4-dioxobutyric acid,

(63) 4-[5-(3-chlorobenzyl)-1-(4-fluorobenzyl)-1H-pyrrol-2-yl]-2,4-dioxobutyric acid,

(64) 4-[5-(benzyl)-1-(4-fluorobenzyl)-1H-pyrrol-2-yl]-2,4-dioxobutyric acid,

(65) 4-[5-(3-chlorobenzyl)-1-(4-fluorobenzyl)-1H-pyrrol-2-yl]-2,4-dioxobutyric acid,

(66) 4-[5-(4-fluorobenzyl)-1-methyl-1H-pyrrol-3-yl]-2,4-dioxobutyric acid,

(67) 4-[5-(3-chlorobenzyl)-1-methyl-1H-pyrrol-3-yl]-2,4-dioxobutyric acid,

(68) 4-[5-(benzyl)-1-methyl-1H-pyrrol-3-yl]-2,4-dioxobutyric acid,

(69) 4-[5-(3-fluorobenzyl)-1-methyl-1H-pyrrol-3-yl]-2,4-dioxobutyric acid,

(70) 4-(5-benzyl-1H-pyrrol-3-yl)-2,4-dioxobutyric acid,

(71) 4-[2,5-bis-(3-chlorobenzyl)-1-H-pyrrol-3-yl]-2,4-dioxobutyric acid,

(72) 4-[1-(4-Fluorobenzyl)-5-phenyl-1H-pyrrol-2-yl]-2,4-dioxobutyric acid ethyl ester,

(73) 4-[1-(4-Fluorobenzyl)-5-phenyl-1H-pyrrol-2-yl]-2,4-dioxobutyric acid,

(74) 4-[4-Dimethylamino-1-(4-fluorobenzyl)-1H-pyrrol-2-yl]-2,4-dioxobutyric acid ethyl ester,

(75) 4-[4-Dimethylamino-1-(4-fluorobenzyl)-1H-pyrrol-2-yl]-2,4-dioxobutyric acid,

(76) 4-[1-(4-Fluorobenzyl)-4-nitro-1H-pyrrol-2-yl]-2,4-dioxobutyric acid,
(77) 4-[4-(Benzylamino)-1-(4-fluorobenzyl)-1H-pyrrol-2-yl]-2,4-dioxobutyric acid,
(78) 4-[5-Nitro-1-(4-fluorobenzyl)-1H-pyrrol-2-yl]-2,4-dioxobutyric
(79) 4-[1-benzyl-1H-pyrrol-3-yl]-2,4-dioxobutyric acid methyl ester,
(80) 4-[1-benzyl-1H-pyrrol-3-yl]-2,4-dioxobutyric acid,
(81) 4-[1-(4-fluorobenzyl)-1H-pyrrol-3-yl]-2,4-dioxobutyric acid,
(82) 4-[1-(3-bromobenzyl)-1H-pyrrol-3-yl]-2,4-dioxobutyric acid,
(83) 4-[1-(4-fluorobenzyl)-4-methyl-1H-pyrrol-3-yl]-2,4-dioxobutyric acid,
(84) 4-[2,4-dimethyl-1-(4-fluorobenzyl)-1H-pyrrol-3-yl]-2,4-dioxobutyric acid,
(85) 4-[1-(3,4-difluorobenzyl)-1H-pyrrol-3-yl]-2,4-dioxobutyric acid,
(86) 4-[1-(3-chlorobenzyl)-1H-pyrrol-3-yl]-2,4-dioxobutyric acid,
(87) 4-[1-(4-chlorobenzyl)-1H-pyrrol-3-yl]-2,4-dioxobutyric acid,
(88) 4-[1-(4-bromobenzyl)-1H-pyrrol-3-yl]-2,4-dioxobutyric acid,
(89) 4-[1-(3,4-dichlorobenzyl)-1H-pyrrol-3-yl]-2,4-dioxobutyric acid,
(90) 4-[1-(2-methylbenzyl)-1H-pyrrol-3-yl]-2,4-dioxobutyric acid,
(91) 4-[1-(3-chlorobenzyl)-4-methyl-1H-pyrrol-3-yl]-2,4-dioxobutyric acid,
(92) 4-[1-(3-trifluoromethylbenzyl)-1H-pyrrol-3-yl]-2,4-dioxobutyric acid,
(93) 4-[1-(4-methylbenzyl)-1H-pyrrol-3-yl]-2,4-dioxobutyric acid,
(94) 4-[1-(4-methoxybenzyl)-1H-pyrrol-3-yl]-2,4-dioxobutyric acid,
(95) 4-[1-(3-methylbenzyl)-1H-pyrrol-3-yl]-2,4-dioxobutyric acid,
(96) 4-{1-[3-(4-fluorophenyl)-propyl]-1H-pyrrol-3-yl}-2,4-dioxobutyric acid,
(97) 4-[1-(4-bromobenzyl)-1-H-pyrrol-3-yl]-2,4-dioxobutyric acid,
(98) 4-[1-(4-chlorobenzyl)-1-H-pyrrol-3-yl]-2,4-dioxobutyric acid,
(99) 4-[4-Benzylmethylamino-1-(4-fluorobenzyl)-1H-pyrrol-2-yl]-2,4-dioxobutyric acid, ethyl ester,
(100) 4-[4-Benzylmethylamino-1-(4-fluorobenzyl)-1H-pyrrol-2-yl]-2,4-dioxobutyric acid,
(101) 4-[4-Phenyl-1-(4-fluorobenzyl)-1H-pyrrol-2-yl]-2,4-dioxobutyric acid ethyl ester,
(102) 4-[4-Phenyl-1-(4-fluorobenzyl)-1H-pyrrol-2-yl]-2,4-dioxobutyric acid,
(103) 4-[1-(4-fluorobenzyl)-4-methanesulfonylamino-1H-pyrrol-3-yl]-2,4-dioxo-butyric acid ethyl ester,
(104) 4-[1-(4-fluorobenzyl)-4-methanesulfonylamino-1H-pyrrol-3-yl]-2,4-dioxo-butyric acid,
(105) 4-[1-(4-Fluorobenzyl)-3-acetylamino-1H-pyrrol-2-yl]-2,4-dioxobutyric acid,
(106) 4-[4-acetylamino-1-(4-fluorobenzyl)-1H-pyrrol-2-yl]-2,4-dioxobutyric acid,
(108) 4-[4-(4-fluorobenzyl)-1H-pyrrol-3-yl]-2,4-dioxobutyric acid,
(109) 4-[1,4-bis-(4-fluorobenzyl)-1H-pyrrol-3-yl]-2,4-dioxobutyric acid,
(110) 4-[5-(3-ethoxycarbonyl-3-oxopropionyl)-1-(4-fluorobenzyl)-1H-pyrazol-3-yl]-2,4-dioxobutyric acid ethyl ester,
(111) 4-[1-(4-fluorobenzyl)-1H-pyrazol-4-yl]-2,4-dioxobutyric acid ethyl ester,
(112) 4-[1-(4-fluorobenzyl)-1H-pyrazol-4-yl]-2,4-dioxobutyric acid,
(113) 4-[4-Dimethylamino-1-(4-fluorobenzyl)-1H-pyrrol-3-yl]-2,4-dioxobutyric acid,
(114) 4-[1-(4-Fluorobenzyl)-5-methyl-1H-pyrazol-4-yl]-2-hydroxy-4-oxobut-2-enoic acid,
(115) 4-[2-(4-fluorobenzyl)-2H-pyrazol-3-yl]-2,4-dioxobutyric acid ethyl ester,
(116) 4-[2-(4-fluorobenzyl)-2H-pyrazol-3-yl]-2,4-dioxobutyric acid,
(117) 1-[1-(4-fluorobenzyl)-3-methyl-1H-pyrazol-4-yl]-2,4-dioxobutyric acid ethyl ester,
(118) 1-[1-(4-fluorobenzyl)-3-methyl-1H-pyrazol-4-yl]-2,4-dioxobutyric acid,
(119) 4-[3-methyl-1-(3-chlorobenzyl)-1H-pyrazol-4-yl]-2,4-dioxobutyric acid ethyl ester,
(120) 4-[3-methyl-1-(3-chlorobenzyl)-1H-pyrazol-4-yl]-2,4-dioxobutyric acid,
(121) 4-[5-methyl-1-(3-chlorobenzyl)-1H-pyrazol-4-yl]-2,4-dioxobutyric acid,
(122) 4-[5-methyl-1-(3-chlorobenzyl)-1H-pyrazol-4-yl]-2,4-dioxobutyric acid ethyl ester,
(123) 4-[5-methyl-1-(3-chlorobenzyl)-1H-pyrazol-4-yl]-2,4-dioxobutyric acid,
(124) 4-[1-(4-fluoro-benzyl)-1H-imidazol-2-yl]-2,4-dioxo-butyric acid,
(125) 4-[1-(4-fluorobenzyl)-1H-imidazol-2-yl]-2,4-dioxo-butyric acid ethyl ester,
(126) 4-[1-(4-fluorobenzyl)-1H-imidazol-2-yl]-2,4-dioxo-butyric acid,
(127) 4-(1-Benzyl-1H-imidazol-2-yl)-2,4-dioxobutyric acid,
(128) 4-[1-(4-fluorobenzyl)-1H-imidazol-4-yl]-2,4-dioxo-butyric acid ethyl ester,
(129) 4-[1-(4-fluorobenzyl)-1H-imidazol-4-yl]-2,4-dioxo-butyric acid,
(130) 4-[1-(4-fluorobenzyl)-1H-indol-2-yl]-2,4-dioxobutyric acid methyl ester,
(131) 4-[1-(4-fluorobenzyl)-1H-indol-2-yl]-2,4-dioxobutyric acid,
(132) 2-hydroxy-4-(1-methyl-1-H-indol-2-yl)-2,4-dioxobutyric acid,
(133) 4-[1-(4-fluorobenzyl)-1H-indol-3-yl]-2,4-dioxobutyric acid,
(134) 1-[1-(4-fluorobenzyl)-1H-indol-3-yl]-2,4-dioxobutyric acid ethyl ester,
(135) 1-[1-(4-fluorobenzyl)-1H-indol-3-yl]-2,4-dioxobutyric acid, (136) 4-[1-(3-fluorobenzyl)-1-H-pyrrol-3-yl]-2,4-dioxobutyric acid,
(137) 4-[4-(3-chlorobenzyl)-1-H-pyrrol-3-yl]-2,4-dioxo-butyric acid,
(138) 4-[4-(4-fluorobenzyl)-1-methyl-1-H-pyrrol-3-yl]-2,4-dioxobutyric acid, (139) 4-[2,5-dimethyl-1-(4-fluorobenzyl)-1-H-pyrrol-3-yl]-2,4-dioxobutyric acid,
(140) 4-[1-(3,5-dichlorobenzyl)-1-H-pyrrol-3-yl]-2,4-dioxobutyric acid,
(141) 4-[1-(3-thiophenemethyl)-1-H-pyrrol-3-yl]-2,4-dioxobutyric acid,
(142) 4-[1-2,4-dimethylbenzyl)-1-H-pyrrol-3-yl]-2,4-dioxobutyric acid,
(143) 4-[1-(3-chloro-5-methyl-benzyl)-1-H-pyrrol-3-yl]-2,4-dioxobutyric acid,
(144) 4-[1-(1-naphthalenemethyl)-1-H-pyrrol-3-yl]-2,4-dioxobutyric acid,
(145) 4-[1-(2-thiophenemethyl)-1-H-pyrrole-3-yl]-2,4-dioxobutyric acid, and
(146) 4-[4-(3-chlorobenzyl)-1-methyl-1-H-pyrrol-3-yl]-2,4-dioxobutyric acid, or a tautomer or a pharmaceutically acceptable salt thereof.

One embodiment of the present invention are compounds of structural formula:

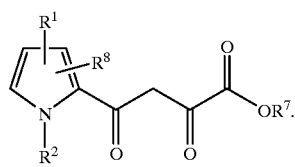

Another embodiment of the present invention are compounds of structural formula:

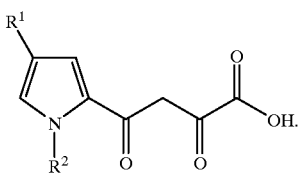

Still another embodiment of the present invention are compounds of structural formula:

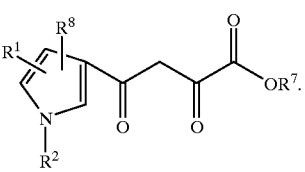

Another embodiment of the present invention are compounds of structural formula:

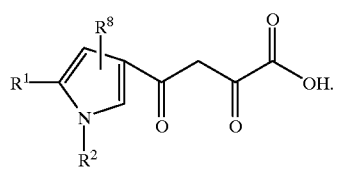

Another embodiment of the present invention are compounds of structural formula:

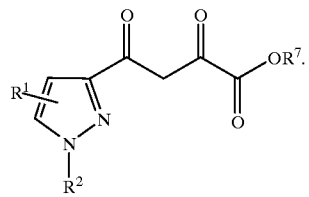

Another embodiment of the present invention are compounds of structural formula:

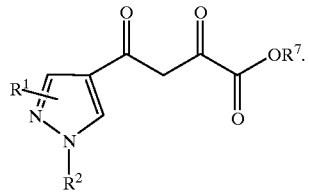

Another embodiment of the present invention are compounds of structural formula:

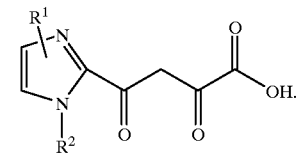

Another embodiment of the present invention are compounds of structural formula:

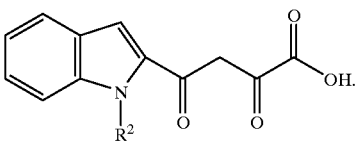

In one class of compounds of the present invention, A is selected from:
(1) pyrrolyl,
(2) imidazolyl,
(3) pyrazolyl, and
(4) indolyl, provided that the nitrogen-containing heteroaromatic ring is substituted by the dioxobutyric moiety in structural formula (I).

In another class of compounds of the present invention, A is pyrazolyl.

In yet another class of compounds of the present invention, A is imidazolyl.

In still another class of compounds of the present invention, A is pyrrolyl.

In another class of compounds of the present invention, A is indolyl and the dioxobutyric acid/ester moeity is attached to the nitrogen containing ring of the indole.

In one class of compounds of the present invention, $R^1$ is selected from:
(1) —H,
(2) —$CH_3$,
(3) —$CF_3$,
(4) -halo, (5) —NO$_2$,
(6) —N(R$^4$)(R$^5$),
(7) -phenyl,
(8) substituted phenyl substituted with 1 or 2 substituents independently selected from:
  (a) halogen,
  (b) C$_{1-6}$ alkyl,
  (c) C$_{1-6}$ alkyloxy-,
  (d) phenyl,
  (e) —CF$_3$,
  (f) —OCF$_3$,
  (g) —CN,
  (h) hydroxy,
  (i) phenyloxy, and
  (j) substituted phenyloxy with 1, 2, or 3 substituents selected from:
    (i) halogen,
    (ii) C$_{1-6}$ alkyl,
    (iii) —CF$_3$, and
    (iv) hydroxy,
(9) phenyl C$_{1-3}$ alkyl-,
(10) substituted phenyl C$_{1-3}$ alkyl-substituted with 1 or 2 substituents independently selected from:
  (a) halogen,
  (b) C$_{1-6}$ alkyl,
  (c) C$_{1-6}$ alkyloxy-,
  (d) phenyl,
  (e) —CF$_3$,
  (f) —OCF$_3$,
  (g) —CN,
  (h) hydroxy,
  (i) phenyloxy, and
  (j) substituted phenyloxy with 1, 2, or 3 substituents selected from:
    (i) halogen,
    (ii) C$_{1-6}$ alkyl,
    (iii) —CF$_3$, and
    (iv) hydroxy,
(11) —C$_{2-5}$ alkenyl-R$^3$,
(12) —C$_{2-5}$ alkynyl-R$^3$, and
(13) —C(O)CH$_2$C(O)C(O)OR$^7$.

In another class of compounds of the present invention, R$^1$ is selected from:
(1) —H,
(2) —CH$_3$,
(3) —CF$_3$,
(4) -halo,
(5) —NO$_2$,
(6) —N(R$^4$)(R$^5$),
(7) -phenyl,
(8) substituted phenyl substituted with 1 or 2 substituents independently selected from:
  (a) halo,
  (b) methyl, and
  (c) methoxy,
(9) phenyl C$_{1-3}$ alkyl-,
(10) substituted phenyl C$_{1-3}$ alkyl-substituted with 1 or 2 substituents independently selected from:
  (a) halo,
  (b) methyl, and
  (c) methoxy,
(11) —C$_{2-5}$ alkenyl-R$^3$, and
(12) —C(O)CH$_2$C(O)C(O)OR$^7$, In yet another class of compounds of the present invention, R$^1$ is selected from:
(1) —H,
(2) —C$_{1-5}$ alkyl,
(3) —CF$_3$,
(4) -halo,
(5) —NO$_2$,
(6) —N(R$^4$)(R$^5$),
(7) -phenyl,
(8) substituted phenyl substituted with 1 substituent independently selected from:
  (a) halo,
  (b) methyl, and
  (c) methoxy,
(9) phenyl C$_{1-3}$ alkyl-,
(10) substituted phenyl C$_{1-3}$ alkyl-substituted with 1 or 2 substituents independently selected from:
  (a) halo,
  (b) methyl, and
  (c) methoxy,
(11) —C$_{2-5}$ alkenyl-R$^3$, and
(12) —C(O)CH$_2$C(O)C(O)OR$^7$.

In yet another class of compounds of the present invention, R$^1$ is selected from:
(1) —H,
(2) —C$_{1-5}$ alkyl,
(3) —CF$_3$,
(4) -halo, wherein halo is selected from: —F, Cl, —Br, and —I;
(5) —NO$_2$,
(6) —N(R$^4$)(R$^5$),
(7) -phenyl,
(8) phenyl C$_{1-3}$ alkyl-,
(9) substituted phenyl C$_{1-3}$ alkyl-substituted with 1 or 2 substituents independently selected from:
  (a) halo, wherein halo is selected from: —F, —Cl, and —Br;
(10) —C$_{2-5}$ alkynyl-R$^3$, and
(11) —C(O)CH$_2$C(O)C(O)OR$^7$.

In another class of compounds of the present invention, R$^1$ is selected from:
(1) —H,
(2) —C$_{1-5}$ alkyl,
(3) —CF$_3$,
(4) -halo, wherein halo is selected from: —F, Cl, —Br, and —I;
(5) —NO$_2$,
(6) —N(R$^4$)(R$^5$),
(7) -phenyl,
(8) phenyl C$_{1-3}$ alkyl-,
(9) substituted phenyl C$_{1-3}$ alkyl-substituted with 1 or 2 substituents independently selected from:
  (a) halo, wherein halo is selected from: —F, —Cl, and —Br, and
(10) —C$_{2-5}$ alkynyl-R$^3$.

In one class of compounds of the present invention, R$^2$ is selected from:
(1) —H,
(2) —R$^3$,
(3) —C$_{1-6}$ alkyl, (4) —$C_{1-6}$ alkyl substituted with $R^3$,
(5) —O—$R^6$,
(6) —O—$C_{1-6}$ alkyl-$OR^6$,
(7) —S(O)n-$R^6$,
(8) —$C_{1-6}$ alkyl ($OR^6$)($R^4$),
(9) —$C_{1-6}$ alkyl-N($R^4$)($R^6$),
(10) —$C_{1-6}$ alkyl S(O)n-$R^6$,
(11) —$C_{1-6}$ alkyl C(O)—$R^6$,
(12) —$C_{1-6}$ alkyl C(S)—$R^6$,
(13) —$C_{1-6}$ alkyl $NR^4$C(O)—$R^6$, and
(14) —$C_{1-6}$ alkyl-C(O)N($R^4$)($R^5$).

In another class of compounds of the present invention, $R^2$ is selected from:
(1) —H,
(2) —$R^3$,
(3) —$C_{1-6}$ alkyl,
(4) —$C_{1-6}$ alkyl substituted with $R^3$,
(5) —O—$R^6$,
(6) —O—$C_{1-6}$ alkyl-$OR^6$,
(7) —S(O)n-$R^6$,
(8) —$C_{1-6}$ alkyl ($OR^6$)($R^4$),
(9) —$C_{1-6}$ alkyl-N($R^4$)($R^6$),
(10) —$C_{1-6}$ alkyl S(O)n-$R^6$,
(11) —$C_{1-6}$ alkyl $NR^4$C(O)—$R^6$, and
(12) —$C_{1-6}$ alkyl-C(O)N($R^4$)($R^5$).

In yet another class of compounds of the present invention, $R^2$ is selected from:
(1) —H,
(2) —$R^3$,
(3) —$C_{1-6}$ alkyl,
(4) —$C_{1-6}$ alkyl substituted with $R^3$,
(5) —O—$R^6$,
(6) —O—$C_{1-6}$ alkyl-$OR^6$,
(7) —$C_{1-6}$ alkyl ($OR^6$)($R^4$),
(8) —$C_{1-6}$ alkyl-N($R^4$)($R^6$),
(9) —$C_{1-6}$ alkyl C(O)—$R^6$,
(10) —$C_{1-6}$ alkyl $NR^4$C(O)—$R^6$, and
(11) —$C_{1-6}$ alkyl-C(O)N($R^4$)($R^5$).

In still another class of compounds of the present invention, $R^2$ is selected from:
(1) —H,
(2) —$R^3$,
(3) —$C_{1-6}$ alkyl,
(4) —$C_{1-6}$ alkyl substituted with $R^3$,
(5) —O—$R^6$,
(6) —O—$C_{1-6}$ alkyl-$OR^6$,
(7) —$C_{1-6}$ alkyl ($OR^6$)($R^4$),
(8) —$C_{1-6}$ alkyl-N($R^4$)($R^6$),
(9) —$C_{1-6}$ alkyl C(O)—$R^6$, and
(10) —$C_{1-6}$ alkyl $NR^4$C(O)—$R^6$.

In one class of compounds of the present invention, $R^3$ is selected from:
(1) phenyl;
(2) substituted phenyl with 1, 2, or 3 substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(3) thienyl;
(4) substituted thienyl substituted on a carbon atom with one or two substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(5) pyridyl;
(6) substituted pyridyl substituted on a carbon atom with one or two substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(7) imidazolyl;
(8) substituted imidazolyl substituted on a carbon atom with one or two substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl, (iii) —CF$_3$, and
(iv) hydroxy;
(9) pyrrolyl;
(10) substituted pyrrolyl substituted on a carbon atom with one or two substituents independently selected from:
(a) halogen,
(b) C$_{1-6}$ alkyl,
(c) C$_{1-6}$ alkyloxy-,
(d) phenyl,
(e) —CF$_3$,
(f) —OCF$_3$,
(g) —CN,
(h) hydroxy,
(i) phenyloxy, and
(j) substituted phenyloxy with 1, 2, or 3 substituents selected from:
(i) halogen,
(ii) C$_{1-6}$ alkyl,
(iii) —CF$_3$, and
(iv) hydroxy;
(11) pyrazolyl;
(12) substituted pyrazolyl substituted on a carbon atom with one or two substituents independently selected from:
(a) halogen,
(b) C$_{1-6}$ alkyl,
(c) C$_{1-6}$ alkyloxy-,
(d) phenyl,
(e) —CF$_3$,
(f) —OCF$_3$,
(g) —CN,
(h) hydroxy,
(i) phenyloxy, and
(j) substituted phenyloxy with 1, 2, or 3 substituents selected from:
(i) halogen,
(ii) C$_{1-6}$ alkyl,
(iii) —CF$_3$, and
(iv) hydroxy;
(13) C$_{3-6}$ cycloalkyl;
(14) substituted C$_{3-6}$ cycloalkyl with 1 or 2 substituents independently selected from:
(a) halogen,
(b) C$_{1-6}$ alkyl,
(c) C$_{1-6}$ alkyloxy-,
(d) —CF$_3$,
(e) —OCF$_3$,
(f) —CN,
(g) =O,
(h) hydroxy;
(15) piperidinyl;
(16) substituted piperidinyl substituted on a carbon atom with one or two substituents independently selected from:
(a) halogen,
(b) C$_{1-6}$ alkyl,
(c) C$_{1-6}$ alkyloxy-,
(d) —CF$_3$,
(e) —OCF$_3$,
(f) —CN,
(g) =O,
(h) hydroxy;
(17) morpholinyl;
(18) substituted morpholinyl substituted at a carbon or nitrogen atom with 1 or 2 independently selected from:
(a) halogen,
(b) C$_{1-6}$ alkyl,
(c) C$_{1-6}$ alkyloxy-,
(d) —CF$_3$,
(e) —OCF$_3$,
(f) —CN,
(g) =O,
(h) hydroxy;
(19) naphthyl;
(20) substituted naphthyl with 1, 2, or 3 substituents independently selected from:
(a) -halogen,
(b) —C$_{1-6}$ alkyl,
(c) —C$_{1-6}$ alkyloxy-,
(d) —CF$_3$,
(e) —OCF$_3$,
(f) —CN, and
(g) -hydroxy;
(21) indolyl;
(22) substituted indolyl substituted on a carbon atom with one or two substituents independently selected from:
(a) -halogen,
(b) —C$_{1-6}$ alkyl,
(c) —C$_{1-6}$ alkyloxy-,
(d) —CF$_3$,
(e) —OCF$_3$,
(f) —CN, and
(g) -hydroxy;
(23) C$_{3-6}$ cycloalkyl fused with a phenyl ring;
(24) substituted C$_{3-6}$ cycloalkyl fused with a phenyl ring substituted on a carbon atom with one or two substituents independently selected from:
(a) halogen,
(b) C$_{1-6}$ alkyl,
(c) C$_{1-6}$ alkyloxy-,
(d) —CF$_3$,
(e) —OCF$_3$,
(f) —CN,
(g) =O, and
(h) hydroxy.

In another class of compounds of the present invention, R$^3$ is selected from:
(1) phenyl,
(2) substituted phenyl with 1, 2, or 3 substituents independently selected from:
(a) halogen,
(b) C$_{1-6}$ alkyl,
(c) C$_{1-6}$ alkyloxy-,
(d) phenyl,
(e) —CF$_3$,
(f) —OCF$_3$,
(g) —CN,
(h) hydroxy,
(i) phenyloxy, and
(j) substituted phenyloxy with 1, 2, or 3 substituents selected from:
(i) halogen,
(ii) C$_{1-6}$ alkyl,
(iii) —CF$_3$, and
(iv) hydroxy,
(3) thienyl,
(4) pyridyl,
(5) imidazolyl,
(6) pyrrolyl,
(7) pyrazolyl, (8) $C_{3-6}$ cycloalkyl,
(9) substituted $C_{3-6}$ cycloalkyl with 1 or 2 substituents independently selected from:
   (a) halogen,
   (b) $C_{1-6}$ alkyl,
   (c) $C_{1-6}$ alkyloxy-,
   (d) —$CF_3$,
   (e) —$OCF_3$,
   (f) —CN,
   (g) =O, and
   (h) hydroxy;
(10) piperidinyl,
(11) morpholinyl,
(12) naphthyl,
(13) indolyl, and
(14) $C_{3-6}$ cycloalkyl fused with a phenyl ring.

In still another class of compounds of the present invention, $R^3$ is selected from:
(1) phenyl;
(2) substituted phenyl with 1, 2, or 3 substituents independently selected from:
   (a) halogen,
   (b) $C_{1-6}$ alkyl,
   (c) $C_{1-6}$ alkyloxy-,
   (d) phenyl,
   (e) —$CF_3$,
   (f) —$OCF_3$,
   (g) —CN,
   (h) hydroxy,
   (i) phenyloxy, and
   (j) substituted phenyloxy with 1, 2, or 3 substituents selected from:
      (i) halogen, wherein halogen is selected from —F, —Cl, and Br,
      (ii) methyl,
      (iii) —$CF_3$, and
      (iv) hydroxy;
(3) $C_{3-6}$ cycloalkyl,
(4) morpholinyl,
(5) substituted morpholinyl substituted with oxo; and
(6) naphthyl.

In one class of compounds of the present invention, $R^4$ is selected from:
(1) —H,
(2) —$C_{1-3}$ alkyl, and
(3) —$CF_3$.

In another class of compounds of the present invention, $R^4$ is selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$,
(7) —$C_{2-3}$ alkenyl-$R^3$,
(8) —$S(O)_n$—$R^3$, and
(9) —$C(O)$—$R^3$.

In still another class of compounds of the present invention, $R^4$ is selected from:
(1) —H,
(2) —$C_{1-3}$ alkyl,
(3) —$CF_3$,
(4) —$R^3$,
(5) —$C_{1-3}$ alkyl-$R^3$,
(6) —$S(O)_n$—$R^3$, and
(7) —$C(O)$—$R^3$.

In yet another class of compounds of the present invention, $R^4$ is selected from:
(1) —H, and
(2) —$C_{1-3}$ alkyl.

In one class of compounds of the present invention, $R^5$ is selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$,
(7) —$C_{2-3}$ alkenyl-$R^3$,
(8) —$S(O)_n$—$R^3$, and
(9) —$C(O)$—$R^3$.

In another class of compounds of the present invention, $R^5$ is selected from:
(1) —H,
(2) —$C_{1-3}$ alkyl,
(3) —$CF_3$, and
(4) —$R^3$.

In yet another class of compounds of the present invention, $R^5$ is selected from:
(1) —H,
(2) —$C_{1-3}$ alkyl,
(3) —$CF_3$,
(4) —$R^3$,
(5) —$C_{1-3}$ alkyl-$R^3$,
(6) —$S(O)_n$—$R^3$, and
(7) —$C(O)$—$R^3$.

In one class of compounds of the present invention, $R^7$ is hydrogen.

In another class of compounds of the present invention, $R^7$ is selected from:
(1) —H, and
(2) $C_{1-4}$ alkyl.

In one class of compounds of the present invention, $R^8$ is selected from:
(1) —H,
(2) —$OCH_3$, and
(3) —$CH_3$.

In another class of compounds of the present invention, $R^8$ is selected from:
(1) —H, and
(2) $CH_3$.

In yet another class of compounds of the present invention, $R^8$ is selected from:
(1) —H, and
(2) $C_{1-6}$ alkyl.

Also included within the present invention are pharmaceutical compositions useful for inhibiting HIV integrase, comprising an effective amount of a compound of this invention, and a pharmaceutically acceptable carrier. Pharmaceutical compositions useful for treating infection by HIV, or for treating AIDS or ARC, are also encompassed by the present invention, as well as a method of inhibiting HIV integrase, and a method of treating infection by HIV, or of treating AIDS or ARC. Additionally, the present invention is directed to a pharmaceutical composition comprising a therapeutically effective amount of a compound of the present invention in combination with a therapeutically effective amount of an AIDS treatment agent selected from:
(1) an AIDS antiviral agent,
(2) an anti-infective agent, and
(3) an immunomodulator.

The compounds of the present invention may have asymmetric centers and may occur, except when specifically noted, as mixtures of stereoisomers or as individual diastereomers, or enantiomers, with all isomeric forms being included in the present invention.

As is recognized by one of ordinary skill in the art, the diketo-acid/ester compounds of the present invention exist as tautomers, and thus by using the phrase "and tautomers thereof" in describing compounds of structural formula (I), Applicants also intend the following tautomeric forms of the same compound (Ia) and (Ib):

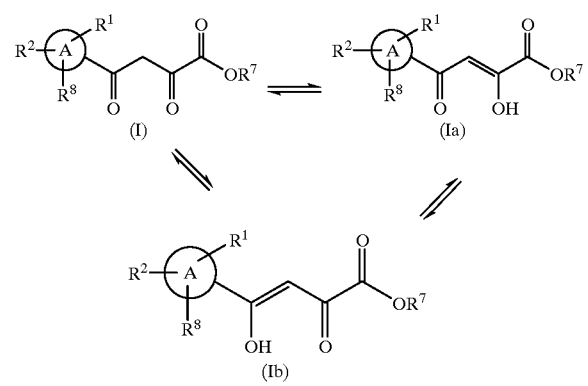

By naming or referring to compound (I) and tautomers thereof, it is understood for the purposes of the present application that the tautomers (Ia) and (Ib) are also intended. Similarly, be referring to compound (Ia), it is understood for the purposes of the present application that the tautomers (I) and (Ib) are also intended. The same holds true for references to tautomer (Ib).

When any variable (e.g., $R^3$, $R^4$, etc.) occurs more than one time in any constituent or in formula I, its definition on each occurrence is independent of its definition at every other occurrence. Also, combinations of substituents and/or variables are permissible only if such combinations result in stable compounds.

The compounds of the present inventions are useful in the inhibition of HIV integrase, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention are commercial products to be sold for these purposes.

The present invention also provides for the use of a compound of structural formula (I) to make a pharmaceutical composition useful for inhibiting HIV integrase and in the treatment of AIDS or ARC.

Compounds of structural formula (I) wherein A is pyrrolyl may be made according to the procedures in Schemes AI–AXI. Compounds of structural formula (I) wherein A is pyrazolyl may be prepared according to the procedures in Schemes BI–BV. Compounds of structural formula (I) wherein A is imidazolyl are prepared according to the procedures in Schemes CI–CII. Schemes DI–D2 illustrate the preparation of the indolyl compounds of the present invention.

SCHEME AI

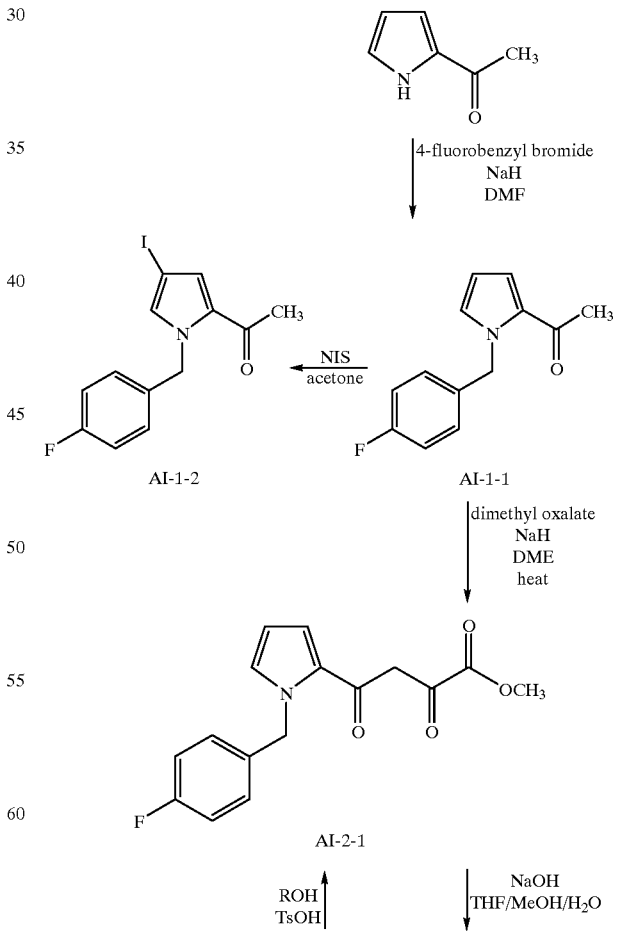

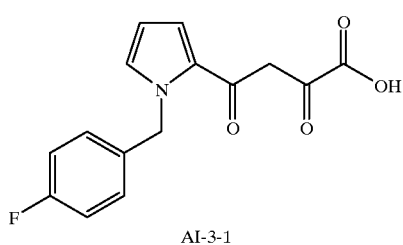
AI-3-1
Scheme AII
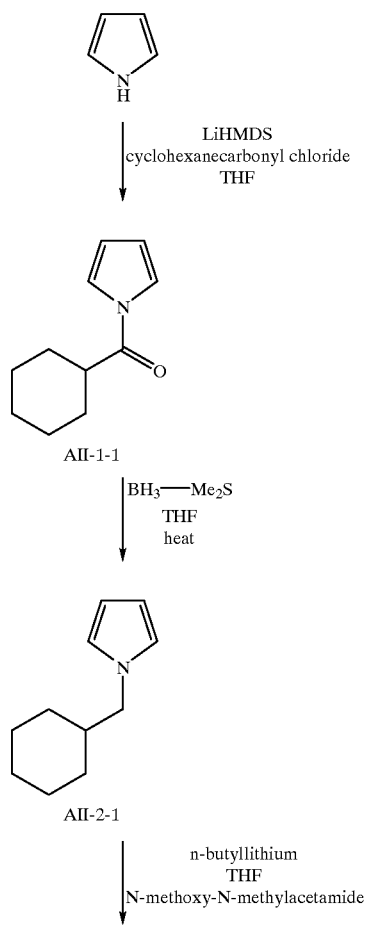
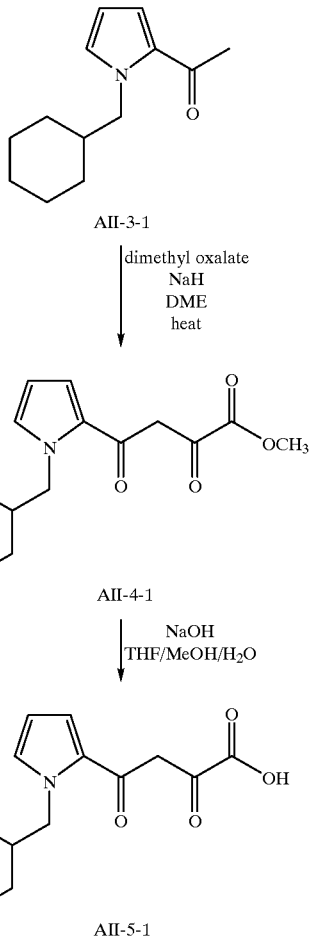

Scheme AIII
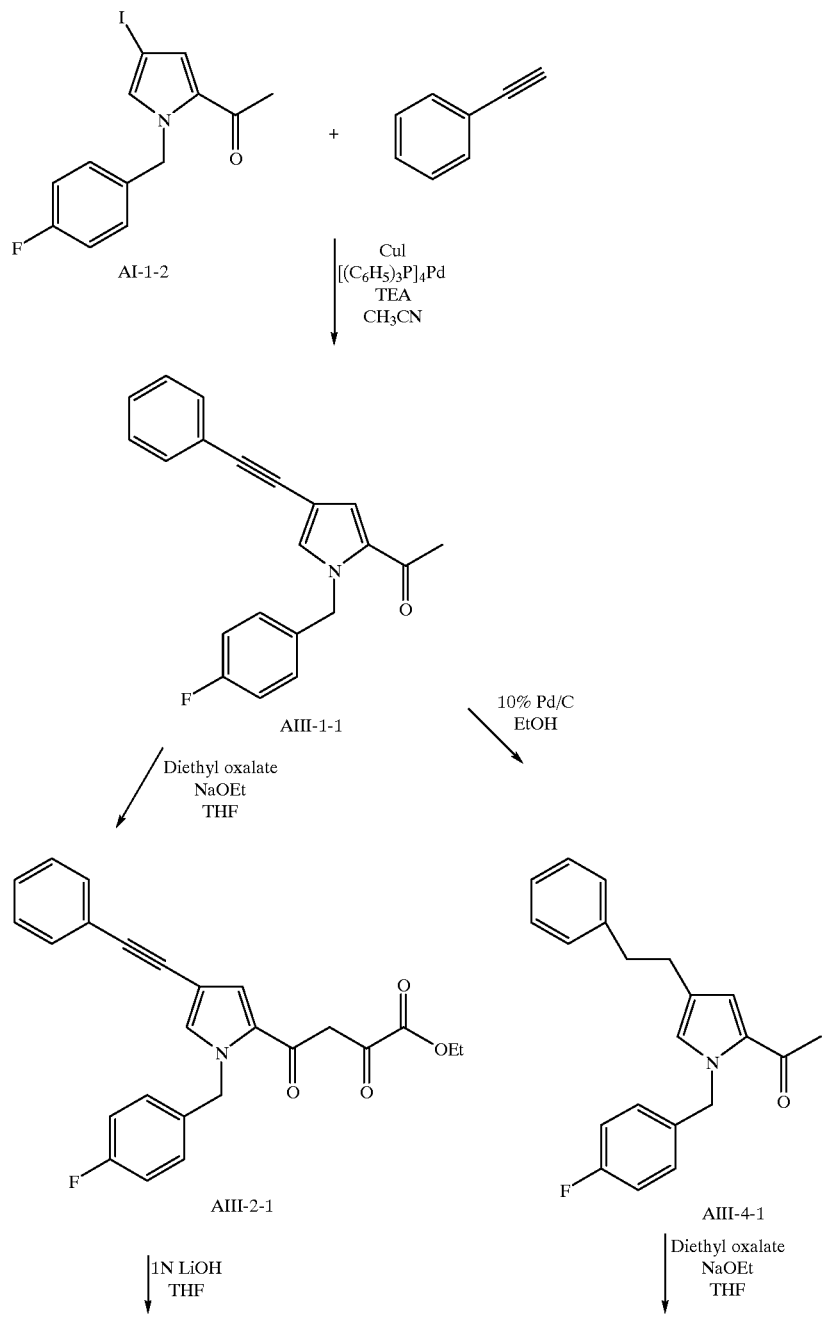

-continued
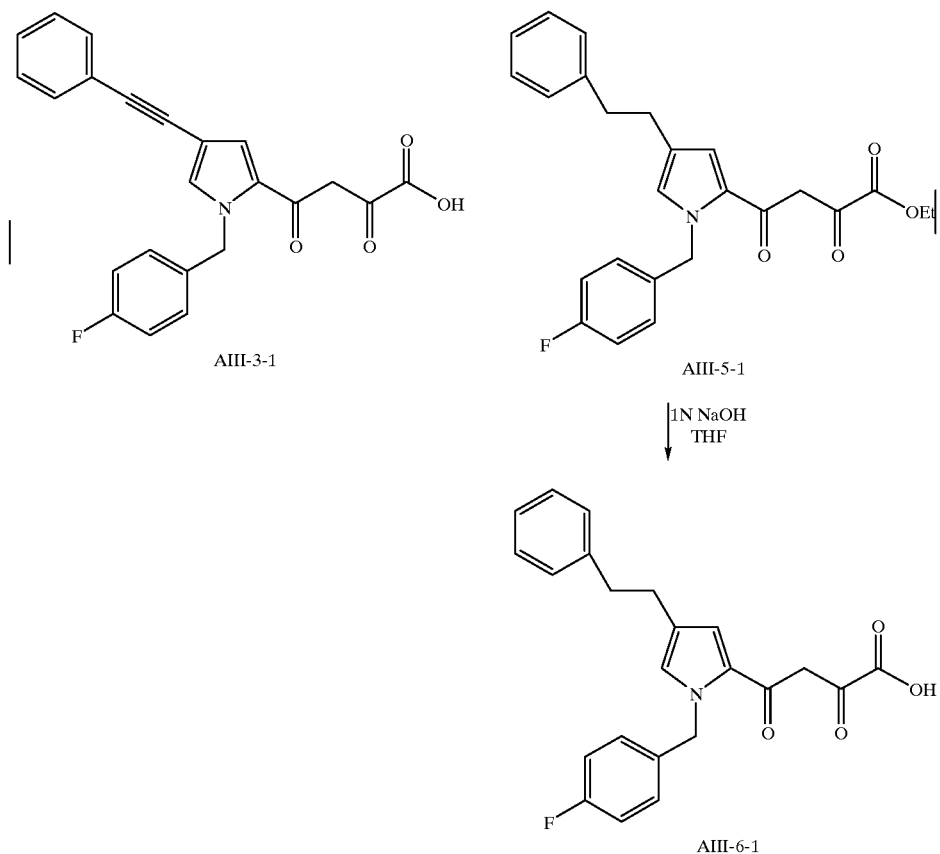
Scheme AIV
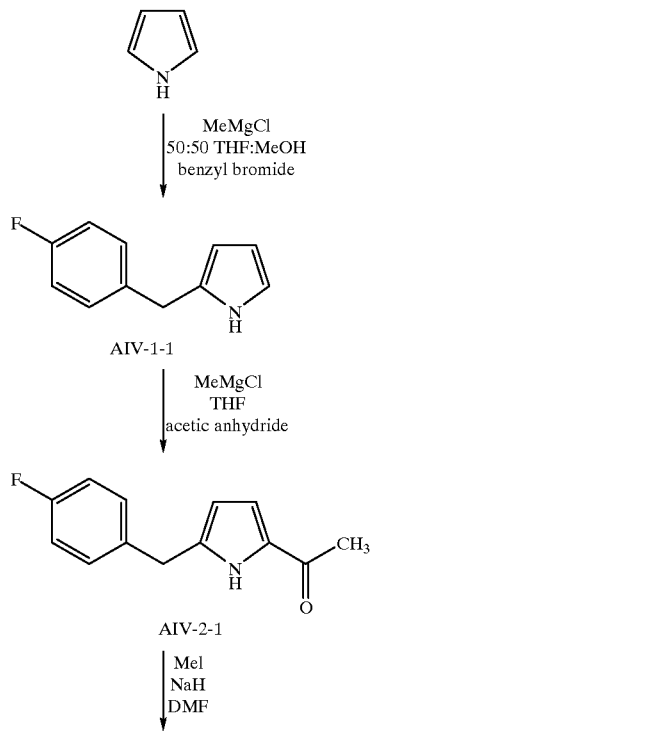

-continued
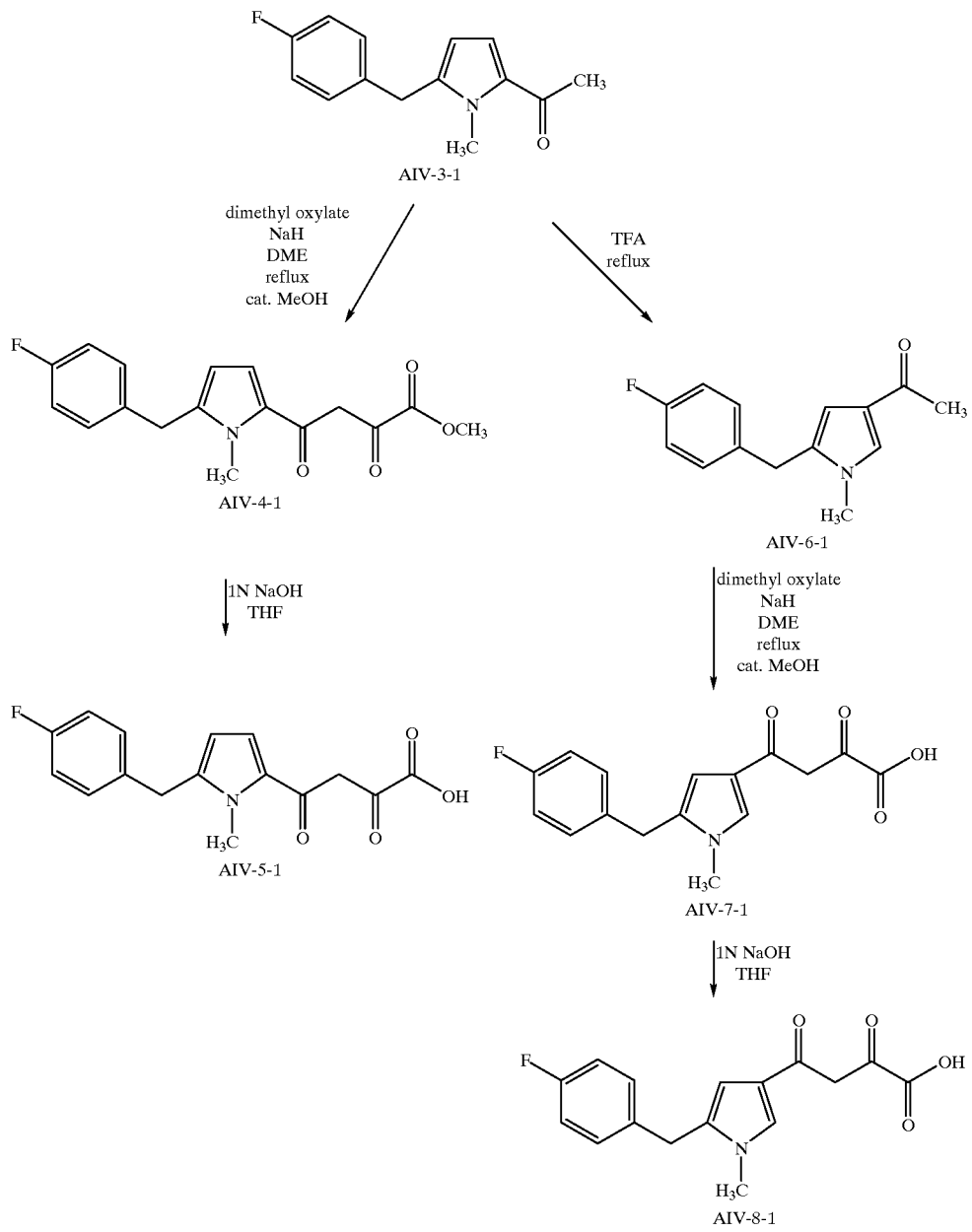
Scheme AV
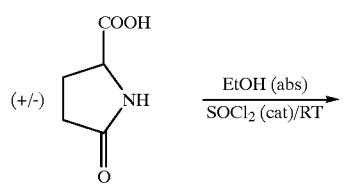
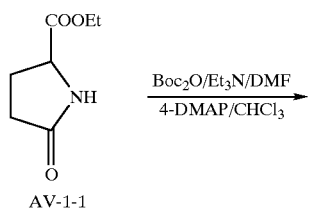

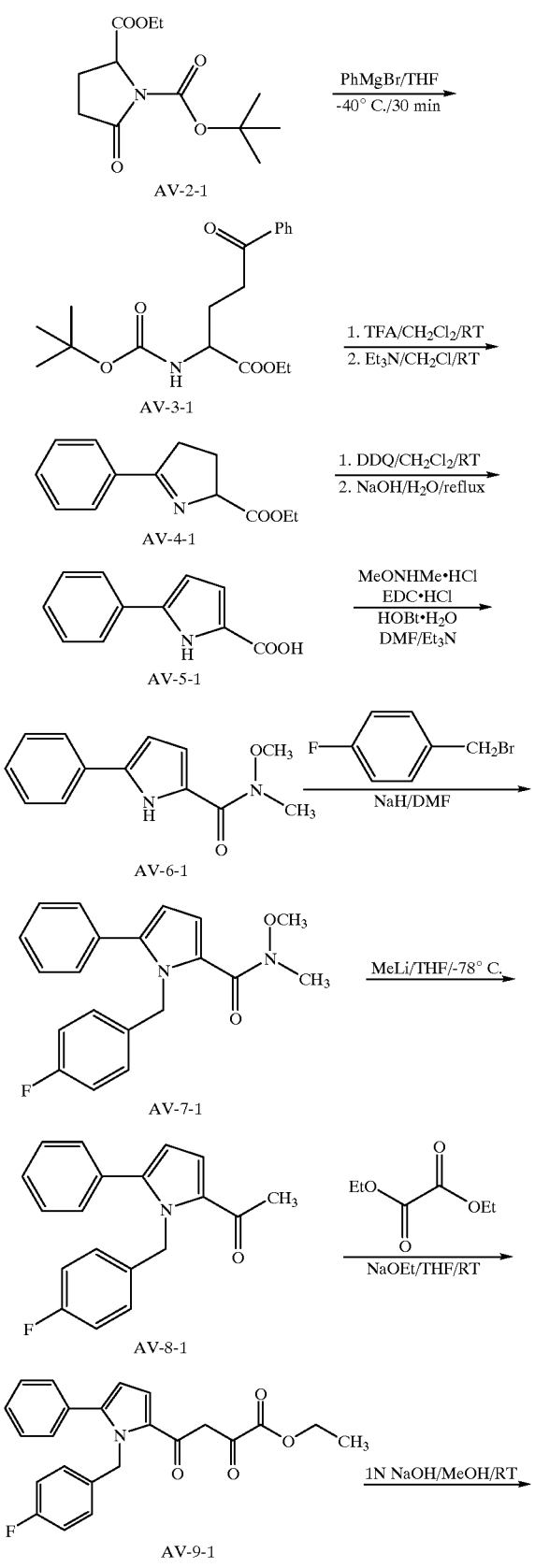
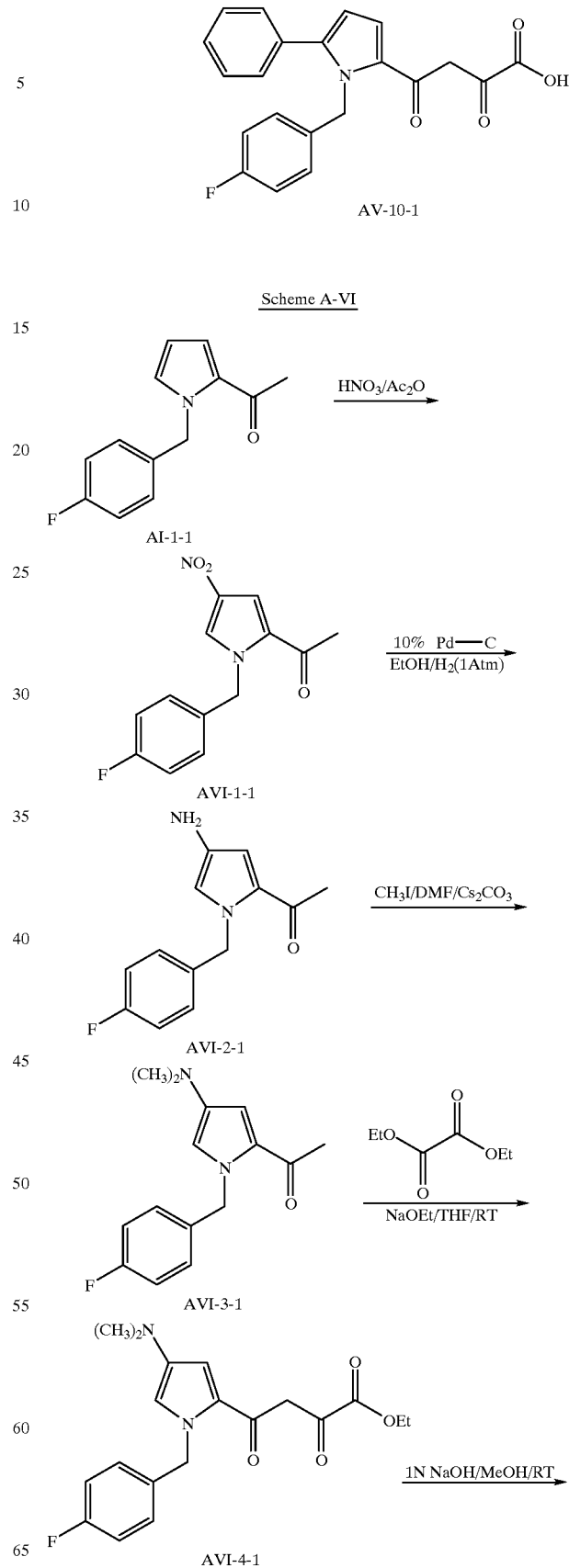
Scheme A-VI

31
-continued
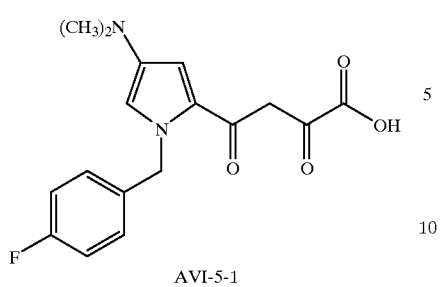
AVI-5-1
32
-continued
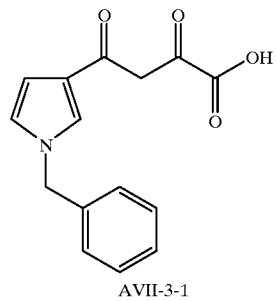
AVII-3-1
SCHEME AVII
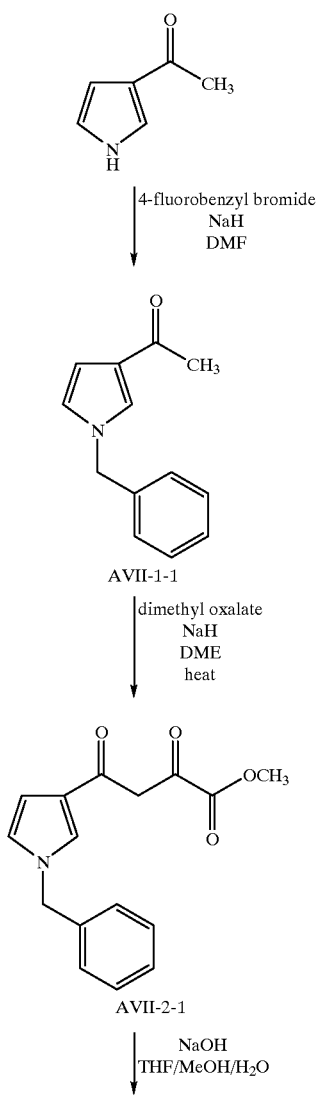
Scheme AVIII
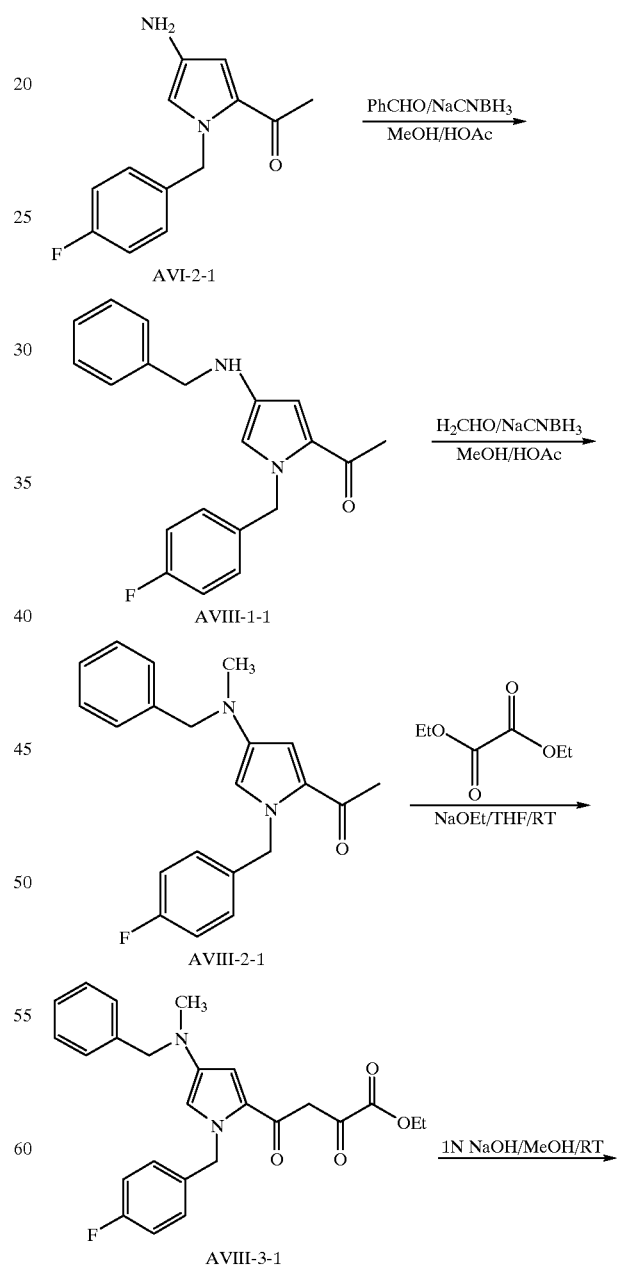

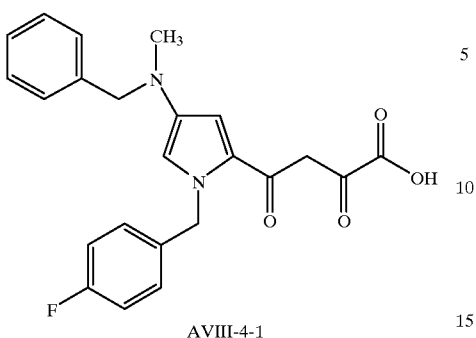
AVIII-4-1
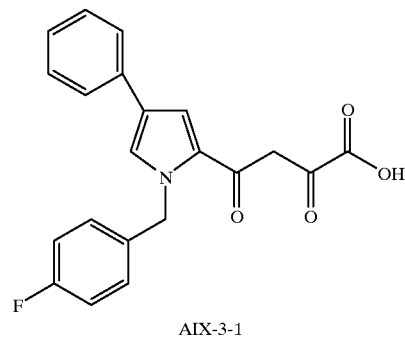
AIX-3-1
Scheme AIX
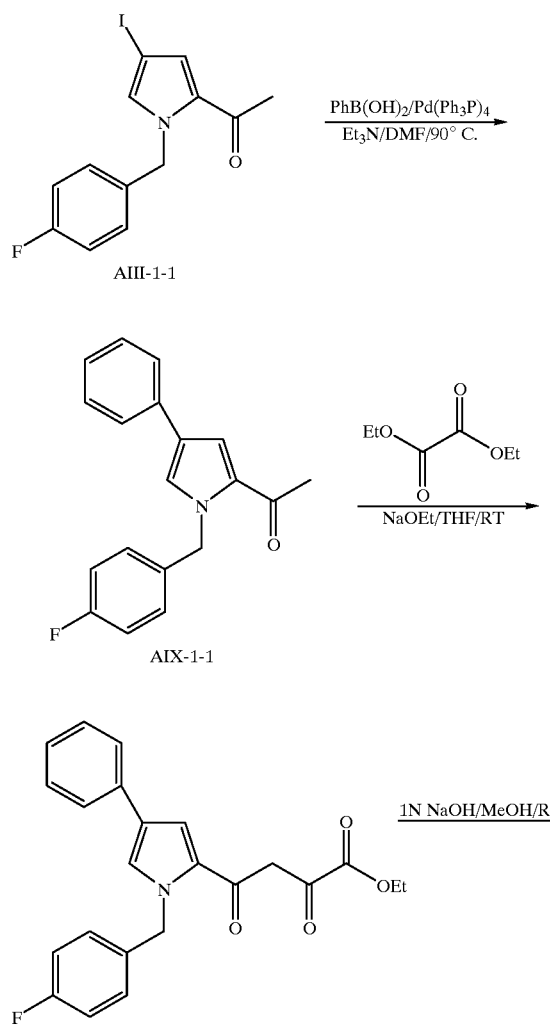
SCHEME AX
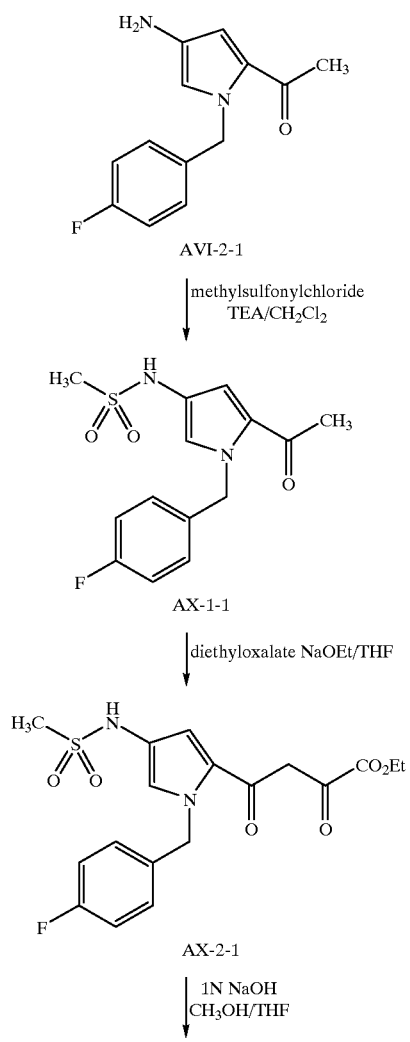

-continued
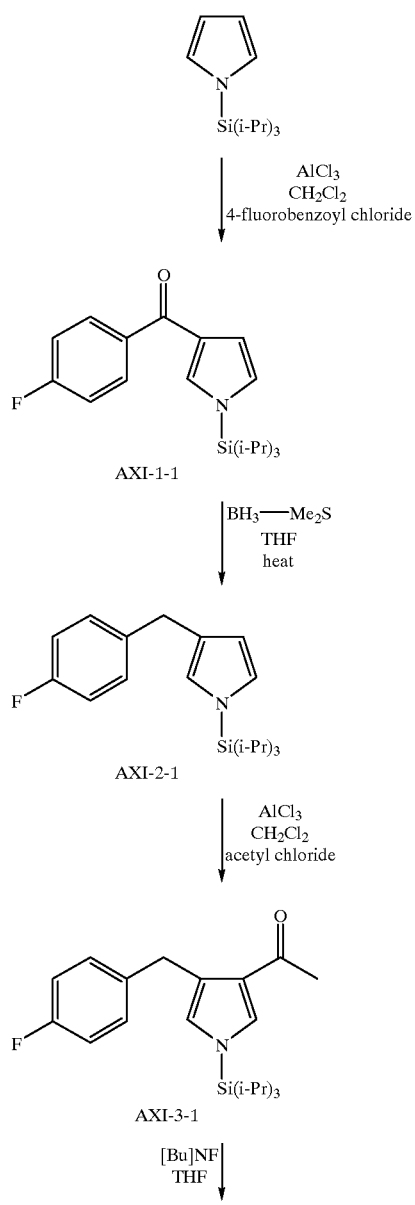
AX-3-1
Scheme AXI
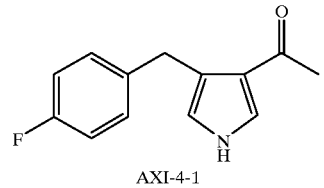
AXI-4-1
1) dimethyl oxalate
   NaH
   DME
   heat
2) NaOH
   THF/MeOH/H$_2$O
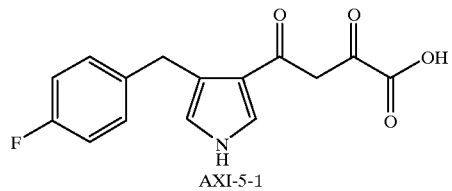
AXI-5-1
Scheme AXI(b)
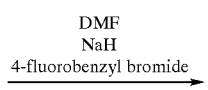
AXI-4-1
DMF
NaH
4-fluorobenzyl bromide
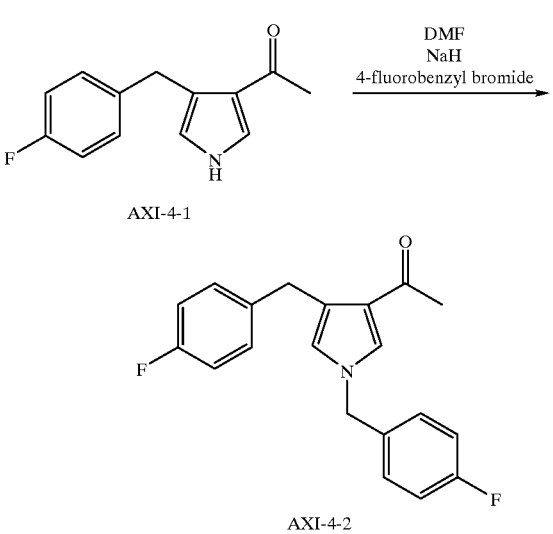
AXI-4-2
1) dimethyl oxalate
   NaH
   DME
   heat
2) NaOH
   THF/MeOH/H$_2$O
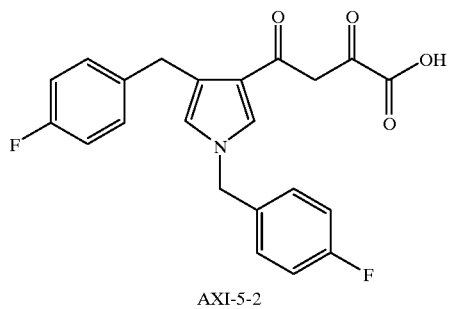
AXI-5-2

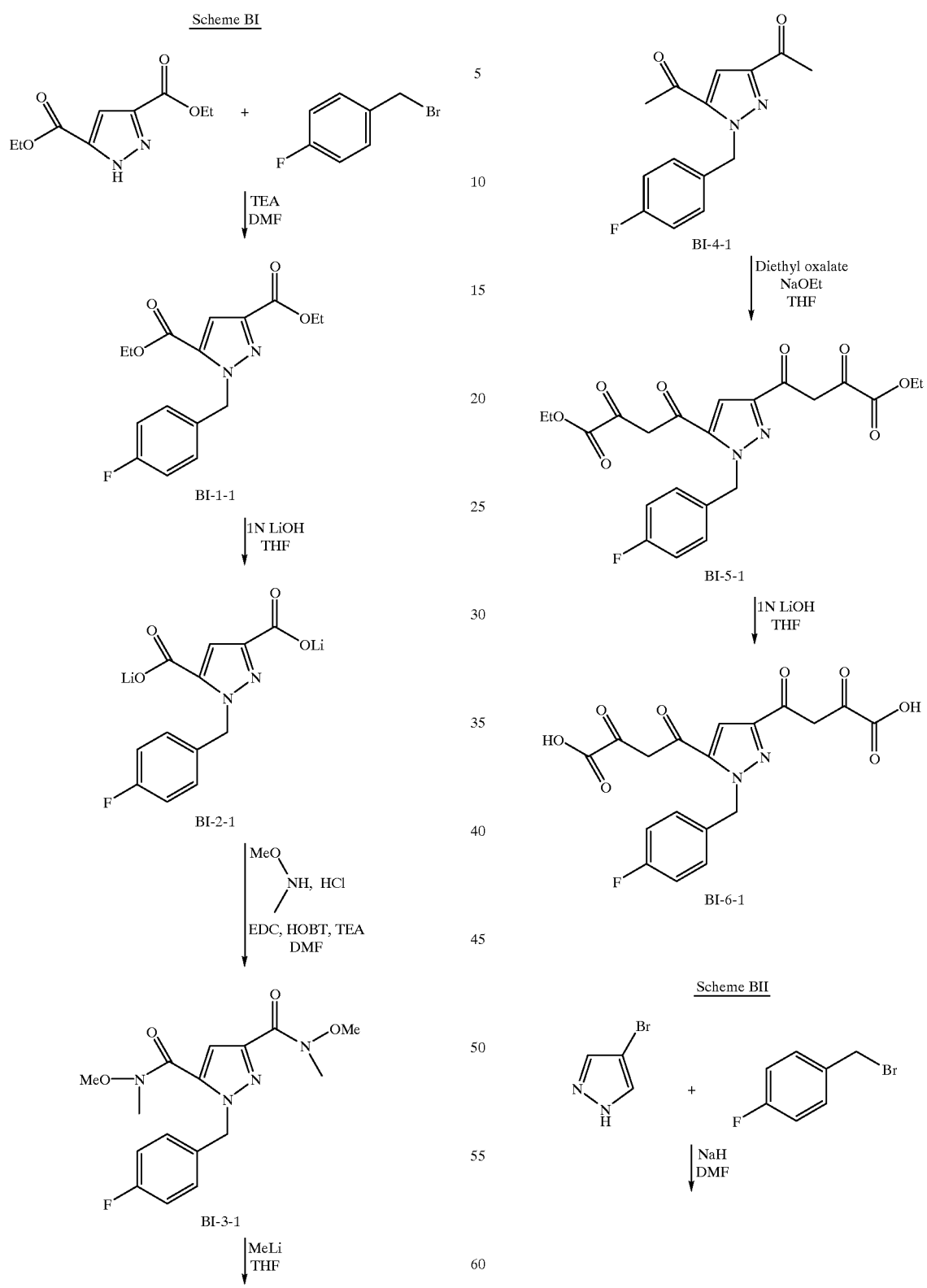

-continued
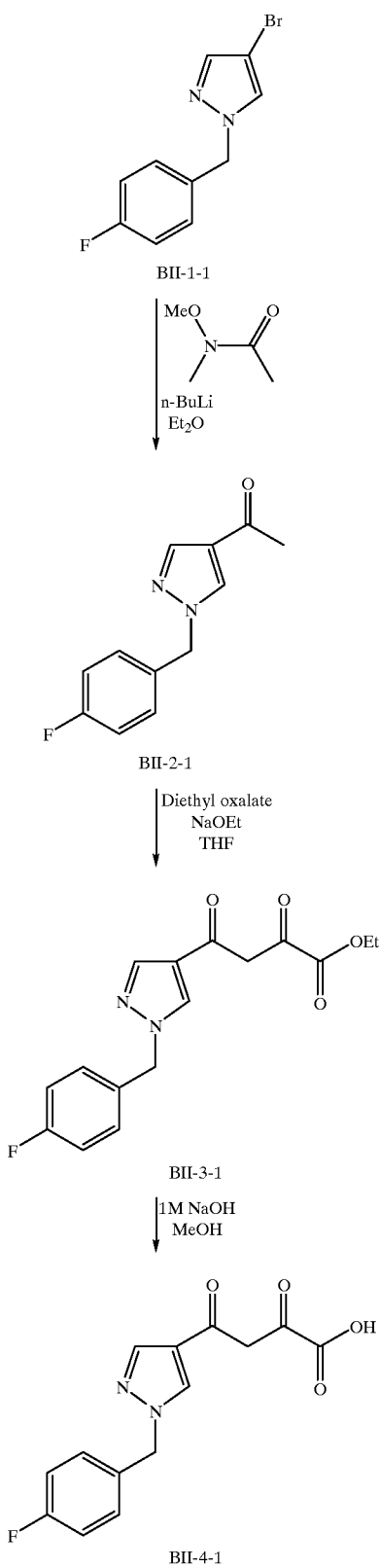
Scheme BIII
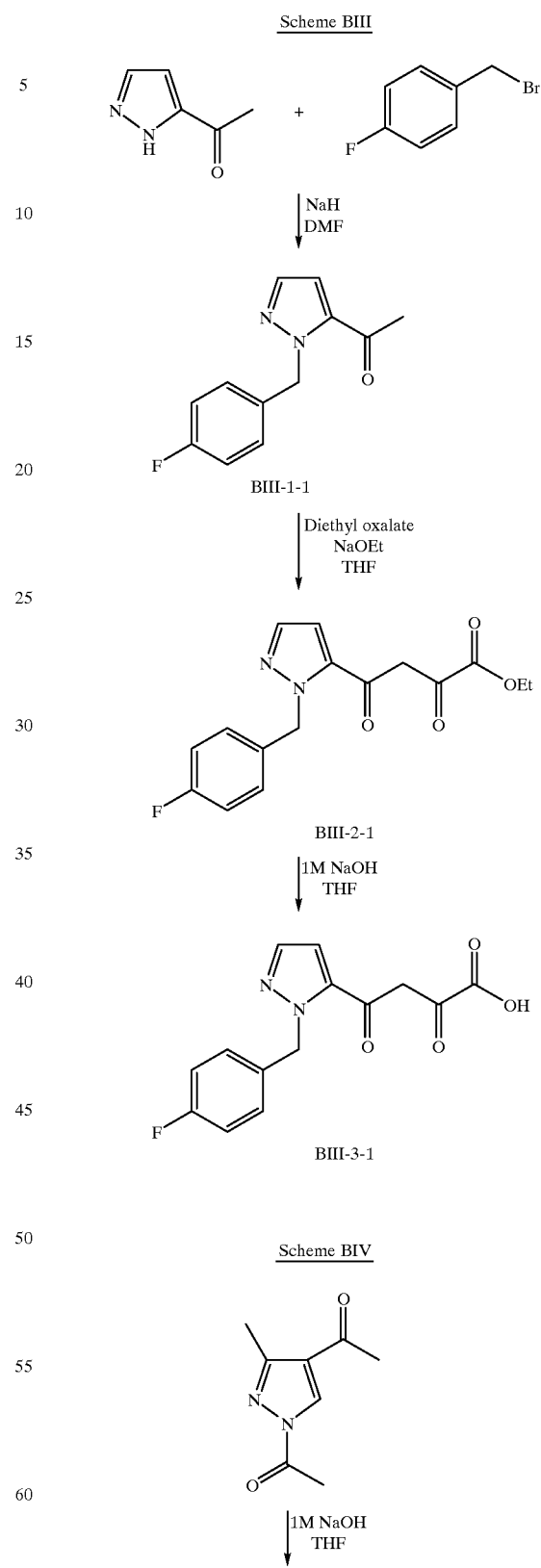

-continued
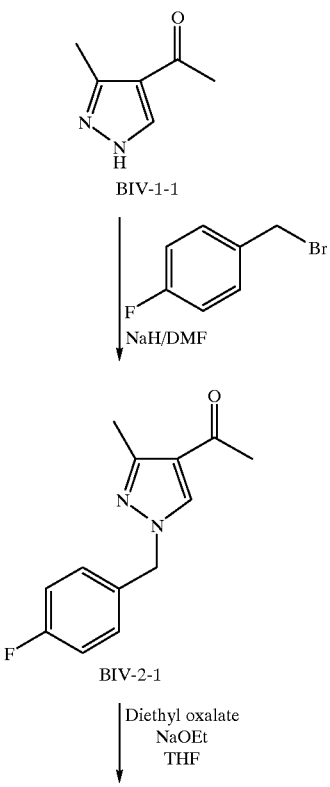
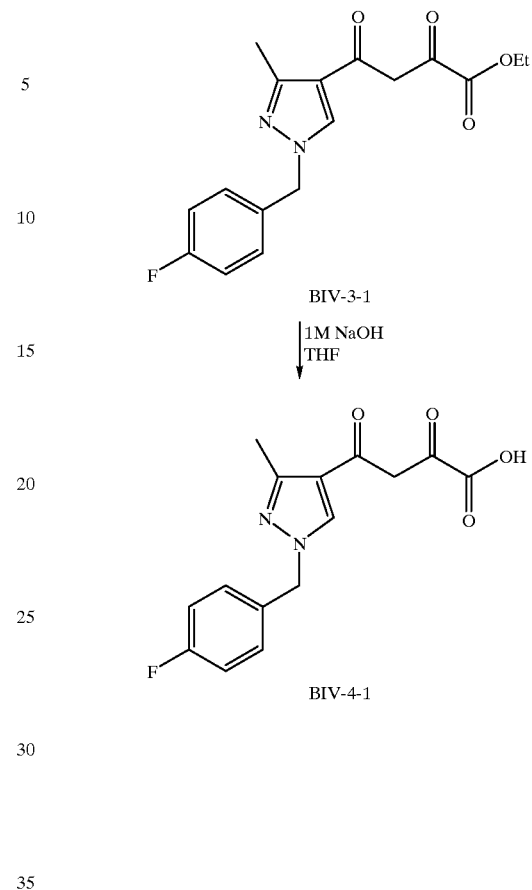
Scheme BV
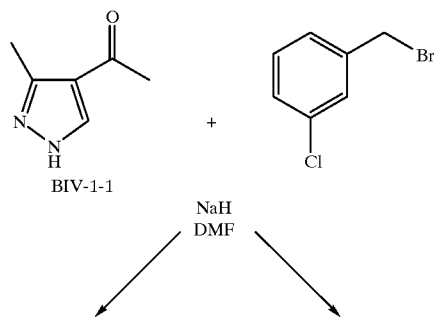

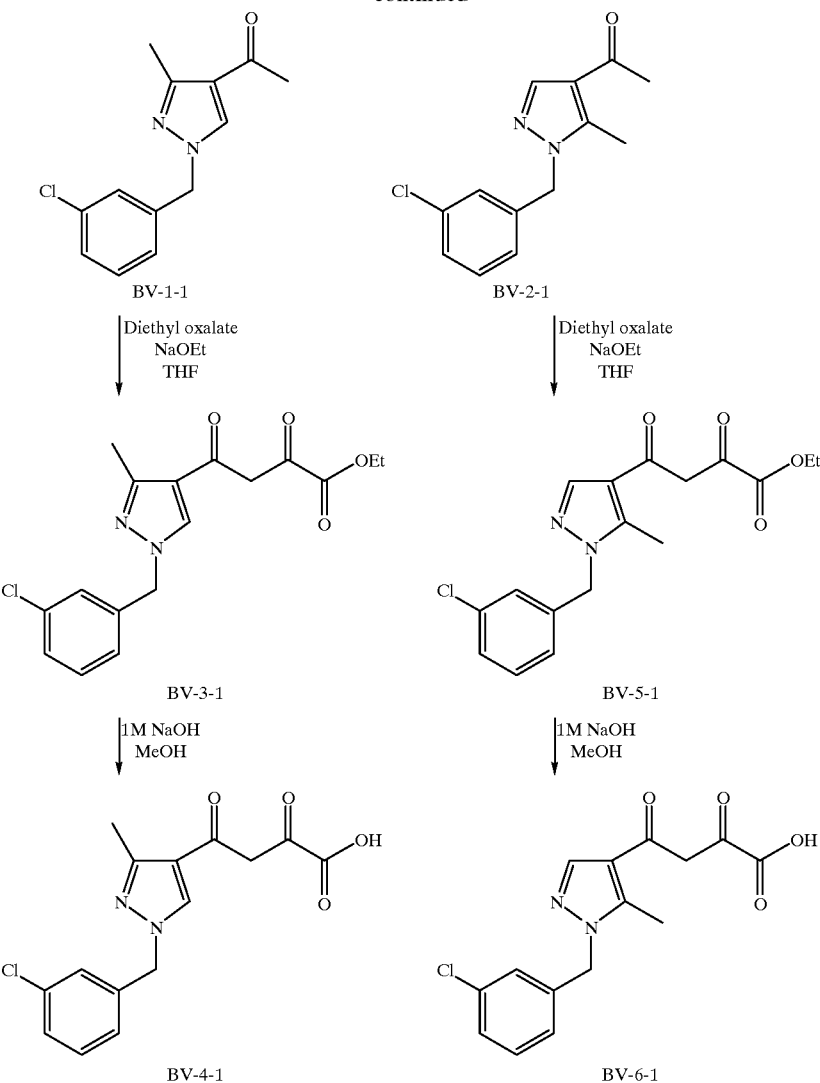
Scheme CI
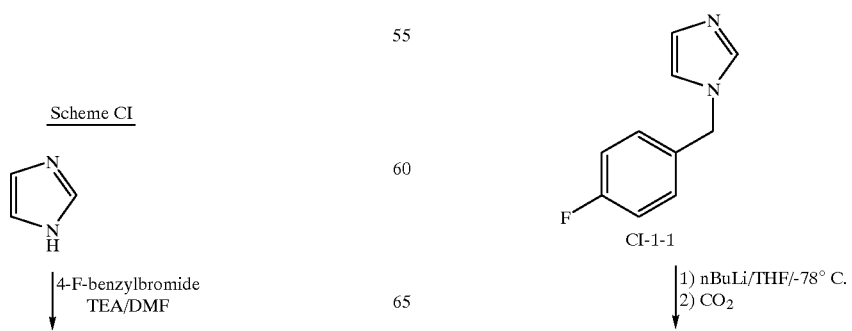

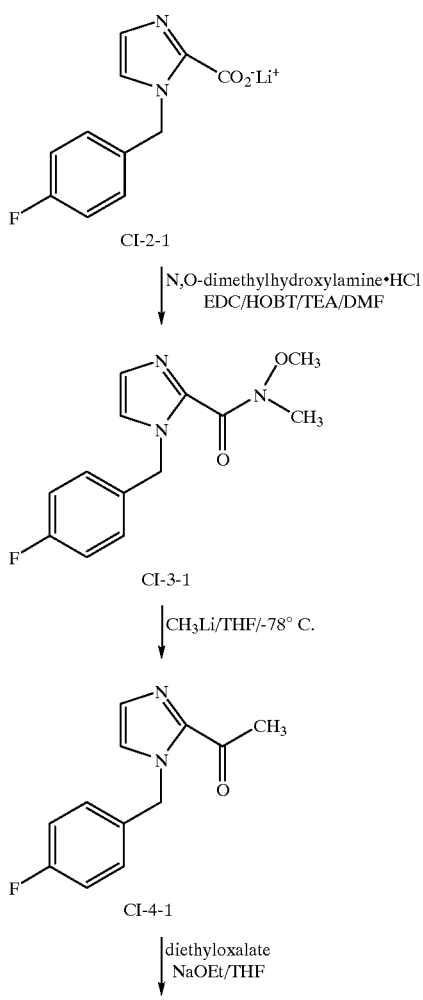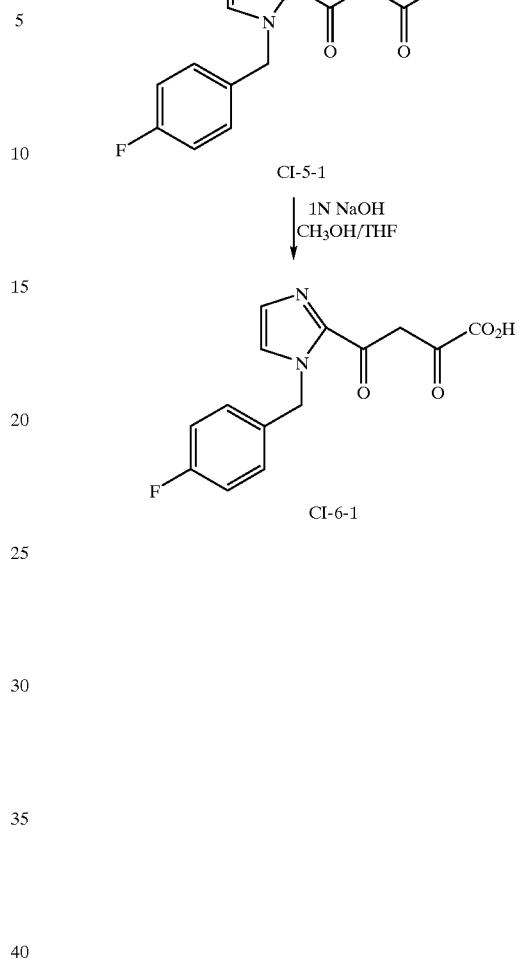
Scheme CII
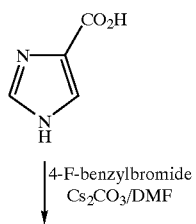

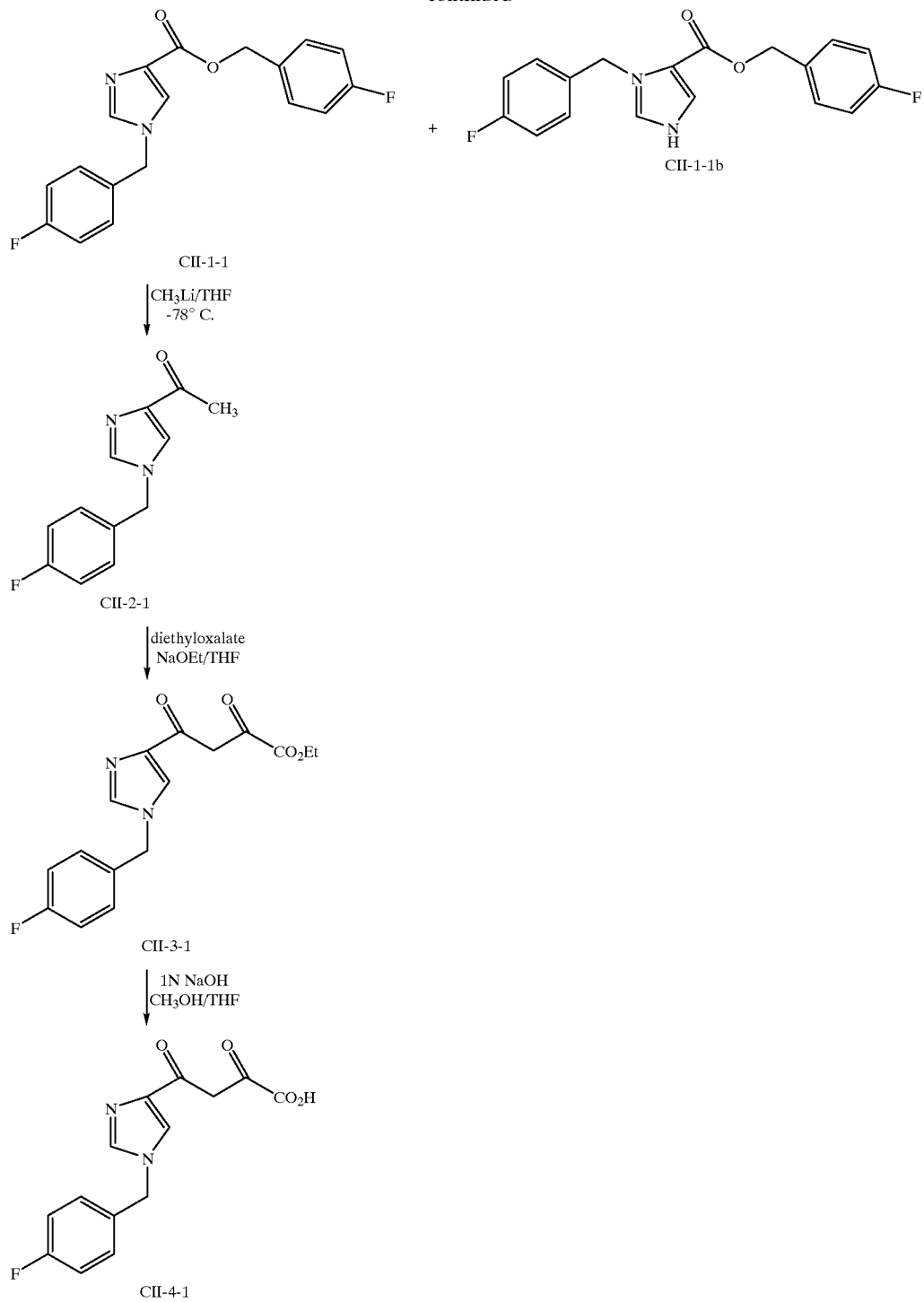

Scheme DI

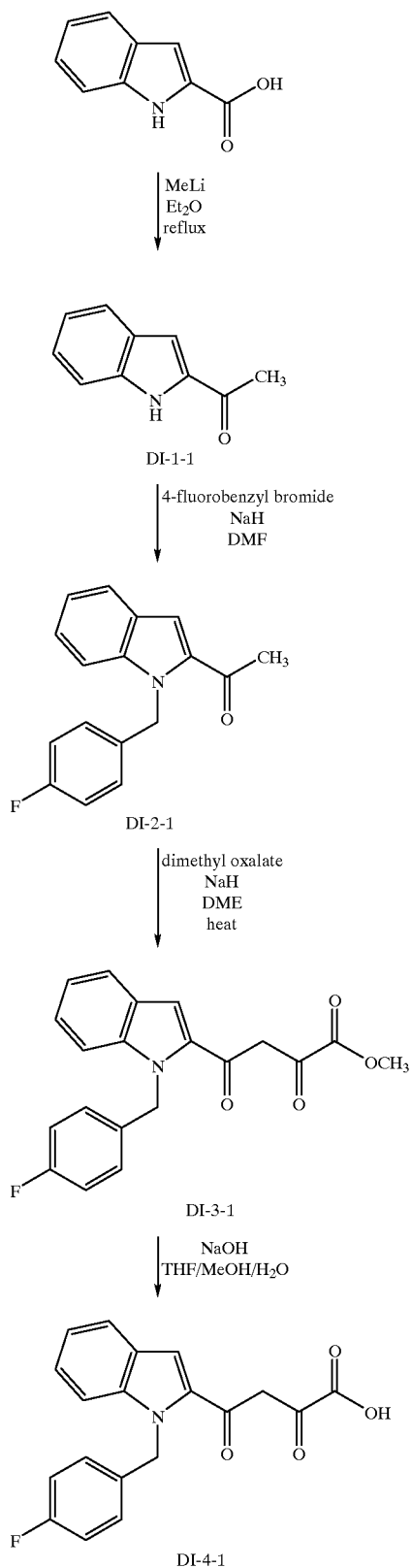

Scheme DII

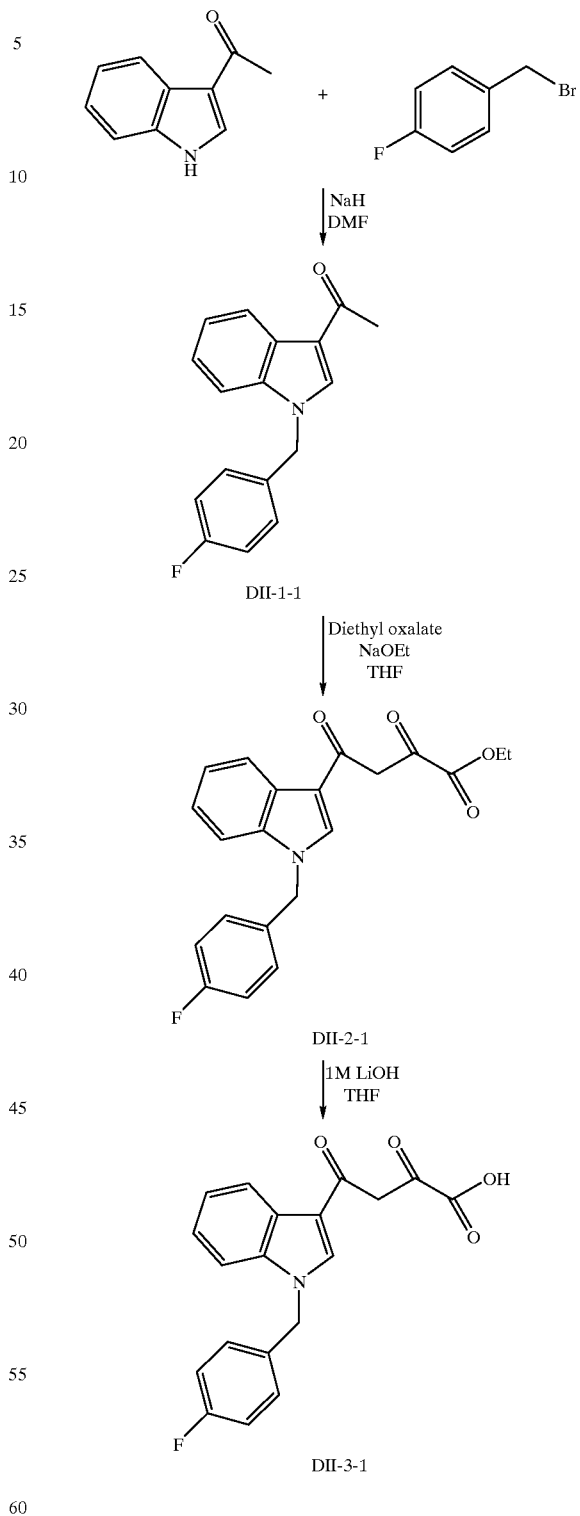

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, e.g. by reacting a free acid with a suitable organic or inorganic base. Where a basic group is present, such as amino, an acidic salt, i.e. hydrochloride, hydrobromide, acetate, pamoate, and the like, can be used as the dosage form.

Also, in the case of an acid (—COOH) or alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

The terms "administration of" and or "administering a" compound should be understood to mean providing a compound of the invention or a prodrug of a compound of the invention to the individual in need of treatment.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of a compound of the present invention.

As used herein, the term "composition" is intended to encompass a product comprising the specified ingredients in the specified amounts, as well as any product which results, directly or indirectly, from combination of the specified ingredients in the specified amounts.

By "pharmaceutically acceptable" it is meant the carrier, diluent or excipient must be compatible with the other ingredients of the formulation and not deleterious to the recipient thereof.

These pharmaceutical compositions may be in the form of orally-administrable suspensions or tablets, nasal sprays, sterile injectible preparations, for example, as sterile injectible aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectible solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

The compounds of this invention can be administered orally to humans in a dosage range of 1 to 1000 mg/kg body weight in divided doses. One preferred dosage range is 0.1 to 200 mg/kg body weight orally in divided doses. Another preferred dosage range is 0.5 to 100 mg/kg body weight orally in divided doses. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV integrase inhibitor compounds with one or more agents useful in the treatment of AIDS. For example, the compounds of this invention may be effectively administered, whether at periods of pre-exposure and/or post-exposure, in combination with effective amounts of the AIDS antivirals, imunomodulators, antiinfectives, or vaccines, such as those in the following table.

ANTIVIRALS

| Drug Name | Manufacturer | Indication |
|---|---|---|
| 097 | Hoechst/Bayer | HIV infection, AIDS, ARC (non-nucleoside reverse transcriptase (RT) inhibitor) |
| Amprenivir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (RT inhibitor) |
| Dextran Suifate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266) ((-)6-Chloro-4(S)-cyclopropylethynyl-4(S)-trifluoro-methyl-1,4-dihydro-2H-3,1-benzoxazin-2-one) STOCRIN, | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VJMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma, in combination with other therapies |

| IMMUNO-MODULATORS | | |
|---|---|---|
| Drug Name | Manufacturer | Indication |
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

| ANTI-INFECTIVES | | |
|---|---|---|
| Drug Name | Manufacturer | Indication |
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |

| OTHER | | |
|---|---|---|
| Drug Name | Manufacturer | Indication |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Megestrol Acetate | Bristol-Myers Squibb | treatment of anorexia assoc. w/AIDS |
| Testosterone | Alza, Smith Kline | AIDS-related wasting |
| Total Enteral Nutrition | Norwich Eaton Pharmaceuticals | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)-2 (S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Indinavir is an inhibitor of HIV protease and is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day.

The following examples are provided to further illustrate details for the preparation and use of the compounds of the present invention. The examples are not intended to be limitations on the scope of the instant invention in any way, and they should not be so construed. Furthermore, the compounds described in the following examples are not to be construed as forming the only genus that is considered as the invention, and any combination of the ocmpounds or their moieties may itself form a genus. Those skilled in the art will readily understand that known variatioons of the conditions and processes of the following preparative procedures can be used to prepare these compounds. All temperatures are in degrees Celsius unless noted otherwise.

Abbreviations: Ac represents acetyl; ACN is acetonitrile; Bn represents benzyl; DME is dimethoxy ethane; DMF is dimethyl formamide; DMSO is dimethyl sulfoxide; EDC represents 1-(3-dimethylaminopropyl-3-ethyl carbodiimide; Et represents ethyl; HOBT represents 1-hydroxybenzotriazole; LiHMDS represents ____; IPA is isopropyl alcohol; Me represents methyl; sat. is saturated; THF is tetrahydrofuran; TLC is thin layer ($SiO_2$) chromatography.

EXAMPLE 1

4-[1-(4-Fluorobenzyl)-1H-pyrrol-2-yl]-2,4-dioxobutyric acid AI-3-1

Step 1: 1-[1-(4-Fluorobenzyl)-1H-pyrrol-2-yl]ethanone AI-1-1

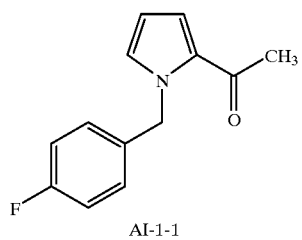

AI-1-1

A solution of 2-acetyl pyrrole (1.09 g, 0.01 mole) in 20 mL of DMF was treated with sodium hydride (0.48 g 60% dispersion in oil, 0.012 mole) followed by 4-fluorobenzyl bromide (1.73 g, 0.012 mole) and stirred overnight at room temperature. The solution was poured into 300 mL saturated $NaHCO_3$ and extracted with EtOAc three times, the combined organic layers were washed with $NaHCO_3$ and dried over $MgSO_4$, filtered and evaporated to give a clear yellow oil that was taken on to the next step without further purification. Rf=0.58 (20% EtOAc/Hexanes). $^1$H NMR (400 MHz, $CDCl_3$) d 7.1 (m, 2H), 7.0 (m, 3H), 6.9 (m, 1H), 6.2 (m, 1H), 5.52 (s, 2H), 2.4 (s, 3H).

Step 2: 4-[1-(4-Fluorobenzyl)-1H-pyrrol-2-yl]-2,4-dioxobutyric acid methyl ester AI-2-1

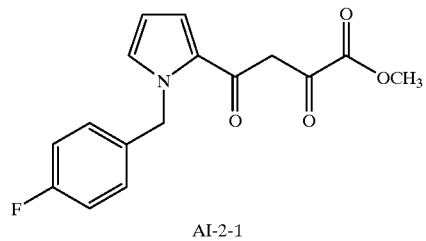

AI-2-1

A solution of 1-[1-(4-fluorobenzyl)-1H-pyrrol-2-yl]ethanone (AI-1-1) (2.17 g, 0.01 mole) in DME (20 mL) was treated with sodium hydride (0.48 g, 60% dispersion in oil) followed by dimethyl oxalate (1.42 g, 0.012 mole) and a drop of methanol and the solution was warmed to reflux overnight. The reaction mixture was poured into 300 mL saturated $NaHCO_3$ and extracted with EtOAc three times, the combined organic layers were washed with $NaHCO_3$ and dried over $MgSO_4$, filtered and evaporated. The residue was crystallized with diethyl ether to give AI-2-1 as yellow-orange crystals. Rf=0.39 (97:3:1 $CHCl_3$/MeOH/HOAc). $^1$H NMR (400 MHz, $CDCl_3$) δ 7.15, (dd, J=1.65, 4.21 Hz, 1H), 7.10 (m, 2H), 7.0 (m, 3H), 6.84 (s, 1H), 6.28 (dd, J=2.57, 4.11 Hz, 1H), 5.6 (s, 2H), 3.9 (s 3H).

Step 3: 4-[1-(4-Fluorobenzyl)-1H-pyrrol-2-yl]-2,4-dioxobutyric acid AI-3-1

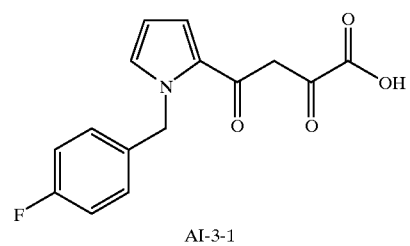

AI-3-1

A solution of AI-1-2 (1.35 g, 0.0045 mole) was dissolved in 1:1 THF/MeOH (20 mL) and treated with 1 N NaOH (22.5 mL, 0.0225 mole) and stirred overnight. The reaction mixture was washed with dilute ether, then acidified to pH2 with 1N HCl and extracted three times with EtOAc. The organic layers were combined, washed with 1 N HCl, dried over $MgSO_4$, filtered and evaporated to dryness. The residue was crystallized from $CHCl_3$ to give AI-3-1 as bright orange-yellow crystals. mp 172° C. decomposed (uncorrected). TLC Rf=0.37 (94:6:6 $CHCl_3$/MeOH/HOAc). $^1$H NMR (400 MHz, $CDCl_3$) δ 7.2 (dd, J=1.65, 4.21 Hz, 1H), 7.09 (m, 3H), 7.0 (m, 2H), 6.86 (s, 1H), 6.3 (dd, J=2.56, 4.21 Hz, 1H), 5.58 (s, 2H). mass spec (FAB, m+1) 290.08.

EXAMPLE 2

4-[1-(4-Methylbenzyl)-1-H-pyrrol-2-yl]-2,4-dioxobutyric acid AI-3-9

Step 1: 1-[1-(4-Methylbenzyl)-1-H-pyrrol-2-yl]ethanone AI-1-3

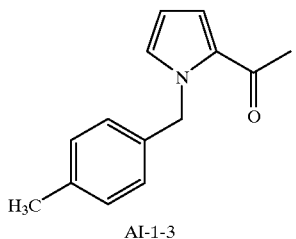

AI-1-3

To a solution of 2-acetyl pyrrole (1.09 g, 10 mmole) in acetone (5 mL) was added 10 N NaOH(aq) (1 mL) and 4-methylbenzyl bromide (1.85 g, 10 mmole). The reaction was stirred at ambient temperature for 12 hours, then the mixture was diluted with Et$_2$O, washed with water, dried with MgSO$_4$, and the solvent evaporated. The residue was purified by preparative silica HPLC using 20% EtOAc/Hex to afford the product as a thick clear oil that solidified upon standing. melting point 52–53° C. (uncorrected). $^1$H NMR (400 MHz, CDCl$_3$) δ 7.11 (d, J=7.8 Hz, 2H), 7.04 (d, J=7.72 Hz, 2H), 7.01 (m, 1H), 6.18 (m, 1H), 5.55 (s, 2H), 2.42 (s, 3H), 2.32 (s, 3H). mass spec (EI, m/z) 213 (M+), 105.

Step 2: 4-[1-(4-Methylbenzyl)-1-H-pyrrol-2-yl]-2,4-dioxobutyric acid ethyl ester AI-2-2

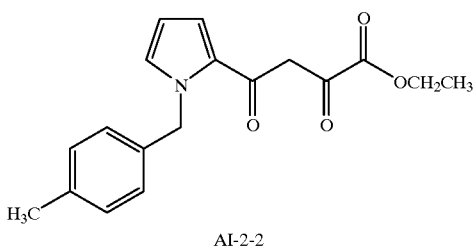

AI-2-2

To a solution of AI-1-3 (639 mg, 3 mmole) and diethyl oxalate (0.814 mL, 6 mmole) in THF (3 mL) was added in portions NaOEt (408 mg, 6 mmole). The reaction was stirred at ambient temperature under a N$_2$ atmosphere for 1.5 hours. The reaction was poured into hexanes (50 mL) and the yellow precipitate was filtered and dried under vacuum. The crude solid was triturated with 1M HCl (50 mL), filtered, and dried under vacuum. The product was further purified by crystallization from EtOAc/Hexanes/Et$_2$O to obtain the product as a yellow powder. melting point 94–97° C. (uncorrected). $^1$H NMR (400 MHz, CDCl$_3$) δ 7.15 (m, 1H), 7.12 (d, J=8.04 Hz, 2H), 7.03 (d, J=8.08 Hz, 2H), 7.01 (m, 1H), 6.85 (s, 1H), 6.26 (dd, J=2.48, 4.08 Hz, 1H), 5.61 (s, 2H), 4.37 (q, J=7.12 Hz, 2H), 2.33 (s, 3H), 1.40 (t, J=7.12 Hz, 3H). mass spec (EI, m/z) 331 (M+), 105.

Step 3: 4-[1-(4-Methylbenzyl)-1-H-pyrrol-2-yl]-2,4-dioxobutyric acid

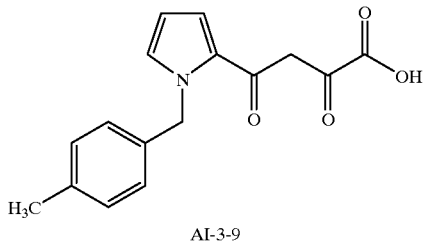

AI-3-9

A solution of AI-2-2 (240 mg, 1 mmol) in 1,4-dioxane (3 mL) and 3N HCl (3 mL) was heated in a sealed tube at 70° C. overnight. The reaction was then allowed to cool to ambient temperature and poured into 1H HCl (25 mL), the solid was filtered, dried under vacuum and the product purified by trituration with Et$_2$O/hexanes to afford AI-3-9 as a yellow solid. melting point 179–181° C. (uncorrected). $^1$H NMR (400 MHz, DMSO) δ 7.50 (s, 1H), 7.41 (d, J=4.28 Hz, 1H), 7.10 (d, J=7.68 Hz, 2H), 6.98 (d, J=7.68 Hz, 2H), 6.83 (s, 1H), 6.30 (dd, J=2.5, 4.1 Hz, 1H), 5.58 (s, 2H), 2.24 (s, 3H). mass spec (FAB, m+1) 286.

EXAMPLE 3

4-[1-(4-Fluorobenzyl)-1-H-pyrrol-2-yl]-2,4-dioxobutyric acid ethyl ester AI-2-3

Step 1: 1-[1-(4-Fluorobenzyl)-4-iodo-1H-pyrrol-2-yl]ethanone AI-1-2

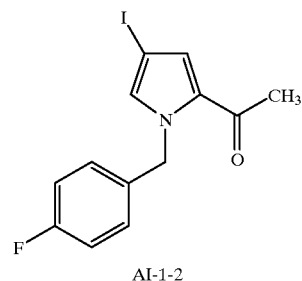

AI-1-2

A solution of 1-[1-(4-fluorobenzyl)-1H-pyrrol-2-yl]ethanone (AI-1-1) (3 g, 13.8 mmole) in acetone (75 mL) was cooled to −78° C. and treated with N-iodosuccinimide (3.73 g, 16.6 mmole). The reaction was slowly warmed and stirred for four days, then evaporated and the residue redissolved in EtOAc, washed with saturated NaHCO$_3$ solution and brine, dried over MgSO$_4$, filtered and evaporated. Silica gel chromatography in 13:87 EtOAc/Hexane gave the title compound as a white crystalline solid. Rf=0.62 (20% EtOAc/Hexanes). $^1$H NMR (400 MHz, CDCl$_3$) δ 7.15 (m, 2H), 7.08 (m, 1H), 7.0 (m, 2H), 6.93 (m, 1H), 5.5 (s, 2H), 2.4 (s, 3H).

Step 2: 4-[1-(4-Fluorobenzyl)-1-H-pyrrol-2-yl]-2,4-dioxobutyric acid ethyl ester AI-2-3

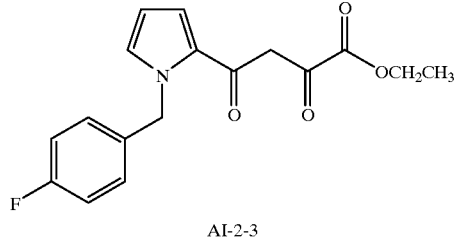

AI-2-3

AI-2-3 was synthesized from AI-1-2 in a manner similar to that described for AI-2-2 to afford the product as a yellow solid. melting point 87–90° C. (uncorrected). $^1$H NMR (400 MHz, CDCl$_3$) δ 7.15 (dd, J=1.6, 4.16 Hz, 1H), 7.09 (m, 2H), 7.01–6.96 (m, 3H), 6.83 (s, 1H), 6.27 (dd, J=2.52, 4.20 Hz, 1H), 5.60 (s, 2H), 4.36 (q, J=7.16 Hz, 2H), 1.38 (t, J=7.16 Hz, 3H). mass spec (EI, m/z) 317 (M+), 109.

EXAMPLE 4

4-[1-(4-Fluorobenzyl)-1H-pyrrol-2-yl]-2,4-dioxobutyric acid isopropyl ester AI-2-4

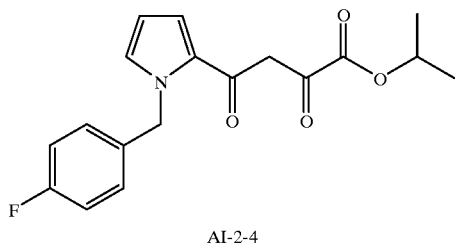

AI-2-4

To a solution of AI-2-3 (317 mg, 1 mmole) in 2-propanol (anhydrous, 20 mL) was added p-toluenesulfonic acid (19 mg, 0.1 mmole) and the mixture was set to reflux for 72 hours. The reaction mixture was then allowed to cool to ambient temperature, diluted with Et$_2$O, washed with a solution of saturated NaHCO$_3$, the organic layer separated and dried with MgSO$_4$, the solvent evaporated and the crude was purified by preparative silica HPLC eluting with 30% EtOAc/hexanes to afford the product as yellow solid. melting point 87–88° C. (uncorrected). $^1$H NMR (400 MHz, CDCl$_3$) δ 7.15–7.08 (m, 3H), 7.00–6.95 (m, 3H), 6.80 (s, 1H), 6.27 (dd, J=2.52, 4.10 Hz, 1H), 5.60 (s, 2H), 5.19 (m, 1H), 1.36 (d, J=6.24 Hz, 6H). mass spec (FAB, m+1) 332.

EXAMPLE 5

4-[1-(4-Fluorobenzyl)-1H-pyrrol-2-yl]-2,4-dioxobutyric acid n-butyl ester AI-2-5

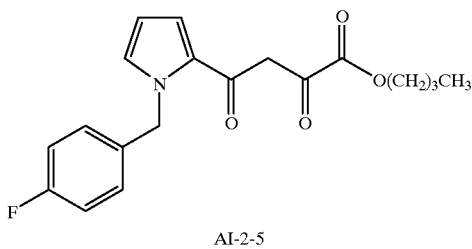

AI-2-5

AI-2-5 was synthesized from AI-2-3 by refluxing for 24 hours in n-butanol in a manner similar to that described for the synthesis of AI-2-4 to afford the product as a yellow solid. melting point 64–65° C. (uncorrected). $^1$H NMR (400 MHz, CDCl$_3$) δ 7.14–7.08 (m, 3H), 7.00–6.95 (m, 3H), 6.81 (s, 1H), 6.26 (dd, J=2.52, 4.12 Hz, 1H), 5.59 (s, 2H), 4.29 (t, J=6.76 Hz, 2H), 1.72 (m, 2H), 1.42 (m, 2H), 0.96 (t, J=7.52 Hz, 3H). mass spec (FAB, m+1) 346.

EXAMPLE 6

4-(1-Benzyl-1H-pyrrol-2-yl)-2,4-dioxobutyric acid AI-3-2

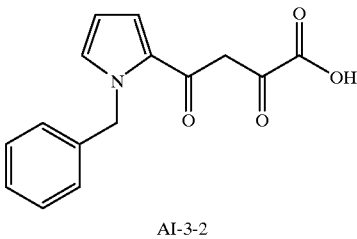

AI-3-2

In a manner similar to that described for AI-3-1, 2-acetyl pyrrole was treated with benzyl bromide and carried through the sequence to yield AI-3-2. mp 150–151° C. (uncorrected). $^1$H NMR (300 MHz, DMSO) δ 7.55 (s, 1H), 7.41 (m, 1H), 7.25 (m, 3H), 7.06 (m, 2H), 6.82 (s, 1H), 6.3 (s, 1H), 5.63 (s, 2H).

EXAMPLE 7

4-(1-Naphthalen-2-ylmethyl-1H-pyrrol-2-yl)-2,4-dioxobutyric acid AI-3-3

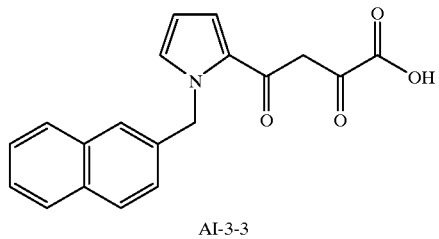

AI-3-3

In a manner similar to that described for AI-3-1, 2-acetyl pyrrole was treated with 2-bromomethylnapthylene and carried through the sequence to yield AI-3-3. mp 160–162° C. (uncorrected). $^1$H NMR (300 MHz, DMSO) δ 7.82 (m, 3H), 7.6 (s, 1H), 7.45 (m, 4H), 7.3 (m, 1H), 6.83 (s, 1H), 6.38 (m, 1H), 5.8 (s, 2H).

EXAMPLE 8

4-(1-Biphenyl-4-ylmethyl-1H-pyrrol-2-yl)-2,4-dioxobutyric acid A-I-3-4

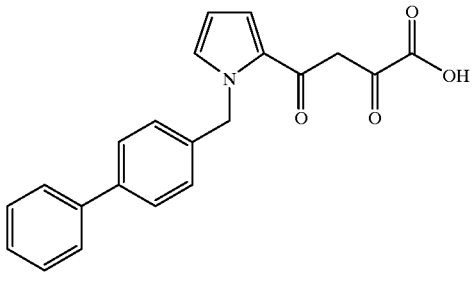

AI-3-4

In a manner similar to that described for AI-3-1, 2-acetyl pyrrole was treated with 4-phenyl benzyl bromide and carried through the sequence to yield AI-3-4. mp 189–191°

C. (uncorrected). ¹H NMR (300 MHz, DMSO) δ 7.75 (m, 5H), 7.58 (m, 3H), 7.48 (m, 1H), 7.3 (m, 2H), 7.0 (s, 1H), 6.45 (m, 1H), 5.8 (s, 2H).

EXAMPLE 9

4-(1-Naphthalen-1-ylmethyl-1H-pyrrol-2-yl)-2,4-dioxobutyric acid AI-3-5

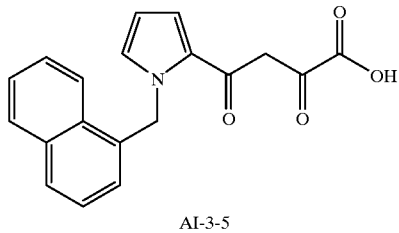

AI-3-5

In a manner similar to that described for AI-3-1, 2-acetyl pyrrole was treated with 1-bromomethyl napthalene and carried through the sequence to yield AI-3-5. mp 172–174° C. (uncorrected). ¹H NMR (300 MHz, DMSO) δ 8.1 (m, 1H), 8.0 (m, 1H), 7.83 (m, 1H), 7.6 (m, 3H), 7.4 (m, 2H), 6.9 (s, 1H), 6.5 (m, 1H), 6.4 (m, 1H), 6.18 (s 2H).

EXAMPLE 10

2,4-Dioxo-4-[1-(4-phenylbutyl)-1H-pyrrol-2-yl]-butyric acid AI-3-6

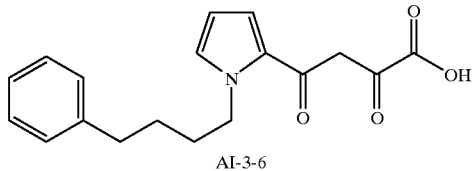

AI-3-6

In a manner similar to that described for AI-3-1, 2-acetyl pyrrole was treated with 4-phenyl butyl chloride and carried through the sequence to yield AI-3-6. mp 119–121° C. (uncorrected). ¹H NMR (300 MHz, DMSO) δ 7.38 (s, 1H), 7.36 (m, 1H), 7.23 (m, 2H), 7.18 (m, 3H), 6.82 (s, 1H), 6.22 (m, 1H), 4.38 (m, 2H), 2.55 (m, 2H), 1.7 (m, 2H), 1.5 (m, 2H).

EXAMPLE 11

4-[1-(4-Chlorobenzyl)-1H-pyrrol-2-yl]-2,4-dioxobutyric acid AI-3-7

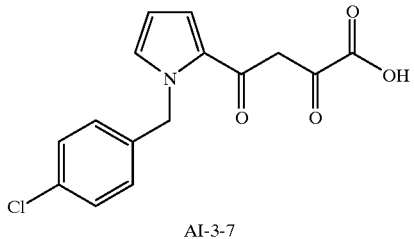

AI-3-7

In a manner similar to that described for AI-3-1, 2-acetyl pyrrole was treated with 4-chlorobenzyl bromide and carried through the sequence to yield AI-3-7. mp 182–184° C. (uncorrected). ¹H NMR (300 MHz, DMSO) δ 7.55 (s, 1H), 7.42 (m, 1H), 7.4 (m, 2H), 7.1 (m, 2H), 6.82 (s, 1H), 6.35 (m, 1H), 5.6 (s, 2H).

EXAMPLE 12

2,4-Dioxo-4-(1-phenethyl-1H-pyrrol-2-yl)-butyric acid AI-3-8

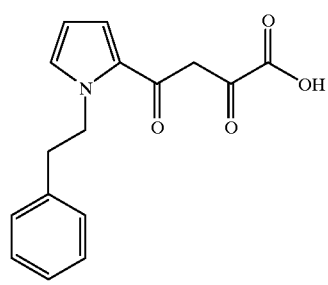

AI-3-8

In a manner similar to that described for AI-3-1, 2-acetyl pyrrole was treated with 2-phenyl 1-bromoethane and carried through the sequence to yield AI-3-8. mp 168–170° C. (uncorrected). ¹H NMR (300 MHz, DMSO) δ 7.35 (m, 1H), 7.2 (m, 6H), 6.85 (s, 1H), 6.18 (m, 1H), 4.6 (m, 2H), 3.0 (m, 2H).

EXAMPLE 13

4-[1-(2-Methylbenzyl)-1H-pyrrol-2-yl]-2,4-dioxobutyric acid AI-3-10

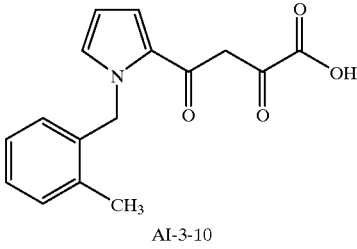

AI-3-10

AI-3-10 was synthesized from 2-acetyl pyrrole and 2-methylbenzyl bromide in a manner similar to that described for AI-3-9 to afford the product as a brownish-yellow solid. melting point 176–178° C. (uncorrected). ¹H NMR (400 MHz, DMSO) δ 7.48 (dd, J=1.52, 4.2 Hz, 1H), 7.36 (dd, J=1.96 Hz, 1H), 7.21 (d, J=6.92 Hz, 1H), 7.15 (dd, J=7.4, 7.4 Hz, 1H), 7.07 (dd, J=7.4, 7.4 Hz, 1), 6.88 (s, 1H), 6.37 (dd, J=2.44, 4.0 Hz, 1H), 6.31, (d, J=7.32 Hz, 1H), 5.64 (s, 2H), 2.31 (s, 3H). mass spec (FAB, m+1) 286.

EXAMPLE 14

4-[1-(3,4-Difluorobenzyl)-1H-pyrrol-2-yl]-2,4-dioxobutyric acid AI-3-11

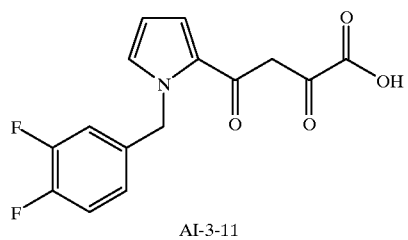

AI-3-11

AI-3-11 was synthesized from 2-acetyl pyrrole and 3,4-difluorobenzyl bromide in a manner similar to that described for AI-3-9 to afford the product as a brownish-yellow solid. melting point 145–148° C. (uncorrected) $^1$H NMR (400 MHz, DMSO) δ 7.56 (d, J=2.2 Hz, 1H), 7.44 (dd, J=1.4, 4.12 Hz, 1H), 7.39 (dd, J=8.6, 19.4 Hz, 1H), 7.19 (ddd, J=2.12, 7.72, 9.96 Hz, 1H), 6.92 (m, 1H), 6.86 (s, 1H), 6.35 (dd, J=2.48, 4.12 Hz, 1H), 5.61 (s, 2H). mass spec (FAB, m+1) 308.

EXAMPLE 15

4-[1-(4-Bromobenzyl)-1H-pyrrol-2-yl]-2,4-dioxobutyric acid AI-3-12

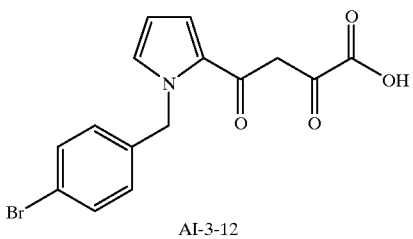

AI-3-12

AI-3-12 was synthesized from 2-acetyl pyrrole and 4-bromobenzyl bromide in a manner similar to that described for AI-3-9 to afford the product as a brownish-yellow solid. melting point 184–185° C. (uncorrected). $^1$H NMR (400 MHz, DMSO) δ 7.54 (d, J=1.68 Hz, 1H), 7.52 (d, J=8.4 Hz, 2H), 7.44 (dd, J=1.4, 4.12 Hz, 1H), 7.04 (d, J=8.4 Hz, 2H), 6.65 (s, 1H), 6.34 (dd, J=2.52, 4.16 Hz, 1H), 5.61 (s, 2H). mass spec (FAB, m+1) 352, 350.

EXAMPLE 16

4-[1-(2-Bromobenzyl)-1H-pyrrol-2-yl]-2,4-dioxobutyric acid AI-3-13

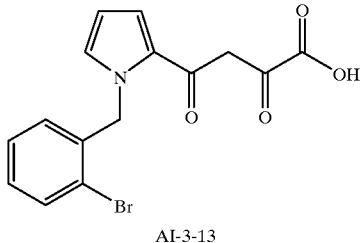

AI-3-13

AI-3-13 was synthesized from 2-acetyl pyrrole and 2-bromobenzyl bromide in a manner similar to that described for AI-3-9 to afford the product as a brownish-yellow solid. melting point 176–180° C. (uncorrected). $^1$H NMR (400 MHz, DMSO) δ 7.66 (dd, J=1.28, 7.88 Hz, 1H), 7.51 (dd, J=1.6, 4.24 Hz, 1H), 7.47 (s, 1H), 7.28 (dd, J=6.7, 6.7 Hz, 1H), 7.21 (dd, J=7.4, 7.4 Hz, 1H), 6.88 (s, 1H), 6.40 (dd, J=2.56, 4.2 Hz, 1H), 6.28 (dd, J=1.4, 7.72 Hz, 1H), 5.68 (s, 2H). mass spec (FAB, m+1).

EXAMPLE 17

4-[1-(3-Bromobenzyl)-1H-pyrrol-2-yl]-2,4-dioxobutyric acid AI-3-14

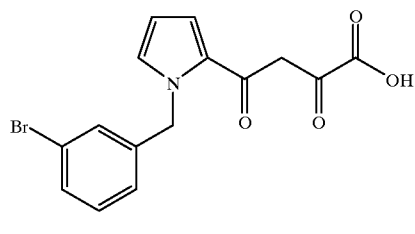

AI-3-14

AI-3-14 was synthesized from 2-acetyl pyrrole and 3-bromobenzyl bromide in a manner similar to that described for AI-3-9 to afford the product as a brownish-yellow solid. melting point 164–166° C. (uncorrected). $^1$H NMR (400 MHz, DMSO) δ 7.54 (broad s, 1H), 7.43 (m, 2H), 7.28–7.24 (m, 2H), 7.05 (d, J=6.76 Hz, 1H), 6.83 (s, 1H), 6.33 (dd, J=2.56, 4.12 Hz, 1H), 5.61 (s, 2H). mass spec (FAB, m+1) 352, 350.

EXAMPLE 18

4-[1-(3-Chlorobenzyl)-1H-pyrrol-2-yl]-2,4-dioxobutyric acid AI-3-15

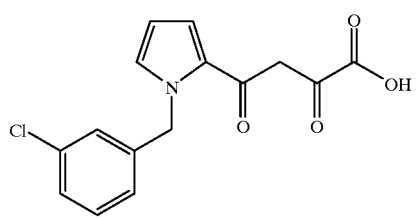

AI-3-15

AI-3-15 was synthesized from 2-acetyl pyrrole and 3-chlorobenzyl bromide in a manner similar to that described for AI-3-9 to afford the product as a brownish-yellow solid. melting point 159–161° C. (uncorrected). $^1$H NMR (400 MHz, DMSO) δ 7.56 (d, J=2.2 Hz, 1H), 7.45 (dd, J=1.48, 4.24 Hz, 1H), 7.38–7.30 (m, 2H), 7.12 (s, 1H), 7.04 (d, J=7.28 Hz, 1H), 6.86 (s, 1H), 6.36 (dd, J=2.48, 4.2 Hz, 1H), 5.65 (s, 2H). mass spec (FAB, m+1) 306.

EXAMPLE 19

4-[1-(3-Methylbenzyl)-1H-pyrrol-2-yl]-2,4-dioxobutyric acid AI-3-16

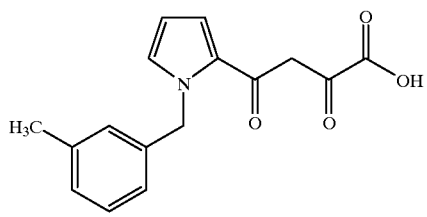

AI-3-16

AI-3-16 was synthesized from 2-acetyl pyrrole and 3-methylbenzyl bromide in a manner similar to that described for AI-3-9 to afford the product as a brownish-yellow solid. melting point 140–141° C. (uncorrected). $^1$H NMR (400 MHz, DMSO) δ 7.50 (d, J=1.92 Hz, 1H), 7.41 (dd, J=1.44, 4.12 Hz, 1H), 7.20 (dd, J=7.64, 7.64 Hz, 1H), 7.06 (d, J=7.6 Hz, 1H), 6.93 (s, 1H), 6.86 (m, 2H), 6.33 (dd, J=2.44, 4.12 Hz, 1H), 5.61 (s, 2H), 2.56 (s, 3H). mass spec (FAB, m+1) 286.

EXAMPLE 20

4-[1-(2-Fluorobenzyl)-1H-pyrrol-2-yl]-2,4-dioxobutyric acid AI-3-17

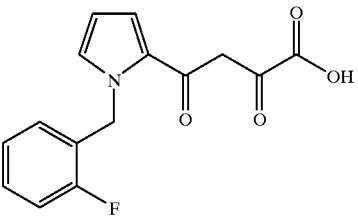

AI-3-17

AI-3-17 was synthesized from 2-acetyl pyrrole and 2-fluorobenzyl bromide in a manner similar to that described for AI-3-9 to afford the product as a brownish-yellow solid. melting point 155–156° C. (uncorrected). $^1$H NMR (400 MHz, DMSO) δ 7.47 (m, 2H), 7.32 (dd, 5.4, 14.0, 1H), 7.22 (dd, J=10.36, 10.36 Hz, 1H), 7.12 (dd, J=8.44, 8.44 Hz, 1H), 6.86 (s, 1H), 6.68 (dd, 7.68, 7.68, 1H), 6.36 (dd, J=2.56, 4.12Hz, 1H), 5.71 (s, 2H). mass spec (FAB, m+1) 290.

EXAMPLE 21

2,4-Dioxo-4-(1-hexyl-1H-pyrrol-2-yl)-butyric acid AI-3-18

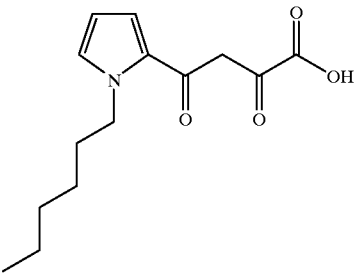

AI-3-18

In a manner similar to that described for AI-3-1, 2-acetyl pyrrole was treated 1-bromo hexane and carried through the sequence to yield AI-3-18.

mp 94.8° C. (uncorrected). TLC Rf=0.68 (94:6:6:6 CHCl$_3$/MeOH/HOAc) $^1$H NMR (400 MHz, CDCl$_3$) δ 7.15 (dd, 1H, J=1.65 Hz, J=4.21 Hz), 7.01 (m, 1H), 6.93 (s, 1H), 6.35 (dd, 1H, J=2.56 Hz, J=4.21 Hz), 4.35 (t, 2H, J=7.33 Hz), 1.77 (m, 2H), 1.28 (m, 6H), 0.88 (t, 3H, J=6.69 Hz).

EXAMPLE 22

4-(1-Biphenyl-2-ylmethy-1H-pyrrol-2-yl)-2,4-dioxobutyric acid

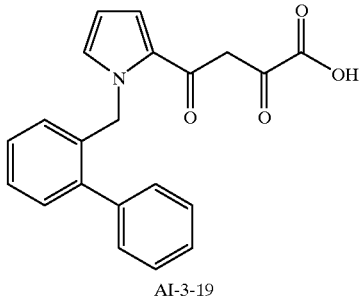

AI-3-19

In a manner similar to that described for AI-3-1, 2-acetyl pyrrole was treated with 1-biphenyl-2-yl bromomethane and carried through the sequence to yield AI-3-19. mp 150–152° C. (uncorrected). $^1$H NMR (400 MHz, CDCl$_3$) δ 7.4 (m, 9H), 6.8 (s, 1H), 6.42 (m, 1H), 6.3 (m, 1H), 5.6 (s, 2H).

EXAMPLE 22

2,4-Dioxo-4-[1-(4-phenoxybutyl)-1H-pyrrol-2-yl]-butyric acid AI-3-20

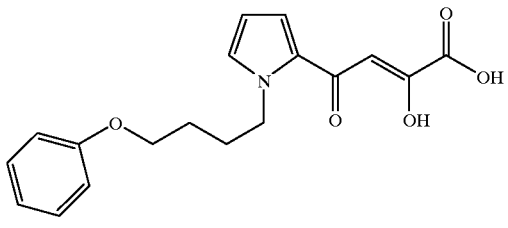

AI-3-20

In a manner similar to that described for AI-3-1, 2-acetyl pyrrole was treated with 4-phenoxy-1-butyl bromide and carried through the sequence to yield AI-3-2. TLC Rf=0.63 (94:6:6 CHCl$_3$/MeOH/HOAc) $^1$H NMR (400 MHz, CDCl$_3$) δ 7.29 (m, 2H), 7.16 (dd, J=1.65 Hz, 4.21 Hz, 1H), 7.05 (m, 1H), 6.94 (m, 1H), 6.93 (s, 1H), 6.87 (m, 2H), 6.25 (dd, J=2.56 Hz, 4.21 Hz 1H), 4.45 (t, J=7.14, 2H), 3.98 (t, J=6.22, 2H), 2.01 (m, 2H), 1.80 (m, 2H).

EXAMPLE 23

4-[1-(3-Fluorobenzyl)-1H-pyrrol-2-yl]-2,4-dioxobutyric acid AI-3-21

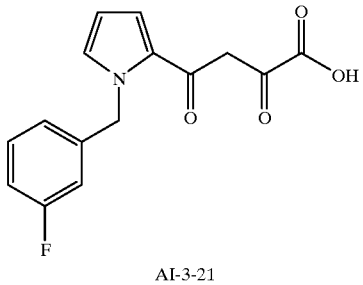

AI-3-21

AI-3-21 was synthesized from 2-acetyl pyrrole and 3-fluorobenzyl bromide in a manner similar to that described for AI-3-9 to afford the product as a brownish-yellow solid. melting point 147–149° C. (uncorrected). $^1$H NMR (400 MHz, DMSO) δ 7.55 (s, 1H), 7.45 (d, J=3.72 Hz, 1H), 7.36 (dd, J=7.72, 14.4 Hz, 1H), 7.08 (ddd, J=2.2, 8.48, 8.48 Hz, 1H), 6.92–6.86 (m, 3H), 6.35 (dd, J=2.48, 4.04 Hz, 1H), 5.66 (s, 2H). mass spec (FAB, m+1) 290.

EXAMPLE 24

4-[1-(2-Chlorobenzyl)-1-pyrrol-2-yl]-2,4-dioxobutyric acid AI-3-22

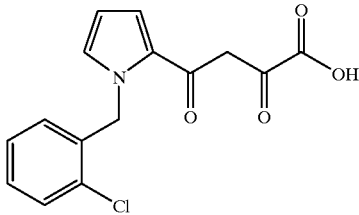

AI-3-22

AI-3-22 was synthesized from 2-acetyl pyrrole and 2-chlorobenzyl bromide in a manner similar to that described for AI-3-9 to afford the product as a brownish-yellow solid. melting point 179–180° C. (uncorrected). $^1$H NMR (400 MHz, DMSO) δ 7.52–7.47 (m, 3H), 7.30 (ddd, J=1.6, 7.44, 7.44 Hz, 1H), 7.24 (ddd, J=1.32, 7.52, 7.52 Hz, 1H), 6.88 (s, 1H), 6.40 (dd, J=2.44, 4.12 Hz, 1H), 6.35 (dd, J=1.48, 7.68 Hz, 1H), 5.79 (s, 2H). mass spec (FAB, m+1) 306.

EXAMPLE 25

4-[1-(4-Fluorobenzyl)-4-iodo-1H-pyrrol-2-yl]-2,4-dioxo-butyric acid

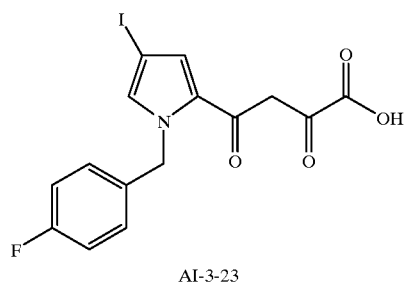

AI-3-23

In a manner similar to that described for AI-3-1, AI-3-23 was prepared from AI-1-2. mass spec (FAB, m+1) 416. $^1$H NMR (400 MHz, D$_6$-DMSO) δ 7.7 (s, 1H), 7.6 (s, 1H), 7.2 (m, 4H), 6.85 (s, 1H), 5.6 (s, 2H).

EXAMPLE 26

4-[1-(4-Methoxybenzyl)-1H-pyrrol-2-yl]-2,4-dioxobutyric acid AI-3-24

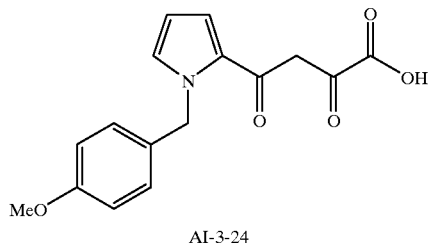

AI-3-24

AI-3-24 was synthesized from 2-acetyl pyrrole and 4-methoxybenzyl chloride in a manner similar to that described for AI-3-9 to afford the product as a brownish-yellow solid. melting point 167–168° C. (uncorrected). $^1$H NMR (400 MHz, DMSO) δ 7.50 (s, 1H), 7.38 (d, J=3.16 Hz, 1H), 7.09 (d, J=8.72 Hz, 2H), 6.86 (d, J=8.72 Hz, 2H), 6.83 (s, 1H), 6.29 (dd, J=2.56, 4.08 Hz, 1H), 5.55 (s, 2H), 3.70 (s, 3H). mass spec (FAB, m+1) 302.

EXAMPLE 27

4-[1-(2,4,5-Trifluorobenzyl)-1H-pyrrol-2-yl]-2,4-dioxobutyric acid AI-3-25

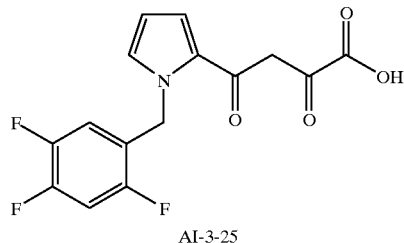

AI-3-25

AI-3-25 was synthesized from 2-acetyl pyrrole and 2,4,5-trifluorobenzyl bromide in a manner similar to that described for AI-3-9 to afford the product as a brownish-yellow solid. melting point 154–156° C. (uncorrected). $^1$H NMR (400 MHz, DMSO) δ 7.6 (m, 1H), 7.48 (m, 2H), 6.86 (s, 1H), 6.78 (m, 1H), 6.36 (dd, J=2.5, 4.1 Hz, 1H), 5.66 (s, 2H).

EXAMPLE 28

4-[1-(2,3-Difluorobenzyl)-1H-pyrrol-2-yl]-2,4-dioxobutyric acid AI-3-26

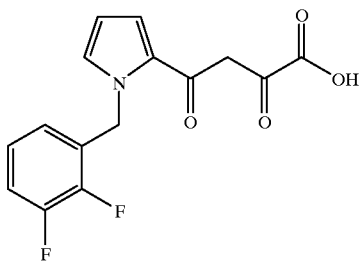

AI-3-26

AI-3-26 was synthesized from 2-acetyl pyrrole and 2,3-difluorobenzyl bromide in a manner similar to that described for AI-3-9 to afford the product as a brownish-yellow solid. melting point 154–156° C. (uncorrected). $^1$H NMR (400 MHz, DMSO) δ 7.51 (s, 1H), 7.45 (m, 1H), 7.35 (m, 1H), 7.12 (m, 1H), 6.86 (s, 1H), 6.48 (m, 1H), 3.38 (dd, J=2.5, 4.1 Hz, 1H), 5.75 (s, 2H). mass spec (FAB, m+1) 308.

EXAMPLE 29

4-[1-(3,5-Difluorobenzyl)-1H-pyrrol-2-yl]-2,4-dioxobutyric acid AI-3-26

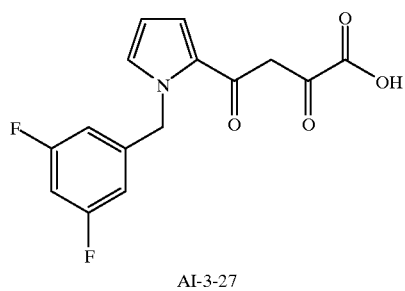

AI-3-27

AI-3-27 was synthesized from 2-acetyl pyrrole and 3,5-difluorobenzyl bromide in a manner similar to that described for AI-3-9 to afford the product as a brownish-yellow solid. melting point 166–168° C. (uncorrected); $^1$H NMR (400 MHz, DMSO) δ 7.58 (s, 1H), 7.48 (m, 1H), 7.14 (m, 1H), 6.88 (s, 1H), 6.75 (m, 2H), 6.38 (dd, J=2.5, 4.0 Hz, 1H), 5.67 (s, 2H). mass spec (FAB, m+1) 308.

EXAMPLE 30

4-[1-(2,5-Difluorobenzyl)-1H-pyrrol-2-yl]-2,4-dioxobutyric acid AI-3-28

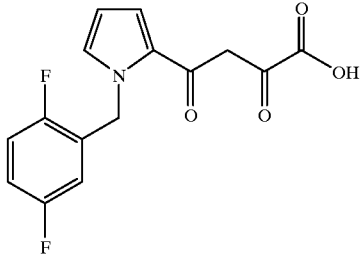

AI-3-28

AI-3-28 was synthesized from 2-acetyl pyrrole and 2,5-difluorobenzyl bromide in a manner similar to that described for AI-3-9 to afford the product as a brownish-yellow solid. melting point 142–146° C. (uncorrected); $^1$H NMR (400 MHz, DMSO) δ 7.50 (m, 2H), 7.30 (m, 1H), 7.17 (m, 1H), 6.86 (s, 1H), 6.38 (m, 2H), 5.69 (s, 2H). mass spec (FAB, m+1) 308.

EXAMPLE 31

4-[1-(2,5,6-Difluorobenzyl)-1H-pyrrol-2-yl]-2,4-dioxobutyric acid AI-3-29

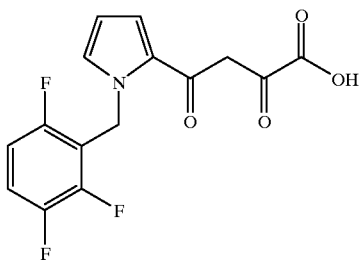

AI-3-29

AI-3-29 was synthesized from 2-acetyl pyrrole and 2,3,6-trifluorobenzyl bromide in a manner similar to that described for AI-3-9 to afford the product as a brownish-yellow solid. melting point 131–133° C. (uncorrected). $^1$H NMR (400 MHz, DMSO) δ 7.50 (m, 1H), 7.40 (m, 1H), 7.37 (s, 1H), 7.15 (m, 1H), 6.84 (s, 1H), 6.29 (dd, J=2.5, 4.1 Hz, 1H), 5.77 (s, 2H). mass spec (FAB, m+1) 326.

EXAMPLES 32–45

In a manner similar to that described for AI-3-1, the following compounds were prepared:

4-[1-(2-Fluorobenzyl)-1H-pyrrol-2-yl]-2,4-dioxobutyric acid

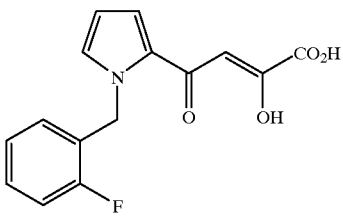

CHN Calc. 62.28, 4.18, 4.84; Fnd. 62.11, 4.37, 4.91. (32)

4-[1-(4-Trifluoromethylbenzyl)-1H-pyrrol-2-yl]-2,4-dioxobutyric acid:

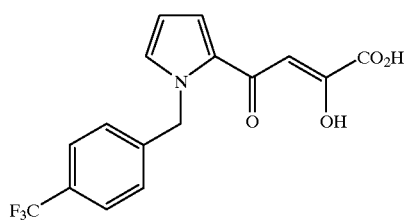

CHN Calc. 56.64, 3.56, 4.12; Fnd. 56.89, 3.75, 4.36. (33)

4-[1-(4-Cyanobenzyl)-1H-pyrrol-2-yl]-2,4-dioxobutyric acid

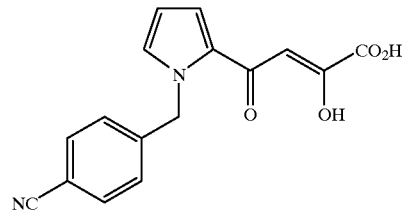

CHN Calc. 64.86, 4.08, 9.45; Fnd. 64.61, 4.32, 9.77. (34)

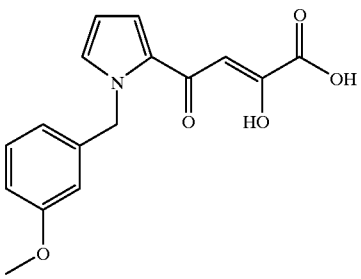

4-[1-(3-Methoxybenzyl)-1H-pyrrol-2-yl]-2,4-dioxobutyric acid CHN Calc. 63.78, 5.02, 4.65; Fnd. 63.99, 5.14, 4.60. (35)

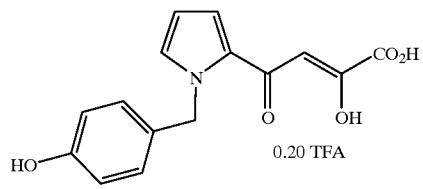

2-hydroxy-4-[1-(4-Hydroxybenzyl)-1H-pyrrol-2-yl]-2,4-dioxobutyric acid CHN Calc. ($C_{15}H_{13}NO_5$ 0.20 TFA) 59.65, 4.29, 4.52; Fnd. 59.50, 4.31, 4.68. (36)

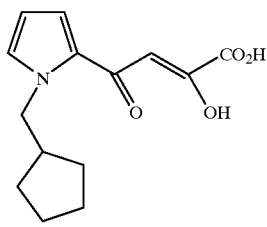

4-(1-Cyclopentylmethyl-1H-pyrrol-2-yl)-2,4-dioxobutyric acid CHN Calc. 63.86, 6.51, 5.32; Fnd. 63.88, 6.27, 5.37 (37)

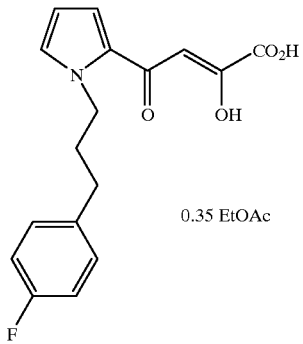

4-{1-[3-(4-Fluorophenyl)propyl]-1H-pyrrol-2-y}-2,4-dioxobutyric acid CHN Calc. ($C_{17}H_{16}NO_4F$ 0.35 EtOAc) 63.47, 5.44, 4.02; 63.16, 5.12, 4.34. (38)

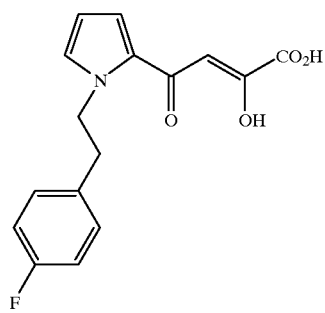

4-{1-[2-(4-Fluorophenyl)ethyl]-1H-pyrrol-2-yl}-2,4-dioxobutyric acid CHN Calc. 63.36, 4.65, 4.62; Fnd. 63.16, 4.64, 4.50. (39)

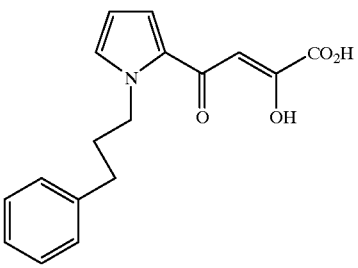

4-[1-(3-Phenylpropyl)-1H-pyrrol-2-yl]-2,4-dioxobutyric acid CHN Calc. ($C_{17}H_{17}NO_4$ 0.1 $H_2O$) 67.80, 5.76, 4.65; Fnd. 67.79, 5.67, 4.70. (40)

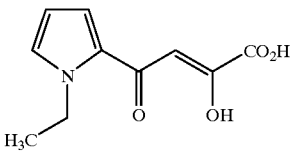

4-(1-Ethyl-1H-pyrrol-2-yl)-2,4-dioxobutyric acid CHN Calc. 57.41, 5.30, 6.70; Fnd. 57.13, 5.33, 6.70. (41)

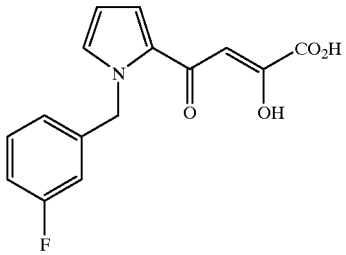

4-[1-(3-Fluoro-benzyl)-1-H-pyrrol-2-yl]-2,4-dioxobutyric acid CHN Calc. ($C_{15}H_{12}FNO_4$ 0.35 $H_2O$) 60.95, 4.33, 4.74; Fnd. 60.89 4.25, 4.78. (42)

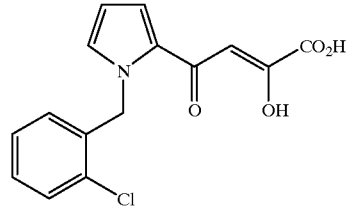

4-[1-(2-Chloro-benzyl)-1-H-pyrrol-2-yl]-2,4-dioxobutyric acid CHN Calc. (C$_{15}$H$_{12}$NO$_4$Cl 0.15 H$_2$O) 58.41, 4.02, 4.54; Fnd. 58.31, 3.94, 4.62. (43)

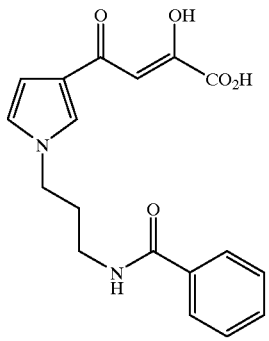

4-[1-(3-Benzoylaminopropyl)-1H-pyrrol-3-yl]-2,4-dioxobutyric acid CHN Calc. (C$_{18}$H$_{18}$N$_2$O$_5$ 0.35 H$_2$O 0.35 TFA) 57.80, 4.94, 7.21; Fnd. 57.80, 4.88, 7.35. (44)

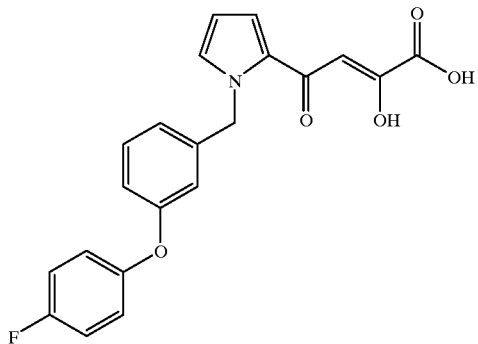

4-{1-[3-(4-Fluorophenoxy)benzyl]-1H-pyrrol-2-yl}-2,4-dioxobutyric acid CHN Calc. 66.14, 4.23, 3.67; Fnd. 66.37, 4.32, 3.69. (45)

EXAMPLE 46

4-(1-Cyclohexylmethyl-1-H-pyrrol-2-yl)-2,4-dioxobutyric acid AII-5-1

Step 1: Cyclohexyl-pyrrol-1-yl-methanone AII-1-1

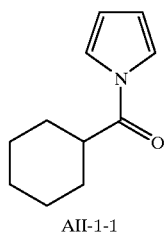

AII-1-1

A solution of pyrrole (2.00 g, 0.0298 mole) in 30 mL THF was cooled to −78° C. and treated with 1.0 M LiHMDS in hexanes (29.8 mL, 0.0298 mole) followed by dropwise addition of cyclopentanecarbonyl chloride (4.00 mL, 0.0298 mole). After five minutes the solution was allowed to warm to room temperature and stirred for four hours. The solution was poured into 200 mL saturated NH$_4$Cl solution and extracted with EtOAc three times. The combined organic layers were washed with NH$_4$Cl and dried over MgSO$_4$, filtered and evaporated to give a crude brown oil. Flash chromatography on silica gel of the crude product, using a 2.5:97.5 EtOAc/Hexane mixture as the eluting solvent, gave AII-1-1 as white crystals. TLC Rf=0.62 (5:95 EtOAc/Hexanes) $^1$H NMR (400 MHz, CDCl$_3$) δ 7.32 (m, 2H), 6.29 (m, 2H), 2.92 (m, 1H), 1.85–1.97 (m, 4H), 1.56–1.76 (m, 3H), 1.24–1.43 (m, 3H).

Step 2: 1-Cyclohexylmethyl-1-H-pyrrole AII-2-1

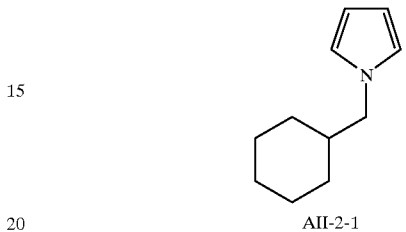

AII-2-1

A solution of AII-1-1 (3.45 g, 0.0195 mole) in 60 mL THF was treated with 1.0 M BH$_3$-Me$_2$S (58.5 mL, 0.0585 mole) and warmed to reflux for three hours. The solution was cooled to 0° C., slowly poured into 300 mL ice cold water and extracted with CH$_2$Cl$_2$ three times. The combined organic layers were washed with water, dried over MgSO$_4$, and evaporated to give a crude yellow oil. Flash chromatography on silica gel of the crude product, using a 2.5:97.5 EtOAc/Hexane mixture as the eluting solvent, gave AII-2-1 as a light yellow oil. TLC Rf=0.71 (5:95 EtOAc/Hexanes) $^1$H NMR (400 MHz, CDCl$_3$) δ 6.60 (t, J=2.01 Hz, 2H), 6.12 (t, J=2.01 Hz, 2H), 3.67 (m, 2H), 1.58–1.72 (m, 6H), 1.15–1.22 (m, 3H), 0.92 (m, 2H).

Step 3: 1-(1-Cyclohexylmethyl-1-H-pyrrol-2-yl)-ethanone AII-3-1

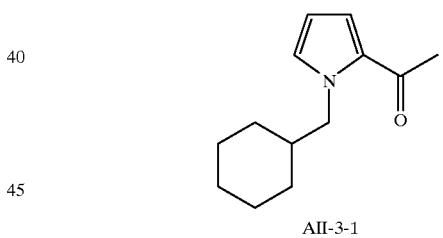

AII-3-1

A solution of AII-2-1 (1.32 g, 0.0081 mole) in 20 mL THF was cooled to −78° C. and treated with 2.5 M n-butyllithium (16.2 mL, 0.0405 mole) over five minutes and stirred overnight at room temperature under argon. The solution was then treated with N-methoxy-N-methylacetamide (4.18 g, 0.0405 mole) and stirred three hours. The solution was poured into 200 mL saturated NH$_4$Cl solution and extracted with Et$_2$O three times. The combined organic layers were washed with NH$_4$Cl and dried over MgSO$_4$, filtered and evaporated to give a crude yellow oil. Flash chromatography on silica gel of the crude product, using a 2.5:97.5 EtOAc/Hexane mixture as the eluting solvent, gave AII-3-1 as a yellow oil. TLC Rf=0.49 (5:95 EtOAc/Hexanes) $^1$H NMR (300 MHz, CDCl$_3$) δ 6.95 (dd, J=1.65, 4.03 Hz, 1H), 6.84 (m, 1H), 6.11 (dd, J=2.65, 4.03 Hz, 1H), 4.13 (d, J=7.32 Hz, 2H), 2.43 (s, 3H), ), 1.58–1.72 (m, 6H), 1.17–1.25 (m, 3H), 0.92 (m, 2H).

Step 4: 4-(1-Cyclohexylmethyl-1-H-pyrrol-2-yl)-2,4-dioxobutyric acid methyl ester AII-4-1

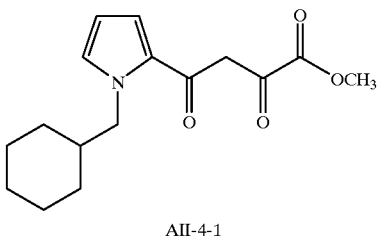

AII-4-1

In a manner similar to that described for AI-2-1, AII-3-1 was treated with NaH and dimethyloxalate to give AII-4-1. TLC Rf=0.62 (2.5:97.5 MeOH/CH$_2$Cl$_2$) $^1$H NMR (400 MHz, CDCl$_3$) δ 7.10 (dd, J=1.65, 4.21 Hz, 1H), 6.92 (m, 1H), 6.85 (s, 1H), 6.19 (dd, J=2.57, 4.21 Hz, 1H), 4.19 (d, J=7.14 Hz, 2H), 1.57–1.72 (m, 6H), 1.17–1.24 (m, 3H), 0.93 (m, 2H).

Step 5: 4-(1-Cyclohexylmethyl-1-H-pyrrol-2-yl)-2,4-dioxobutyric acid AII-5-1

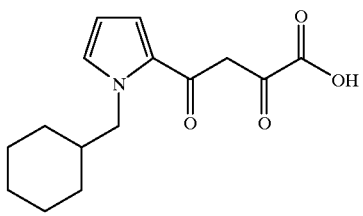

AII-5-1

In a manner similar to that described for AI-3-1, AII-4-1 was treated with NaOH to give AII-5-1. TLC Rf=0.65 (94:6:6 CHCl$_3$/MeOH/HOAc) $^1$H NMR (400 MHz, CDCl$_3$) δ 7.15 (dd, J=1.65, 4.21 Hz, 1H), 6.96 (m, 1H), 6.93 (s, 1H), 6.22 (dd, J=2.56, 4.21 Hz, 1H), 4.18 (d, J=7.13 Hz, 2H), 1.57–1.72 (m, 6H), 1.16–1.23 (m, 3H), 0.96 (m, 2H).

EXAMPLE 47

4-[1-(4-Fluorobenzyl)-4-phenylethynyl-1-H-pyrrol-2-yl]-2,4-dioxobutyric acid AIII-3-1

Step 1: 1-[1-(4-Fluorobenzyl)-4-phenylethynyl-1H-pyrrol-2-yl]ethanone AIII-1-1

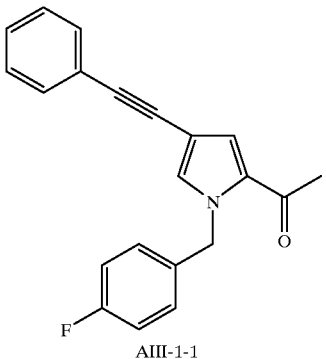

AIII-1-1

A mixture of AI-1-2 (0.49 g, 1.43 mmol), phenylacetylene (0.218 g, 0.235 mls, 2.14 mmol), copper(I) iodide (0.022 g, 0.116 mmol), tetrakis(triphenylphosphine)-palladium(0) (0.1 g, 0.086 mmol) and triethylamine (5 ml) were combined in 2 mL acetonitrile and heated to reflux for 4 hrs. After cooling, the solvent was removed in vacuo and the residue partitioned between ethyl acetate/H$_2$O and extracted. The combined organic extracts were washed with H$_2$O, brine, dried over Na$_2$SO$_4$, filtered and the solvent removed. The resulting brown oil was purified by radial disc chromatography twice, first using 2:1 hexane/CH$_2$Cl$_2$ followed by straight ethyl acetate, then straight CH$_2$Cl$_2$ to afford the title compound. $^1$H NMR (400 MHz, CDCl$_3$) δ 2.42 (s, 3H), 5.52 (s, 2H), 6.99 (t, 2H, J=8.7 Hz), 7.11–7.16 (m, 4H), 7.29–7.47 (m, 3H), 7.45–7.48 (m, 2H).

Step 2: [1-(4-Fluorobenzyl)-4-phenylethynyl-1H-pyrrol-2-yl-2,4-dioxobutyric acid ethyl ester AIII-2-1

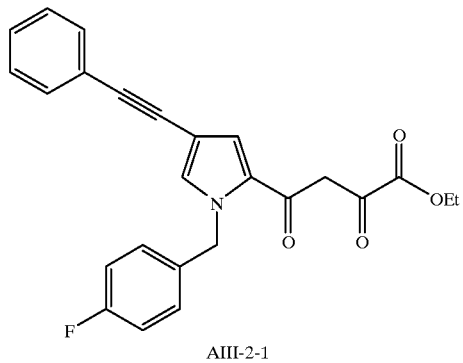

AIII-2-1

A solution of AIII-1-1 (0.264 g, 0.83 mmol) in 10 mL THF was treated with diethyl oxalate (0.243 g, 1.66 mmol) and sodium ethoxide (0.113 g, 1.66 mmol). After stirring for 1 hr, the reaction was poured into 20 mL 10% citric acid and extracted with ethyl acetate. The combined organic extracts were washed with H$_2$O, brine, dried over Na$_2$SO$_4$ filtered, and the solvent removed in vacuo to give the title compound as a yellow oil. $^1$H NMR (400 MHz, CDCl$_3$) δ 1.36 (t, 3H, J=7.1 Hz), 4.34 (q, 2H, J=7.2 Hz), 5.55 (s, 2H), 6.80 (s, 1H), 6.99 (t, 2H, J=8.7 Hz), 7.12–7.18 (m, 2H), 7.19 (d, 1H, J=1.65 Hz), 7.25 (d, 1H, J=1.65 Hz), 7.29–7.35 (m, 3H), 7.44–7.48 (m, 2H).

Step 3: [1-(4-Fluorobenzyl)-4-phenylethynyl-1H-pyrrol-2-yl]-2,4-dioxobutyric acid AIII-3-1

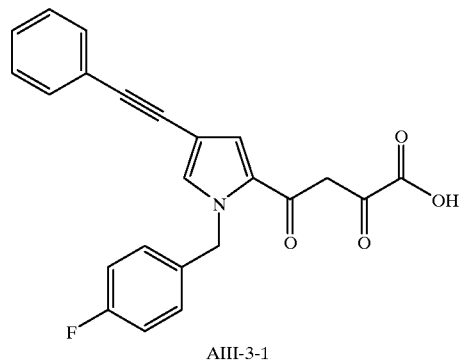

AIII-3-1

In a similar manner to AI-3-1, AIII-2-1 (0.347 g, 0.83 mmol) was reacted with 1.66 mL 1M LiOH in 5 mls THF to give the title compound as a yellow resin. $^1$H NMR (400 MHz, CDCl$_3$) δ 6.86 (s, 1H), 7.01 (t, 2H, J=8.6 Hz), 7.12–7.19 (m, 2H), 7.21 (d, 1H, J=1.65 Hz), 7.28 (d, 2H, J=1.65 Hz), 7.30–7.36 (m, 4H), 7.43–7.50 (m, 2H) FAB MS: m/z 390 (M$^+$+H).

EXAMPLE 48

4-[1-(4-Fluorobenzyl)-4-phenethyl-1H-pyrrol-2-yl]-2,4-dioxobutyric acid

Step 1: 1-[1-(4-Fluorobenzyl)-4-phenethyl-1H-pyrrol-2-yl]ethanone AIII-4-1

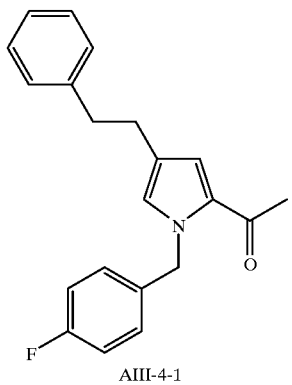

AIII-4-1

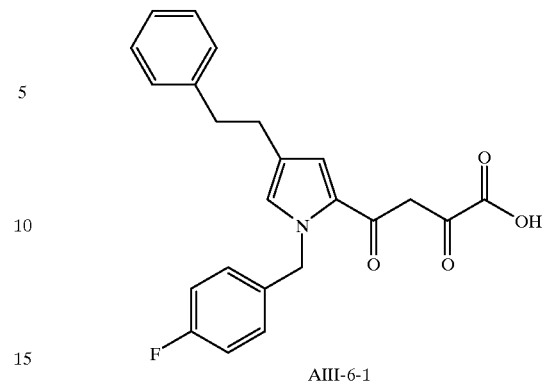

AIII-6-1

AIII-1-1 (0.15 g, 0.47 mmol) was dissolved in 10 ml absolute ethanol, and to it was added 10% Pd/C (0.03 g, 20 wt-%). The reaction vessel was purged with hydrogen (via balloon) and allowed to stir for 6 hr. The catalyst was filtered and the solvent removed in vacuo. NMR of this crude mixture showed about 20% starting material. The product was purified by radial disc chromatography ($CH_2Cl_2$) to obtain the title compound as a resin. $^1$H NMR (400 MHz, $CDCl_3$) δ 2.35 (s, 3H), 2.72–2.79 (m, 2H), 2.82–2.89 (m, 2H), 5.42 (s, 2H), 6.57 (d, 1H, J=1.8 Hz), 6.79 (d, 1H, J=1.8 Hz), 6.94 (t, 2H, J=8.7 Hz), 7.00–7.07 (m, 2H), 7.12–7.30 (m, 5H).

Step 2: 4-[1-(4-Fluorobenzyl)-4-phenethyl-1H-pyrrol-2-yl]-2,4-dioxobutyric acid ethyl ester AIII-5-1

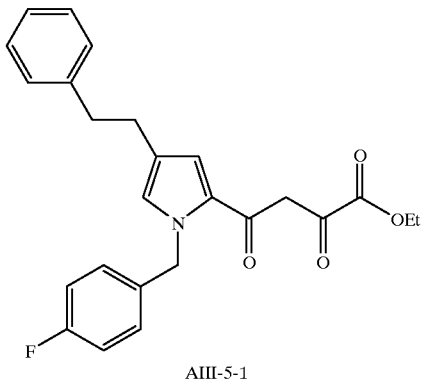

AIII-5-1

In a similar manner to AIII-2-1, AIII-4-1 (0.1 g, 0.31 mmol) was reacted with diethyl oxalate (0.091 g, 0.084 ml, 0.62 mmol) and sodium ethoxide (0.042 g, 0.62 mmol) in 5 mL THF to give the title compound, which was used in the next reaction without further purification. $^1$H NMR (400 MHz, $CDCl_3$) δ 1.37 (t, 3H, J=7.14 Hz), 2.76 (t, 1H, J=7.7 Hz), 2.86 (t, 1H, J=7.7 Hz), 4.35 (q, 2H, J=7.14 Hz), 5.48 (s, 2H), 6.67 (s, 1H), 6.77 (s, 1H), 6.92–7.06 (m, 5H), 7.11–7.29 (m, 5H).

Step 3: 4-[1-(4-Fluorobenzyl)-4-phenethyl-1H-pyrrol-2-yl]-2,4-dioxobutyric acid AIII-6-1

In a manner similar to AI-3-1, AIII-5-1 was reacted with 0.5 ml 1N NaoH in 3 mL THF for 2 hr to give the title compound as a yellow solid. MP=135–137° C.; $^1$H NMR (400 MHz, $CDCl_3$) δ 2.75–2.82 (m, 1H), 2.84–2.91 (m, 1H), 5.47 (s, 2H), 6.71 (d, 1H, J=1.3 Hz), 6.86 (s, 1H), 6.95–7.08 (m, 4H), 7.11–7.16 (m, 2H), 7.17–7.23 (m, 1H), 7.24–7.32 (m, 3H).

EXAMPLE 49

4-[5-(4-Fluorobenzyl)-1-methyl-1-H-pyrrol-2-yl]-2,4-dioxobutyric acid AIV-5-1

Step 1: 2-(4-Fluorobenzyl)-1H-pyrrole AIV1-1

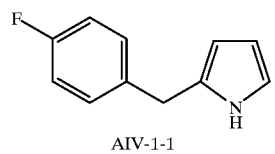

AIV-1-1

MeMgCl (3N in THF, 43.8 mL, 0.131 mole) was added dropwise to a solution of 50:50 THF:$CH_2Cl_2$ and pyrrole (9.31 g, 0.139 mole) at 0° C. followed by quick addition of 4-fluorobenzyl bromide and stirred at room temperature overnight. The solution was poured into 300 mL of saturated $NH_4Cl$ and extracted five times with $Et_2O$. The combined organic layers were dried over $NaSO_4$, filtered and evaporated to give a dark brown oil that was distilled under vacuum to give analytically pure AIV-1-1. $^1$H NMR (400 MHz, $CDCl_3$) δ 7.77 (broad s, 1H), 7.17–7.13 (m, 2H), 7.00–6.95 (m, 2H), 6.67 (s, 1H), 6.15–6.14 (d, 1H, J=2.7 Hz), 5.97 (m, 1H), 3.94 (s, 2H).

Step 2: 1-[5-(4-Fluorobenzyl)-1H-pyrrol-2-yl]ethanone AIV-2-1

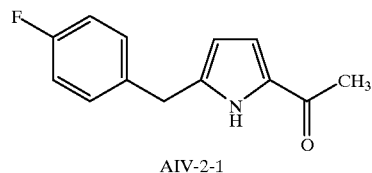

AIV-2-1

MeMgCl (2.95 mL, 0.0284 mole) was added dropwise to a solution of AIV-1-1 in THF (35 mL) at 0° C. After ten minutes acetic anhydride (2.95 mL, 0.0312 mole) was added and the reaction was stirred for 1 hour. The solution was poured into saturated $NH_4Cl$ and extracted three times with EtOAc. The combined organic layers were dried over NaSO$_4$, filtered and evaporated to give a brown oil. Silica gel chromatography using 85:15 Hexane/EtOAc gave AIV-2-1 as a light yellow powder. TLC: Rf=0.30 (80:20 Hexanes/EtOAc) $^1$H NMR (400 MHz, CDCl$_3$) δ 9.72 (broad s, 1H), 7.18–7.14 (m, 2H), 7.00–6.95 m, 2H), 6.85–6.83 (m, 1H), 6.01–5.99 (m, 1H), 3.97 (s, 2H), 2.37 (s, 2H).

Step 3: 1-[5-(4-Fluorobenzyl)-1-methyl-1H-pyrrol-2-yl]ethanone AIV-3-1

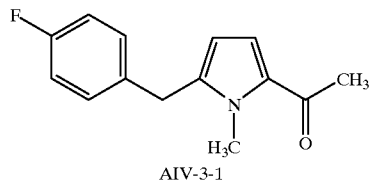

AIV-3-1

NaH (0.098 g, 0.00244 mole) was added to a solution of AIV-2-1 in DMF (25 mL) at 0° C. followed by subsequent addition of MeI (0.53 g, 0.00244 mole). The ice bath was removed and the reaction was stirred for one hour. The solution was poured into NH$_4$Cl and extracted three times with EtOAc. The combined organic layers were dried over NaSO$_4$, filtered and evaporated to give AIV-3-1 as a brown oil. TLC: Rf=0.43 (80:20 Hexanes/EtOAc) $^1$H NMR (400 MHz, CDCl$_3$) δ 7.11–7.07 (m, 2H), 7.01–6.97 (m, 2H), 6.93–6.92 (m, 1H), 5.90–5.89 (m, 1H), 3.93 (s, 2H), 3.79 (s, 3H), 2.42 (s, 3H).

Step 4: 4-[5-(4-Fluorobenzyl)-1-methyl-1-H-pyrrol-2-yl]-2,4-dioxobutyric acid methyl ester AIV-4-1

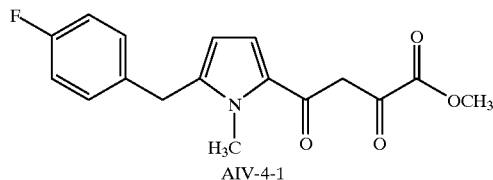

AIV-4-1

A solution of AIV-3-1 (0.222 g, 0.000961 mole) in DME (10 mL) was treated with sodium hydride (0.058 g, 0.00144 mole) followed by dimethyl oxalate (0.113 g, 0.000961 mole) and methanol (200 mL) and the solution was warmed to reflux for 1.5 hours. The reaction was poured into 30 mL of 1 N HCl and extracted thr ee times with EtOAc. The combined organic layers were dried over NaSO$_4$, filtered and evaporated to give AIV-4-1 as a brown solid. TLC: Rf=0.39 (97:3:1 CH$_2$Cl$_2$/MeOH/HOAc) $^1$H NMR (400 MHz, CDCl$_3$) δ 7.12–7.07 (m, 3H), 7.04–6.99 (m, 2H), 6.83 (s, 1H), 5.99–5.98 (d, 1H, j=4.21), 3.97 (s, 2H), 3.915 (s, 3H), 3.85 (s, 3H).

Step 5: 4-[5-(4-Fluorobenzyl)-1-methyl-1H-pyrrol-2-yl]-2,4-dioxobutyric acid AIV-5-1

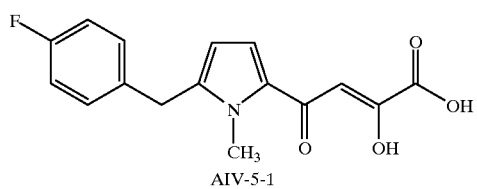

AIV-5-1

AIV-4-1 was dissolved in THF (15 inL) and 1 N NaOH (5 mL) was added. After two hours the reaction was acidified with 1 N HCl. This mixture was extracted three times with EtOAc, dried over NaSO$_4$, filtered and evaporated to give a brown solid. Prepped on HPLC using a gradient of 5:95–95:5 CH$_3$CN/water over 45 minutes to give AIV-5-1 as a yellow solid. TLC Rf=0.52 (93:7:7 CHCl$_3$/MeOH/HOAc) $^1$H NMR (400 MHz, CDCl$_3$) δ 7.128–7.086 (m, 3H), 7.04–6.99 (t, 2H j=9), 6.90 (s, 1H), 6.03–6.02 (d, 1H, j=4.39 Hz), 3.98 (s, 2H), 3.85 (s, 3H).

EXAMPLE 50

4-[5-(3-Chlorobenzyl)-1-methyl-1H-pyrrol-2-yl]-2,4-dioxobutyric acid AIV-5-2

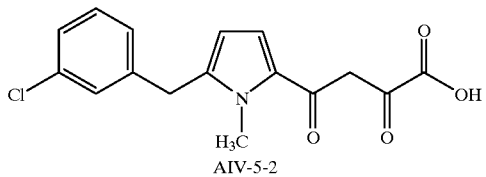

AIV-5-2

In a manner similar to that described for AIV-5-1, pyrrole was alkylated with 3-chlorobenzyl bromide and carried through the sequence to give AIV-5-2. TLC: Rf=0.52 (93:7:7 CHCl$_3$/MeOH/HOAc) $^1$H NMR (400 MHz, DMSO) δ 7.39–7.29 (m, 4H), 7.18–7.16 (d, 1H, j=6.7 Hz), 6.81 (s, 1H), 6.04–6.03 (d, 1H, j=4.2 Hz), 4.10 (s, 1H), 3.82 (s, 1H).

EXAMPLE 51

4-[5-(4-Fluorobenzyl)-1H-pyrrol-2-yl]-2,4-dioxobutyric acid AIV-5-3

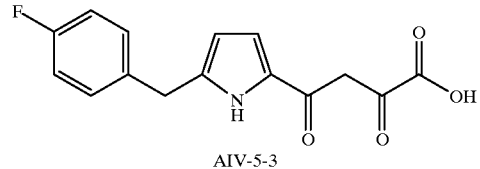

AIV-5-3

AIV-5-3 was prepared in a manner similar to that described for AIV-5-1, with the exception that the methylation step was omitted. TLC: Rf=0.28 (93:7:7 CHCl$_3$/MeOH/HOAc) $^1$H NMR (400 MHz, DMSO) δ 12.19 (s, 1H), 7.32–7.28 (m, 2H) 7.17 (s, 1H), 7.14–7.10 (t, 2H, j=8.8 Hz), 6.79 (s, 1H), 6.06–6.04 (m, 1H) 3.97 (s, 1H).

EXAMPLE 52

4-[5-(3-Chlorobenzyl)-1H-pyrrol-2-yl]-2,4-dioxobutyric acid AIV-5-4

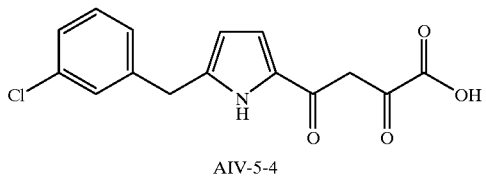

AIV-5-4

AIV-5-4 was prepared in a manner similar to that described for AIV-5-1, with the exception that the methylation step was omitted. TLC: Rf=0.44 (93:7:7 CHCl$_3$/MeOH/HOAc) $^1$H NMR (400 MHz, DMSO) δ 12.21 (s, 1H), 7.36–7.18 (m, 5H), 6.80 (s, 1H), 6.10 (s, 1H), 3.99 (s, 1H).

EXAMPLE 53

4-[5-(Benzyl)-1H-pyrrol-2-yl]-2,4-dioxobutyric acid AIV-5-5

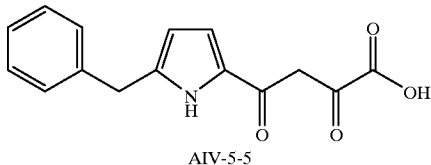

AIV-5-5

AIV-5-5 was prepared in a manner similar to that described for AIV-5-1 with the exception that the methylation step was omitted. TLC: Rf=0.34 (93:7:7 CHCl$_3$/MeOH/HOAc) $^1$H NMR (400 MHz, DMSO) δ 12.20 (s, 1H), 7.32–7.18 (m, 6H), 6.80 (s, 1H), 6.05 (m, 1H), 3.98 (s, 2H).

EXAMPLE 54

4-[5-(3-Fluorobenzyl)-1H-pyrrol-2-yl]-2,4-dioxobutyric acid AIV-5-6

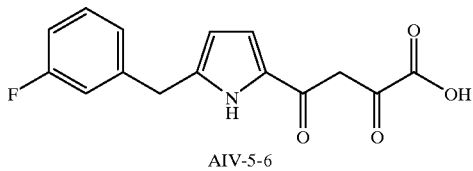

AIV-5-6

AIV-5-6 was prepared in a manner similar to that described for AIV-5-1, with the exception that the methylation step was omitted. TLC: Rf=0.34 (93:7:7 CHCl$_3$/MeOH/HOAc) $^1$H NMR (400 MHz, DMSO) δ 12.21 (s, 1H), 7.35–7.33 (dd, 1H, j=8.1 Hz, 1.6 Hz), 7.19 (d, 1H, j=2.2 Hz), 7.12–7.10 (d, 2H, j=6.6 Hz), 7.04 (m, 1H), 6.80 (s, 1H), 6.10–6.09 (dd, 1H, j=3.8 Hz, 2.1 Hz), 4.00 (s, 1H).

EXAMPLE 55

4-[5-(4-Fluorobenzyl)-1-(4-fluorobenzyl)-1H-pyrrol-2-yl]-2,4-dioxobutyric acid AIV-5-7

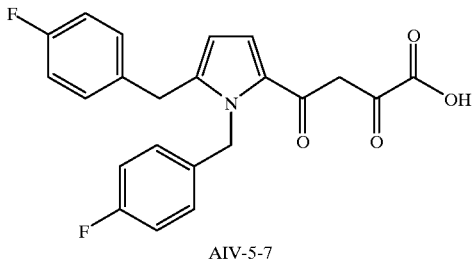

AIV-5-7

AIV-5-7 was prepared in a manner similar to that described for AIV-5-1, except that 4-fluorobenzyl bromide was substituted for methyl iodide in the N-alkylation step. TLC: Rf=0.60 (93:7:7 CHCl$_3$/MeOH/HOAc) $^1$H NMR (400 MHz, CDCl$_3$) δ 7.21–7.20 (d, 1H, j=4.2 Hz) 7.049–6.96 (m, 6H), 6.93 (s, 1H), 6.90–6.86 (dd, 2H j=8.4 Hz, 5.3 Hz), 6.07–6.06 (d, 1H j=4.2 Hz), 5.60 (s, 2H), 3.85 (s, 2H).

EXAMPLE 56

4-[5-(3-Chlorobenzyl)-1-(4-fluorobenzyl)-1H-pyrrol-2-yl]-2,4-dioxobutyric acid AIV-5-8

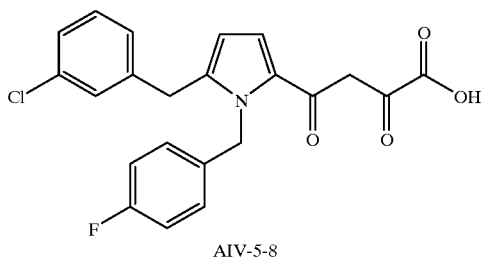

AIV-5-8

AIV-5-8 was prepared in a manner similar to that described for AIV-5-1, except that 4-fluorobenzyl bromide was substituted for methyl iodide in the N-alkyation step. $^1$H NMR (400 MHz, DMSO) δ 7.46–7.45 (d, 1H j=4.2 Hz), 7.28–7.22 (m, 2H), 7.12–7.04 (m, 4H), 6.92–6.88 (m, 2H), 6.85 (s, 1H), 6.14–6.13 (d, 1H, j=4.2 Hz), 5.69 (s, 2H), 3.99 (s, 2H). mass spec.: (FAB, m+1) 414.10.

EXAMPLE 57

4-[5-(Benzyl)-1-(4-fluorobenzyl)-1H-pyrrol-2-yl]-2,4-dioxobutyric acid AIV-5-9

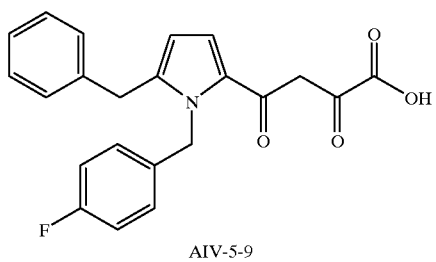

AIV-5-9

AIV-5-9 was prepared in a manner similar to that described for AIV-5-1, except that 4-fluorobenzyl bromide was substituted for methyl iodide in the N-alkyation step. $^1$H NMR (400 MHz, CDCl$_3$) δ 7.31–7.27 (m, 2H), 7.24 (m, 1H), 7.22–7.21 (d, 1H j=4.2 Hz), 7.08–7.06 (m, 2H), 7.00–6.96 (m, 2H), 6.92 (s, 1H), 6.90–6.87 (m, 2H), 6.11–1.10 (d, 1H, j=4.2 Hz), 5.60 (s, 2H) 3.88 (s, 2H). mass spec.: (FAB, m+1) 380.

EXAMPLE 58

4-[5-(3-Chlorobenzyl)-1-(4-fluorobenzyl)-1H-pyrrol-2-yl]-2,4-dioxobutyric acid AIV-5-10

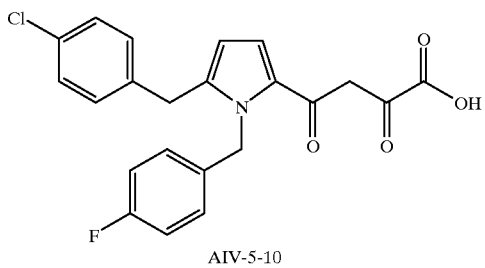

AIV-5-10

AIV-5-10 was prepared in a manner similar to that described for AIV-5-1, except that 4-fluorobenzyl bromide was substituted for methyl iodide in the N-alkyation step. $^1$H NMR (400 MHz, CDCl$_3$) δ 7.27 (m, 1H), 7.25–7.24 (m, 1H), 7.21–7.20 (d, 1H, j=4.2 Hz), 7.01–6.95 (m, 4H), 6.93 (s, 1H), 6.89–6.85 (m, 2H), 6.08–6.07 (d, 1H, j=4.2 Hz), 5.59 (s, 2H), 3.84 (s, 2H). mass spec.: (FAB, m+1) 414.

EXAMPLE 59

4-[5-(4-Fluorobenzyl)-1-methyl-1H-pyrrol-3-yl]-2,4-dioxobutyric acid AIV-8-1

Step 1: 1-[5-(4-Fluorobenzyl)-1-methyl-1H-pyrrol-3-yl]ethanone AIV-6-1

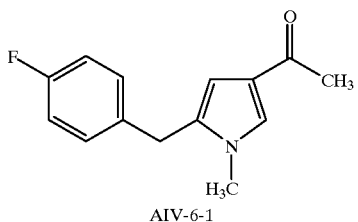

AIV-6-1

AIV-3-1 was dissolved in TFA 10 mL and was refluxed for two days. Cooled and removed TFA under reduced pressure. Dissolved brown oil in saturated NaHCO$_3$ and extracted three times with EtOAc, dried over NaSO$_4$, filtered and evaporated to give AIV-6-1 as a green oily solid. TLC: Rf=0.33 (60:40 Hexanes/EtOAc) $^1$H NMR (400 MHz, CDCl$_3$) δ 7.21–7.20 (d, 1H, j=1.83 Hz), 7.12–7.09 (m, 2H), 7.01–6.96 (m, 2H), 6.33–6.22 (d, 1H, j=1.8 Hz), 3.88 (s, 2H), 3.45 (s, 3H), 2.36 (s, 3H).

Step 2: 4-[5-(4-Fluorobenzyl)-1-methyl-1H-pyrrol-3-yl]-2,4-dioxobutyric acid AIV-8-1

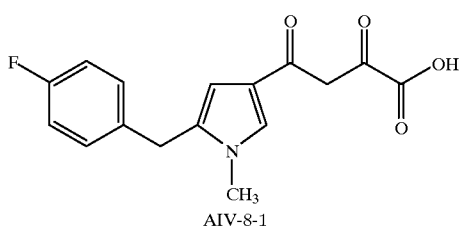

AIV-8-1

In a manner similar to that described for AIV-5-1, AIV-6-1 was treated with NaH and dimethyl oxalate followed by hydrolysis with NaOH to give AIV-8-1. $^1$H NMR (400 MHz, CDCl$_3$) δ 7.42 (d, 2H, j=1.8 Hz), 7.13–7.10 (m, 2H), 7.04–6.99 (m, 2H), 6.72–6.71 (d, 1H, j=1.7 Hz), 6.38 (s, 1H), 3.91 (s, 2H), 3.51 (s, 3H). mass spec.: (FAB, m+1) 304.19.

EXAMPLE 60

4-[5-(3-Chlorobenzyl)-1-methyl-1H-pyrrol-3-yl]-2,4-dioxobutyric acid AIV-8-2

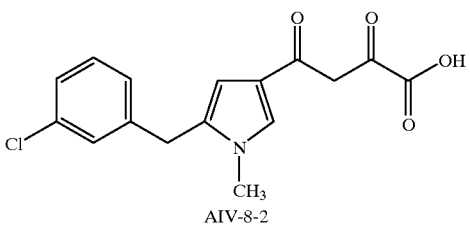

AIV-8-2

In a manner similar to that described for AIV-8-1, pyrrole was alkylated with 3-chlorobenzyl bromide and carried through the sequence to give AIV-8-2. $^1$H NMR (400 MHz, CDCl$_3$) δ 7.43–7.42 (d, 1H, j=1.8 Hz), 7.25–7.24 (m, 2H), 7.14 (s, 1H), 7.04–7.03 (m, 1H), 6.72 (s, 1H), 6.42–6.41 (d, 1H, j=1.1 Hz), 3.92 (s, 2H), 3.50 (s, 3H). mass spec.: (FAB, m+1) 320.2.

EXAMPLE 61

4-[5-(Benzyl)-1-methyl-1H-pyrrol-3-yl]-2,4-dioxobutyric acid AIV-8-3

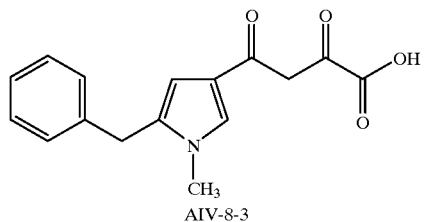

AIV-8-3

In a manner similar to that described for AIV-8-1, pyrrole was alkylated with benzyl bromide and carried through the sequence to give AIV-8-3. $^1$H NMR (400 MHz, CDCl$_3$) δ 7.43–7.42 (d, 1H, j=1.8), 7.34–7.30 (m, 2H), 7.27 (m, 1H), (d, 2H, j=7.1 Hz), 6.72 (s, 1H), 6.41–6.40 (d, 1H, j=1.8), 3.94 (s, 2H), 3.50 (s, 3H). mass spec.: (FAB, m+1) 286.3.

EXAMPLE 62

4-[5-(3-Fluorobenzyl)-1-methyl-1H-pyrrol-3-yl]-2,4-dioxobutyric acid AIV-8-4

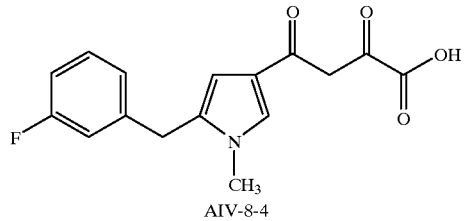

AIV-8-4

In a manner similar to that described for AIV-8-1, pyrrole was alkylated with 3-fluorobenzyl bromide and carried through the sequence to give AIV-8-4. ¹H NMR (400 MHz, CDCl₃) δ 7.43 (d, 1H, j=1.8 Hz), 7.32–7.28 (m, 1H), 6.98–6.93 (m, 2H), 6.86–6.83 (d, 1H, j=9.5 Hz), 6.72 (s, 1H), 6.43–6.42 (d, 1H, j=1.3 Hz), 3.94 (s, 2H), 3.50 (S, 3H). mass spec.: (FAB, m+1) 304.2.

EXAMPLE 63

4-(5-Benzyl-1H-pyrrol-3-yl)-2,4-dioxobutyric acid AIV-8-5

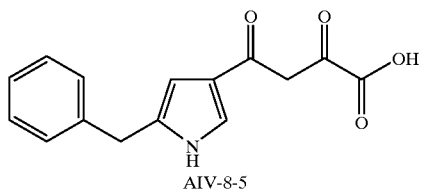

AIV-8-5

In a manner similar to that described for AIV-8-1, with the exception that the N-alkylation step was omitted, pyrrole was alkyated with benzyl bromide and carried through the sequence to give AIV-8-5. TLC: Rf=0.18 (93:7:7 CHCl₃/MeOH/HOAc) ¹H NMR (400 MHz, CDCl₃) δ 8.43 (s, 1H), 7.48 (dd, 1H, j=3.1 Hz, 1.8 Hz), 7.41–7.18 (m, 5H), 6.78 (s, 1H), 6.47 (d, 1H), j=0.7 Hz), 3.98 (s, 1H).

EXAMPLE 64

4-[2,5-Bis-(3-chlorobenzyl)-1-H-pyrrol-3-yl]-2,4-dioxobutyric acid AIV-8-6

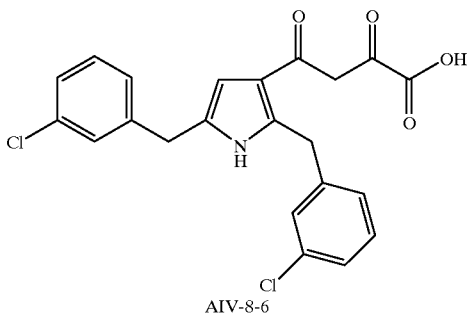

AIV-8-6

In a manner similar to that described for AIV-5-1 pyrrole was alkyated with 3-chlorobenzyl bromide and the minor 2,5-bis 3-chlorobenzyl alkylated product was isolated. Treatment with MeMgCl followed by acetic anyhydride as described for AIV-2-1 gave the 3-acylated product that was carried through the sequence to give AIV-8-6. TLC: Rf=0.42 (93:7:7 CHCl₃/MeOH/HOAc) ¹H NMR (400 MHz, CDCl₃) δ 9.10 (s, 1H), 7.26–7.21 (m, 3H), 7.08–6.97 (m, 5H), 6.90 (d, 1H, j=2.6 Hz), 6.77 (s, 1H), 3.92 (s, 2H), 3.77 (s, 2H).

EXAMPLE 65

4-[1-(4-Fluorobenzyl)-5-phenyl-1H-pyrrol-2-yl]-2,4-dioxobutyric acid AV-10-1

Step 1: (+/-) 5-Oxo-pyrrolidine-2-carboxylic acid ethyl ester AV-1-1

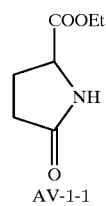

AV-1-1

To a 2L round bottomed flask with a stirring bar was added pyroglutamic acid (50 g, 387.2 mmol) and 1L of absolute ethanol. To this well stirred mixture was added thionyl chloride (10.0 mL, 137.1 mmol) dropwise over 15 minutes. The resulting mixture was stirred at ambient temperature 24 h. The resulting solution was concentrated in vacuo to give a colorless oil. This material was dissolved in EtOAc and washed with aqueous NaHCO₃ (2×) and brine. Drying (MgSO₄), filtration and removal of the solvent in vacuo gave 5-oxo-pyrrolidine-2-carboxylic acid ethyl ester AV-1-1 as an oil which crystallized on standing. ¹H NMR (CDCl₃) δ 1.30 (3H, t, j=7.3 Hz), 2.18 to 2.60 (4H, complex multiplet), 4.21 (3H, m), 3.37 (1H, br s).

Step 2: (+/-) 5-Oxo-pyrrolidine-1,2-dicarboxylic acid, 1-tert-butyl ester 2-ethyl ester AV-2-1

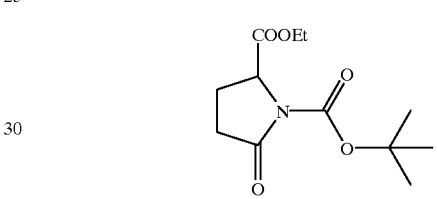

AV-2-1

To a 1L round bottomed flask with a stirring bar and an argon inlet was added gave 5-oxo-pyrrolidine-2-carboxylic acid ethyl ester AV-1-1 (18.6 g, 118.34 mmol) CHCl₃ (300 mL), di-tert-butyldicarbonate (30.99 g, 142.01 mmol), Et₃N (16.5 mL, 118.34 mmol), and 4-dimethylaminopyridine (14.46 g, 118.34 mmol). The mixture was stirred at ambient temperature 18 h. The solvent was removed in vacuo and the residue was dissolved in 750 mL of EtOAc. The EtOAc solution was washed with 10% aqueous citric acid, aqueous NaHCO₃, H₂O, and brine. Drying (MgSO₄), filtration and removal of the solvent in vacuo gave an oil. This material was chromatographed on 300 g of silica gel using 1:1 EtOAc-hexane as eluant. There was obtained (+/-) 5-oxo-pyrrolidine-1,2-dicarboxylic acid, 1-tert-butyl ester 2-ethyl ester AV-2-1 as an oil. ¹H NMR (CDCl₃) δ 1.27 (3H, t, j=7.3 Hz), 1.50 (9H, s), 2.08 (1H, m), 2.45 to 2.71 (3H, complex multiplet), 4.27 (2H, q, j=7.3 Hz), 4.60 (1H, dd, j=3, 9 Hz).

Step 3: (+/-) 2-Tert-butoxycarbonylamino-5-oxo-5-phenyl-pentanoic acid ethyl ester AV-3-1

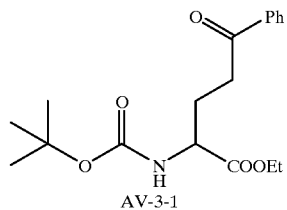

AV-3-1

To an oven dried 500 mL, three-necked round bottomed flask with a stirring bar, argon inlet and septum was added 5-oxo-pyrrolidine-1,2-dicarboxylic acid, 1-tert-butyl ester 2-ethyl ester AV-2-1 (6.50 g, 25.25 mmol) and 100 mL of dry THF. This solution was cooled to −40° C. and a solution of phenyl magnesium bromide (25.3 mL of a 1M solution in THF) was added slowly with a syringe. The mixture was aged 15 m at −40° C., the cooling bath was removed and the mixture was warmed to 20° C. The reaction was quenched by the addition of 150 mL of saturated aqueous NH$_4$Cl solution. This mixture was stirred 30m. The mixture was extracted with EtOAc. The organic extract was washed with brine, dried (MgSO$_4$), filtered and concentrated in vacuo to give 2-tert-butoxycarbonylamino-5-oxo-5-phenyl-pentanoic acid ethyl ester AV-3-1 which was used in the subsequent step without purification.

Step 4: (+/−) 5-Phenyl-3,4-dihydro-2H-pyrrole-2-carboxylic acid ethyl ester AV-4-1

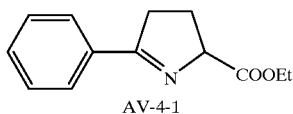

AV-4-1

To a 500 mL round bottomed flask with a stirring bar and a nitrogen inlet was added tert-butoxycarbonylamino-5-oxo-5-phenyl-pentanoic acid ethyl ester AV-3-1 (8.09 g, 22.76 mmol) and 100 mL of CH$_2$Cl$_2$. This solution was cooled in an ice bath and 100 mL of trifluoroacetic acid was added. The ice bath was allowed to expire and the mixture was stirred at ambient temperature 24 h. The solvents were removed in vacuo and the residue was redissolved in 300 mL of CHCl$_3$ and concentrated a second time. The resulting residue was dissolved in 100 mL of CH$_2$Cl$_2$ and this solution was cooled in an ice bath. Et$_3$N (50 mL) was added and the mixture was stirred 3 h. The solvents were removed in vacuo and the residue was dissolved in 300 mL of EtOAc. This solution was washed with H$_2$O and brine. Drying (MgSO$_4$), filtration and removal of the solvent in vacuo gave an oil. This material was chromatographed on silica gel using 1:4 EtOAc-hexane as eluant. 5-Phenyl-3,4-dihydro-2H-pyrrole-2-carboxylic acid ethyl ester AV-4-1 was obtained as a colorless oil. $^1$H NMR (CDCl$_3$) δ 1.31 (3H, t, j=7.1 Hz), 2.22 (2H, m), 3.00 (1H, m), 3.17 (1H, m), 4.23 (2H, d, j=7.1), 4.92 (1H, m), 7.41 (3H, m), 7.89 (2H, dd, j=2.7, 4.0).

Step 5: 5-Phenyl-1H-pyrrole-2-carboxylic acid AV-5-1

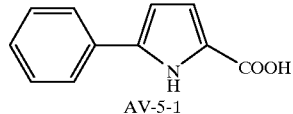

AV-5-1

To a 1L round bottomed flask with a stirring bar and an argon inlet was added 5-phenyl-3,4-dihydro-2H-pyrrole-2-carboxylic acid ethyl ester AV-4-1 (4.84 g, 22.28 mmol), dry CH$_2$Cl$_2$ (220 mL) and DDQ (5.06 g, 22.28 mmol). This solution was stirred at ambient temperature 1 h. The solvent was removed in vacuo. Aqueous NaOH (10% w/v, 440 mL) was added and the mixture was heated at reflux 24 h. The cooled, black solution was poured onto crushed ice and the mixture was acidified with conc. HCl. This mixture was extracted with EtOAc (2×). The combined extracts were washed with brine, dried (MgSO$_4$), filtered and concentrated in vacuo. The crude product was chromatographed on silica gel using 2.5% MeOH in EtOAc as eluant to give 5-phenyl-1H-pyrrole-2-carboxylic acid AV-5-1 as an off white solid. $^1$H NMR (CDCl$_3$) δ 6.59 (1H, dd, j=2.7, 3.9 Hz), 7.13 (1H, dd, j=2.7, 3.9 Hz), 7.34 (1H, m), 7.41 (2H, m), 7.59 (2H, m), 9.40 (1H, br s).

Step 6: 5-Phenyl-1H-pyrrole-2-carboxylic acid methoxymethylamide AV-6-1

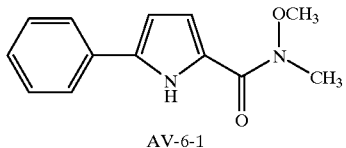

AV-6-1

To a 200 mL round bottomed flask with a stirring bar and an argon inlet was added 5-phenyl-1H-pyrrole-2-carboxylic acid AV-5-1 (2.45 g, 13.09 mmol), N,O-dimethylhydroxylamine hydrochloride (1.40 g, 14.40 mmol), N-ethyl-N'-dimethylaminopropylcarbodiimide hydrochloride (2.76 g, 14.40 mmol), hydroxybenztriazole hydrate (1.94 g, 14.40 mmol) and dry, degassed DMF (25 mL). This well stirred mixture was warmed gently until all of the solids dissolved. Et$_3$N (5.6 mL, 40.00 mmol) was added in one portion. The resulting mixture was stirred at ambient temperature 18 h. The solvents were removed in vacuo at +80° C. The residue was partitioned between saturated aqueous NaHCO$_3$ and EtOAc. The layers were separated and the organic phase was washed with H$_2$O (2×) and brine. Drying (MgSO$_4$), filtration and removal of the solvent in vacuo gave a solid. This material was chromatographed on silica gel using 35% EtOAc in hexane as eluant to give 5-phenyl-1H-pyrrole-2-carboxylic acid methoxymethylamide AV-6-1 as a solid. $^1$H NMR (CDCl$_3$) δ 3.36 (3H, s), 3.80 (3H, s), 6.58 (1H, dd, j=2.2, 4.0 Hz), 6.94 (1H, dd, j=2.2, 4.0 Hz), 7.30 (1H, m), 7.41 (2H, m), 7.58 (2H, m), 9.63 (1H, br s).

Step 7: 1-(4-Fluorobenzyl)-5-phenyl-1H-pyrrole-2-carboxylic acid methoxy-methyl-amide AV-7-1

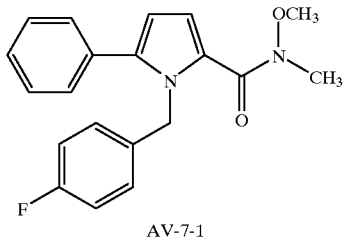

AV-7-1

To a 100 mL round bottomed flask containing 5-phenyl-1H-pyrrole-2-carboxylic acid methoxymethylamide AV-6-1 (0.692 g, 3.01 mmol) was added a stirring bar and an argon inlet was attached. THF (15 mL) was added and, when all of the solids had dissolved, NaH-oil suspension (0.132 g of a 60% w/w suspension, 3.31 mmol) was added. This mixture was stirred 15 min at ambient temperature then 4-fluorobenzylbromide (0.41 mL, 3.31 mmol) was added. The resulting mixture was stirred 24 h at ambient temperature. The mixture was diluted with EtOAc and the solution was washed with 1N HCl, water and brine. Drying (MgSO$_4$), filtration and removal of the solvent in vacuo gave an oil. This material was chromatographed on silica gel using 25% EtOAc in hexanes a eluant to give 1-(4-fluorobenzyl)-5-phenyl-1H-pyrrole-2-carboxylic acid methoxy-methyl-amide AV-7-1. $^1$H NMR (CDCl$_3$) δ 3.21 (3H, s), 3.47 (3H, s), 5.52 (2H, s), 6.24 (1H, d, j=3.9 Hz), 6.75 to 6.90 (5H, m), 6.94 (1H, d, j=3.9 Hz), 7.38 (4H, m).

Step 8: 1-[1-(4-Fluorobenzyl)-5-phenyl-1H-pyrrol-2-yl] ethanone AV-8-1

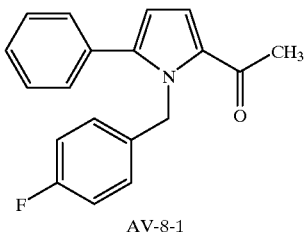

AV-8-1

To a 100 mL round bottomed flask with a stirring bar and an argon inlet was added 1-(4-fluorobenzyl)-5-phenyl-1H-pyrrole-2-carboxylic acid methoxy-methylamide AV-7-1 (0.726 g, 2.16 mmol) and dry THF (20 mL). This solution was cooled to −78° C. and methyllithium (3.39 mL of a 1.4 M solution in Et$_2$O, 4.75 mmol). The mixture was stirred 30 min at −78° C. then the reaction was quenched with saturated aqueous NH$_4$Cl solution. The mixture was warmed to room temperature and stirred 2 h. The layers were separated and the aqueous phase was extracted with EtOAc. The combined organic fractions were dried (MgSO$_4$), filtered and concentrated in vacuo. The crude product was chromatographed on silica gel using 15% EtOAc in hexanes as eluant to give 1-[1-(4-fluorobenzyl)-5-phenyl-1H-pyrrol-2-yl]ethanone AV-8-1 as an oil. $^1$H NMR (CDCl$_3$) δ 2.42 (3H, s), 5.59 (2H, s), 6.29 (1H, d, j=4.2 Hz), 6.78 to 6.91 (4H, m), 7.12 (1H, d, j=4.2 Hz), 7.29 (2H, m), 7.38 (3H, m).

Step 9: 4-[1-(4-Fluorobenzyl)-5-phenyl-1H-pyrrol-2-yl]-2,4-dioxobutyric acid ethyl ester AV-9-1

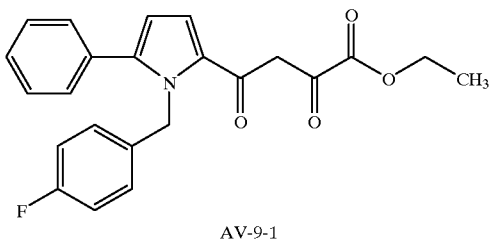

AV-9-1

To a 100 mL round bottomed flask with a stirring bar and an argon inlet was added 1-[1-(4-fluorobenzyl)-5-phenyl-1H-pyrrol-2-yl]ethanone AV-8-1 (0.628 g, 2.14 mmol), dry THF (10 mL), diethyl oxalate (0.41 mL, 3.00 mmol) and NaOEt (0.204 g, 3.00 mmol). The resulting mixture was stirred 1 h at ambient temperature. The mixture was diluted with EtOAc and washed with 1N HCl, H$_2$O (2×) and brine. Drying (MgSO$_4$) filtration and removal of the solvent in vacuo gave 4-[1-(4-fluorobenzyl)-5-phenyl-1H-pyrrol-2-yl]-2,4-dioxobutyric acid ethyl ester AV-9-1 as an oil. This material was used without further purification. $^1$H NMR (CDCl$_3$) δ 1.38 (3H, t, j=7.1 Hz), 4.38 (2H, q, j=7.1 Hz), 5.65 (2H, s), 6.38 (1H, d, j=4.1 Hz), 6.79 to 6.94 (4H, m), 7.29 (2H, m), 7.39 (3H, m).

Step 10: 4-[1-(4-Fluorobenzyl)-5-phenyl-1H-pyrrol-2-yl]-2,4-dioxobutyric acid AV-10-1

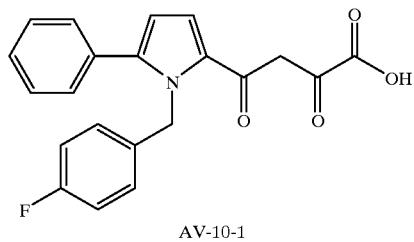

AV-10-1

To a 200 mL round bottomed flask with a stirring bar and an argon inlet was added 4-[1-(4-fluorobenzyl)-5-phenyl-1H-pyrrol-2-yl]-2,4-dioxobutyric acid ethyl ester AV-9-1 (0.84 g, 2.14 mmol) and MeOH (72 mL). To this solution was added aqueous NaOH (11 mL of a 1N solution). The mixture was stirred at ambient temperature 18 h. The organic solvents were removed in vacuo and the aqueous residue was washed with Et$_2$O then acidified with 1N HCl. The mixture was extracted with Et$_2$O and the Et$_2$O extract was washed with brine, dried (MgSO$_4$), filtered and concentrated in vacuo. The crude solid was recrystallized from a mixture of EtOAc and hexane to give 4-[1-(4-fluorobenzyl)-5-phenyl-1H-pyrrol-2-yl]-2,4-dioxobutyric acid AV-10-1 as a white, crystalline solid. MP: 151–152° C. (dec). $^1$H NMR (CDCl$_3$) δ 5.63 (2H, s), 6.42 (1H, d, j=4.4 Hz), 6.80 (2H, m), 6.94 (3H, m), 7.29 (2H, m), 7.40 (2H, m).

EXAMPLE 66

4-[4-Dimethylamino-1-(4-fluorobenzyl)-1H-pyrrol-2-yl]-2,4-dioxobutyric acid A-VI-5-1

Step 1: 1-[1-(4-Fluorobenzyl)-4-nitro-1H-pyrrol-2-yl]ethanone AVI-1-1

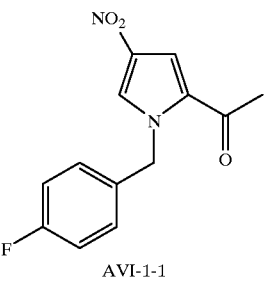

AVI-1-1

To a 500 mL round bottomed flask with a stirring bar and a drying tube was added 1-[1-(4-fluorobenzyl)-1H-pyrrol-2-yl]ethanone AI-1-1 (11.64 g, 53.58 mmol) and acetic anhydride (230 mL). This solution was cooled to −78° C. and concentrated nitric acid (3.7 mL of 15.9 N solution, 58.24 mmol) was added with a pipette. The cooling bath was allowed to expire and the mixture warmed to 0° C. over 7 h. The acetic anhydride was removed in vacuo and the residue was taken up in EtOAc (500 mL). This solution was washed with saturated aqueous NaHCO$_3$ solution (2×) and brine. Drying (MgSO$_4$), filtration and removal of the solvent in vacuo gave a solid. This material was chromatographed on silica gel using 20% EtOAc in hexane as eluant. An impure yellow crystalline solid was obtained. This material was recrystallized from Et$_2$O/hexane to give white crystals of 1-[1-(4-fluorobenzyl)-4-nitro-1H-pyrrol-2-yl]ethanone AVI-1-1. $^1$H NMR (CDCl$_3$) δ 2.55 (3H, s), 5.54 (2H, s), 7.06 (2H, m), 7.20 (2H, m), 7.47 (1H, d, j=1.8 Hz), 7.63 (1H, d, j=1.8 Hz).

Step 2: 1-[4-Amino-1-(4-fluorobenzyl)-1H-pyrrol-2-yl]ethanone AVI-2-1

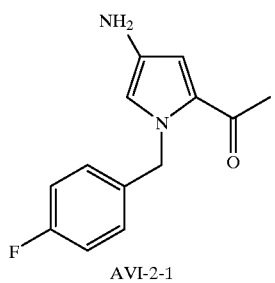

AVI-2-1

To a 1L round bottomed flask with a stirring bar and a balloon hydrogenation adapter was added 1-[1-(4-fluorobenzyl)-4-nitro-1H-pyrrol-2-yl]ethanone AVI-1-1 (8.00 g, 30.51 mmol) absolute EtOH (640 mL) and 10% Pd-C (2.24 g, 2.11 mmol). This mixture was hydrogenated at ambient temperature 24 h. The catalyst was removed by filtration and the EtOH was removed in vacuo. The semi-solid residue was chromatographed on silica gel using EtOAc as eluant to give 1-[4-amino-1-(4-fluorobenzyl)-1H-pyrrol-2-yl]ethanone AVI-2-1 as a yellow crystalline solid. $^1$H NMR (CDCl$_3$) δ 2.34 (3H, s), 3.01 (2H, br s), 5.42 (2H, s), 6.46 (1H, d, j=2.0 Hz), 6.50 (1H, d, j=2.0 Hz), 6.98 (2H, m), 7.12 (2H, m).

Step 3: 1-[4-Dimethylamino-1-(4-fluorobenzyl)-1H-pyrrol-2-yl]ethanone AVI-3-1

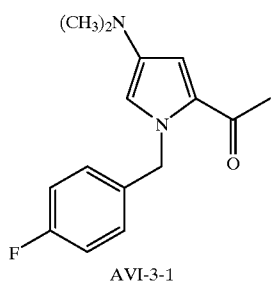

AVI-3-1

To a 100 mL round bottomed flask with a stirring bar and a nitrogen inlet was added 1-[4-amino-1-(4-fluorobenzyl)-1H-pyrrol-2-yl]ethanone AVI-2-1 (0.50 g, 2.15 mmol), dry DMF (20 mL), finely powdered Cs$_2$CO$_3$ (3.26 g, 10 mmol) and MeI (0.31 mL, 5.00 mmol). The resulting mixture was stirred 1h at ambient temperature. The solids were removed by filtration and the solvent was removed in vacuo. The residue was dissolved in EtOAc and washed with water (3×) and brine. Drying (MgSO$_4$), filtration and removal of the solvent in vacuo gave an oil. This material was chromatographed on silica gel using 50% EtOAc-hexanes as eluant to give 1-[4-dimethylamino-1-(4-fluorobenzyl)-1H-pyrrol-2-yl]ethanone AVI-3-1 as an oil. $^1$H NMR (CDCl$_3$) δ 2.36 (3H, s), 2.70 (6H, s), 5.46 (2H, s), 6.36 (1H, d, j=2.0 Hz), 6.50 (1H, d, j=2.0 Hz), 6.98 (2H, m), 7.11 (2H, m).

Step 4: 4-[4-Dimethylamino-1-(4-fluorobenzyl)-1H-pyrrol-2-yl]-2,4-dioxobutyric acid ethyl ester AVI-4-1

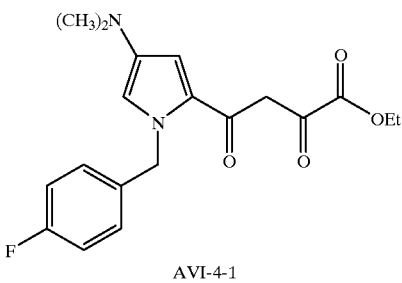

AVI-4-1

In a manner substantially similar to that described for Example AV-9-1, 1-[4-dimethylamino-1-(4-fluorobenzyl)-1H-pyrrol-2-yl]ethanone AVI-3-1 was used to prepare 4-[4-dimethylamino-1-(4-fluorobenzyl)-1H-pyrrol-2-yl]-2,4-dioxobutyric acid ethyl ester AVI-4-1 which was used in the next step without further purification.

Step 5: 4-[4-Dimethylamino-1-(4-fluorobenzyl)-1H-pyrrol-2-yl]-2,4-dioxobutyric acid AVI-5-1

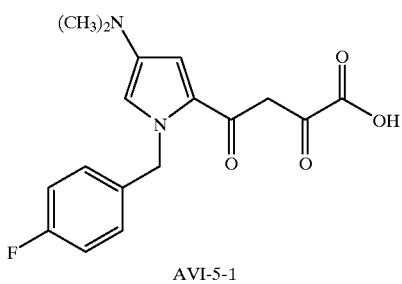

AVI-5-1

In a manner substantially similar to that described for Example AV-10-1 4-[4-dimethylamino-1-(4-fluorobenzyl)-1H-pyrrol-2-yl]-2,4-dioxobutyric acid ethyl ester AVI-4-1 was used to prepare 4-[4-dimethylamino-1-(4-fluorobenzyl)-1H-pyrrol-2-yl]-2,4-dioxobutyric acid AVI-5-1. $^1$H NMR (DMSO-d$_6$-CDCl$_3$ 1:1) δ 3.12 (6H, s), 5.61 (2H, s), 7.06 (2H, m), 7.19 (2H, m), 7.60 (1H, br s), 7.68 (1H, br s).

EXAMPLES 67–69

The following compounds was prepared in a manner similar to that described for AVI-5-1:

4-[1-(4-Fluorobenzyl)-4-nitro-1H-pyrrol-2-yl]-2,4-dioxobutyric acid CHN Calc.
(C$_{15}$H$_{11}$FN$_2$O$_6$.0.8H$_2$O) 51.65, 3.64, 8.03; Fnd. 51.65, 3.42, 7.88. (67)

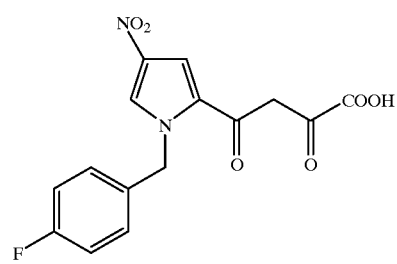

4-[4-(Benzylamino)-1-(4-fluorobenzyl)-1H-pyrrol-2-yl]-2,4-dioxobutyric acid CHN Calc. ($C_{22}H_{19}FN_2O_4 \cdot 0.33$ CHCl$_3$) 61.83, 4.49, 6.45; Fnd. 62.07, 4.27, 5.74. (68)

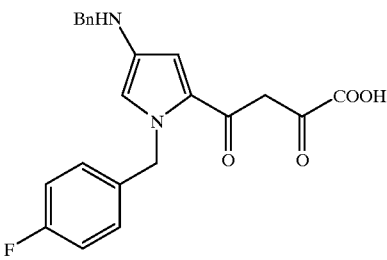

4-[5-Nitro-1-(4-fluorobenzyl)-1H-pyrrol-2-yl]-2,4-dioxobutyric acid CHN Calc. 53.90, 3.32, 8.38; Fnd. 53.77, 3.24, 8.20. (69)

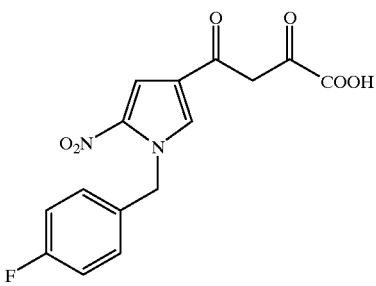

EXAMPLE 70

4-[1-Benzyl-1H-pyrrol-3-yl]-2,4-dioxobutyric acid AVII-3-1

Step 1: 1-[1-Benzyl-1H-pyrrol-3-yl]ethanone AVII-1-1

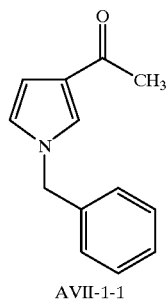

AVII-1-1

To a solution of 3-acetylpyrrole (545 mg, 5.00 mmol) in DMF (10 mL) at 0° C. was added benzyl bromide (0.60 mL, 5.05 mmol) followed by NaH (260 mg of a 60% suspension in mineral oil, 6.50 mmol). After stirring at 0° C. for 20 min and room temperature for 1 h, the reaction mixture was treated with sat. NH$_4$Cl (10 mL) and poured onto sat. NH$_4$Cl (50 mL). The resulting mixture was extracted with Et$_2$O (3×50 mL). The combined organic extracts were washed with sat. NaCl (50 mL) and dried (MgSO$_4$). Concentration followed by medium-pressure liquid chromatography on silica gel, eluting with 2:1/hexanes:EtOAc, afforded the product as a clear oil. $^1$H NMR (400 MHz, CDCl$_3$) δ 7.35–7.29 (m, 4H), 7.13–7.27 (m, 2H), 6.66–6.61 (m, 2H), 5.07 (s, 2H), 2.38 (s, 3H). mass spec (EI, M$^+$) 199.

Step 2: 4-[1-Benzyl-1H-pyrrol-3-yl]-2,4-dioxobutyric acid methyl ester AVII-2-1

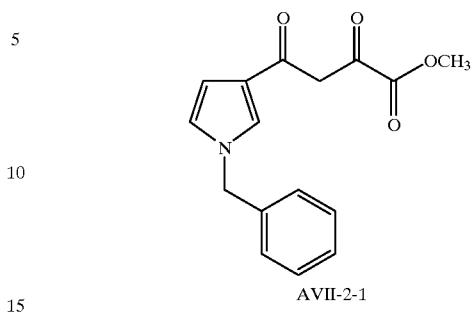

AVII-2-1

To a solution of AVII-1-1 (900 mg, 4.52 mmol) in THF (10 mL) was added dimethyl oxalate (795 mg, 6.74 mmol) followed by NaH (270 mg of a 60% suspension in mineral oil, 6.76 mmol). Methanol (2 drops) was added and the reaction mixture was heated to reflux. After 1 h, 1 N HCl (20 mL) was added and the mixture extracted with CH$_2$Cl$_2$ (3×20 mL). The combined organic extracts were washed with sat. NaCl (20 mL) and dried (MgSO$_4$). Concentration followed by medium-pressure liquid chromatography on silica gel, eluting with 5:5:1/CH$_2$Cl$_2$:hexanes:EtOAc, afforded the product as a yellow solid. $^1$H NMR (400 MHz, CDCl$_3$) δ 7.44 (m, 1H), 7.40–7.32 (m, 3H), 7.19–7.15 (m, 2H), 6.72–6.68 (m, 3H), 5.09 (s, 2H), 3.91 (s, 3H).

Step 3: 4-[1-Benzyl-1H-pyrrol-3-yl]-2,4-dioxobutyric acid AVII-3-1

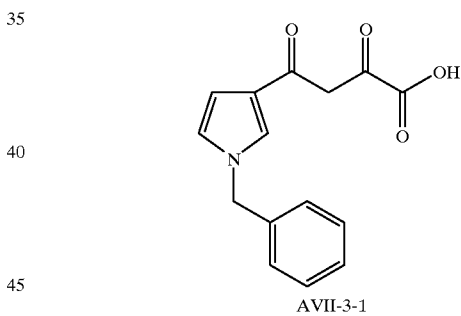

AVII-3-1

To a solution of AVII-2-1 (450 mg, 1.58 mmol) in THF (3.2 mL) was added 1 N NaOH (2.4 mL). After stirring 14 h at room temperature, the mixture was poured onto 1 N NaOH (10 mL) and extracted with Et$_2$O (5×10 mL). The Et$_2$O extracts were discarded. The aqueous phase was treated with 3 N HCl (20 mL), extracted with CH$_2$Cl$_2$ (3×20 mL) and the combined organic extracts dried (MgSO$_4$). Concentration provided a yellow solid which was recrystallized from benzene to afford the desired product as a light yellow solid. mp 151–152° C. (uncorrected) $^1$H NMR (400 MHz, d$_6$-DMSO) δ 8.04 (d, J=1.6 Hz, 1H), 7.40–7.25 (m, 5H), 7.01 (m, 1H), 6.74 (s, 1H), 6.62 (m, 1H), 5.18 (s, 2H). mass spec (negative mode electrospray, M–H) 270.

EXAMPLES 71–85

In a manner similar to that described for AVII-3-1, the following compounds were prepared:

EXAMPLE 71

4-[1-(4-Fluorobenzyl)-1H-pyrrol-3-yl]-2,4-dioxobutyric acid AVII-3-2 (71)

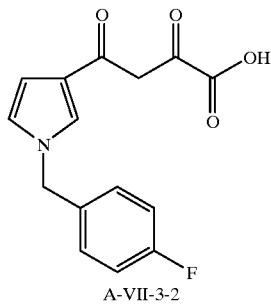

A-VII-3-2 mp 145–146° C. (uncorrected) $^1$H NMR (400 MHz, d$_6$-DMSO) δ 8.04 (m, 1H), 7.40–7.35 (m, 2H), 7.22–7.17 (m, 2H), 7.01 (m, 1H), 6.73 (s, 1), 6.62 (m, 1H), 5.17 (s, 2H). mass spec (negative mode electrospray, M–H) 288.

EXAMPLE 72

4-[1-(3-Bromobenzyl)-1H-pyrrol-3-yl]-2,4-dioxobutyric acid AVII-3-3

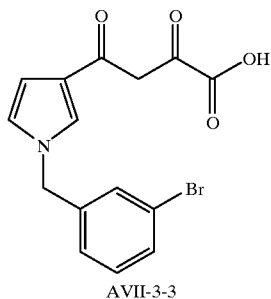

AVII-3-3 mp 159–160° C. (uncorrected) $^1$H NMR (400 MHz, d$_6$-DMSO) δ 8.07 (m, 1H), 7.56–7.50 (m, 2H), 7.36–7.28 (m, 2H), 7.04 (m, 1H), 6.74 (s, 1H), 6.6 (m, 1H), 5.18 (s, 2H). mass spec (negative mode electrospray, M–H) 348, 350.

EXAMPLE 73

4-[1-(4-Fluorobenzyl)-4-methyl-1H-pyrrol-3-yl]-2,4-dioxobutyric acid AVII-H3-4

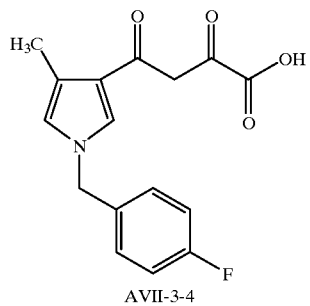

AVII-3-4

AVII-3-4 was prepared in a manner similar to AVII-3-1, starting with 4-methyl-3-acetyl pyrrole. mp 162–163° C. (uncorrected) $^1$H NMR (400 MHz, d$_6$-DMSO) δ 8.10 (m, 1H), 7.37 (dd, J=5.5, 7.6 Hz, 2H), 7.18 (dd, J=7.6, 8.9 Hz, 2H), 6.77 (m, 1H), 6.72 (s, 1H), 5.10 (s, 2H), 2.20 (s, 3H). mass spec (negative mode electrospray, M–H) 302.

EXAMPLE 74

4-[2,4-Dimethyl-1-(4-fluorobenzyl)-1H-pyrrol-3-yl]-2,4-dioxobutyric acid AVII-3-5

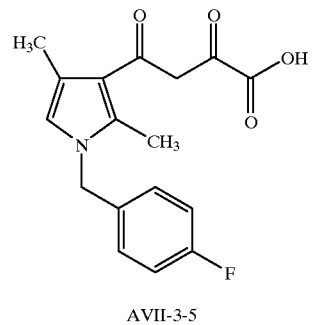

AVII-3-5

AVII-3-5 was prepared in a manner similar to AVII-3-1, starting with 2,4-dimethyl-3-acetyl pyrrole. mp 184–185° C. (uncorrected) $^1$H NMR (400 MHz, d$_6$-DMSO) δ 7.20–7.12 (m, 4H), 6.74 (s, 1H), 6.62 (s, 1H), 5.13 (s, 2H), 2.41 (s, 3H), 2.19 (s, 3H). mass spec (negative mode electrospray, M–H) 316.

EXAMPLE 75

4-[1-(3,4-Difluorobenzyl)-1H-pyrrol-3-yl]-2,4-dioxobutyric acid AVII-3-6

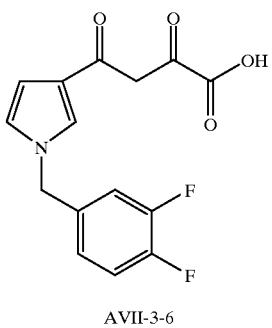

AVII-3-6 mp 143–144° C. (uncorrected) $^1$H NMR (400 MHz, d$_6$-DMSO) δ 8.05 (s, 1H), 7.43 (m, 2H), 7.17 (m, 1H), 7.03 (dd, J=3.0, 1.8 Hz, 1H), 6.73 (s, 1H), 6.61 (dd, J=3.0, 1.8 Hz, 1H), 5.16 (s, 2H), 3.3 bs, 1H). mass spec (negative mode electrospray, M–H) 306.

EXAMPLE 76

4-[1-(3-Chlorobenzyl)-1H-pyrrol-3-yl]-2,4-dioxobutyric acid AVII-3-7

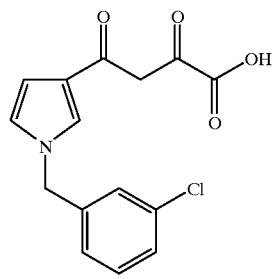

AVII-3-7 mp 159–160° C. (uncorrected) $^1$H NMR (400 MHz, $d_6$-DMSO) δ 8.07 (m, 1H), 7.38 (m, 3H), 7.26 (m, 1H), 7.04 (m, 1H), 6.74 (s, 1H), 6.63 (m, 1H), 5.19 (s, 1H). mass spec (negative mode electrospray, M–H) 304, 306.

EXAMPLE 77

4-[1-(4-Chlorobenzyl)-1H-pyrrol-3-yl]-2,4-dioxobutyric acid AVII-3-8

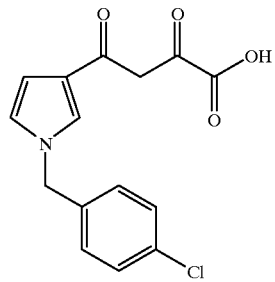

A-VII-3-8 mp 170–171° C. (uncorrected) $^1$H NMR (400 MHz, $d_6$-DMSO) δ 8.03 (t, J=1.8 Hz, 1H), 7.43–7.40 (m, 2H), 7.34 (m, 1H), 7.31 (m, 1H), 7.00 (dd, J=2.8, 1.8 Hz, 1H), 6.72 (s, 1H), 6.61 (dd, J=2.8, 1.8 Hz, 1H). mass spec (negative mode electrospray, M–H) 304.

EXAMPLE 78

4-[1-(4-Bromobenzyl)-1H-pyrrol-3-yl]-2,4-dioxobutyric acid AVII-3-9

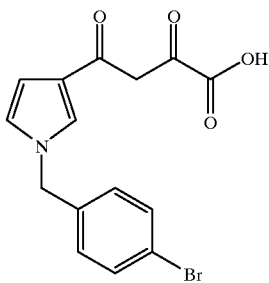

AVII-3-9 mp 184–185° C. (uncorrected) $^1$H NMR (400 MHz, $d_6$-DMSO) δ 8.04 (t, J=2.0 Hz, 1H), 7.59–7.54 (m, 2H), 7.28–7.23 (m, 2H), 7.01 (dd, J=2.0, 2.9 Hz, 1H), 6.74 (s, 1H), 6.62 (dd, J=2.0, 2.9 Hz, 1H), 5.17 (s, 2H). mass spec (negative mode electrospray, M–H) 348, 350.

EXAMPLE 79

4-[1-(3,4-Dichlorobenzyl)-1H-pyrrol-3-yl]-2,4-dioxobutyric acid AVII-3-10

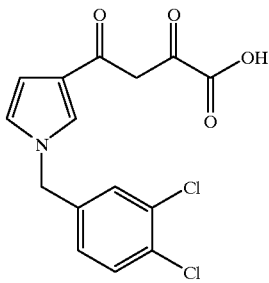

A-II-3-10 mp 175–176° C. (uncorrected) $^1$H NMR (400 MHz, $d_6$-DMSO) δ 8.06 (t, J=1.9 Hz, 1H), 7.62 (d, J=8.2 Hz, 1H), 7.61 (s, 1H), 7.28 (dd, J=8.2, 2.0 Hz, 1H), 7.04 (dd, J=2.9, 1.9 Hz, 1H), 6.73 (s, 1H), 6.62 (dd, J=2.9, 1.9 Hz, 1H), 5.18 (s, 2H), 3.36–3.20 (bs, 1H). mass spec (negative mode electrospray, M–H) 338, 340.

EXAMPLE 80

4-[1-(2-Methylbenzyl)-1H-pyrrol-3-yl]-2,4-dioxobutyric acid AVII-3-11

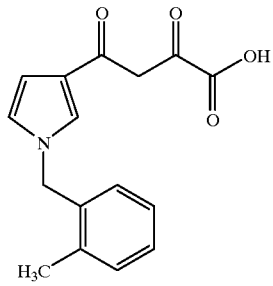

AVII-3-11 mp 119–120° C. (uncorrected) $^1$H NMR (400 MHz, $d_6$-DMSO) δ 7.91 (t, J=1.9 Hz, 1H), 7.24–7.15 (m, 2H), 6.94 (d, J=7.4 Hz, 1H), 6.91 (dd, J=2.9, 1.9 Hz, 1H), 6.72 (s, 1H), 6.64 (dd, J=2.9, 1.9 Hz, 1H), 5.21 (s, 2H), 3.45–3.21 (bs, 1H), 2.25 (s, 3H). mass spec (negative mode electrospray, M−H) 284.

EXAMPLE 81

4-[1-(3-Chlorobenzyl)-4-methyl-1H-pyrrol-3-yl]-2,4-dioxobutyric acid AVII-3-12

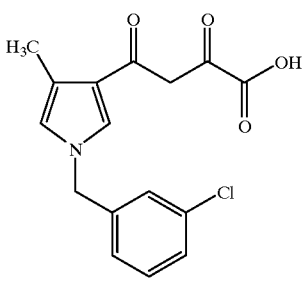

AVII-3-12

AVII-3-12 was prepared in a manner similar to AVII-3-1, starting with 4-methyl-3-acetyl pyrrole. mp 148–149° C. (uncorrected) $^1$H NMR (400 MHz, $d_6$-DMSO) δ 8.09 (d, J=2.2 Hz, 1H), 7.41–7.35 (m, 2H), 7.26 (m, 1H), 6.79 (dd, J=2.1, 1.1 Hz, 1H), 6.72 (s, 1H), 5.09 (s, 2H), 3.40–3.30 (bs, 1H), 2.19 (s, 3H). mass spec (negative mode electrospray, M−H) 318, 320.

EXAMPLE 82

4-[1-(3-Trifluoromethylbenzyl)-1H-pyrrol-3-yl]-2,4-dioxobutyric acid AVII-3-13

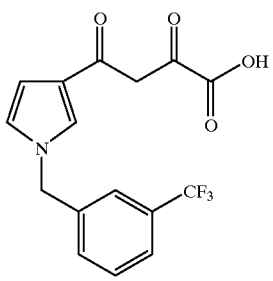

AVII-3-13 mp 145–146° C. (uncorrected) $^1$H NMR (400 MHz, $d_6$-DMSO) δ 8.09 (t, J=1.9 Hz, 1H), 7.70–7.66 (m, 2H), 7.63–7.58 (m, 2H), 7.06 (m, 1H), 6.73 (s, 1H), 6.63 (dd, J=4.7, 1.7 Hz, 1H), 5.28 (s, 2H), 3.40–3.20 (bs, 1H). mass spec (negative mode electrospray, M−H) 338.

EXAMPLE 83

4-[1-(4-Methylbenzyl)-1H-pyrrol-3-yl]-2,4-dioxobutyric acid AVII-3-14

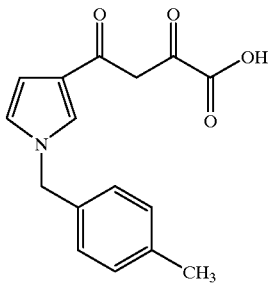

AVII-3-14 mp 164–165° C. (uncorrected) $^1$H NMR (400 MHz, $d_6$-DMSO) δ 8.00 (t, J=1.9 Hz, 1H), 7.20–7.14 (m, 4H), 6.97 (dd, J=2.9, 1.9 Hz, 1H), 6.72 (s, 1H), 6.59 (dd, J=2.9, 1.9 Hz, 1H), 5.11 (s, 2H), 3.37–3.27 (bs, 1H), 2.26 (s, 3H). mass spec (negative mode electrospray, M−H) 284.

EXAMPLE 84

4-[1-(4-Methoxybenzyl)-1H-pyrrol-3-yl]-2,4-dioxobutyric acid AVII-3-15

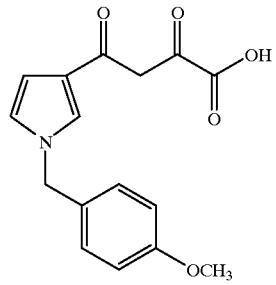

AVII-3-15 mp 137–138° C. (uncorrected) 1H NMR (400 MHz, $d_6$-DMSO) δ 7.99 (t, J=1.9 Hz, 1H), 7.27–7.25 (m, 2H), 6.97 (dd, J=2.9, 1.9 Hz, 1H), 6.90 (m, 2H), 6.71 (s, 1H), 6.58 (dd, J=2.9, 1.9 Hz, 1H), 5.08 (s, 2H). mass spec (negative mode electrospray, M−H) 300.

EXAMPLE 85

4-[1-(3-Methylbenzyl)-1H-pyrrol-3-yl]-2,4-dioxobutyric acid AVII-3-16

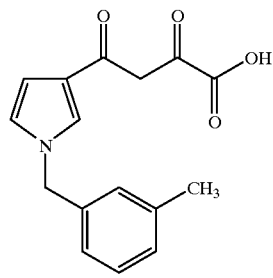

AVII-3-16

Rf=0.49 (94:6:1 $CH_2Cl_2$/MeOH/HOAc) $^1$H NMR (400 MHz, $CDCl_3$) δ 7.46 (s, 1H), 7.25 (m, 2H), 7.15 (d, J=7.5 Hz, 1H), 6.98 (m, 2H), 6.25 (s, 1H), 6.23 (m, 1H), 6.20 (m, 1H), 5.05 (s, 2H), 2.33 (s, 3H).

EXAMPLES 86–88

The following compounds were prepared in a manner similar to AVII-3-1:

EXAMPLE 86

4-{1-[3-(4-Fluorophenyl)-propyl]-1H-pyrrol-3-yl}-2,4-dioxobutyric acid

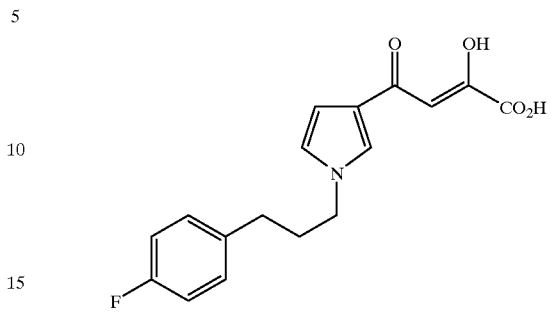

CHN Calc. ($C_{17}H_{16}FNO_4$ 0.2 water) 63.62, 5.15, 4.36; Fnd. 63.54, 5.07, 4.00.

EXAMPLE 87

4-[1-(4-Bromobenzyl)-1-H-pyrrol-3-yl]-2,4-dioxobutyric acid

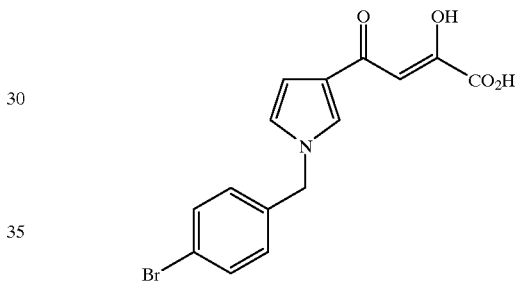

CHN Calc. 51.45, 3.45, 4.00; Fnd. 51.53, 3.50, 3.92.

EXAMPLE 88

4-[1-(4-Chlorobenzyl)-1-H-pyrrol-3-yl]-2,4-dioxobutyric acid

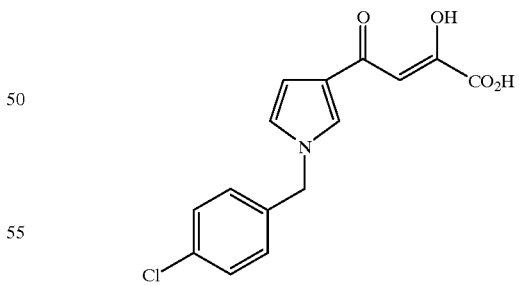

CHN Calc. 58.93, 3.96, 4.58; Fnd. 58.79, 4.04, 4.47.

EXAMPLE 89

4-[4-Benzylmethylamino-1-(4-fluorobenzyl)-1H-pyrrol-2-yl]-2,4-dioxobutyric acid AVIII-4-1

Step 1: 1-[4-Benzylamino-1-(4-fluorobenzyl)-1H-pyrrol-2-yl]ethanone AVIII-1-1

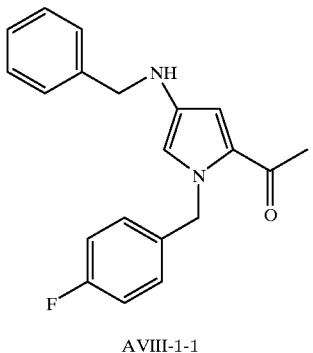

AVIII-1-1

To a 100 mL round bottomed flask with a stirring bar, addition funnel and an argon inlet was added 1-[4-amino-1-(4-fluorobenzyl)-1H-pyrrol-2-yl]ethanone AVI-2-1 (1.00 g, 4.31 mmol), MeOH (20 mL), benzaldehyde (0.875 mL, 8.61 mmol) and sodium cyanoborohydride (0.541 g, 8.61 mmol). The addition funnel was charged with a solution of glacial acetic acid (0.246 mL, 4.31 mmol) in MeOH (20 mL). The acetic acid solution was added dropwise to the reaction mixture over 1.5 h. When the addition was complete, the resulting mixture was stirred at ambient temperature 18 h. The solvents were removed in vacuo and the residue was partitioned between EtOAc (100 mL) and water. The layers were separated and the organic phase was washed with saturated aqueous NaHCO$_3$, aqueous sodium potassium tartrate and brine. Drying (MgSO$_4$), filtration and removal of the solvent in vacuo gave an oil. This material was chromatographed on silica gel using 30% EtOAc in hexanes as eluant to give 1-[4-Benzylamino-1-(4-fluorobenzyl)-1H-pyrrol-2-yl]ethanone AVIII-1-1 as a crystalline solid. $^1$H NMR (CDCl$_3$) δ 2.34 (3H, s), 3.35 (1H, br s), 4.16 (2H, s), 5.41 (2H, s), 6.36 (1H, d, j=2.2 Hz), 6.49 (1H, d, j=2.2 Hz), 6.93 (2H, m), 7.06 (2H, m), 7.30 to 7.37 (5H, complex multiplet).

Step 2: 1-[4-Benzylmethylamino-1-(4-fluorobenzyl)-1H-pyrrol-2-yl]ethanone AVIII-2-1

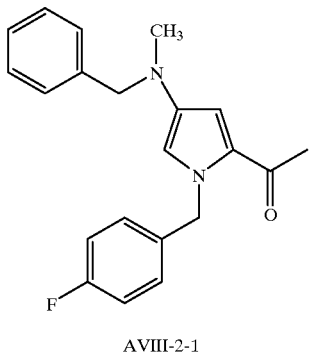

AVIII-2-1

To a 100 mL round bottomed flask with a stirring bar and an addition funnel topped by an argon inlet was added 1-[4-benzylamino-1-(4-fluorobenzyl)-1H-pyrrol-2-yl]ethanone AVIII-1-1 (0.472 g, 1.46 mmol), MeOH (20 mL), formalin (1.19 mL of 37% aqueous solution, 14.64 mmol) and sodium cyanoborohydride (0.628 g, 10.00 mmol). The addition funnel was charged with a solution of glacial acetic acid (0.57 mL, 10.0 mmol) in MeOH (20 mL). The acetic acid solution was added dropwise to the reaction mixture over 1.5 h. When the addition was complete, the resulting mixture was stirred at ambient temperature 18 h. The solvents were removed in vacuo and the residue was partitioned between EtOAc (100 mL) and water. The layers were separated and the organic phase was washed with saturated aqueous NaHCO$_3$, aqueous sodium potassium tartrate and brine. Drying (MgSO$_4$), filtration and removal of the solvent in vacuo gave an oil. This material was chromatographed on silica gel using 30% EtOAc in hexanes as eluant to give 1-[4-benzylmethylamino-1-(4-fluorobenzyl)-1H-pyrrol-2-yl]ethanone AVIII-2-1 as a crystalline solid. $^1$H NMR (CDCl$_3$) δ 2.25 (3H, s), 2.36 (3H, s), 4.16 (2H, s), 5.43 (2H, s), 6.33 (1H, d, j=2.2 Hz), 6.53 (1H, d, j=2.2 Hz), 6.93 (2H, m), 7.06 (2H, m), 7.27 to 7.32 (5H, complex multiplet).

Step 3: 4-[4-Benzylmethylamino-1-(4-fluorobenzyl)-1H-pyrrol-2-yl]-2,4-dioxobutyric acid ethyl ester A-VIII-3-1

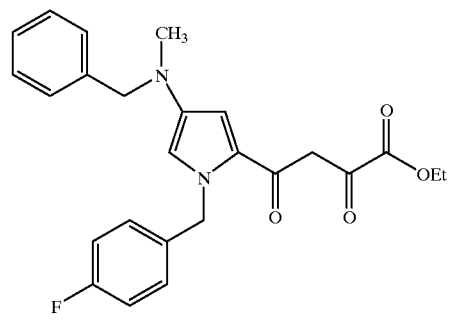

A-VIII-3-1

In a manner substantially similar to that described for Example A-V-9-1 1-[4-benzylmethylamino-1-(4-fluorobenzyl)-1H-pyrrol-2-yl]ethanone A-VIII-2-1 was used to prepare 4-[4-benzylmethylamino-1-(4-fluorobenzyl)-1-pyrrol-2-yl]-2,4-dioxobutyric acid ethyl ester A-VIII-3-1 which was used in the next step without further purification.

Step 4: 4-[4-Benzylmethylamino-1-(4-fluorobenzyl)-1H-pyrrol-2-yl]-2,4-dioxobutyric acid AVI-5-1

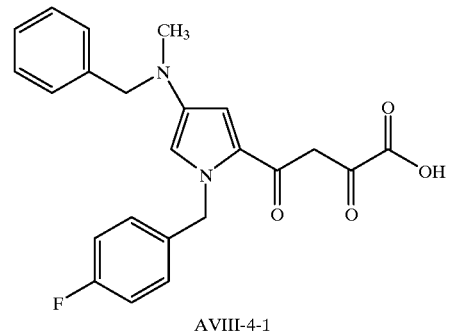

AVIII-4-1

In a manner substantially similar to that described for Example AV-10-1 4-[4-benzylmethylamino-1-(4-fluorobenzyl)-1H-pyrrol-2-yl]-2,4-dioxobutyric acid ethyl ester AVIII-3-1 was used to prepare 4-[4-benzylmethylamino-1-(4-fluorobenzyl)-1H-pyrrol-2-yl]-2,4-dioxobutyric acid AVIII-4-1. $^1$H NMR (CDCl$_3$) δ 2.79 (3H, s), 4.23 (2H, s), 5.48 (2H, s), 6.54 (1H, d, j=2.0 Hz), 6.74 (1H, d, j=2.0 Hz), 7.00 (4H, m), 7.28 (5H, m).

EXAMPLE 90

4-[4-Dimethylamino-1-(4-fluorobenzyl)-1H-pyrrol-2-yl]-2,4-dioxobutyric acid A-IX-3-1

Step 1: 1-[1-(4-Fluorobenzyl)-4-phenyl-1H-pyrrol-2-yl]ethanone AIX-1-1

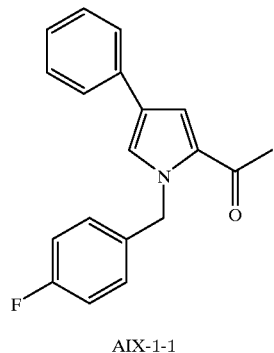

AIX-1-1

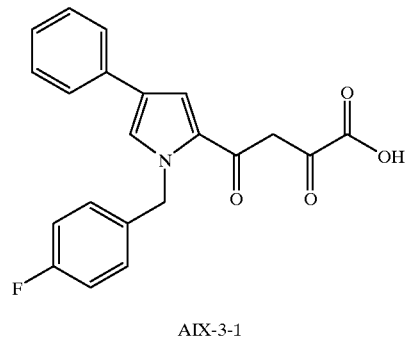

AIX-3-1

To a 100 mL round bottomed flask with a stirring bar, reflux condenser and an argon inlet was added 1-[1-(4-fluorobenzyl)-4-iodo-1H-pyrrol-2-yl]ethanone AIII-1-1 (1.00 g, 2.91 mmol), phenylboronic acid (0.431 g, 3.54 mmol), tetrakis(triphenylphosphine)palladium° (0.20 g, 0.17 mmol), barium hydroxide (1.37 g, 4.37 mmol), DME (40 mL), and $H_2O$ (5 mL). This well stirred mixture was heated at reflux 4 h. The reaction mixture was cooled to 20° C. and diluted with EtOAc. This solution was washed with $H_2O$, 1N HCl, $H_2O$, and brine. Drying ($MgSO_4$), filtration and removal of the solvent in vacuo gave an amorphous material. The crude product was chromatographed on silica gel using 15% EtOAc in hexanes as eluant to give 1-[1-(4-fluorobenzyl)-4-phenyl-1H-pyrrol-2-yl]ethanone AIX-1-1 as an oil. $^1$H NMR (CDCl$_3$) δ 2.47 (3H, s), 5.57 (2H, s), 6.98 (2H, m), 7.13 to 7.28 (5H, complex multiplet), 7.36 (2H, m), 7.51 (2H, m).

Step 2: 4-[4-Phenyl-1-(4-fluorobenzyl)-1H-pyrrol-2-yl]-2,4-dioxobutyric acid ethyl ester AIX-2-1

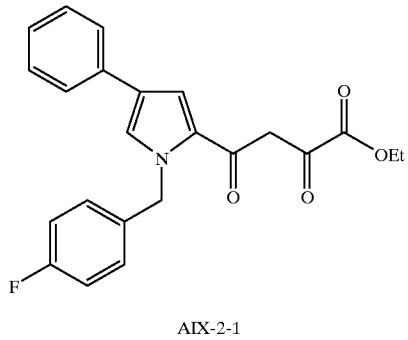

AIX-2-1

In a manner substantially similar to that described for Example AV-9-1, 1-[1-(4-fluorobenzyl)-4-phenyl-1H-pyrrol-2-yl]ethanone AIX-1-1 was used to prepare 4-[4-phenyl-1-(4-fluorobenzyl)-1H-pyrrol-2-yl]-2,4-dioxobutyric acid ethyl ester AIX-2-1 which was used in the next step without further purification.

Step 3: 4-[4-Phenyl-1-(4-fluorobenzyl)-1H-pyrrol-2-yl]-2,4-dioxobutyric acid AIX-3-1

In a manner substantially similar to that described for Example AV-10-1 4-[4-phenyl-1-(4-fluorobenzyl)-1H-pyrrol-2-yl]-2,4-dioxobutyric acid ethyl ester AIX-2-1 was used to prepare 4-[4-phenyl-1-(4-fluorobenzyl)-1H-pyrrol-2-yl]-2,4-dioxobutyric acid AIX-3-1. $^1$H NMR (DMSO-d$_6$) δ 5.66 (2H, s), 6.93 (1H, s), 7.05 (2H, m), 7.23 (3H, m), 7.36 (2H, m), 7.59 (3H, m), 7.65 (1H, d, j=1.7 Hz).

EXAMPLE 91

4-[1-(4-Fluorobenzyl)-4-methanesulfonylamino-1H-pyrrol-3-yl]-2,4-dioxobutyric acid AX-3-1

Step 1: N-[4-Acetyl-1-(4-fluorobenzyl)-1H-pyrrol-3-yl]-methanesulfonamide AX-1-1

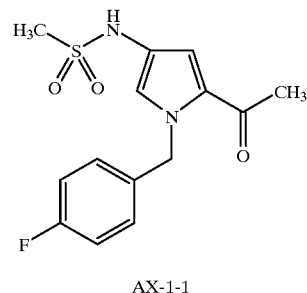

AX-1-1

A solution of 1-[4-amino-1-(4-fluoro-benzyl)-1H-pyrrol-3-yl]-ethanone AVI-2-1 (0.5 g, 2.15 mmole) in 10 ml of $CH_2Cl_2$ was cooled to 0° C. and treated with triethylamine (0.25 mL, 3.22 mmole) followed by methane sulfonylchloride (0.45 mL, 3.22 mmole) dropwise via syringe. The reaction was completed in two hours and was diluted with $CH_2Cl_2$ and washed with 10% citric acid. Organic layer was dried over $MgSO_4$, filtered and concentrated in vacuo to afford a light pink semi-solid residue. This material was chromatographed on silica gel using 50% EtOAc/Hex as eluant to give AX-1-1 as a white crystalline solid. $^1$H NMR (400 MHz, CDCl$_3$) δ 7.12 (m, 2H), 6.96 (m, 2H), 6.94 (d, J=1.8Hz, 1H), 6.85 (d, J=1.8 Hz, 1H), 5.97 (s, b, 1H), 5.49 (s, 2H), 2.97 (s, 3H), 2.39 (s, 3H).

Step 2: 4-[1-(4-Fluorobenzyl)-4-methanesulfonylamino-1H-pyrrol-3-yl]-2,4-dioxo-butyric acid ethyl ester AX-2-1

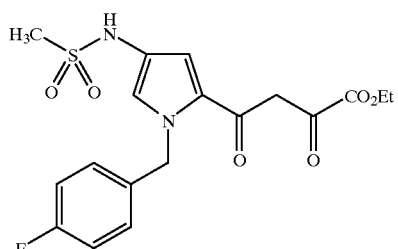

AX-2-1

A solution of AX-1-1 (460 mg, 1.48 mmole) in 10 ml dried THF was treated with diethyl oxalate (0.40 ml, 2.96 mmole) and sodium ethoxide (200 mg, 2.96 mmole) at room temperature over night under $N_2$ atmosphere. The reaction mixture was poured into 20 ml of 1N HCl solution and extracted twice with EtOAc. Combined extracts were washed with brine and dried over $MgSO_4$, filtered and evaporated to give a yellow brown residue that was flashed chromatographed using 100% EtOAc as eluant to give AX-2-1 as a yellow crystalline solid. $^1$H NMR (400 MHz, $CDCl_3$) δ 7.13 (m, 2H), 6.97 (m, 4H), 6.75 (s, 1H), 5.92 (s, br, 1H), 5.56 (s, 2H), 4.34–4.40 (q, 2H), 2.97 (s, 3H), 1.39 (t, 3H).

Step 3: 4-[1-(4-Fluorobenzyl)-4-methanesulfonylamino-1H-pyrrol-3-yl]-2,4-dioxo-butyric acid AX-3-1

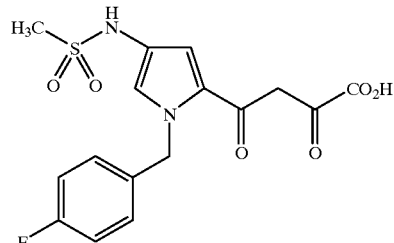

AX-3-1

A solution of AX-2-1 (200 mg, 0.48 mmole) was dissolved in 6 ml of $CH_3OH$ and 6 ml of 1N NaOH for 3 hours. The reaction mixture was washed with ether and acidified to pH 1–2 with 1N HCl and extracted three times with EtOAc. Combined extracts were washed with brine, dried over $MgSO_4$, filtered and evaporated to give an oily residue that was triturated with 20% $Et_2O$/Hex to afford AX-3-1 as a yellow crystalline solid.

m.p.: 160° C. decomposed $^1$H NMR (400 MHz, DMSO-$d_6$) δ 9.33 (s, 1H), 7.39 (s, 1H), 7.12–7.17 (m, 5H), 6.75 (s, 1H), 5.58 (s, 2H), 2.92 (s, 3H).

EXAMPLES 92–94

The following compounds were prepared in a manner similar to that described for AX-3-1:

EXAMPLE 92

4-[1-(4-Fluorobenzyl)-3-acetylamino-1H-pyrrol-2-yl]-2,4-dioxobutyric acid

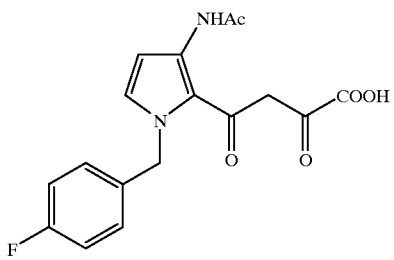

CHN Calc. 58.96, 4.37, 8.09; Fnd. 59.20, 4.30, 8.06.

EXAMPLE 93

4-[4-Acetylamino-1-(4-fluorobenzyl)-1H-pyrrol-2-yl]-2,4-dioxobutyric acid

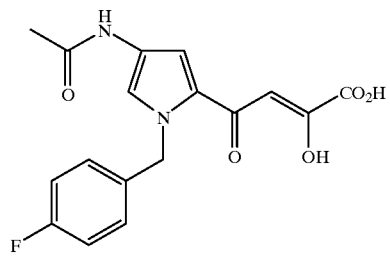

CHN Calc. ($C_{17}H_{15}FN_2O_5$ 0.3 $H_2O$) 58.05, 4.47, 7.97; Fnd. 58.09, 4.40, 8.06.

EXAMPLE 94

4-[1-(4-Fluorobenzyl)-4-(2-oxo-piperidin-1-yl)-1H-pyrrol-2-yl]-2,4-dioxobutyric acid

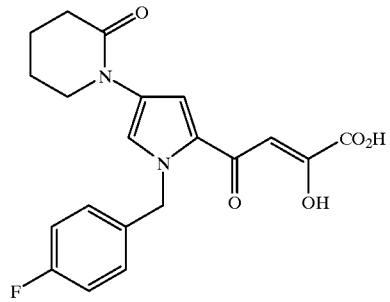

CHN Calc. ($C_{20}H_{19}FN_2O_5$ 0.4 $H_2O$) 61.03, 5.07, 7.12; Fnd. 60.96, 5.00, 7.22.

EXAMPLE 95

4-[4-(4-Fluorobenzyl)-1H-pyrrol-3-yl]-2,4-dioxo-butyric acid AXI-5-1

Step 1: (4-Fluorophenyl)-(1-triisopropylsilanyl-1H-pyrrol-3-yl)methanone AXI-1-1

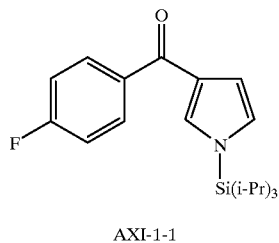

AXI-1-1

A stirred slurry of AlCl₃ (99.99% anhydrous powder, 3.28 g, 0.0246 mole) in anhydrous CH₂Cl₂ (45 mL) was treated with 4-fluorobenxoyl chloride (2.64 mL, 0.0224 mole) added dropwise at 0° C. After 0.5 h, a solution of 1-(triisopropylsilyl)pyrrole (5.55 mL, 0.0224 mole) in CH₂Cl₂ (11 mL) was added. The mixture was stirred for 0.5 h at 0° C. then 3 h at room temperature and then poured into 300 mL cold saturated NH₄Cl solution. The organic phase was separated and combined with two CH₂Cl₂ extracts of the aqueous phase. The combined organic layers were washed with NH₄Cl solution and dried over MgSO₄, filtered and evaporated to give a crude brown oil. Flash chromatography on silica gel of the crude product, using a 5:95 EtOAc/Hexane mixture as the eluting solvent, gave AXI-1-1 as a yellow oil. TLC Rf=0.54 (10:90 EtOAc/Hexanes) ¹H NMR (400 MHz, CDCl₃) δ 7.87 (m, 2H), 7.32 (m, 1H), 7.13 (m, 2H), 6.78 (m, 2H), 1.48 (m, 3H), 1.12 (d, J=7.51 Hz, 18H).

Step 2: 3-(4-Fluorobenzyl)-1-triisopropylsilanyl-1H-pyrrole AXI-2-1

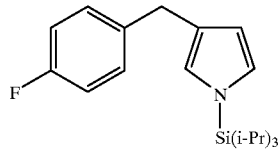

AXI-2-1

In a similar manner to AII-2-1, AXI-1-1 (3.50 g, 0.0101 mole) was refluxed with 1.0 M BH₃-Me₂S (30.3, 0.0303 mole) in 100 mL anhydrous THF to give AXI-2-1 as a light yellow solid. TLC Rf=0.57 (5:95 EtOAc/Hexanes) ¹H NMR (400 MHz, CDCl₃) δ 7.15 (m, 2H), 6.94 (m, 2H), 6.71 (t, J=2.38 Hz, 1H), 6.50 (m, 1H), 6.09 (m, 1H), 3.82 (s, 2H), 1.41 (m, 3H), 1.08 (d, J=7.51, 18H).

Step 3: 1-[4-(4-Fluorobenzyl)-1-triisopropylsilanyl-1H-pyrrol-3-yl]ethanone AXI-3-1

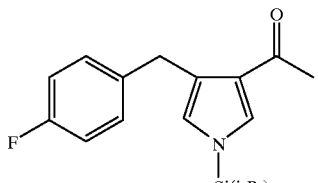

AXI-3-1

In a similar manner to AXI-1-1, AXI-2-1 was acylated using freshly distilled acetyl chloride to give AXI-3-1 as a light yellow solid. TLC Rf=0.41 (10:90 EtOAc/Hexanes) ¹H NMR (400 MHz, CDCl₃) δ 7.31 (m, 1H), 7.17 (m, 2H), 6.93 (m, 2H), 6.30 (t, J=1.10 Hz, 1H), 4.08 (s, 1H), 2.37 (s, 3H), 1.42 (m, 3H), 1.08 (d, J=7.51 Hz, 18H).

Step 4: 1-[4-(4-Fluorobenzyl)-1H-pyrrol-3-yl]ethanone AXI-4-1

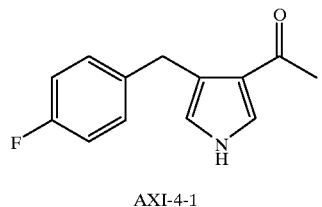

AXI-4-1

A solution of AXI-3-1 (0.145 g, 0.387 mmol) in dry THF (0.5 mL) was treated with tetra-n-butylammonium fluoride (0.397 μL 1.0 M in THF, 0.387 mmol) at room temperature for one hour. The reaction was quenched with saturated NaHCO₃, extracted with EtOAc, dried over MgSO₄, filtered and concentrated to give the product as a yellow solid. TLC Rf=0.15 (10:90 EtOAc/Hexanes) ¹H NMR (400 MHz, CDCl₃) δ 8.2 (bs, 1H), 7.38 (s, 1H), 7.22 (m, 2H), 6.95 (m, 2H), 6.34 (s, 1H), 4.1 (s, 2H), 2.4 (s, 3H).

Step 5: 1-[1,4-Bis-(4-fluorobenzyl)-1H-pyrrol-3-yl]ethanone AXI-4-2

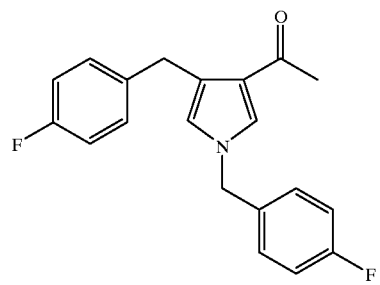

AXI-4-2

In a similar manner to AIV-3-1, AXI-4-1 was alkylated using 4-fluorobenzyl bromide to give AXI-4-2 as a light brown oil. TLC Rf=0.69 (40:60 EtOAc/Hexanes) ¹H NMR (400 MHz, CDCl₃) δ 7.17–7.21 (m, 3H), 7.04–7.12 (m, 4H), 6.93 (m, 2H), 6.20 (s, 1H), 4.94 (s, 2H), 4.06 (s, 2H), 2.34 (s, 3H).

Step 6: 4-[4-(4-Fluorobenzyl)-1H-pyrrol-3-yl]-2,4-dioxobutyric acid AXI-5-1

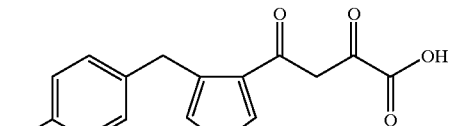

AXI-5-1

AXI-4-1 was carried on to the diketo acid AXI-5-1 as described for AI-3-1. TLC Rf=0.41 (94:6:6 CHCl₃/MeOH/HOAc) ¹H NMR (400 MHz, CDCl₃) δ 8.4 (bs, 1H), 7.4 (s, 1H), 7.2 (m, 2H), 6.96 (m, 2H), 6.41 (s, 1H), 4.1 (s, 2H).

EXAMPLE 96

4-[1,4-Bis-(4-fluorobenzyl)-1H-pyrrol-3-yl]-2,4-dioxobutyric acid AXI-5-2

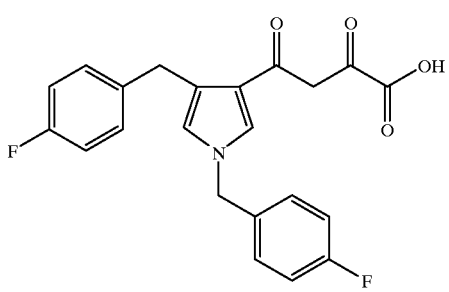

AXI-5-2

AXI-4-2 was carried on to the diketo acid AXI-5-2 as described for AI-3-1. TLC Rf=0.66 (94:6:6 CHCl₃/MeOH/HOAc) ¹H NMR (400 MHz, CDCl₃) δ 7.41 (s, 1H), 7.04–7.19 (m, 6H), 6.96 (m, 2H), 6.70 (s, 1H), 6.28 (s,1H), 4.97 (s, 2H), 4.07 (s, 2H).

EXAMPLE 97

4-[5-(3-Carboxy-3-oxo-propionyl)-1-(4-fluorobenzyl)-1H-pyrazol-3-yl]-2,4-dioxobutyric acid BI-6-1

Step 1: 1-(4-Fluorobenzyl)-1H-pyrazol-3,5-dicarboxylic acid diethyl ester BI-1-1

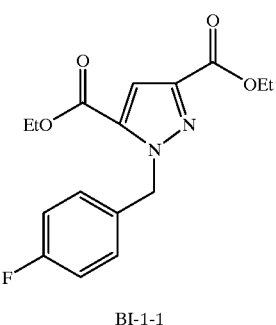

BI-1-1

A mixture of 1H-pyrrole-2,4-dicarboxylic acid diethyl ester (0.424 g, 2 mmol), 4-fluorobenzyl bromide (0.378 g, 0.25 ml, 2 mmol) and triethylamine (0.303 g, 0.417 ml, 3 mmol) was dissolved in 5 ml dry DMF and stirred for 18 hr. The solvent was removed in vacuo and the resulting residue partitioned between ethyl acetate/H₂O and extracted. The combined organics were washed with H₂O, brine, dried over Na₂SO₄, filtered and the solvent removed. TLC showed about 30% unreacted pyrrole. Further purification by column chromatography (2:1 hexane/ethyl acetate) gave 0.335 gr (50%) of the title compound as a colorless oil. ¹H NMR (400 MHz, CDCl₃) d 1.34 (t, 3H, J=7.14), 1.41 (t, 3H, J=7.14 Hz, 4.32 (q, 2H, J=7.14 Hz), 4.42 (q, 2H, J=7.14 Hz), 5.80 (s, 2H), 6.98 (t, 2H, J=8.7 Hz), 7.29 (m, 2H), 7.36 (s, 1H).

Step 2: 1-(4-Fluorobenzyl)-1H-pyrazol-3,5-dicarboxylic acid dilithium salt BI-2-1

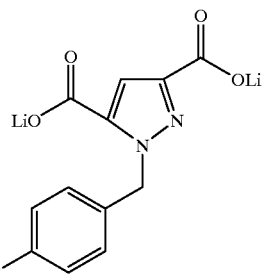

BI-2-1

BI-1-1 (0.2 g, 0.62 mmol) was dissolved in 2 ml THF, and to it was added LiOH (1.3 ml of a 1M soln.). After stirring 18 hr, the solvent was removed in vacuo and 3×5 ml toluene added and removed to eliminate water. The crude material was used in the next reaction without further purification.

Step 3: 1-(4-Fluorobenzyl)-1H-pyrazol-2,4-dicarboxylic acid bis-(methoxymethylamide) BI-3-1

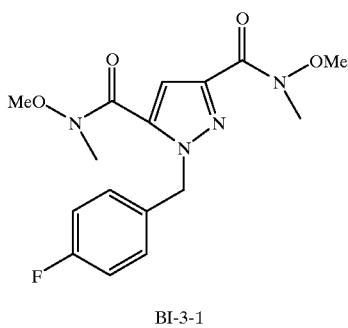

BI-3-1

A mixture of BI-2-1 from the previous example, N,O-dimethylhydroxylamine hydrochloride (0.121 g, 1.24 mmol), 1-ethyl-3-(3-dimethylaminopropyl)carbodiimide hydrochloride (0.238 g, 1.24 mmol), 1-hydroxybenzotriazole hydrate (0.167 g, 1.24 mmol), and triethylamine (0.125 g, 0.173 ml, 1.24 mmol) were combined in 3 ml DMF and stirred for 18 hr. The solvent was removed in vacuo and the residue partitioned between ethyl acetate/H₂O and extracted. The combined organic extracts were washed with H₂O, brine, dried over Na₂SO₄, filtered and the solvent removed. Further purification via radial disc chromatography (1:1 hexane/ethyl acetate) afforded the title compound as a colorless oil. ¹H NMR (400 MHz, CDCl₃) δ 3.27 (s, 3H), 3.43 (s, 3H), 3.46 (s, 3H), 3.75 (s, 3H), 6.91–7.00 (m, 3H), 7.22–7.32 (m, 3H).

Step 4: 1-[5-Acetyl-1-(4-fluorobenzyl)-1-H-pyrazol-3-yl]ethanone BI-4-1

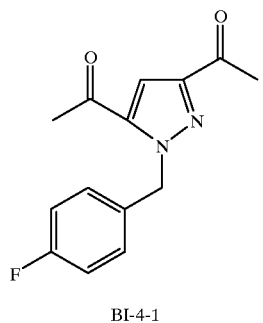

BI-4-1

BI-3-1 (0.142 g, 0.41 mmol) was dissolved in 5 ml dry THF and cooled to −78° C. To this was added methyl lithium (1.158 ml of a 1.4M solution in diethyl ether, 1.64 mmol). The mixture was stirred for 1 hr, then quenched by the addition of excess 10% aqueous citric acid solution. After warming to room temperature, the mixture was poured into 10 ml H$_2$O and extracted with ethyl acetate. The combined organic extracts were washed with H$_2$O, brine, dried over Na$_2$SO$_4$, filtered and the solvent removed to get the title compound as an oil. $^1$H NMR (400 MHz, CDCl$_3$) δ 2.50 (s, 3H), 2.63 (s, 3H), 5.74 (s, 2H), 6.99 (t, 2H, J=8.8 Hz), 7.28–7.37 (m, 3H).

Step 5: 4-[5-(3-Ethoxycarbonyl-3-oxopropionyl)-1-(4-fluorobenzyl)-1H-pyrazol-3-yl]-2,4-dioxobutyric acid ethyl ester BI-5-1

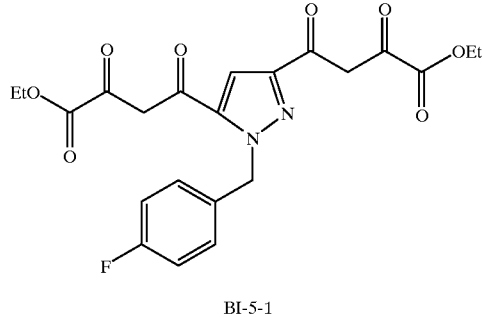

BI-5-1

In a similar manner to AIII-2-1, BI-4-1 (0.094 g, 0.36 mmol) was reacted with diethyl oxalate (0.212 g, 0.196 ml, 1.44 mmol) and sodium ethoxide (0.096 g, 1.44 mmol) to give the title compound as a yellow solid. $^1$H NMR (400 MHz, CDCl$_3$) δ 1.38 (t, 3H, J=7.33 Hz), 1.42 (t, 3H, J=7.14 Hz), 4.36 (q, 2H, J=7.14 Hz), 4.41 (q, 2H, J=7.14 Hz), 5.84 (s, 2H), 6.85 (s, 1H), 7.00 (t, 2H, J=2.0 Hz), 7.29–7.36 (m, 3H), 7.54 (s, 1H).

Step 6: 4-[5-(3-Carboxy-3-oxopropionyl)-1-(4-fluorobenzyl)-1H-pyrazol-3-yl]-2,4-dioxobutyric acid BI-6-1

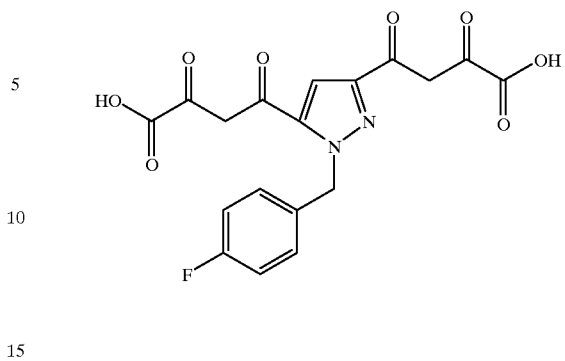

In a similar manner to AI-3-1, BI-5-1 (0.157 g, 0.35 mmol) was reacted with LiOH (0.7 ml of a 1M solution in H$_2$O) in 5 ml THF to give the title compound as a light tan solid. MP=215–217° C. $^1$H NMR (400 MHz, CDCl$_3$) δ 5.84 (s, 2H), 7.00 (t, 2H, J=8.7 Hz), 7.29–7.37 (m, 4H), 7.55 (s, 1H); FAB MS: m/z 405 (M$^+$+H).

EXAMPLE 98

4-[1-(4-Fluorobenzyl)-1H-pyrazol-4-yl]-2,4-dioxobutyric acid BII-4-1

Step 1: 4-Bromo-1-(4-fluorobenzyl)-1H-pyrazole BII-1-1

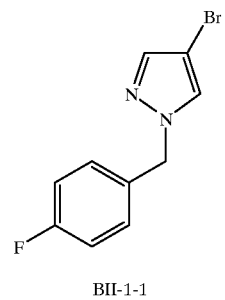

BII-1-1

4-Bromopyrazole (0.441 g, 3 mmol) was added to a slurry of sodium hydride (0.072 g, 0.12 gr of a 60% oil dispersion, 3 mmol) in 5 ml DMF and stirred for 15 min, after which 4-fluorobenzyl bromide (0.568 g, 0.374 ml, 3 mmol) was added and the reaction was stirred for 18 hr. The solvent was then removed in vacuo and the residue partitioned between ethyl acetate/H$_2$O and extracted. The combined organic extracts were washed with H$_2$O, brine, dried over Na$_2$SO$_4$, filtered and the solvent removed to afford title compound as a colorless oil. $^1$H NMR (400 MHz, CDCl$_3$) δ 5.23 (s, 2H), 7.04 (t, 2H, J=8.6 Hz), 7.18–7.25 (m, 2H), 7.36 (s, 1H), 7.49 (s, 1H).

Step 2: 1-[1-(4-Fluorobenzyl)-1H-pyrazol-4-yl]ethanone BII-2-1

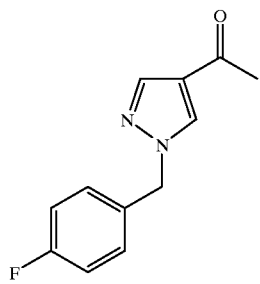

BII-2-1

BII-1-1 (0.686 g, 2.7 mmol) was dissolved in 8 ml diethyl ether and cooled to −78° C. To this was added butyllithium (1.85 ml of a 1.6M solution in hexane, 2.95 mmol) and the reaction was allowed to stir for 1 hr, after which time N-methoxy-N-methyl-acetamide (0.33 g, 0.33 ml, 3.22 mmol) was added and the mixture allowed to warm to room temperature. After stirring for 2 hr, the reaction was quenched with 10% citric acid solution and extracted with H$_2$O, brine, dried over Na$_2$SO$_4$, filtered and the solvent removed. Purification by radial disc chromatography (4:1 hexane/ethyl acetate) the title compound as a colorless oil.
Step 3: 4-[1-(4-Fluorobenzyl)-1H-pyrazol-4-yl]-2,4-dioxobutyric acid ethyl ester BII-3-1

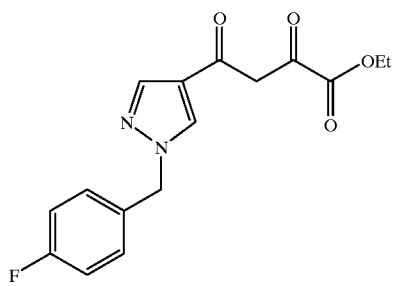

BII-3-1

In a manner analogous to AIII-2-1, BII-2-1 was reacted with diethyl oxalate (0.152 g, 0.142 ml. 1.04 mmol) and sodium ethoxide (0.071 g, 1.04 mmol) to yield the title compound as a white solid. $^1$H NMR (400 MHz, CDCl$_3$) δ 1.40 (t, 3H, J=7.14 Hz), 4.38 (q, 2H, J=7.14 Hz), 5.31 (s, 2H), 6.66 (s, 1H), 7.08 (t, 2H, J=8.61 Hz), 7.24–7.31 (m, 2H), 7.94 (2, 1H), 8.02 (s, 1H).
Step 4: 4-[1-(4-Fluorobenzyl)-1H-pyrazol-4-yl]-2,4-dioxobutyric acid BII-4-1

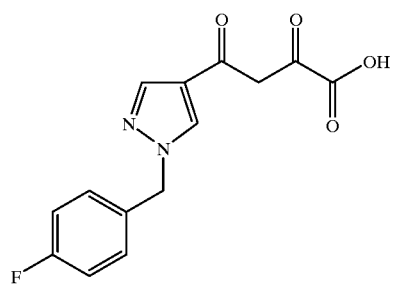

BII-4-1

In a similar manner to AI-3-1, BII-3-1 (0.17 g, 0.53 mmol) was reacted in 5 ml MeOH containing 2 ml 1M NaOH to give a light tan solid after triturating the crude material with CH$_2$Cl$_2$. MP=191–192° C. $^1$H NMR (400 MHz, CDCl$_3$) δ 5.31 (s, 2H), 6.71 (d, 1H, J =0.73 Hz), 7.08 (t, 2H, J=8.6 Hz), 7.24–7.33 (m, 2H), 7.99 (s, 1H), 8.03 (s, 1H) FAB MS: m/z 291 (M$^+$+H).

EXAMPLES 99 & 100

The following compound were prepared in a manner similar to that described for BII-4-1:

EXAMPLE 99

4-[4-Dimethylamino-1-(4-fluorobenzyl)-1H-pyrrol-3-yl]-2,4-dioxobutyric acid

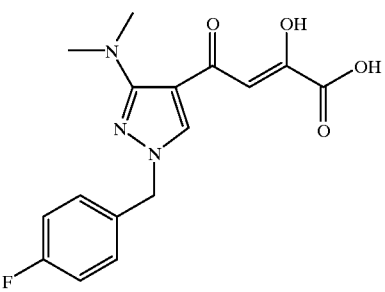

CHN Calc. (C16H$_{16}$N$_3$O$_4$F 0.5 EtOAc) 57.28, 5.34, 11.14; Fnd. 56.93, 5.01, 11.43.

EXAMPLE 100

4-[1-(4-Fluorobenzyl)-5-methyl-1H-pyrazol-4-yl]-2-hydroxy-4-oxobut-2-enoic acid

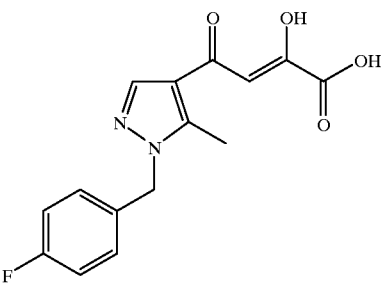

CHN Calc. (C$_{15}$H$_{13}$N$_2$O$_4$F 0.4 MeOH) 58.33, 4.64, 8.84; Fnd 57.95, 4.40, 8.44.

EXAMPLE 101

4-[2-(4-Fluorobenzyl)-2H-pyrazol-3-yl]-2,4-dioxo-butyric acid BIII-3-1

Step 1: 1-[2-(4-Fluorobenzyl)-2H-pyrazol-3-yl]ethanone BIII-1-1

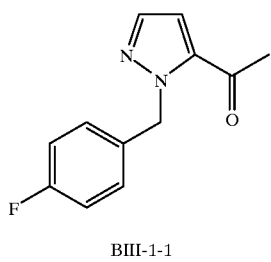

BIII-1-1

1-(2H-Pyrazol-3-yl)ethanone hydrochloride (0.44 g, 3 mmol) was dissolved in 8 ml DMF, and to it was added sodium hydride (0.144 g, 0.24 g of a 60% oil dispersion, 6 mmol). After stirring for 5 min, 4-fluorobenzyl bromide (0.567 g, 0.374 ml, 3 mmol) was added and the reaction allowed to stir for 2 hr. It was then poured into 10 ml $H_2O$ and extracted with ethyl acetate. The combined organic extracts were washed with $H_2O$, brine, dried over $Na_2SO_4$, filtered and the solvent removed. Further purification by radial disc chromatography (3:1 hexane/ethyl acetate) yielded the title compound as a colorless oil. $^1$H NMR (400 MHz, CDCl$_3$) δ 2.58 (s, 3H), 5.33 (s, 2H), 6.80 (d, 1H, J=2.4 Hz), 7.05 (t, 2H, J=8.6 Hz), 7.19–7.28 (m, 2H), 7.35 (d, 1H, J=2.4 Hz).

Step 2: 4-[2-(4-Fluorobenzyl)-2H-pyrazol-3-yl]-2,4-dioxobutyric acid ethyl ester BIII-2-1

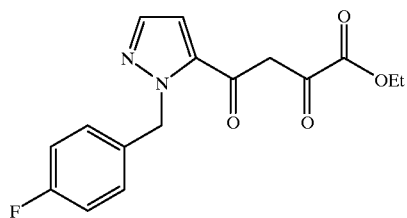

BIII-2-1

In a similar manner to AIII-2-1, BIII-1-1 (0.474 g, 2.2 mmol) was reacted with diethyl oxalate (0.635 g, 0.59 ml, 4.4 mmol) and sodium ethoxide (0.295 g, 4.4 mmol) to give the title compound, which was used in the next reaction without further purification. $^1$H NMR (400 MHz, CDCl$_3$) δ 1.38 (t, 3H, J=7.14 Hz), 4.36 (q, 2H, J=7.14 Hz), 5.36 (s, 2H), 6.90 (d, 1H, J=2.38 Hz), 7.06 (t, 2H, J=8.61 Hz), 7.22–7.28 (m, 3H), 7.40 (d, 1H, J=2.38 Hz).

Step 3: 4-[2-(4-Fluorobenzyl)-2H-pyrazol-3-yl]-2,4-dioxobutyric acid BIII-3-1

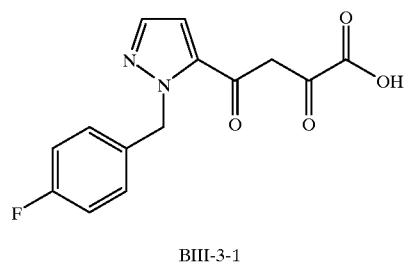

BIII-3-1

In a similar manner to AI-3-1, BIII-2-1 (crude from previous reaction) was reacted with 1N NaOH (3 ml) in 20 ml THF to yield the title compound as a light tan solid after trituration in diethyl ether. MP=157–159° C.; $^1$H NMR (400 MHz, CDCl$_3$) δ 5.35 (s, 2H), 6.90 (d, 1H, J=2.57 Hz), 7.06 (t, 2H, J=8.61 Hz), 7.22–7.31 (m, 3H), 7.42 (d, 1H, J=2.38 Hz) FAB MS: m/z 291 (M$^+$+H).

EXAMPLE 102

1-[1-(4-Fluorobenzyl)-3-methyl-1H-pyrazol-4-yl]-2,4-dioxobutyric acid BIV-3-1

Step 1: 1-(3-Methyl-1H-pyrazol-4-yl)ethanone BIV-1-1

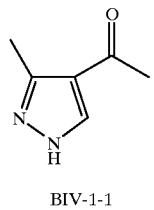

BIV-1-1

A mixture of 1-(4-acetyl-5-methylpyrazol-1-yl)ethanone (1 g, 6 mmol, Maybridge) and 10 ml 1N NaOH were dissolved in 40 ml THF and stirred 4 days. The solvent was removed in vacuo and the residue partitioned between ethyl acetate/$H_2O$ and extracted. The combined organic extracts were washed with $H_2O$, brine, dried over $Na_2SO_4$, filtered and the solvent removed to get the title compound. $^1$H NMR (400 MHz, CDCl$_3$) δ 2.43 (s, 3H), 2.60 (s, 3H), 7.96 (s, 1H).

Step 2: 1-[1-(4-Fluorobenzyl)-3-methyl-1H-pyrazol-4-yl]ethanone BIV-2-1

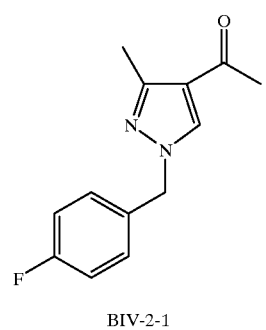

BIV-2-1

In a similar manner to BIII-1-1, BIV-1-1 (0.248 g, 2 mmol) was reacted with sodium hydride (0.096 g, 0.16 gr of a 60% oil dispersion, 4 mmol) and 4-fluorobenzyl bromide (0.378 g, 0.249 ml, 2 mmol) for 2 hr. Subsequent work-up and purification by preparative HPLC (Chiralcel OD 25×2, 75% hexane/1% diethylamine, 25% EtOH) yielded the title compound and 1-[1-(4-fluorobenzyl)-5-methyl-1H-pyrazol-4-yl]ethanone as white solids. $^1$H NMR (400 MHz, CDCl$_3$) δ 2.36 (s, 3H), 2.49 (s, 3H), 5.21 (s, 2H), 7.07 (t, 2H, J=8.4 Hz), 7.24 (dd, 2H, J=8.4, 4.9 Hz), 7.73 (s, 1H).

Step 3: 1-[1-(4-Fluorobenzyl)-3-methyl-1H-pyrazol-4-yl]-2,4-dioxobutyric acid ethyl ester BIV-3-1

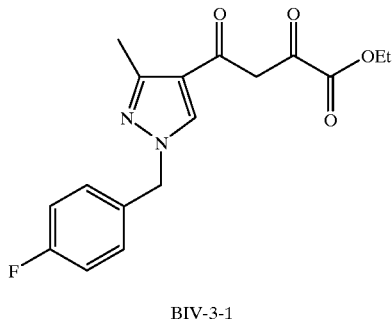

BIV-3-1

In a similar manner to AIII-2-1, BIV-2-1 (0.168 g, 0.72 mmol) was reacted with diethyl oxalate (0.211 g, 0.196 ml, 1.44 mmol) and sodium ethoxide (0.098 g, 1.44 mmol) in 5 ml THF to give the title compound as a yellow solid. $^1$H NMR (400 MHz, CDCl$_3$) δ 1.37 (t, 3H, J=7.14 Hz), 2.52 (s, 3H), 4.35 (q, 2H, J=7.14 Hz), 5.23 (s, 2H), 6.61 (s, 1H), 7.06 (t, 2H, J=8.61 Hz), 7.21–7.32 (m, 2H), 7.89 (s, 1H).

Step 4: 1-[1-(4-Fluorobenzyl)-3-methyl-1H-pyrazol-4-yl]-2,4-dioxobutyric acid BIV-4-1

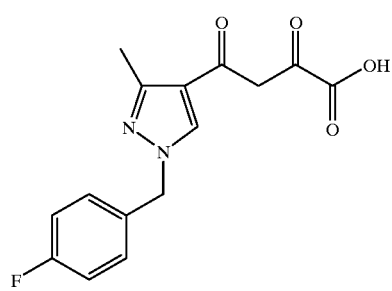

BIV-4-1

In a similar manner to AI-3-1, BIV-3-1 (0.234 g, 0.68 m mmol) was reacted with 2 ml NaOH in 10 ml THF to afford the title compound as a light tan solid. MP=187–188° C.; $^1$H NMR (400 MHz, CDCl$_3$) δ 2.53 (s, 3H), 5.23 (s, 2H), 6.64 (2, 1H), 7.08 (t, 2H, J=8.61), 7.23–7.31 (m, 2H), 7.88 (s, 1H).

EXAMPLE 103

4-[3-Methyl-1-(3-chlorobenzyl)-1H-pyrazol-4-yl]-2,4-dioxobutyric acid BV-4-1

Step 1: 1-[1-(3-Chlorobenzyl)-3-methyl-1H-pyrazol-4-yl]ethanone BV-1-1 and 1-[1-(3-chlorobenzyl)-5-methyl-1H-pyrazol-4-yl]ethanone BV-2-1

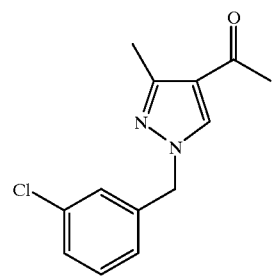

BV-1-1

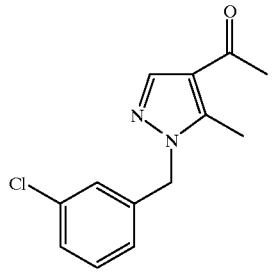

BV-2-1

In a similar manner to BIV-2-1, BIV-1-1 (0.271 g, 2.2 mmol) was reacted with 3-chlorobenzyl bromide (0.493 g, 0.315 ml, 2.4 mmol) and sodium hydride (0.063 g, 0.105 gr of a 60% oil dispersion, 2.6 mmol) in 5 ml THF for 2 hr and purified by preparative HPLC (Chiralpak AD 25×2, 75% hexane/1% diethylamine, 25% 2-propanol) to yield the faster eluting 1-[1-(3-chlorobenzyl)-3-methyl-1H-pyrazol-4-yl]ethanone and the slower eluting 1-[1-(3-chlorobenzyl)-5-methyl-1H-pyrazol-4-yl]ethanone, both as clear oils. 1-[1-(3-chlorobenzyl)-3-methyl-1H-pyrazol-4-yl]ethanone BV-1-1: $^1$H NMR (400 MHz, CDCl$_3$) δ 2.38 (s, 3H), 2.49 (s, 3H), 5.21 (s, 2H), 7.12 (dt, 1H, J=6.2, 2.2, 1.6 Hz), 7.22 (s, 1H), 7.31–7.34 (m, 2H), 7.78 (s, 1H) 1-[1-(3-chlorobenzyl)-5-methyl-1H-pyrazol-4-yl]ethanone BV-2-1: $^1$H NMR (400 MHz, CDCl$_3$) δ 2.45 (s, 3H), 2.52 (s, 3H), 5.28 (s, 2H), 6.87–7.02 (m, 1H), 7.10 (s, 1H), 7.22–7.30 (m, 2H), 7.90 (s, 1H).

Step 2: 4-[3-Methyl-1-(3-chlorobenzyl)-1H-pyrazol-4-yl]-2,4-dioxobutyric acid ethyl ester BV-3-1

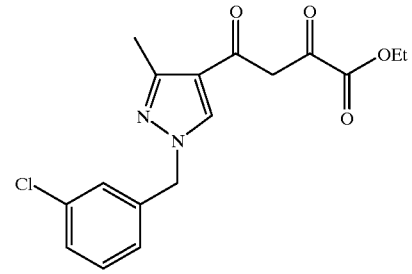

BV-3-1

In a similar manner to AIII-2-1, BV-1-1 (0.255 g, 1 mmol) was reacted with diethyl oxalate (0.321 g, 0.298 ml, 2.2 mmol) and sodium ethoxide (0.15 g, 2.2 mmol) to give the title compound, which was used without further purification. $^1$H NMR (400 MHz, CDCl$_3$) δ 1.38 (t, 3H, J=7.14 Hz), 2.53 (s, 3H), 4.35 (q, 2H, J=7.14 Hz), 5.24 (s, 2H), 6.63 (s, 1H), 7.11–7.18 (m, 1H), 7.23 (s, 1H), 7.29–7.35 (m, 2H), 7.93 (s, 1H).

Step 3: 4-[3-Methyl-1-(3-chlorobenzyl)-1H-pyrazol-4-yl]-2,4-dioxobutyric acid BV-4-1

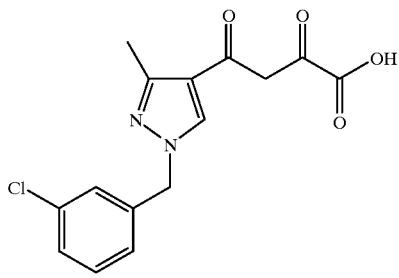

BV-4-1

In a similar manner to AI-3-1, 4-[3-methyl-1-(3-chlorobenzyl)-1H-pyrazol-4-yl]-2,4-dioxobutyric acid ethyl ester (crude from above) was reacted with 5 ml 1N NaOH in 20 ml methanol for two hours to give the title compound as a light tan solid. MP=183–184° C. $^1$H NMR (400 MHz, CDCl$_3$) δ 2.54 (s, 3H), 5.23 (s, 2H), 6.67 (s, 1H), 7.12–7.18 (m, 1H), 7.25 (s, 1H), 7.31–7.36 (m, 2H), 7.97 (2, 1H).

EXAMPLE 104

4-[5-Methyl-1-(3-chlorobenzyl)-1H-pyrazol-4-yl]-2,4-dioxobutyric acid

Step 1: 4-[5-Methyl-1-(3-chlorobenzyl)-1H-pyrazol-4-yl]-2,4-dioxobutyric acid ethyl ester BV-5-1

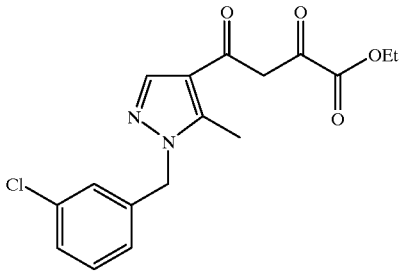

BV-5-1

In a similar manner to AIII-2-1, BV-2-1 (0.158 g, 0.64 mmol) was reacted with diethyl oxalate (0.199 g, 0.185 ml, 1.36 mmol) and sodium ethoxide (0.092 g, 1.36 mmol) to give the title compound, which was used without further purification. $^1$H NMR (400 MHz, CDCl$_3$) δ 1.40 (t, 3H, J=7.14 Hz), 2.58 (s, 3H), 4.38 (q, 2H, J=7.14 Hz), 5.31 (s, 2H), 6.75 (s, 1H), 6.98–7.04 (m, 1H), 7.12 (s, 1H), 7.25–7.31 (m, 2H), 7.99 (s, 1H).

Step 2: 4-[5-Methyl-1-(3-chlorobenzyl)-1H-pyrazol-4-yl]-2,4-dioxobutyric acid BV-6-1

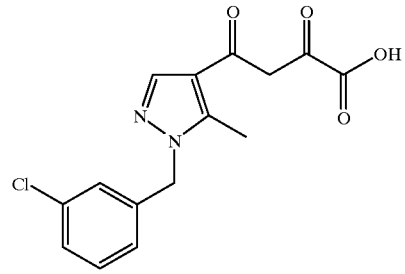

BV-6-1

In a similar manner to AI-3-1, BV-5-1 (crude from above) was reacted with 2 ml 1N NaOH in 10 ml methanol for two hours to give the title compound as a white solid after ether trituration. MP(uncorrected)168–169° C.

$^1$H NMR (400 MHz, CDCl$_3$) δ 2.53 (s, 3H), 5.23 (2, 2H), 6.67 (s, 1H), 7.12–7.18 (m, 1H), 7.25 (s, 1H), 7.31–7.36 (m, 2H), 7.97 (s, 1H).

EXAMPLE 105

4-[1-(4-Fluoro-benzyl)-1H-imidazol-2-yl]-2,4-dioxo-butyric acid CI-6-1

Step 1: 1-(4-Fluoro-benzyl)-1H-imidazole CI-1-1

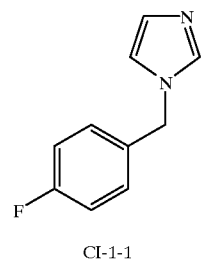

CI-1-1

To a solution of imidazole (10 g, 0.146 mole) in 80 ml of DMF at 0° C. was added triethylamine (25.5 ml, 0.176 mole) followed by a solution of 4-Fluorobenzylbromide (22 ml, 0.176 mole) in 30 ml of DMF added dropwise via addition funnel. The ice bath was removed and the reaction was allowed to warm to room temperature overnight. The solvent was evaporated under reduced pressure in vacuo. The residue was partitioned with H$_2$O and CH$_2$Cl$_2$. The organic layer was washed with saturated NaHCO$_3$, brine, dried over MgSO$_4$, filtered and evaporated to afford a crude oil. This material was chromatographed on silica gel using 50–100% EtOAc/Hex as eluant. Obtained CI-1-1 as an oil. $^1$H NMR (400 MHz, CDCl$_3$) δ 7.53 (s, 1H), 7.09–7.15 (m, 5H), 6.88 (s, 1H), 5.09 (s, 2H).

Step 2: 1-(4-Fluorobenzyl)-1H-imidazole-2-carboxylic lithium salt CI-2-1

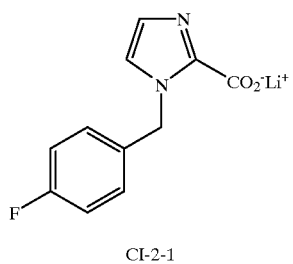

CI-2-1

A solution of CI-1-1 (8.81 g, 0.05 mole) in 120 ml dried THF at −78° C. under $N_2$ was added a solution of 2.5M nBuLi in Hexanes (21 ml, 0.052 mole) dropwise via syringe over 40 minutes. This resulting mixture was aged for 1 hour at −78° C. and small chunks of dried ice were added (6.6 g, 0.15 mole). The ice bath was removed and the reaction warmed to ambient temperature for 4 hours. The homogeneous solution was concentrated in vacuo to give a gummy foam which was triturated with ether to obtain CI-2-1 as a solid salt. $^1$H NMR (400 MHz, DMSO-$d_6$) δ 7.34 (t, 2H), 7.22 (s, 1H), 7.11 (t, 2H), 6.83 (s, 1H), 5.74 (s, 2H).

Step 3: 1-(4-Fluorobenzyl)-1H-imidazole-2-carboxylic acid methoxy-methyl-amide CI-3-1

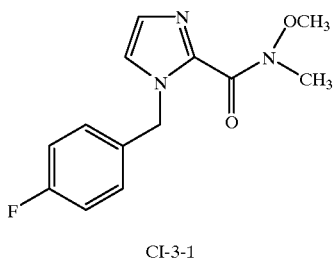

CI-3-1

A solution of CI-2-1 (7.0 g, 0.031 mole) was treated with EDC.HCl (6.5 g, 0.034 mole), HOBT.$H_2O$ (4.6 g, 0.034 mole), N,O-dimethylhydroxyamine.HCl (3.31 g, 0.034 mole), and triethylamine (12.9 ml, 0.092 mole) in 60 ml of DMF and stirred over the weekend under $N_2$. The DMF was removed under reduced pressure in vacuo. The residue was partitioned with saturated $NaHCO_3$ and extracted three times with EtOAc. Combined organics layers were washed with $H_2O$ and brine, dried over $MgSO_4$, filtered and evaporated to afford a yellow oil. This crude material was chromatographed on silica gel using 70–100% EtOAc/Hex as eluant. Obtained CI-3-1 as an oil. $^1$H NMR (400 MHz, $CDCl_3$) δ 7.19–7.23 (m, 2H), 7.09 (s, 1H), 6.97–7.04 (m, 3H), 5.42 (s, 2H), 3.81 (s, 3H), 3.48 (s, 3H).

Step 4: 1-[1-(4-Fluorobenzyl)-1H-imidazol-2-yl]ethanone CI-4-1

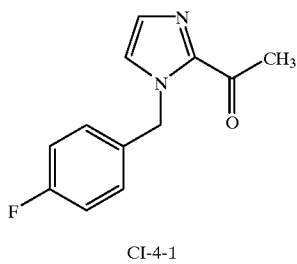

CI-4-1

A solution of CI-3-1 (2.0 g, 0.0076 mole) in 60 ml dried THF at −78° C. was treated with a solution of 1.4M $CH_3Li$ (6.5 ml, 0.0091 mole) in $Et_2O$ dropwise via syringe under $N_2$ atmosphere. The ice bath was removed after addition was completed and the reaction was warmed to 0° C. for 2 hours. The reaction was quenched with 75 ml of saturated $NH_4Cl$ solution and extracted with three times EtOAc. Combined organics layers were washed with brine, dried over $MgSO_4$, filtered and evaporated to give an oil. This crude material was chromatographed on silica gel using 70% EtOAc/Hex as eluant. Obtained CI-4-1 as an oil. $^1$H NMR (400 MHz, $CDCl_3$) δ 7.16–7.20 (m, 3H), 7.06 (s, 1H), 6.99–7.04 (t, 2H), 5.58 (s, 2H), 2.66 (s, 3H).

Step 5: 4-[1-(4-Fluorobenzyl)-1H-imidazol-2-yl]-2,4-dioxobutyric acid ethyl ester CI-5-1

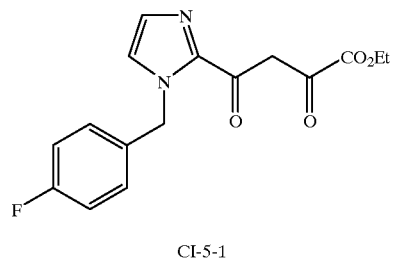

CI-5-1

A solution of CI-4-1 (0.5 g, 0.0023 mole) in 8 ml dried THF was treated with diethyl oxalate (0.62 ml, 0.0046 mole) and sodium ethoxide (0.31 g, 0.0046 mmole) at room temperature over night under $N_2$ atmosphere. The reaction mixture was poured into 10 ml of 0.5 N HCl solution and extracted twice with EtOAc. The combined extracts were washed with brine and dried over $MgSO_4$, filtered and evaporated to give a crude residue. This crude material was chromatographed on silica gel using 50% EtOAc/Hex as eluant. Obtained CI-5-1 as a beige solid. $^1$H NMR (400 MHz, $CDCl_3$) δ 7.19–7.23 (m, 3H), 7.13 (s, 1H), 7.01 (t, 2H), 5.69 (s, 2H), 4.33–4.37 (q, 2H), 1.36 (t, 3H).

Step 6: 4-[1-(4-Fluorobenzyl)-1H-imidazol-2-yl]-2,4-dioxobutyric acid CI-6-1

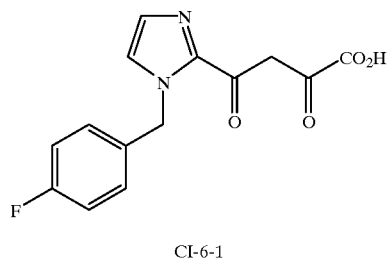

CI-6-1

A solution of CI-5-1 (0.3 g, 0.0009 mole) was dissolved in 7 ml of $CH_3OH$, 7 ml of THF and 3 ml of 1N NaOH and stirred for 3 hours. The reaction mixture was washed with ether and acidified to pH 1–2 with 1N HCl and extracted three times with EtOAc. The combined extracts were washed with brine, dried over $MgSO_4$, filtered and evaporated to give a crystalline solid, that was stirred in hot EtOAc and filtered to obtained CI-6-1 as a light beige solid. m.p.: 163–164° C. $^1$H NMR (400 MHz, $CDCl_3$) δ 7.20 (m, 3H), 7.13 (s, 1H), 7.01 (t, 3H), 5.69 (s, 2H).

EXAMPLE 106

In a manner similar to that described for CI-6-1, the following compound was prepared:

129

4-(1-Benzyl-1H-imidazol-2-yl)-2,4-dioxobutyric acid

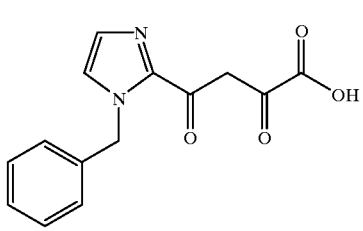

CHN Calc. 61.76, 4.44, 10.29; Fnd. 61.80, 4.58, 10.17

EXAMPLE 107

4-[1-(4-Fluorobenzyl)-1H-imidazol-4-yl]-2,4-dioxobutyric acid CII-4-1

Step 1: 1-(4-Fluorobenzyl)-1H-imidazole-4-carboxylic acid 4-fluorobenzyl ester CII-1-1a; and 3-(4-fluorobenzyl)-3H-imidazole-4-carboxylic acid 4-fluorobenzyl ester CII-1-1b

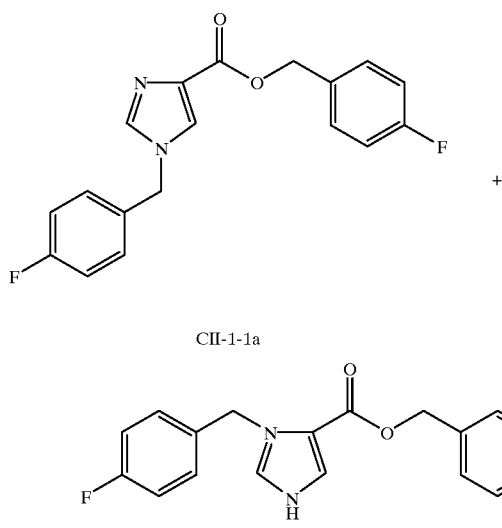

A suspension of 1H-imidazole-4-carboxylic acid (1.0 g, 0.0089 mole) in 25 ml of DMF was treated with $Cs_2CO_3$ (8.72 g, 0.026 mole) followed by 4-fluorobenzyl bromide (3.33 ml, 0.026 mole) and stirred overnight at room temperature under $N_2$ atmosphere. DMF was removed under reduced pressure in vacuo. The residue was partitioned with $H_2O$ and three times with EtOAc. Combined extracts were washed with brine, dried over $MgSO_4$, filtered and evaporated to give a crude oil. This material was chromatographed on silica gel with 50% EtOAc/Hex as eluant to afford a 1:1 mixture of CII-1-1a and CII-1-1b. $^1H$ NMR (400 MHz, $CDCl_3$) δ 7.54–7.57 (d, J=9.7 Hz, 2H), 7.40 (m, 2H), 7.14 (m, 2H), 6.99 (m, 4H), 5.28 (s, 2H), 5.09 (s, 2H).

Step 2: 1-[1-(4-Fluorobenzyl)-1H-imidazol-4-yl]-ethanone CII-2-1

130

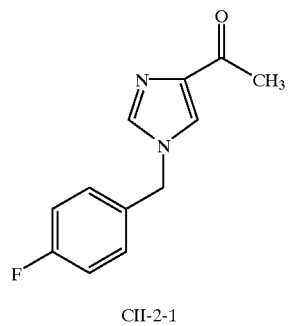

CII-2-1

A solution of CII-1-1 (0.9 g, 0.0027 mole) in 10 ml dried THF at −78° C. was treated with a solution of 1.4M $CH_3Li$ (2.35 ml, 0.0032 mole) in $Et_2O$ dropwise via syringe under $N_2$ atmosphere. The ice bath was removed after addition was completed and the reaction was warmed to room temperature over the weekend. The reaction was quenched with 10 ml of 1N HCl. The solution was basified with saturated $NaHCO_3$ and extracted with EtOAc three times. Combined organics layers were washed with brine, dried over $MgSO_4$, filtered and evaporated to give CII-2-1 as a crystalline solid. $^1H$ NMR (400 MHz, $CDCl_3$) δ 7.53 (d, 2H), 7.15 (m, 2H), 7.04 (m, 2H), 5.1 (s, 2H), 2.5 (s, 3H).

Step 3: 4-[1-(4-Fluorobenzyl)-1H-imidazol-4-yl]-2,4-dioxobutyric acid ethyl ester CII-3-1

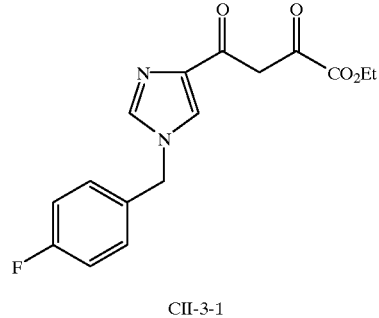

CII-3-1

A solution of CII-2-1 (75 mg, 0.34 mmole) in 3 ml dried THF was treated with diethyl oxalate (0.092 ml, 0.68 mmole) and sodium ethoxide (47 mg, 0.68 mmole) at room temperature over night under $N_2$ atmosphere. The reaction mixture was poured into 10 ml of 1N HCl solution and extracted twice with EtOAc. The combined extracts were washed with brine and dried over $MgSO_4$, filtered and evaporated to give CII-3-1 as a bright yellow oil. Used as is without further purification. $^1H$ NMR (400 MHz, $CDCl_3$) δ 7.78 (s, 1H), 7.69 (s, 1H), 7.22 (m, 2H), 7.10 (m, 3H), 5.19 (m, 2H), 4.35 (m, 2H), 1.4 (m, 3H).

Step 4: 4-[1-(4-Fluorobenzyl)-1H-imidazol-4-yl]-2,4-dioxobutyric acid CII-4-1

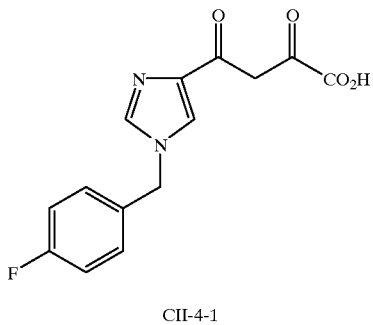

CII-4-1

A solution of CII-3-1 (70 mg, 0.2 mmole) was dissolved in 3 ml of CH₃OH and 3 ml of 1N NaOH for 3 hours. The reaction mixture was washed with ether, acidified to pH 1–2 with 1N HCl and extracted three times with EtOAc. The combined extracts were washed with brine, dried over MgSO₄, filtered and evaporated to give an oily residue that was triturated with 20% Et₂O/Hex to afford CII-4-1 as a yellow crystalline solid. ¹H NMR (400 MHz, CDCl₃) δ 8.24 (s, 1H), 8.07 (s, 1H), 7.44 (m, 2H), 7.19 (m, 2H), 6.92 (s, 1H), 5.28 (s, 2H).

EXAMPLE 108

4-[1-(4-Fluorobenzyl)-1H-indol-2-yl]-2,4-dioxobutyric acid DI-4-1

Step 1: 1-(1H-indol-2-yl)ethanone DI-1-1

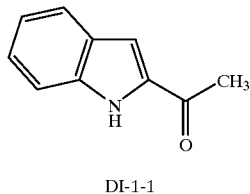

DI-1-1

A solution of 2-carboxy indole (3 g, 16.9 mmol) in anhydrous ether (50 mL) was cooled to 0° C. and treated with Methyl Lithium (1.4 M, 48.3 mL) A white solid precipitated. After addition was complete the reaction was warmed to reflux for two hours, quenched by pouring into ice water, and extracted with Et₂O. The organic layers were combined, washed with saturated sodium bicarbonate solution and brine, dried over MgSO₄, filtered and evaporated to give DI-1-1 as a white solid. Rf=0.53 (20% EtOAc/Hexanes)

¹H NMR (400 MHz, CDCl₃) δ 9.1 (bs, 1 h), 7.72 (d, J=7.78 Hz, 1H), 7.42 (d, J=8.4 Hz, 1H), 7.36 (m, 1H), 7.2 (m, 1H), 7.15 (m, 1H), 2.6 (s, 3H).

Step 2: 1-[1-(4-Fluorobenzyl)-1H-indol-2-yl]ethanone DI-2-1

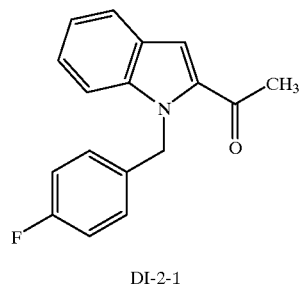

DI-2-1

In a manner similar to that described for the preparation of AI-1-1, DI-1-1 was treated with 4-fluorobenzyl bromide to give DI-2-1 as a yellow oil. Rf=0.67 (20% EtOAc/Hexanes) ¹H NMR (400 MHz, CDCl₃) δ 7.73 (d, J=8.06 Hz, 1H), 7.36 (m, 3H), 7.18 (m, 1H), 7.02 (m, 2H), 6.9 (m, 2H), 5.8 (s, 2H), 2.6 (s, 3H).

Step 3: 4-[1-(4-Fluorobenzyl)-1H-indol-2-yl]-2,4-dioxobutyric acid

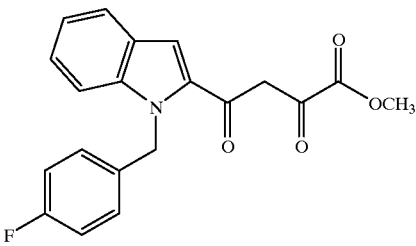

methyl ester DI-3-1

In a manner similar to that described for the preparation of AI-2-1, DI-2-1 was treated with dimethyl oxalate and sodium hydride to give DI-3-1 as a yellow solid. Rf=0.26 (97:3:1 CHCl₃/MeOH/HOAc). ¹H NMR (400 MHz, CDCl₃) d 7.75 (d, J=8.05 Hz, 1H), 7.52 (s, 1H), 7.38 (m, 2H), 7.2 (m, 1H), 7.09 (s, 1H), 7.05 (m, 2H), 6.95 (m, 2H), 3.95 (s, 3H).

Step 4: 4-[1-(4-Fluorobenzyl)-1H-indol-2-yl]-2,4-dioxobutyric acid DI-4-1

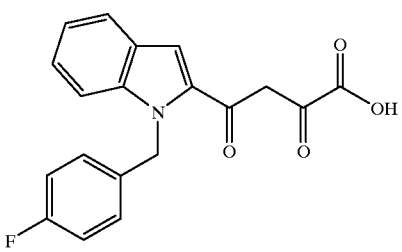

DI-4-1

In a manner similar to that described for the preparation of A-I-3-1, DI-3-1 was treated with sodium hydroxide to give DI-4-1 as bright yellow crystals after crystallization from EtOAc. ¹H NMR (400 MHz, DMSO-D6) δ 7.90 (s, 1H), 7.77 (d, J=7.88 Hz, 1H), 7.62 (d, J=8.42 Hz, 1H), 7.4 (m, 1H), 7.2 (m, 1H), 7.1 (m, 5H), 5.9 (s, 2H). mass spec (FAB, M+1) 340.03.

EXAMPLE 109

The following compound was prepared in a manner similar to that described for DI-4-1:

2-Hydroxy-4-(1-methyl-1-H-indol-2-yl)-2,4-dioxobutyric acid

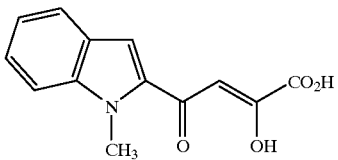

CHN Calc. ($C_{13}H_{11}NO_4$ 0.15 $H_2O$) 62.97, 4.59, 5.65; Fnd. 63.05, 4.45, 5.80.

EXAMPLE 110

4-[1-(4-Fluorobenzyl)-1H-indol-3-yl]-2,4-dioxobutyric acid DII-3-1

Step 1: 1-[1-(4-Fluorobenzyl)-1H-indol-3-yl]ethanone DII-1-1

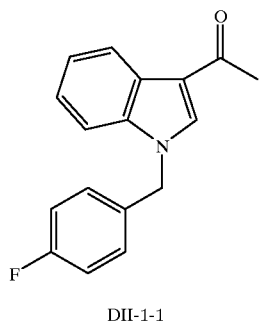

DII-1-1

In a similar manner to BIII-1-1, 3-acetylindole (0.318 g, 2 mmol) was treated with 4-fluorobenzyl bromide (0.378 g, 0.244 ml, 2 mmol) and sodium hydride (0.048 g, 0.08 gr of a 60% oil dispersion, 2 mmol) in 2 ml DMF for one hour to give the title compound as a white solid. $^1$H NMR (400 MHz, CDCl$_3$) δ 2.52 (s, 3H) 5.33 (s, 2H), 7.03 (t, 2H, J=8.61 Hz), 7.11–7.18 (m, 2H), 7.24–7.35 (m, 2H), 7.74 (s, 1H), 8.39 (d, 1H, J=7.5 Hz).

Step 2: 1-[1-(4-Fluorobenzyl)-1H-indol-3-yl]-2,4-dioxobutyric acid ethyl ester DII-2-1

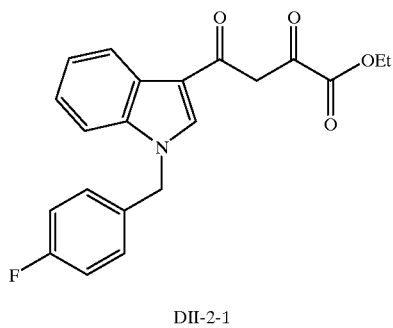

DII-2-1

In a similar manner to AIII-2-1, DII-1-1 (0.267 g, 1 mmol) was reacted with diethyl oxalate (0.292 g, 0.271 ml, 2 mmol) and sodium ethoxide (0.136 g, 2 mmol) to yield the title compound as a yellow solid after trituration in diethyl ether.

$^1$H NMR (400 MHz, CDCl$_3$) δ 1.41 (t, 3H, J=7.14 Hz), 4.39 (q, 2H, J=7.14 Hz), 5.35 (s, 2H), 6.83 (s, 1H), 7.05 (t, 2H, J=8.6 Hz), 7.13–7.20 (m, 2H), 7.30–7.39 (m, 3H), 7.88 (s, 1H), 8.40 (d, 1H, J=7.51 Hz).

Step 3: 1-[1-(4-Fluorobenzyl)-1H-indol-3-yl]-2,4-dioxobutyric acid DII-3-1

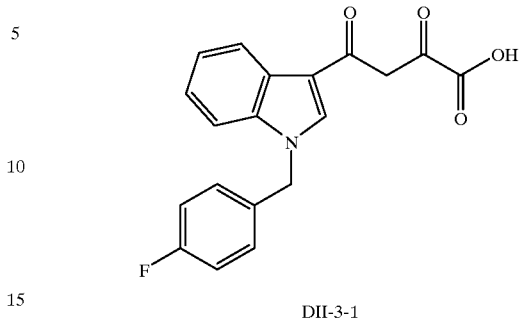

DII-3-1

In a similar manner to AI-3-1, DII-2-1 (0.1 g, 0.27 mmol) was hydrolyzed using 0.54 ml 1M LiOH (5.4 mmol) in 2 ml THF to give the title compound as a yellow solid. MP=161–162° C. $^1$H NMR (400 MHz, CDCl$_3$) δ 5.36 (s, 2H), 6.92 (s, 1H), 7.07 (t, 2H, J=8.61 Hz), 7.15–7.23 (m, 2H), 7.31–7.39 (m, 3H), 7.95 (s, 1H), 8.30 (d, 1H, J=6.59 Hz).

EXAMPLE 111

HIV Integrase Assay: Strand Transfer Catalyzed by Recombinant Integrase and Preintegration Complexes Assays for the strand transfer activity of integrase were conducted according to Wolfe, A. L. et al., J. Virol. 70, 1424 (1996), and Farnet, C. M. and Bushman F. D. (1997) Cell; 88, 483 for recombinant integrase and preintegration complexes, respectively, hereby incorporated by reference for these purposes.

Representative compounds tested in the integrase assay demonstrated IC50's less than 1 micromolar. Further, representative compounds tested in the preintegration complex assay also demonstrated IC50's of less than 1 micromolar.

EXAMPLE 112

Assay for Inhibition of HIV Replication

Assays for the inhibition of acute HIV infection of T-lymphoid cells was conducted according to Vacca, J. P. et al., (1994), Proc. Natl. Acad. Sci. USA 91, 4906, herein incorporated by reference for these purposes.

Representative compounds tested in the present assay demonstrated $IC_{95}$s of less than 10 micromolar.

EXAMPLE 113

Oral Composition

As a specific embodiment of an oral composition of a compound of this invention, 50 mg of a compound of the present invention is formatted with sufficient finely divided lactose to provide a total amount of 580 to 590 mg to fill a size 0 hard gelatin capsule.

While the foregoing specification teaches the principles of the present invention, with examples provided for the purpose of illustration, it will be understood that the practice of the invention encompasses all of the usual variations, adoptions, or modifications, as come within the scope of the following claims and their equivalents.

What is claimed:

1. A compound of structural formula (I):

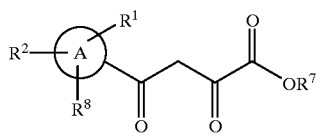

and tautomers and pharmaceutically acceptable salts thereof, wherein:

A is a five-membered heteroaromatic ring containing 1 or 2 nitrogen atoms and substituted on carbon or nitrogen by $R^1$, $R^2$ and $R^8$; the heteroaromatic ring may optionally be fused with a phenyl ring to form a fused ring system, provided that when A is a fused ring system, the nitrogen-containing heteroaromatic ring is substituted by the dioxobutyric acid/ester moiety;

$R_1$ is selected from:
(1) —H,
(2) —$C_{1-5}$ alkyl,
(3) —$CF_3$,
(4) -halo,
(5) —$NO_2$,
(6) —$N(R^4)(R^5)$,
(7) —$R^6$,
(8) —$C_{2-5}$ alkenyl-$R^3$,
(9) —$C_{2-5}$ alkynyl-$R^3$,
(10) —O—$R^6$,
(11) —O—$C_{1-6}$ alkyl, and
(12) —C(O)$CH_2$C(O)C(O)$OR^7$;

$R^2$ is selected from:
(1) —H,
(2) —$R^3$,
(3) —$C_{1-6}$ alkyl,
(4) —$C_{1-6}$ alkyl substituted with $R^3$,
(5) —O—$R^6$,
(6) —O—$C_{1-6}$ alkyl-$OR^6$,
(7) —S(O)n-$R^6$,
(8) —$C_{1-6}$ alkyl ($OR^6$)($R^4$),
(9) —$C_{1-6}$ alkyl-$N(R^4)(R^6)$,
(10) —$C_{1-6}$ alkyl S(O)n-$R^6$,
(11) —$C_{1-6}$ alkyl C(O)—$R^6$,
(12) —$C_{1-6}$ alkyl C(S)—$R^6$,
(13) —$C_{1-6}$ alkyl $NR^4C(O)$—$R^6$, and
(14) —$C_{1-6}$ alkyl-C(O)$N(R^4)(R^5)$;

each $R^3$ is independently selected from:
(1) a 5 or 6 membered aromatic or heteroaromatic ring, containing 0, 1, 2, 3, or 4 heteroatoms selected from oxygen, nitrogen and sulfur, unsubstituted or substituted on a nitrogen or carbon atom by 1 to 5 substituents selected from:
(a) halogen,
(b) $C_{1-6}$ alkyl,
(c) $C_{1-6}$ alkyloxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
(i) halogen,
(ii) $C_{1-6}$ alkyl,
(iii) —$CF_3$, and
(iv) hydroxy;
(2) a 3 to 6 membered saturated ring containing 0 or 1 heteroatoms selected from oxygen, nitrogen or sulfur, unsubstituted or substituted with 1 to 5 substituents selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;
(3) unsubstituted or substituted hexahydrothieno[3,4-d]imidazolyl with one or two substituents selected from:
(a) oxo,
(b) halogen,
(c) $C_{1-6}$ alkyl,
(d) $C_{1-6}$ alkyloxy-,
(e) —$CF_3$,
(f) —$OCF_3$,
(g) —CN, and
(h) hydroxy;
(4) a 5 or 6 membered aromatic or heteroaromatic ring, containing 0, 1, or 2 heteroatoms selected from oxygen, nitrogen and sulfur, fused with a phenyl ring; wherein the ring system is unsubstituted or substituted on a nitrogen or carbon atom by 1 to 3 substituents selected from:
(a) -halogen,
(b) —$C_{1-6}$ alkyl,
(c) —$C_{1-6}$ alkyloxy-,
(d) —$CF_3$,
(e) —$OCF_3$,
(f) —CN, and
(g) -hydroxy;
(5) a 3 to 6 membered saturated ring containing 0 or 1 heteroatoms selected from oxygen, nitrogen or sulfur, fused with a phenyl ring, unsubstituted or substituted with 1 or 2 substituents selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy; and
(6) a 5 to 6 membered ring containing 0, 1 or 2 heteroatoms selected from oxygen, nitrogen or sulfur, containing 2 or 3 double bonds, unsubstituted or substituted with 1 or 2 substituents selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;

each $R^4$ is independently selected from:
(1) —H,
(2) —$C_{1-3}$ alkyl,
(3) —$CF_3$,
(4) —$R^3$, (5) —$C_{2-3}$ alkenyl,
(6) —$C_{1-3}$ alkyl-$R^3$,
(7) —$C_{2-3}$ alkenyl-$R^3$,
(8) —$S(O)_n$—$R^3$, and
(9) —$C(O)$—$R^3$;

each $R^5$ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$,
(7) —$C_{2-3}$ alkenyl-$R^3$,
(8) —$S(O)_n$—$R^3$, and
(9) —$C(O)$—$R^3$;

each $R^6$ is independently selected from:
(1) —$C_{1-3}$ alkyl-$R^3$, and
(2) —$R^3$;

$R^7$ is selected from:
(1) —H, and
(2) $C_{1-6}$ alkyl;

$R^8$ is selected from:
(1) —H,
(2) $C_{1-6}$ alkyl-oxy, and
(3) $C_{1-6}$ alkyl; and each n is independently selected from 0, 1 and 2; and further provided that when $R^7$ is $C_{1-6}$ alkyl, then $R^2$ is not —H or —$C_{1-6}$ alkyl.

2. The compound according to claim 1, and tautomers and pharmaceutically acceptable salts thereof, wherein:

A is selected from:
(1) pyrrolyl,
(2) imidazolyl,
(3) pyrazolyl, and
(4) indolyl, provided that the nitrogen-containing heteroaromatic ring is substituted by the dioxobutyric moiety in structural formula (I);

$R^1$ is selected from:
(1) —H,
(2) —$CH_3$,
(3) —$CF_3$,
(4) -halo,
(5) —$NO_2$,
(6) —$N(R^4)(R^5)$,
(7) -phenyl,
(8) substituted phenyl substituted with 1 or 2 substituents independently selected from:
(a) halogen,
(b) $C_{1-6}$ alkyl,
(c) $C_{1-6}$ alkyloxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
(i) halogen,
(ii) $C_{1-6}$ alkyl,
(iii) —$CF_3$, and
(iv) hydroxy,
(9) phenyl $C_{1-3}$ alkyl-,
(10) substituted phenyl $C_{1-3}$ alkyl-substituted with 1 or 2 substituents independently selected from:
(a) halogen,
(b) $C_{1-6}$ alkyl,
(c) $C_{1-6}$ alkyloxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
(i) halogen,
(ii) $C_{1-6}$ alkyl,
(iii) —$CF_3$, and
(iv) hydroxy,
(11) —$C_{2-5}$ alkenyl-$R^3$,
(12) —$C_{2-5}$ alkynyl-$R^3$, and
(13) —$C(O)CH_2C(O)C(O)OR^7$;

$R^2$ is selected from:
(1) —H,
(2) —$R^3$,
(3) —$C_{1-6}$ alkyl,
(4) —$C_{1-6}$ alkyl substituted with $R^3$,
(5) —O—$R^6$,
(6) —O—$C_{1-6}$ alkyl-$OR^6$,
(7) —$S(O)n$-$R^6$,
(8) —$C_{1-6}$ alkyl $(OR^6)(R^4)$,
(9) —$C_{1-6}$ alkyl-$N(R^4)(R^6)$,
(10) —$C_{1-6}$ alkyl $S(O)n$-$R^6$,
(11) —$C_{1-6}$ alkyl $C(O)$—$R^6$,
(12) —$C_{1-6}$ alkyl $C(S)$—$R^6$,
(13) —$C_{1-6}$ alkyl $NR^4C(O)$—$R^6$, and
(14) —$C_{1-6}$ alkyl-$C(O)N(R^4)(R^5)$;

each $R^3$ is independently selected from:
(1) phenyl;
(2) substituted phenyl with 1, 2, or 3 substituents independently selected from:
(a) halogen,
(b) $C_{1-6}$ alkyl,
(c) $C_{1-6}$ alkyloxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
(i) halogen,
(ii) $C_{1-6}$ alkyl,
(iii) —$CF_3$, and
(iv) hydroxy;
(3) thienyl;
(4) substituted thienyl substituted on a carbon atom with one or two substituents independently selected from:
(a) halogen,
(b) $C_{1-6}$ alkyl,
(c) $C_{1-6}$ alkyloxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
(i) halogen, (ii) $C_{1-6}$ alkyl,
(iii) —$CF_3$, and
(iv) hydroxy;
(5) pyridyl;
(6) substituted pyridyl substituted on a carbon atom with one or two substituents independently selected from:
(a) halogen,
(b) $C_{1-6}$ alkyl,
(c) $C_{1-6}$ alkyloxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
(i) halogen,
(ii) $C_{1-6}$ alkyl,
(iii) —$CF_3$, and
(iv) hydroxy;
(7) imidazolyl;
(8) substituted imidazolyl substituted on a carbon atom with one or two substituents independently selected from:
(a) halogen,
(b) $C_{1-6}$ alkyl,
(c) $C_{1-6}$ alkyloxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
(i) halogen,
(ii) $C_{1-6}$ alkyl,
(iii) —$CF_3$, and
(iv) hydroxy;
(9) pyrrolyl;
(10) substituted pyrrolyl substituted on a carbon atom with one or two substituents independently selected from:
(a) halogen,
(b) $C_{1-6}$ alkyl,
(c) $C_{1-6}$ alkyloxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
(i) halogen,
(ii) $C_{1-6}$ alkyl,
(iii) —$CF_3$, and
(iv) hydroxy;
(11) pyrazolyl;
(12) substituted pyrazolyl substituted on a carbon atom with one or two substituents independently selected from:
(a) halogen,
(b) $C_{1-6}$ alkyl,
(c) $C_{1-6}$ alkyloxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
(i) halogen,
(ii) $C_{1-6}$ alkyl,
(iii) —$CF_3$, and
(iv) hydroxy;
(13) $C_{3-6}$ cycloalkyl;
(14) substituted $C_{3-6}$ cycloalkyl with 1 or 2 substituents independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;
(15) piperidinyl;
(16) substituted piperidinyl substituted on a carbon atom with one or two substituents independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;
(17) morpholinyl;
(18) substituted morpholinyl substituted at a carbon or nitrogen atom with 1 or 2 independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;
(19) naphthyl;
(20) substituted naphthyl with 1, 2, or 3 substituents independently selected from:
(a) -halogen,
(b) —$C_{1-6}$ alkyl,
(c) —$C_{1-6}$ alkyloxy-,
(d) —$CF_3$,
(e) —$OCF_3$,
(f) —CN, and
(g) -hydroxy;
(21) indolyl;
(22) substituted indolyl substituted on a carbon atom with one or two substituents independently selected from:
(a) -halogen,
(b) —$C_{1-6}$ alkyl,
(c) —$C_{1-6}$ alkyloxy-,
(d) —$CF_3$,
(e) —$OCF_3$,
(f) —CN, and (g) -hydroxy;
(23) $C_{3-6}$ cycloalkyl fused with a phenyl ring;
(24) substituted $C_{3-6}$ cycloalkyl fused with a phenyl ring substituted on a carbon atom with one or two substituents independently selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O, and
  (h) hydroxy;
each $R^4$ is independently selected from:
  (1) —H,
  (2) —$C_{1-3}$ alkyl, and
  (3) —$CF_3$;
each $R^5$ is independently selected from:
  (1) —H,
  (2) —$C_{1-3}$ alkyl,
  (3) —$CF_3$,
  (4) —$R^3$,
  (5) —$C_{2-3}$ alkenyl,
  (6) —$C_{1-3}$ alkyl-$R^3$,
  (7) —$C_{2-3}$ alkenyl-$R^3$,
  (8) —$S(O)_n$—$R^3$, and
  (9) —C(O)—$R^3$;
each $R^6$ is independently selected from:
  (1) —$C_{1-3}$ alkyl-$R^3$, and
  (2) —$R^3$;
$R^7$ is H;
$R^8$ is selected from:
  (1) —H,
  (2) —$OCH_3$, and
  (3) —$CH_3$; and
each n is independently selected from 0, 1 and 2.

3. The compound according to claim 2, and tautomers and pharmaceutically acceptable salts thereof, wherein:
A is selected from:
  (1) pyrrolyl,
  (2) imidazolyl,
  (3) pyrazolyl, and
  (4) indolyl, provided that the nitrogen-containing heteroaromatic ring is substituted by the dioxobutyric moiety in structural formula (I);
$R^1$ is selected from:
  (1) —H,
  (2) —$CH_3$,
  (3) —$CF_3$,
  (4) -halo,
  (5) —$NO_2$,
  (6) —$N(R^4)(R^5)$,
  (7) -phenyl,
  (8) substituted phenyl substituted with 1 or 2 substituents independently selected from:
    (a) halo,
    (b) methyl, and
    (c) methoxy,
  (9) phenyl $C_{1-3}$ alkyl-,
  (10) substituted phenyl $C_{1-3}$ alkyl-substituted with 1 or 2 substituents independently selected from:
    (a) halo,
    (b) methyl, and
    (c) methoxy,
  (11) —$C_{2-5}$ alkenyl-$R^3$, and
  (12) —$C(O)CH_2C(O)C(O)OR^7$;

$R^2$ is selected from:
  (1) —H,
  (2) —$R^3$,
  (3) —$C_{1-6}$ alkyl,
  (4) —$C_{1-6}$ alkyl substituted with $R^3$,
  (5) —O—$R^6$,
  (6) —O—$C_{1-6}$ alkyl-$OR^6$,
  (7) —$S(O)n-R^6$,
  (8) —$C_{1-6}$ alkyl $(OR^6)(R^4)$,
  (9) —$C_{1-6}$ alkyl-$N(R^4)(R^6)$,
  (10) —$C_{1-6}$ alkyl $S(O)n-R^6$,
  (11) —$C_{1-6}$ alkyl $NR^4C(O)$—$R^6$, and
  (12) —$C_{1-6}$ alkyl-$C(O)N(R^4)(R^5)$;
each $R^3$ is independently selected from:
  (1) phenyl,
  (2) substituted phenyl with 1, 2, or 3 substituents independently selected from:
    (a) halogen,
    (b) $C_{1-6}$ alkyl,
    (c) $C_{1-6}$ alkyloxy-,
    (d) phenyl,
    (e) —$CF_3$,
    (f) —$OCF_3$,
    (g) —CN,
    (h) hydroxy,
    (i) phenyloxy, and
    (j) substituted phenyloxy with 1, 2, or 3 substituents selected from:
      (i) halogen,
      (ii) $C_{1-6}$ alkyl,
      (iii) —$CF_3$, and
      (iv) hydroxy,
  (3) thienyl,
  (4) pyridyl,
  (5) imidazolyl,
  (6) pyrrolyl,
  (7) pyrazolyl,
  (8) $C_{3-6}$ cycloalkyl,
  (9) substituted $C_{3-6}$ cycloalkyl with 1 or 2 substituents independently selected from:
    (a) halogen,
    (b) $C_{1-6}$ alkyl,
    (c) $C_{1-6}$ alkyloxy-,
    (d) —$CF_3$,
    (e) —$OCF_3$,
    (f) —CN,
    (g) =O, and
    (h) hydroxy;
  (10) piperidinyl,
  (11) morpholinyl,
  (12) naphthyl,
  (13) indolyl, and
  (14) $C_{3-6}$ cycloalkyl fused with a phenyl ring;
each $R^4$ is independently selected from:
  (1) —H,
  (2) —$C_{1-3}$ alkyl, and
  (3) —$CF_3$;
each $R^5$ is independently selected from:
  (1) —H,
  (2) —$C_{1-3}$ alkyl,
  (3) —$CF_3$, and
  (4) —$R^3$,
each $R^6$ is independently selected from:
  (1) —$C_{1-3}$ alkyl-$R^3$, and
  (2) —$R^3$;
$R^7$ is H; and R⁸ is selected from:
  (1) —H, and
  (2) CH₃; and
each n is independently selected from 0, 1 and 2.

4. The compound according to claim 1 of structural formula:

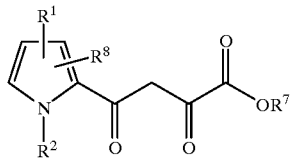

and tautomers and pharmaceutically acceptable salts thereof, wherein:

R¹ is selected from:
  (1) —H,
  (2) —C₁₋₅ alkyl,
  (3) —CF₃,
  (4) -halo,
  (5) —NO₂,
  (6) —N(R⁴)(R⁵),
  (7) -phenyl,
  (8) substituted phenyl substituted with 1 or 2 substituents independently selected from:
    (a) halo,
    (b) methyl, and
    (c) methoxy,
  (9) phenyl C₁₋₃ alkyl-,
  (10) substituted phenyl C₁₋₃ alkyl-substituted with 1 or 2 substituents independently selected from:
    (a) halo,
    (b) methyl, and
    (c) methoxy,
  (11) —C₂₋₅ alkenyl-R³,
  (12) —C₂₋₅ alkynyl-R³, and
  (13) —C(O)CH₂C(O)C(O)OR⁷

R² is selected from:
  (1) —H,
  (2) —R³,
  (3) —C₁₋₆ alkyl,
  (4) —C₁₋₆ alkyl substituted with R³,
  (5) —O—R⁶,
  (6) —O—C₁₋₆ alkyl-OR⁶,
  (7) —S(O)n-R⁶,
  (8) —C₁₋₆ alkyl (OR⁶)(R⁴),
  (9) —C₁₋₆ alkyl-N(R⁴)(R⁶),
  (10) —C₁₋₆ alkyl S(O)n-R⁶,
  (11) —C₁₋₆ alkyl C(O)—R⁶,
  (12) —C₁₋₆ alkyl C(S)—R⁶,
  (13) —C₁₋₆ alkyl NR⁴C(O)—R⁶, and
  (14) —C₁₋₆ alkyl-C(O)N(R⁴)(R⁵);

each R³ is independently selected from:
  (1) phenyl,
  (2) substituted phenyl with 1, 2, or 3 substituents independently selected from:
    (a) halogen,
    (b) C₁₋₆ alkyl,
    (c) C₁₋₆ alkyloxy-,
    (d) phenyl,
    (e) —CF₃,
    (f) —OCF₃,
    (g) —CN,
    (h) hydroxy,
    (i) phenyloxy, and
    (j) substituted phenyloxy with 1, 2, or 3 substituents selected from:
      (i) halogen,
      (ii) C₁₋₆ alkyl,
      (iii) —CF₃, and
      (iv) hydroxy,
  (3) thienyl,
  (4) substituted thienyl substituted on a carbon atom with one or two substituents independently selected from:
    (a) halogen,
    (b) C₁₋₆ alkyl,
    (c) C₁₋₆ alkyloxy-,
    (d) phenyl,
    (e) —CF₃,
    (f) —OCF₃,
    (g) —CN,
    (h) hydroxy,
    (i) phenyloxy, and
    (j) substituted phenyloxy with 1, 2, or 3 substituents selected from:
      (i) halogen,
      (ii) C₁₋₆ alkyl,
      (iii) —CF₃, and
      (iv) hydroxy;
  (5) pyridyl,
  (6) substituted pyridyl substituted on a carbon atom with one or two substituents independently selected from:
    (a) halogen,
    (b) C₁₋₆ alkyl,
    (c) C₁₋₆ alkyloxy-,
    (d) phenyl,
    (e) —CF₃,
    (f) —OCF₃,
    (g) —CN,
    (h) hydroxy,
    (i) phenyloxy, and
    (j) substituted phenyloxy with 1, 2, or 3 substituents selected from:
      (i) halogen,
      (ii) C₁₋₆ alkyl,
      (iii) —CF₃, and
      (iv) hydroxy,
  (7) imidazolyl,
  (8) substituted imidazolyl substituted on a carbon atom with one or two substituents independently selected from:
    (a) halogen,
    (b) C₁₋₆ alkyl,
    (c) C₁₋₆ alkyloxy-,
    (d) phenyl,
    (e) —CF₃,
    (f) —OCF₃,
    (g) —CN,
    (h) hydroxy,
    (i) phenyloxy, and
    (j) substituted phenyloxy with 1, 2, or 3 substituents selected from:
      (i) halogen,
      (ii) C₁₋₆ alkyl,
      (iii) —CF₃, and
      (iv) hydroxy;
  (9) pyrrolyl,
  (10) substituted pyrrolyl substituted on a carbon atom with one or two substituents independently selected from:

(a) halogen,
(b) $C_{1-6}$ alkyl,
(c) $C_{1-6}$ alkyloxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
  (i) halogen,
  (ii) $C_{1-6}$ alkyl,
  (iii) —$CF_3$, and
  (iv) hydroxy,
(11) pyrazolyl,
(12) substituted pyrazolyl substituted on a carbon atom with one or two substituents independently selected from:
(a) halogen,
(b) $C_{1-6}$ alkyl,
(c) $C_{1-6}$ alkyloxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
  (i) halogen,
  (ii) $C_{1-6}$ alkyl,
  (iii) —$CF_3$, and
  (iv) hydroxy,
(13) $C_{3-6}$ cycloalkyl,
(14) substituted $C_{3-6}$ cycloalkyl with 1 or 2 substituents independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy,
(15) piperidinyl,
(16) substituted piperidinyl substituted on a carbon atom with one or two substituents independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy,
(17) morpholinyl,
(18) substituted morpholinyl substituted at a carbon or nitrogen atom with 1 or 2 independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy,
(19) naphthyl,
(20) substituted naphthyl with 1, 2, or 3 substituents independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy,
(21) indolyl,
(22) substituted indolyl substituted on a carbon atom with one or two substituents independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy,
(23) $C_{3-6}$ cycloalkyl fused with a phenyl ring,
(24) substituted $C_{3-6}$ cycloalkyl fused with a phenyl ring substituted on a carbon atom with one or two substituents independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;

each $R^4$ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$,
(7) —$C_{2-3}$ alkenyl-$R^3$,
(8) —$S(O)_n$—$R^3$, and
(9) —$C(O)$—$R^3$;

each $R^5$ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$,
(7) —$C_{2-3}$ alkenyl-$R^3$,
(8) —$S(O)_n$—$R^3$, and
(9) —$C(O)$—$R^3$;

each $R^6$ is independently selected from:
(1) —$C_{1-3}$ alkyl-$R^3$, and
(2) —$R^3$;

$R^7$ is selected from:
(1) —H, and
(2) $C_{1-6}$ alkyl;

$R^8$ is selected from:
(1) —H, and
(2) $C_{1-6}$ alkyl; and each n is independently selected from 0, 1 and 2;
and further provided that when $R^7$ is $C_{1-6}$ alkyl, then $R^2$ is not —H or —$C_{1-6}$ alkyl.

5. The compound according to claim 4 of structural formula:

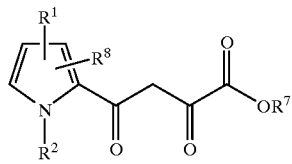

and tautomers and pharmaceutically acceptable salts thereof, wherein:

$R^1$ is selected from:
(1) —H,
(2) —$C_{1-5}$ alkyl,
(3) —$CF_3$,
(4) -halo,
(5) —$NO_2$,
(6) —$N(R^4)(R^5)$,
(7) -phenyl,
(8) substituted phenyl substituted with 1 substituent independently selected from:
  (a) halo,
  (b) methyl, and
  (c) methoxy,
(9) phenyl $C_{1-3}$ alkyl-,
(10) substituted phenyl $C_{1-3}$ alkyl-substituted with 1 or 2 substituents independently selected from:
  (a) halo,
  (b) methyl, and
  (c) methoxy,
(11) —$C_{2-5}$ alkenyl-$R^3$, and
(12) —$C(O)CH_2C(O)C(O)OR^7$;

$R^2$ is selected from:
(1) —H,
(2) —$R^3$,
(3) —$C_{1-6}$ alkyl,
(4) —$C_{1-6}$ alkyl substituted with $R^3$,
(5) —O—$R^6$,
(6) —O—$C_{1-6}$ alkyl-$OR^6$,
(7) —$C_{1-6}$ alkyl $(OR^6)(R^4)$,
(8) —$C_{1-6}$ alkyl-$N(R^4)(R^6)$,
(9) —$C_{1-6}$ alkyl $C(O)$—$R^6$,
(10) —$C_{1-6}$ alkyl $NR^4C(O)$—$R^6$, and
(11) —$C_{1-6}$ alkyl-$C(O)N(R^4)(R^5)$;

each $R^3$ is independently selected from:
(1) phenyl,
(2) substituted phenyl with 1, 2, or 3 substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-2}$ alkyl,
    (iii) —$CF_3$, and
    (iv) hydroxy;
(3) thienyl,
(4) pyridyl,
(5) imidazolyl,
(6) pyrrolyl,
(7) pyrazolyl,
(8) $C_{3-6}$ cycloalkyl,
(10) piperidinyl,
(11) morpholinyl,
(12) substituted morpholinyl substituted with a substituent selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O,
  (h) hydroxy;
(12) naphthyl,
(13) indolyl, and
(14) $C_{3-6}$ cycloalkyl fused with a phenyl ring;

each $R^4$ is independently selected from:
(1) —H,
(2) —$C_{1-3}$ alkyl,
(3) —$CF_3$,
(4) —$R^3$,
(5) —$C_{1-3}$ alkyl-$R^3$,
(6) —$S(O)_n$—$R^3$, and
(7) —$C(O)$—$R^3$;

each $R^5$ is independently selected from:
(1) —H,
(2) —$C_{1-3}$ alkyl,
(3) —$CF_3$,
(4) —$R^3$,
(5) —$C_{1-3}$ alkyl-$R^3$,
(6) —$S(O)_n$—$R^3$, and
(7) —$C(O)$—$R^3$;

each $R^6$ is independently selected from:
(1) —$C_{1-3}$ alkyl-$R^3$, and
(2) —$R^3$;

$R^7$ is selected from:
(1) —H, and
(2) $C_{1-4}$ alkyl;

$R^8$ is selected from:
(1) —H, and
(2) —$CH_3$; and each n is independently selected from 0, 1 and 2;
and further provided that when $R^7$ is $C_{1-4}$ alkyl, then $R^2$ is not —H or —$C_{1-6}$ alkyl.

6. The compound according to claim 5 of structural formula:

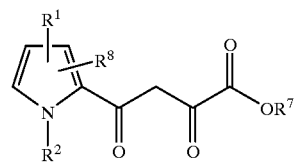

and tautomers and pharmaceutically acceptable salts thereof, wherein:

$R^1$ is selected from:
(1) —H,
(2) —$C_{1-5}$ alkyl, (3) —CF$_3$,
(4) -halo, wherein halo is selected from: —F, Cl, —Br, and —I;
(5) —NO$_2$,
(6) —N(R$^4$)(R$^5$),
(7) -phenyl,
(8) phenyl C$_{1-3}$ alkyl-,
(9) substituted phenyl C$_{1-3}$ alkyl-substituted with 1 or 2 substituents independently selected from:
 (a) halo, wherein halo is selected from: —F, —Cl and —Br;
(10) —C$_{2-5}$ alkynyl-R$^3$, and
(11) —C(O)CH$_2$C(O)C(O)OR$^7$;
R$^2$ is selected from:
(1) —H,
(2) —R$^3$,
(3) —C$_{1-6}$ alkyl,
(4) —C$_{1-6}$ alkyl substituted with R$^3$,
(5) —O—R$^6$,
(6) —O—C$_{1-6}$ alkyl-OR$^6$,
(7) —C$_{1-6}$ alkyl (OR$^6$)(R$^4$),
(8) —C$_{1-6}$ alkyl-N(R$^4$)(R$^6$),
(9) —C$_{1-6}$ alkyl C(O)—R$^6$, and
(10) —C$_{1-6}$ alkyl NR$^4$C(O)—R$^6$;
each R$^3$ is independently selected from:
(1) phenyl;
(2) substituted phenyl with 1, 2, or 3 substituents independently selected from:
 (a) halogen,
 (b) C$_{1-6}$ alkyl,
 (c) C$_{1-6}$ alkyloxy-,
 (d) phenyl,
 (e) —CF$_3$,
 (f) —OCF$_3$,
 (g) —CN,
 (h) hydroxy,
 (i) phenyloxy, and
 (j) substituted phenyloxy with 1, 2, or 3 substituents selected from:
  (i) halogen, wherein halogen is selected from —F, —Cl, and Br,
  (ii) methyl,
  (iii) —CF$_3$, and
  (iv) hydroxy;
(3) C$_{3-6}$ cycloalkyl,
(4) morpholinyl,
(5) substituted morpholinyl substituted with oxo; and
(6) naphthyl;
each R$^4$ is independently selected from:
(1) —H, and
(2) —C$_{1-3}$ alkyl,
each R$^5$ is independently selected from:
(1) —H,
(2) —C$_{1-3}$ alkyl,
(3) —CF$_3$,
(4) —R$^3$,
(5) —C$_{1-3}$ alkyl-R$^3$,
(6) —S(O)$_n$—R$^3$, and
(7) —C(O)—R$^3$;
each R$^6$ is independently selected from:
(1) —C$_{1-3}$ alkyl-R$_3$, and
(2) —R$^3$;
R$^7$ is —H;
R$^8$ is selected from:
(1) —H, and
(2) —CH$_3$; and each n is independently selected from 0, 1 and 2.
7. The compound according to claim 6 of structural formula:

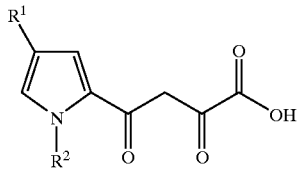

and tautomers and pharmaceutically acceptable salts thereof, wherein:
R$^1$ is selected from:
(1) —H,
(2) —C$_{1-5}$ alkyl,
(3) —CF$_3$,
(4) -halo; wherein halo is selected from: —F, Cl, —Br, and —I;
(5) —NO$_2$,
(6) —N(R$^4$)(R$^5$),
(7) -phenyl,
(8) phenyl C$_{1-3}$ alkyl-,
(9) substituted phenyl C$_{1-3}$ alkyl-substituted with 1 or 2 substituents independently selected from:
 (a) halo, wherein halo is selected from: —F, —Cl, and —Br, and
(10) —C$_{2-5}$ alkynyl-R$^3$;
R$^2$ is selected from:
(1) —H,
(2) —R$^3$,
(3) —C$_{1-6}$ alkyl,
(4) —C$_{1-6}$ alkyl substituted with R$^3$,
(5) —O—R$^6$,
(6) —O—C$_{1-6}$ alkyl-OR$^6$,
(7) —C$_{1-6}$ alkyl (OR$^6$)(R$^4$),
(8) —C$_{1-6}$ alkyl-N(R$^4$)(R$^6$),
(9) —C$_{1-6}$ alkyl C(O)—R$^6$, and
(10) —C$_{1-6}$ alkyl NR$^4$C(O)—R$^6$;
each R$^3$ is independently selected from:
(1) phenyl,
(2) substituted phenyl with 1, 2, or 3 substituents independently selected from:
 (a) halogen,
 (b) C$_{1-6}$ alkyl,
 (c) C$_{1-6}$ alkyloxy-,
 (d) phenyl,
 (e) —CF$_3$,
 (f) —OCF$_3$,
 (g) —CN,
 (h) hydroxy,
 (i) phenyloxy, and
 (j) substituted phenyloxy with 1, 2, or 3 substituents selected from:
  (i) halogen, wherein halogen is selected from —F, —Cl, and Br,
  (ii) methyl,
  (iii) —CF$_3$, and
  (iv) hydroxy,
(3) C$_{3-6}$ cycloalkyl,
(4) morpholinyl,
(5) substituted morpholinyl substituted with oxo, and
(6) naphthyl;
each R$^4$ is independently selected from:
(1) —H, and (2) —$C_{1-3}$ alkyl;
each $R^5$ is independently selected from:
(1) —H,
(2) —$C_{1-3}$ alkyl,
(3) —$CF_3$,
(4) —$R^3$,
(5) —$C_{1-3}$ alkyl-$R^3$,
(6) —$S(O)_n$—$R^3$, and
(7) —$C(O)$—$R^3$;
each $R^6$ is independently selected from:
(1) —$C_{1-3}$ alkyl-$R^3$, and
(2) —$R^3$; and
each n is independently selected from 0, 1 and 2.

8. The compound according to claim 6 of structural formula:

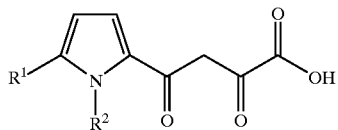

and tautomers and pharmaceutically acceptable salts thereof, wherein:
$R^1$ is selected from:
(1) —H,
(2) —$C_{1-5}$ alkyl,
(3) —$CF_3$,
(4) -halo, wherein halo is selected from: —F, Cl, —Br, and —I;
(5) —$NO_2$,
(6) —$N(R^4)(R^5)$,
(7) -phenyl,
(8) phenyl $C_{1-3}$ alkyl-,
(9) substituted phenyl $C_{1-3}$ alkyl-substituted with 1 or 2 substituents independently selected from:
(a) halo, wherein halo is selected from: —F, —Cl, and —Br, and
(10) —$C_{2-5}$ alkynyl-$R^3$;
$R^2$ is selected from:
(1) —H,
(2) —$R^3$,
(3) —$C_{1-6}$ alkyl,
(4) —$C_{1-6}$ alkyl substituted with $R^3$,
(5) —O—$R^6$,
(6) —O—$C_{1-6}$ alkyl-$OR^6$,
(7) —$C_{1-6}$ alkyl $(OR^6)(R^4)$,
(8) —$C_{1-6}$ alkyl-$N(R^4)(R^6)$,
(9) —$C_{1-6}$ alkyl $C(O)$—$R^6$, and
(10) —$C_{1-6}$ alkyl $NR^4C(O)$—$R^6$;
each $R^3$ is independently selected from:
(1) phenyl,
(2) substituted phenyl with 1, 2, or 3 substituents independently selected from:
(a) halogen,
(b) $C_{1-6}$ alkyl,
(c) $C_{1-6}$ alkyloxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
(i) halogen, wherein halogen is selected from —F, —Cl, and Br, (ii) methyl,
(iii) —$CF_3$, and
(iv) hydroxy,
(3) $C_{3-6}$ cycloalkyl,
(4) morpholinyl,
(5) substituted morpholinyl substituted with oxo, and
(6) naphthyl;
each $R^4$ is independently selected from:
(1) —H, and
(2) —$C_{1-3}$ alkyl;
each $R^5$ is independently selected from:
(1) —H,
(2) —$C_{1-3}$ alkyl,
(3) —$CF_3$,
(4) —$R^3$,
(5) —$C_{1-3}$ alkyl-$R^3$,
(6) —$S(O)_n$—$R^3$, and
(7) —$C(O)$—$R^3$,
each $R^6$ is independently selected from:
(1) —$C_{1-3}$ alkyl-$R^3$, and
(2) —$R^3$;
each n is independently selected from 0, 1 and 2.

9. The compound according to claim 1 of structural formula:

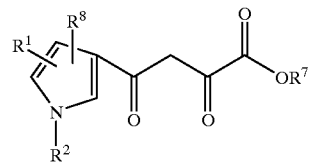

and tautomers and pharmaceutically acceptable salts thereof, wherein:
$R^1$ is selected from:
(1) —H,
(2) —$C_{1-5}$ alkyl,
(3) —$CF_3$,
(4) -halo,
(5) —$NO_2$,
(6) —$N(R^4)(R^5)$,
(7) -phenyl,
(8) substituted phenyl substituted with 1 or 2 substituents independently selected from:
(a) halo,
(b) methyl, and
(c) methoxy,
(9) phenyl $C_{1-3}$ alkyl-,
(10) substituted phenyl $C_{1-3}$ alkyl-substituted with 1 or 2 substituents independently selected from:
(a) halo,
(b) methyl, and
(c) methoxy,
(11) —$C_{2-5}$ alkenyl-$R^3$,
(12) —$C_{2-5}$ alkynyl-$R^3$, and
(13) —$C(O)CH_2C(O)C(O)OR^7$;
$R^2$ is selected from:
(1) —H,
(2) —$R^3$,
(3) —$C_{1-6}$ alkyl,
(4) —$C_{1-6}$ alkyl substituted with $R^3$,
(5) —O—$R^6$,
(6) —O—$C_{1-6}$ alkyl-$OR^6$,
(7) —$S(O)n$-$R^6$,
(8) —$C_{1-6}$ alkyl $(OR^6)(R^4)$, (9) —$C_{1-6}$ alkyl-N($R^4$)($R^6$),
(10) —$C_{1-6}$ alkyl S(O)n-$R^6$,
(11) —$C_{1-6}$ alkyl C(O)—$R^6$,
(12) —$C_{1-6}$ alkyl C(S)—$R^6$,
(13) —$C_{1-6}$ alkyl $NR^4$C(O)—$R^6$, and
(14) —$C_{1-6}$ alkyl-C(O)N($R^4$)($R^5$);

each $R^3$ is independently selected from:
(1) phenyl;
(2) substituted phenyl with 1, 2, or 3 substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(3) thienyl;
(4) substituted thienyl substituted on a carbon atom with one or two substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(9) pyrrolyl;
(10) substituted pyrrolyl substituted on a carbon atom with one or two substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(11) pyrazolyl;
(12) substituted pyrazolyl substituted on a carbon atom with one or two substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(13) $C_{3-6}$ cycloalkyl;
(14) substituted $C_{3-6}$ cycloalkyl with 1 or 2 substituents independently selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O, and
  (h) hydroxy;
(15) piperidinyl;
(16) substituted piperidinyl substituted on a carbon atom with one or two substituents independently selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O, and
  (h) hydroxy;
(17) morpholinyl;
(18) substituted morpholinyl substituted at a carbon or nitrogen atom with 1 or 2 independently selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O, and
  (h) hydroxy;
(19) naphthyl;
(20) substituted naphthyl with 1, 2, or 3 substituents independently selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O, and
  (h) hydroxy;
(21) indolyl;
(22) substituted indolyl substituted on a carbon atom with one or two substituents independently selected from:
  (a) halogen,
  (b) $C_{1-6}$ alkyl, (c) $C_{1-6}$ alkyloxy-,
(d) —$CF_3$,
(e) —$OCF_3$,
(f) —CN,
(g) =O, and
(h) hydroxy;
(23) $C_{3-6}$ cycloalkyl fused with a phenyl ring;
(24) substituted $C_{3-6}$ cycloalkyl fused with a phenyl ring substituted on a carbon atom with one or two substituents independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;
each $R^4$ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$,
(7) —$C_{2-3}$ alkenyl-$R^3$,
(8) —$S(O)_n$—$R^3$, and
(9) —C(O)—$R^3$;
each $R^5$ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$,
(7) —$C_{23}$ alkenyl-$R^3$,
(8) —$S(O)_n$—$R^3$, and
(9) —C(O)—$R^3$;
each $R^6$ is independently selected from:
(1) —$C_{1-3}$ alkyl-$R^2$, and
(2) —$R^3$;
$R^7$ is selected from:
(1) —H, and
(2) $C_{1-6}$ alkyl;
$R^8$ is selected from:
(1) —H, and
(2) $C_{1-6}$ alkyl; and
each n is independently selected from 0, 1 and 2;
and further provided that when $R^7$ is $C_{1-6}$ alkyl, then $R^2$ is not —H or —$C_{1-6}$ alkyl.

10. The compound according to claim 9 of structural formula:

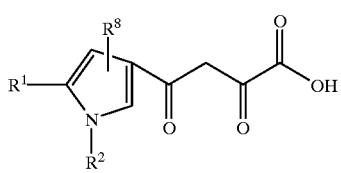

and tautomers and pharmaceutically acceptable salts thereof, wherein:
$R^1$ is selected from:
(1) —H,
(2) —$C_{1-5}$ alkyl,
(3) —$CF_3$,
(4) -halo, wherein halo is selected from: —F, Cl, —Br, and —I;
(5) —$NO_2$,
(6) —$N(R^4)(R^5)$,
(7) -phenyl,
(8) phenyl $C_{1-3}$ alkyl-,
(9) substituted phenyl $C_{1-3}$ alkyl-substituted with 1 or 2 substituents independently selected from:
(a) halo, wherein halo is selected from: —F, —Cl, and —Br, and
(10) —$C_{2-5}$ alkynyl-$R^3$;
$R^2$ is selected from:
(1) —H,
(2) —$R^3$,
(3) —$C_{1-6}$ alkyl,
(4) —$C_{1-6}$ alkyl substituted with $R^3$,
(5) —O—$R^6$,
(6) —O—$C_{1-6}$ alkyl-$OR^6$,
(7) —$C_{1-6}$ alkyl $(OR^6)(R^4)$,
(8) —$C_{1-6}$ alkyl-$N(R^4)(R^6)$,
(9) —$C_{1-6}$ alkyl C(O)—$R^6$, and
(10) —$C_{1-6}$ alkyl $NR^4C(O)$—$R^6$;
each $R^3$ is independently selected from:
(1) phenyl,
(2) substituted phenyl with 1, 2, or 3 substituents independently selected from:
(a) halogen,
(b) $C_{1-6}$ alkyl,
(c) $C_{1-6}$ alkyloxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
(i) halogen, wherein halogen is selected from —F, —Cl, and Br,
(ii) methyl,
(iii) —$CF_3$, and
(iv) hydroxy,
(3) $C_{3-6}$ cycloalkyl,
(4) morpholinyl,
(5) substituted morpholinyl substituted with oxo; and
(6) naphthyl;
each $R^4$ is independently selected from:
(1) —H, and
(2) —$C_{1-3}$ alkyl;
each $R^5$ is independently selected from:
(1) —H,
(2) —$C_{1-3}$ alkyl,
(3) —$CF_3$,
(4) —$R^3$,
(5) —$C_{1-3}$ alkyl-$R^3$,
(6) —$S(O)_n$—$R^3$, and
(7) —C(O)—$R^3$;
each $R^6$ is independently selected from:
(1) —$C_{1-3}$ alkyl-$R^3$, and
(2) —$R^3$;
$R^8$ is selected from:
(1) —H, and
(2) $CH_3$; and
each n is independently selected from 0, 1 and 2.

11. The compound according to claim 1 of structural formula:

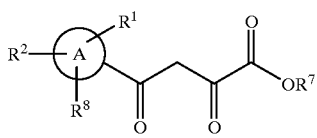 (I)

and tautomers and pharmaceutically acceptable salts thereof, wherein:

A is pyrazolyl;

$R^1$ is selected from:
(1) —H,
(2) —$C_{1-5}$ alkyl,
(3) —$CF_3$,
(4) -halo,
(5) —$NO_2$,
(6) —$N(R^4)(R^5)$,
(7) -phenyl,
(8) substituted phenyl substituted with 1 or 2 substituents independently selected from:
  (a) halo,
  (b) methyl, and
  (c) methoxy,
(9) phenyl $C_{1-3}$ alkyl-,
(10) substituted phenyl $C_{1-3}$ alkyl-substituted with 1 or 2 substituents independently selected from:
  (a) halo,
  (b) methyl, and
  (c) methoxy,
(11) —$C_{2-5}$ alkenyl-$R^3$,
(12) —$C_{2-5}$ alkynyl-$R^3$, and
(13) —$C(O)CH_2C(O)C(O)OR^7$;

$R^2$ is selected from:
(1) —H,
(2) —$R^3$,
(3) —$C_{1-6}$ alkyl,
(4) —$C_{1-6}$ alkyl substituted with $R^3$,
(5) —O—$R^6$,
(6) —O—$C_{1-6}$ alkyl-$OR^6$,
(7) —$S(O)n$-$R^6$,
(8) —$C_{1-6}$ alkyl $(OR^6)(R^4)$,
(9) —$C_{1-6}$ alkyl-$N(R^4)(R^6)$,
(10) —$C_{1-6}$ alkyl $S(O)n$-$R^6$,
(11) —$C_{1-6}$ alkyl $C(O)$—$R^6$,
(12) —$C_{1-6}$ alkyl $C(S)$—$R^6$,
(13) —$C_{1-6}$ alkyl $NR^4C(O)$—$R^6$, and
(14) —$C_{1-6}$ alkyl-$C(O)N(R^4)(R^5)$;

each $R^3$ is independently selected from:
(1) phenyl;
(2) substituted phenyl with 1, 2, or 3 substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(3) thienyl;
(4) substituted thienyl substituted on a carbon atom with one or two substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(5) pyridyl;
(6) substituted pyridyl substituted on a carbon atom with one or two substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(7) imidazolyl;
(8) substituted imidazolyl substituted on a carbon atom with one or two substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(9) pyrrolyl;
(10) substituted pyrrolyl substituted on a carbon atom with one or two substituents independently selected from:
  (a) halogen,
  (b) $C_{1-6}$ alkyl,
  (c) $C_{1-6}$ alkyloxy-,
  (d) phenyl,
  (e) —$CF_3$, (f) —OCF$_3$,
(g) —CN,
(h) hydroxy,
(i) phenyloxy, and
(j) substituted phenyloxy with 1, 2, or 3 substituents selected from:
  (i) halogen,
  (ii) C$_{1-6}$ alkyl,
  (iii) —CF$_3$, and
  (iv) hydroxy;

(11) pyrazolyl;
(12) substituted pyrazolyl substituted on a carbon atom with one or two substituents independently selected from:
  (a) halogen,
  (b) C$_{1-6}$ alkyl,
  (c) C$_{1-6}$ alkyloxy-,
  (d) phenyl,
  (e) —CF$_3$,
  (f) —OCF$_3$,
  (g) —CN,
  (h) hydroxy,
  (i) phenyloxy, and
  (j) substituted phenyloxy with 1, 2, or 3 substituents selected from:
    (i) halogen,
    (ii) C$_{1-6}$ alkyl,
    (iii) —CF$_3$, and
    (iv) hydroxy;

(13) C$_{3-6}$ cycloalkyl;
(14) substituted C$_{3-6}$ cycloalkyl with 1 or 2 substituents independently selected from:
  (a) halogen,
  (b) C$_{1-6}$ alkyl,
  (c) C$_{1-6}$ alkyloxy-,
  (d) —CF$_3$,
  (e) —OCF$_3$,
  (f) —CN,
  (g) =O, and
  (h) hydroxy;

(15) piperidinyl;
(16) substituted piperidinyl substituted on a carbon atom with one or two substituents independently selected from:
  (a) halogen,
  (b) C$_{1-6}$ alkyl,
  (c) C$_{1-6}$ alkyloxy-,
  (d) —CF$_3$,
  (e) —OCF$_3$,
  (f) —CN,
  (g) =O, and
  (h) hydroxy;

(17) morpholinyl;
(18) substituted morpholinyl substituted at a carbon or nitrogen atom with 1 or 2 independently selected from:
  (a) halogen,
  (b) C$_{1-6}$ alkyl,
  (c) C$_{1-6}$ alkyloxy-,
  (d) —CF$_3$,
  (e) —OCF$_3$,
  (f) —CN,
  (g) =O, and
  (h) hydroxy;

(19) naphthyl;
(20) substituted naphthyl with 1, 2, or 3 substituents independently selected from:
  (a) halogen,
  (b) C$_{1-6}$ alkyl,
  (c) C$_{1-6}$ alkyloxy-,
  (d) —CF$_3$,
  (e) —OCF$_3$,
  (f) —CN,
  (g) =O, and
  (h) hydroxy;

(21) indolyl;
(22) substituted indolyl substituted on a carbon atom with one or two substituents independently selected from:
  (a) halogen,
  (b) C$_{1-6}$ alkyl,
  (c) C$_{1-6}$ alkyloxy-,
  (d) —CF$_3$,
  (e) —OCF$_3$,
  (f) —CN,
  (g) =O, and
  (h) hydroxy;

(23) C$_{3-6}$ cycloalkyl fused with a phenyl ring;
(24) substituted C$_{3-6}$ cycloalkyl fused with a phenyl ring substituted on a carbon atom with one or two substituents independently selected from:
  (a) halogen,
  (b) C$_{1-6}$ alkyl,
  (c) C$_{1-6}$ alkyloxy-,
  (d) —CF$_3$,
  (e) —OCF$_3$,
  (f) —CN,
  (g) =O, and
  (h) hydroxy;

each R$^4$ is independently selected from:
  (1) —H,
  (2) —C$_{1-3}$ alkyl,
  (3) —CF$_3$,
  (4) —R$^3$,
  (5) —C$_{2-3}$ alkenyl,
  (6) —C$_{1-3}$ alkyl-R$^3$,
  (7) —C$_{2-3}$ alkenyl-R$^3$,
  (8) —S(O)$_n$—R$^3$, and
  (9) —C(O)—R$^3$;

each R$^5$ is independently selected from:
  (1) —H,
  (2) —C$_{1-3}$ alkyl,
  (3) —CF$_3$,
  (4) —R$^3$,
  (5) —C$_{2-3}$ alkenyl,
  (6) —C$_{1-3}$ alkyl-R$^3$,
  (7) —C$_{2-3}$ alkenyl-R$^3$,
  (8) —S(O)$_n$—R$^3$, and
  (9) —C(O)—R$^3$;

each R$^6$ is independently selected from:
  (1) —C$_{1-3}$ alkyl-R$^3$, and
  (2) —R$^3$;

R$^7$ is selected from:
  (1) —H, and
  (2) C$_{1-6}$ alkyl;

R$^8$ is selected from:
  (1) —H, and
  (2) C$_{1-6}$ alkyl; and each n is independently selected from 0, 1 and 2;
and further provided that when R$^7$ is C$_{1-6}$ alkyl, then R$^2$ is not —H or —C$_{1-6}$ alkyl.

12. The compound according to claim 11 wherein:
R$^1$ is selected from:

(1) —H,
(2) —C$_{1-5}$ alkyl,
(3) —CF$_3$,
(4) -halo, wherein halo is selected from: —F, Cl, —Br, and —I;
(5) —NO$_2$,
(6) —N(R$^4$)(R$^5$),
(7) -phenyl,
(8) phenyl C$_{1-3}$ alkyl-,
(9) substituted phenyl C$_{1-3}$ alkyl-substituted with 1 or 2 substituents independently selected from:
  (a) halo, wherein halo is selected from: —F, —Cl, and —Br, and
(10) —C$_{2-5}$ alkynyl-R$^3$;
R$^2$ is selected from:
(1) —H,
(2) —R$^3$,
(3) —C$_{1-6}$ alkyl,
(4) —C$_{1-6}$ alkyl substituted with R$^3$,
(5) —O—R$^6$,
(6) —O—C$_{1-6}$ alkyl-OR$^6$,
(7) —C$_{1-6}$ alkyl (OR$^6$)(R$^4$),
(8) —C$_{1-6}$ alkyl-N(R$^4$)(R$^6$),
(9) —C$_{1-6}$ alkyl C(O)—R$^6$, and
(10) —C$_{1-6}$ alkyl NR$^4$C(O)—R$^6$;
each R$^3$ is independently selected from:
(1) phenyl,
(2) substituted phenyl with 1, 2, or 3 substituents independently selected from:
  (a) halogen,
  (b) C$_{1-6}$ alkyl,
  (c) C$_{1-6}$ alkyloxy-,
  (d) phenyl,
  (e) —CF$_3$,
  (f) —OCF$_3$,
  (g) —CN,
  (h) hydroxy,
  (i) phenyloxy, and
  (j) substituted phenyloxy with 1, 2, or 3 substituents selected from:
    (i) halogen, wherein halogen is selected from —F, -Cl, and Br,
    (ii) methyl,
    (iii) —CF$_3$, and
    (iv) hydroxy,
(3) C$_{3-6}$ cycloalkyl,
(4) morpholinyl,
(5) substituted morpholinyl substituted with oxo, and
(6) naphthyl;
each R$^4$ is independently selected from:
(1) —H, and
(2) —C$_{1-3}$ alkyl;
each R$^5$ is independently selected from:
(1) —H,
(2) —C$_{1-3}$ alkyl,
(3) —CF$_3$,
(4) —R$^3$,
(5) —C$_{1-3}$ alkyl-R$^3$,
(6) —S(O)$_n$—R$^3$, and
(7) —C(O)—R$^3$;
each R$^6$ is independently selected from:
(1) —C$_{1-3}$ alkyl-R$^3$, and
(2) —R$^3$;
each R$^7$ is independently selected from:
(1) —H,
(2) —CH$_2$CH$_3$, and
(3) —CH$_3$; and
R$^8$ is selected from:
(1) —H, and
(2) —CH$_3$; and
each n is independently selected from 0, 1 and 2;
and further provided that when R$^7$ is —CH$_2$CH$_3$ or —CHCH$_3$, then R$^2$ is not —H or —C$_{1-6}$ alkyl;
and tautomers and pharmaceutically acceptable salts thereof.

13. The compound according to claim 12 of structural formula:

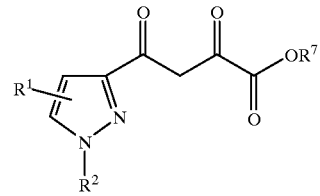

and tautomers and pharmaceutically acceptable salts thereof.

14. The compound according to claim 12 of structural formula:

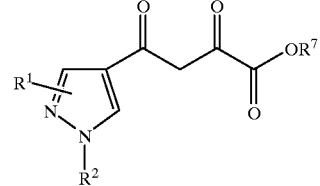

and tautomers and pharmaceutically acceptable salts thereof.

15. The compound according to claim 1 of structural formula:

(I)

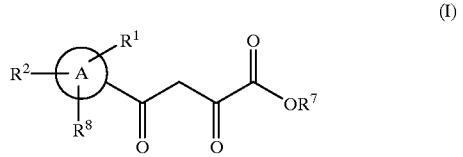

and tautomers and pharmaceutically acceptable salts thereof, wherein:
A is imidazolyl;
R$^1$ is selected from:
(1) —H,
(2) —C$_{1-5}$ alkyl,
(3) —CF$_3$,
(4) -halo,
(5) —NO$_2$,
(6) —N(R$^4$)(R$^5$),
(7) -phenyl,
(8) substituted phenyl substituted with 1 or 2 substituents independently selected from:
  (a) halo,
  (b) methyl, and
  (c) methoxy,
(9) phenyl C$_{1-3}$ alkyl-,
(10) substituted phenyl C$_{1-3}$ alkyl-substituted with 1 or 2 substituents independently selected from:
  (a) halo,
  (b) methyl, and
  (c) methoxy,

(11) —$C_{2-5}$ alkenyl-$R^3$,
(12) —$C_{2-5}$ alkynyl-$R^3$, and
(13) —$C(O)CH_2C(O)C(O)OR^7$;

$R^2$ is selected from:
(1) —H,
(2) —$R^3$,
(3) —$C_{1-6}$ alkyl,
(4) —$C_{1-6}$ alkyl substituted with $R^3$,
(5) —O—$R^6$,
(6) —O—$C_{1-6}$ alkyl-$OR^6$,
(7) —$S(O)n-R^6$,
(8) —$C_{1-6}$ alkyl $(OR^6)(R^4)$,
(9) —$C_{1-6}$ alkyl-$N(R^4)(R^6)$,
(10) —$C_{1-6}$ alkyl $S(O)n-R^6$,
(11) —$C_{1-6}$ alkyl $C(O)$—$R^6$,
(12) —$C_{1-6}$ alkyl $C(S)$—$R^6$,
(13) —$C_{1-6}$ alkyl $NR^4C(O)$—$R^6$, and
(14) —$C_{1-6}$ alkyl-$C(O)N(R^4)(R^5)$;

each $R^3$ is independently selected from:
(1) phenyl;
(2) substituted phenyl with 1, 2, or 3 substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(3) thienyl;
(4) substituted thienyl substituted on a carbon atom with one or two substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(5) pyridyl;
(6) substituted pyridyl substituted on a carbon atom with one or two substituents independently selected from:
  (a) halogen,
  (b) $C_{1-6}$alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(7) imidazolyl;
(8) substituted imidazolyl substituted on a carbon atom with one or two substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(9) pyrrolyl;
(10) substituted pyrrolyl substituted on a carbon atom with one or two substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(11) pyrazolyl
(12) substituted pyrazolyl substituted on a carbon atom with one or two substituents independently selected from:
  (a) halogen,
  (b) $C_{1-6}$alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(13) $C_{3-6}$ cycloalkyl;
(14) substituted $C_{3-6}$ cycloalkyl with 1 or 2 substituents independently selected from:

(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;
(15) piperidinyl;
(16) substituted piperidinyl substituted on a carbon atom with one or two substituents independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;
(17) morpholinyl,
(18) substituted moipholinyl substituted at a carbon or nitrogen atom with 1 or 2 independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;
(19) naphthyl;
(20) substituted naphthyl with 1, 2, or 3 substituents independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;
(21) indolyl;
(22) substituted indolyl substituted on a carbon atom with one or two substituents independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;
(23) $C_{3-6}$ cycloalkyl fused with a phenyl ring;
(24) substituted $C_{3-6}$ cycloalkyl fused with a phenyl ring substituted on a carbon atom with one or two substituents independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;

each $R^4$ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$,
(7) —$C_{2-3}$ alkenyl-$R^3$,
(8) —$S(O)_n$—$R^3$, and
(9) —C(O)—$R^3$;
each $R^5$ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$,
(7) —$C_{2-3}$ alkenyl-$R^3$,
(8) —$S(O)_n$—$R^3$, and
(9) —C(O)—$R^3$;
each $R^6$ is independently selected from:
(1) —$C_{1-3}$ alkyl-$R^3$, and
(2) —$R^3$;
$R^7$ is selected from:
(1) —H, and
(2) $C_{1-6}$ alkyl;
$R^8$ is selected from:
(1) —H, and
(2) $C_{1-6}$ alkyl; and
each n is independently selected from 0, 1 and 2;
and further provided that when $R^7$ is $C_{1-6}$ alkyl, then $R^2$ is not —H or —$C_{1-6}$ alkyl.

16. The compound according to claim 15 of structural formula:

and tautomers and pharmaceutically acceptable salts thereof, wherein:
$R^1$ is selected from:
(1) —H,
(2) —$C_{1-5}$ alkyl,
(3) —$CF_3$,
(4) -halo, wherein halo is selected from: —F, Cl, —Br, and —I;
(5) —$NO_2$,
(6) —$N(R^4)(R^5)$,
(7) -phenyl,
(8) phenyl $C_{1-3}$ alkyl-,
(9) substituted phenyl $C_{1-3}$ alkyl-substituted with 1 or 2 substituents independently selected from:
(a) halo, wherein halo is selected from: —F, —Cl, and —Br, and
(10) —$C_{2-5}$ alkynyl-$R^3$;
$R^2$ is selected from:
(1) —H,
(2) —$R^3$,
(3) —$C_{1-6}$ alkyl,
(4) —$C_{1-6}$ alkyl substituted with $R^3$,
(5) —O—$R^6$, (6) —O—$C_{1-6}$ alkyl-$OR^6$,
(7) —$C_{1-6}$ alkyl $(OR^6)(R^4)$,
(8) —$C_{1-6}$ alkyl-$N(R^4)(R^6)$,
(9) —$C_{1-6}$ alkyl C(O)—$R^6$, and
(10) —$C_{1-6}$ alkyl $NR^4C(O)$—$R^6$;

each $R^3$ is independently selected from:
(1) phenyl,
(2) substituted phenyl with 1, 2, or 3 substituents independently selected from:
 (a) halogen,
 (b) $C_{1-6}$ alkyl,
 (c) $C_{1-6}$ alkyloxy-,
 (d) phenyl,
 (e) —$CF_3$,
 (f) —$OCF_3$,
 (g) —CN,
 (h) hydroxy,
 (i) phenyloxy, and
 (j) substituted phenyloxy with 1, 2, or 3 substituents selected from:
  (i) halogen, wherein halogen is selected from —F, —Cl, and Br,
  (ii) methyl,
  (iii) —$CF_3$, and
  (iv) hydroxy,
(3) $C_{3-6}$ cycloalkyl,
(4) morpholinyl,
(5) substituted morpholinyl substituted with oxo, and
(6) naphthyl;

each $R^4$ is independently selected from:
(1) —H, and
(2) —$C_{1-3}$ alkyl;

each $R^5$ is independently selected from:
(1) —H,
(2) —$C_{1-3}$ alkyl,
(3) —$CF_3$,
(4) —$R^3$,
(5) —$C_{1-3}$ alkyl-$R^3$,
(6) —$S(O)_n$—$R^3$, and
(7) —C(O)—$R^3$;

each $R^6$ is independently selected from:
(1) —$C_{1-3}$ alkyl-$R^3$, and
(2) —$R^3$; and each n is independently selected from 0, 1 and 2.

17. The compound according to claim 1 of structural formula:

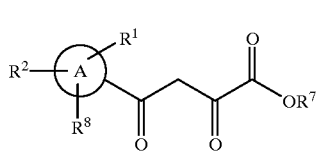

(I)

and tautomers and pharmaceutically acceptable salts thereof, wherein:
A is indolyl and the dioxobutyric acid/ester moeity is attached to the nitrogen containing ring of the indole;
$R^1$ is selected from:
(1) —H,
(2) —$C_{1-5}$ alkyl,
(3) —$CF_3$,
(4) -halo,
(5) —$NO_2$,
(6) —$N(R^4)(R^5)$,
(7) -phenyl,
(8) substituted phenyl substituted with 1 or 2 substituents independently selected from:
 (a) halo,
 (b) methyl, and
 (c) methoxy,
(9) phenyl $C_{1-3}$ alkyl-,
(10) substituted phenyl $C_{1-3}$ alkyl-substituted with 1 or 2 substituents independently selected from:
 (a) halo,
 (b) methyl, and
 (c) methoxy,
(11) —$C_{2-5}$ alkenyl-$R^3$,
(12) —$C_{2-5}$ alkynyl-$R^3$, and
(13) —$C(O)CH_2C(O)C(O)OR^7$;

$R^2$ is selected from:
(1) —H,
(2) —$R^3$,
(3) —$C_{1-6}$ alkyl,
(4) —$C_{1-6}$ alkyl substituted with $R^3$,
(5) —O—$R^6$,
(6) —O—$C_{1-6}$ alkyl-$OR^6$,
(7) —$S(O)n$-$R^6$,
(8) —$C_{1-6}$ alkyl $(OR^6)(R^4)$,
(9) —$C_{1-6}$ alkyl-$N(R^4)(R^6)$,
(10) —$C_{1-6}$ alkyl $S(O)n$-$R^6$,
(11) —$C_{1-6}$ alkyl C(O)—$R^6$,
(12) —$C_{1-6}$ alkyl C(S)—$R^6$,
(13) —$C_{1-6}$ alkyl $NR^4C(O)$—$R^6$, and
(14) —$C_{1-6}$ alkyl-$C(O)N(R^4)(R^5)$;

each $R^3$ is independently selected from:
(1) phenyl;
(2) substituted phenyl with 1, 2, or 3 substituents independently selected from:
 (a) halogen,
 (b) $C_{1-6}$ alkyl,
 (c) $C_{1-6}$ alkyloxy-,
 (d) phenyl,
 (e) —$CF_3$,
 (f) —$OCF_3$,
 (g) —CN,
 (h) hydroxy,
 (i) phenyloxy, and
 (j) substituted phenyloxy with 1, 2, or 3 substituents selected from:
  (i) halogen,
  (ii) $C_{1-6}$ alkyl,
  (iii) —$CF_3$, and
  (iv) hydroxy;
(3) thienyl;
(4) substituted thienyl substituted on a carbon atom with one or two substituents independently selected from:
 (a) halogen,
 (b) $C_{1-6}$ alkyl,
 (c) $C_{1-6}$ alkyloxy-,
 (d) phenyl,
 (e) —$CF_3$,
 (f) —$OCF_3$,
 (g) —CN,
 (h) hydroxy,
 (i) phenyloxy, and
 (j) substituted phenyloxy with 1, 2, or 3 substituents selected from:
  (i) halogen,
  (ii) $C_{1-6}$ alkyl,
  (iii) —$CF_3$, and (iv) hydroxy;
(5) pyridyl;
(6) substituted pyridyl substituted on a carbon atom with one or two substituents independently selected from:
 (a) halogen,
 (b) $C_{1-6}$ alkyl,
 (c) $C_{1-6}$ alkyloxy-,
 (d) phenyl,
 (e) —$CF_3$,
 (f) —$OCF_3$,
 (g) —CN,
 (h) hydroxy,
 (i) phenyloxy, and
 (j) substituted phenyloxy with 1, 2, or 3 substituents selected from:
  (i) halogen,
  (ii) $C_{1-6}$ alkyl,
  (iii) —$CF_3$, and
  (iv) hydroxy;
(7) imidazolyl;
(8) substituted imidazolyl substituted on a carbon atom with one or two substituents independently selected from:
 (a) halogen,
 (b) $C_{1-6}$ alkyl,
 (c) $C_{1-6}$ alkyloxy-,
 (d) phenyl,
 (e) —$CF_3$,
 (f) —$OCF_3$,
 (g) —CN,
 (h) hydroxy,
 (i) phenyloxy, and
 (j) substituted phenyloxy with 1, 2, or 3 substituents selected from:
  (i) halogen,
  (ii) $C_{1-6}$ alkyl,
  (iii) —$CF_3$, and
  (iv) hydroxy;
(9) pyrrolyl;
(10) substituted pyrrolyl substituted on a carbon atom with one or two substituents independently selected from:
 (a) halogen,
 (b) $C_{1-6}$ alkyl,
 (c) $C_{1-6}$ alkyloxy-,
 (d) phenyl,
 (e) —$CF_3$,
 (f) —$OCF_3$,
 (g) —CN,
 (h) hydroxy,
 (i) phenyloxy, and
 (j) substituted phenyloxy with 1, 2, or 3 substituents selected from:
  (i) halogen,
  (ii) $C_{1-6}$ alkyl,
  (iii) —$CF_3$, and
  (iv) hydroxy;
(11) pyrazolyl;
(12) substituted pyrazolyl substituted on a carbon atom with one or two substituents independently selected from:
 (a) halogen,
 (b) $C_{1-6}$ alkyl,
 (c) $C_{1-6}$ alkyloxy-,
 (d) phenyl,
 (e) —$CF_3$,
 (f) —$OCF_3$,
 (g) —CN,
 (h) hydroxy,
 (i) phenyloxy, and
 (j) substituted phenyloxy with 1, 2, or 3 substituents selected from:
  (i) halogen,
  (ii) $C_{1-6}$ alkyl,
  (iii) —$CF_3$, and
  (iv) hydroxy;
(13) $C_{3-6}$ cycloalkyl,
(14) substituted $C_{3-6}$ cycloalkyl with 1 or 2 substituents independently selected from:
 (a) halogen,
 (b) $C_{1-6}$ alkyl,
 (c) $C_{1-6}$ alkyloxy-,
 (d) —$CF_3$,
 (e) —$OCF_3$,
 (f) —CN,
 (g) =O, and
 (h) hydroxy;
(15) piperidinyl;
(16) substituted piperidinyl substituted on a carbon atom with one or two substituents independently selected from:
 (a) halogen,
 (b) $C_{1-6}$ alkyl,
 (c) $C_{1-6}$ alkyloxy-,
 (d) —$CF_3$,
 (e) —$OCF_3$,
 (f) —CN,
 (g) =O, and
 (h) hydroxy;
(17) morpholinyl,
(18) substituted morpholinyl substituted at a carbon or nitrogen atom with 1 or 2 independently selected from:
 (a) halogen,
 (b) $C_{1-6}$ alkyl,
 (c) $C_{1-6}$ alkyloxy-,
 (d) —$CF_3$,
 (e) —$OCF_3$,
 (f) —CN,
 (g) =O, and
 (h) hydroxy;
(19) naphthyl;
(20) substituted naphthyl with 1, 2, or 3 substituents independently selected from:
 (a) halogen,
 (b) $C_{1-6}$ alkyl,
 (c) $C_{1-6}$ alkyloxy-,
 (d) —$CF_3$,
 (e) —$OCF_3$,
 (f) —CN,
 (g) =O, and
 (h) hydroxy;
(21) indolyl;
(22) substituted indolyl substituted on a carbon atom with one or two substituents independently selected from:
 (a) halogen,
 (b) $C_{1-6}$ alkyl,
 (c) $C_{1-6}$ alkyloxy-,
 (d) —$CF_3$,
 (e) —$OCF_3$,
 (f) —CN,
 (g) =O, and (h) hydroxy;
(23) $C_{3-6}$ cycloalkyl fused with a phenyl ring;
(24) substituted $C_{3-6}$ cycloalkyl fused with a phenyl ring substituted on a carbon atom with one or two substituents independently selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O, and
  (h) hydroxy;
each $R^4$ is independently selected from:
  (1) —H,
  (2) —$C_{1-3}$ alkyl,
  (3) —$CF_3$,
  (4) —$R^3$,
  (5) —$C_{2-3}$ alkenyl,
  (6) —$C_{1-3}$ alkyl-$R^3$,
  (7) —$C_{2-3}$ alkenyl-$R^3$,
  (8) —$S(O)_n$—$R^3$, and
  (9) —$C(O)$—$R^3$;
each $R^5$ is independently selected from:
  (1) —H,
  (2) —$C_{1-3}$ alkyl,
  (3) —$CF_3$,
  (4) —$R^3$,
  (5) —$C_{2-3}$ alkenyl,
  (6) —$C_{1-3}$ alkyl-$R^3$,
  (7) —$C_{2-3}$ alkenyl-$R^3$,
  (8) —$S(O)_n$—$R^3$, and
  (9) —$C(O)$—$R^3$;
each $R^6$ is independently selected from:
  (1) —$C_{1-3}$ alkyl-$R^3$, and
  (2) —$R^3$;
$R^7$ is selected from:
  (1) —H, and
  (2) $C_{1-6}$ alkyl;
$R^8$ is selected from:
  (1) —H, and
  (2) $C_{1-6}$ alkyl; and
each n is independently selected from 0, 1 and 2;
and further provided that when $R^7$ is $C_{1-6}$ alkyl, then $R^2$ is not —H or —$C_{1-6}$ alkyl.

18. The compound according to claim 17 of structural formula:

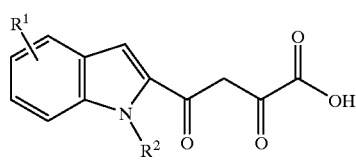

or a tautomer or a pharmaceutically acceptable salt thereof, wherein:
$R^1$ is selected from:
  (1) —H,
  (2) —$C_{1-5}$ alkyl,
  (3) —$CF_3$,
  (4) -halo, wherein halo is selected from: —F, Cl, —Br, and —I;
  (5) —$NO_2$,
  (6) —$N(R^4)(R^5)$,
  (7) -phenyl,
  (8) phenyl $C_{1-3}$ alkyl-,
  (9) substituted phenyl $C_{1-3}$ alkyl-substituted with 1 or 2 substituents independently selected from:
    (a) halo, wherein halo is selected from: —F, —Cl, and —Br, and
  (10) —$C_{2-5}$ alkynyl-$R^3$;
$R^2$ is selected from:
  (1) —H,
  (2) —$R^3$,
  (3) —$C_{1-6}$ alkyl,
  (4) —$C_{1-6}$ alkyl substituted with $R^3$,
  (5) —O—$R^6$,
  (6) —O—$C_{1-6}$ alkyl-$OR^6$,
  (7) —$C_{1-6}$ alkyl $(OR^6)(R^4)$,
  (8) —$C_{1-6}$ alkyl-$N(R^4)(R^6)$
  (9) —$C_{1-6}$ alkyl $C(O)$—$R^6$, and
  (10) —$C_{1-6}$ alkyl $NR^4C(O)$—$R^6$;
each $R^3$ is independently selected from:
  (1) phenyl,
  (2) substituted phenyl with 1, 2, or 3 substituents independently selected from:
    (a) halogen,
    (b) $C_{1-6}$ alkyl,
    (c) $C_{1-6}$ alkyloxy-,
    (d) phenyl,
    (e) —$CF_3$,
    (f) —$OCF_3$,
    (g) —CN,
    (h) hydroxy,
    (i) phenyloxy, and
    (j) substituted phenyloxy with 1, 2, or 3 substituents selected from:
      (i) halogen, wherein halogen is selected from —F, —Cl, and Br,
      (ii) methyl,
      (iii) —$CF_3$, and
      (iv) hydroxy,
  (3) $C_{3-6}$ cycloalkyl,
  (4) morpholinyl,
  (5) substituted morpholinyl substituted with oxo, and
  (6) naphthyl;
each $R^4$ is independently selected from:
  (1) —H, and
  (2) —$C_{1-3}$ alkyl;
each $R^5$ is independently selected from:
  (1) —H,
  (2) —$C_{1-3}$ alkyl,
  (3) —$CF_3$,
  (4) —$R^3$,
  (5) —$C_{1-3}$ alkyl-$R^3$,
  (6) —$S(O)_n$—$R^3$, and
  (7) —$C(O)$—$R^3$;
each $R^6$ is independently selected from:
  (1) —$C_{1-3}$ alkyl-$R^3$, and
  (2) —$R^3$; and
each n is independently selected from 0, 1 and 2.

19. The compound according to claim 17 of structural formula:

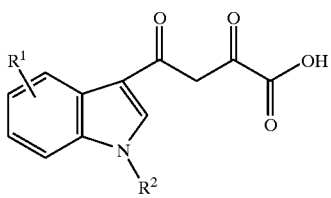

or a tautomer or a pharmaceutically acceptable salt thereof, wherein:

$R^1$ is selected from:
(1) —H,
(2) —$C_{1-5}$ alkyl,
(3) —$CF_3$,
(4) -halo, wherein halo is selected from: —F, Cl, —Br, and —I,
(5) —$NO_2$,
(6) —$N(R^4)(R^5)$,
(7) -phenyl,
(8) phenyl $C_{1-3}$ alkyl-,
(9) substituted phenyl $C_{1-3}$ alkyl-substituted with 1 or 2 substituents independently selected from:
  (a) halo, wherein halo is selected from: —F, —Cl, and —Br, and
(10) —$C_{2-5}$ alkynyl-$R^3$;

$R^2$ is selected from:
(1) —H,
(2) —$R^3$,
(3) —$C_{1-6}$ alkyl,
(4) —$C_{1-6}$ alkyl substituted with $R^3$,
(5) —O—$R^6$,
(6) —O—$C_{1-6}$ alkyl-$OR^6$,
(7) —$C_{1-6}$ alkyl $(OR^6)(R^4)$,
(8) —$C_{1-6}$ alkyl-$N(R^4)(R^6)$,
(9) —$C_{1-6}$ alkyl C(O)—$R^6$, and
(10) —$C_{1-6}$ alkyl $NR^4C(O)$—$R^6$;

each $R^3$ is independently selected from:
(1) phenyl,
(2) substituted phenyl with 1, 2, or 3 substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen, wherein halogen is selected from —F, —Cl, and Br,
    (ii) methyl,
    (iii) —$CF_3$, and
    (iv) hydroxy,
(3) $C_{3-6}$ cycloalkyl,
(4) morpholinyl,
(5) substituted morpholinyl substituted with oxo, and
(6) naphthyl;

each $R^4$ is independently selected from:
(1) —H, and
(2) —$C_{1-3}$ alkyl;

each $R^5$ is independently selected from:
(1) —H,
(2) —$C_{1-3}$ alkyl,
(3) —$CF_3$,
(4) —$R^3$,
(5) —$C_{1-3}$ alkyl-$R^3$,
(6) —$S(O)_n$—$R^3$, and
(7) —$C(O)$—$R^3$;

each $R^6$ is independently selected from:
(1) —$C_{1-3}$ alkyl-$R^3$, and
(2) —$R^3$; and each n is independently selected from 0, 1 and 2.

20. The compound according to claim 1 selected from:
(1) 4-[1-(4-fluorobenzyl)-1H-pyrrol-2-yl]-2,4-dioxobutyric acid methyl ester,
(2) 4-[1-(4-fluorobenzyl)-1H-pyrrol-2-yl]-2,4-dioxobutyric acid,
(3) 4-[1-(4-methylbenzyl)-1-H-pyrrol-2-yl]-2,4-dioxobutyric acid ethyl ester,
(4) 4-[1-(4-methylbenzyl)-1-H-pyrrol-2-yl]-2,4-dioxobutyric acid,
(5) 4-[1-(4-fluorobenzyl)-1-H-pyrrol-2-yl]-2,4-dioxobutyric acid ethyl ester,
(6) 4-[1-(4-fluorobenzyl)-1H-pyrrol-2-yl]-2,4-dioxobutyric acid isopropyl ester,
(7) 4-[1-(4-fluorobenzyl)-1H-pyrrol-2-yl]-2,4-dioxobutyric acid n-butyl ester,
(8) 4-(1-benzyl-1H-pyrrol-2-yl)-2,4-dioxobutyric acid, 2
(9) 4-(1-naphthalen-2-ylmethyl-1H-pyrrol-2-yl)-2,4-dioxobutyric acid,
(10) 4-(1-biphenyl-4-ylmethyl-1H-pyrrol-2-yl)-2,4-dioxobutyric acid,
(11) 4-(1-naphthalen-1-ylmethyl-1H-pyrrol-2-yl)-2,4-dioxobutyric acid,
(12) 2,4-dioxo-4-[1-(4-phenylbutyl)-1H-pyrrol-2-yl]-butyric acid,
(13) 4-[1-(4-chlorobenzyl)-1H-pyrrol-2-yl]-2,4-dioxobutyric acid,
(14) 2,4-dioxo-4-(1-phenethyl-1H-pyrrol-2-yl)-butyric acid,
(15) 4-[1-(2-methylbenzyl)-1H-pyrrol-2-yl]-2,4-dioxobutyric acid,
(16) 4-[1-(3,4-difluorobenzyl)-1H-pyrrol-2-yl]-2,4-dioxobutyric acid,
(17) 4-[1-(4-bromobenzyl)-1H-pyrrol-2-yl]-2,4-dioxobutyric acid,
(18) 4-[1-(2-bromobenzyl)-1H-pyrrol-2-yl]-2,4-dioxobutyric acid,
(19) 4-[1-(3-bromobenzyl)-1H-pyrrol-2-yl]-2,4-dioxobutyric acid,
(20) 4-[1-(3-chlorobenzyl)-1H-pyrrol-2-yl]-2,4-dioxobutyric acid,
(21) 4-[1-(3-methylbenzyl)-1H-pyrrol-2-yl]-2,4-dioxobutyric acid,
(22) 4-[1-(2-fluorobenzyl)-1H-pyrrol-2-yl]-2,4-dioxobutyric acid,
(23) 2,4-dioxo-4-(1-hexyl-1H-pyrrol-2-yl)-butyric acid,
(24) 4-(1-biphenyl-2-ylmethyl-1H-pyrrol-2-yl)-2,4-dioxobutyric acid,
(25) 2,4-dioxo-4-[1-(4-phenoxybutyl)-1H-pyrrol-2-yl]-butyric acid,
(26) 4-[1-(3-fluorobenzyl)-1H-pyrrol-2-yl]-2,4-dioxobutyric acid,
(27) 4-[1-(2-chlorobenzyl)-1H-pyrrol-2-yl]-2,4-dioxobutyric acid,

(28) 4-[1-(4-fluorobenzyl)-4-iodo-1H-pyrrol-2-yl]-2,4-dioxo-butyric acid,
(29) 4-[1-(4-methoxybenzyl)-1H-pyrrol-2-yl]-2,4-dioxobutyric acid,
(30) 4-[1-(2,4,5-trifluorobenzyl)-1H-pyrrol-2-yl]-2,4-dioxobutyric acid,
(31) 4-[1-(2,3-difluorobenzyl)-1H-pyrrol-2-yl]-2,4-dioxobutyric acid,
(32) 4-[1-(3,5-difluorobenzyl)-1H-pyrrol-2-yl]-2,4-dioxobutyric acid,
(33) 4-[1-(2,5-difluorobenzyl)-1H-pyrrol-2-yl]-2,4-dioxobutyric acid,
(34) 4-[1-(2,5,6-difluorobenzyl)-1H-pyrrol-2-yl]-2,4-dioxobutyric acid,
(35) 4-[1-(2-fluorobenzyl)-1H-pyrrol-2-yl]-2,4-dioxobutyric acid,
(36) 4-[1-(4-trifluoromethylbenzyl)-1H-pyrrol-2-yl]-2,4-dioxobutyric acid,
(37) 4-[1-(4-cyanobenzyl)-1H-pyrrol-2-yl]-2,4-dioxobutyric acid,
(38) 4-[1-(3-methoxybenzyl)-1H-pyrrol-2-yl]-2,4-dioxobutyric acid,
(39) 2-hydroxy-4-[1-(4-hydroxybenzyl)-1H-pyrrol-2-yl]-2,4-dioxobutyric acid,
(40) 4-(1-cyclopentylmethyl-1H-pyrrol-2-yl)-2,4-dioxobutyric acid,
(41) 4-{1-[3-(4-fluorophenyl)propyl]-1H-pyrrol-2-yl}-2,4-dioxobutyric acid,
(42) 4-{1-[2-(4-fluorophenyl)ethyl]-1H-pyrrol-2-yl}-2,4-dioxobutyric acid,
(43) 4-[1-(3-phenylpropyl)-1H-pyrrol-2-yl]-2,4-dioxobutyric acid,
(44) 4-(1-ethyl-1H-pyrrol-2-yl)-2,4-dioxobutyric acid,
(45) 4-[1-(3-fluorobenzyl)-1-H-pyrrol-2-yl]-2,4-dioxobutyric acid,
(46) 4-[1-(2-chlorobenzyl)-1-H-pyrrol-2-yl]-2,4-dioxobutyric acid,
(47) 4-[1-(3-benzoylaminopropyl)-1H-pyrrol-3-yl]-2,4-dioxobutyric acid,
(48) 4-{1-[3-(4-fluorophenoxy)benzyl]-1H-pyrrol-2-yl}]-2,4-dioxobutyric acid,
(49) 4-(1-cyclohexylmethyl-1-H-pyrrol-2-yl)-2,4-dioxobutyric acid methyl ester
(50) 4-(1-cyclohexylmethyl-1-H-pyrrol-2-yl)-2,4-dioxobutyric acid,
(51) 4-[1-(4-fluorobenzyl)-4-phenylethynyl-1H-pyrrol-2-yl-2,4-dioxobutyric acid ethyl ester,
(52) 4-[1-(4-fluorobenzyl)-4-phenylethynyl-1H-pyrrol-2-yl]-2,4-dioxobutyric acid,
(53) 4-[1-(4-fluorobenzyl)-4-phenethyl-1H-pyrrol-2-yl]-2,4-dioxobutyric acid ethyl ester,
(54) 4-[1-(4-fluorobenzyl)-4-phenethyl-1H-pyrrol-2-yl]-2,4-dioxobutyric acid,
(55) 4-[5-(4-fluorobenzyl)-1-methyl-1H-pyrrol-2-yl]-2,4-dioxobutyric acid methyl ester,
(56) 4-[5-(4-fluorobenzyl)-1-methyl-1H-pyrrol-2-yl]-2,4-dioxobutyric acid,
(57) 4-[5-(3-chlorobenzyl)-1-methyl-1H-pyrrol-2-yl]-2,4-dioxobutyric acid,
(58) 4-[5-(4-fluorobenzyl)-1H-pyrrol-2-yl]-2,4-dioxobutyric acid,
(59) 4-[5-(3-chlorobenzyl)-1H-pyrrol-2-yl]-2,4-dioxobutyric acid,
(60) 4-[5-(benzyl)-1H-pyrrol-2-yl]-2,4-dioxobutyric acid,
(61) 4-[5-(3-fluorobenzyl)-1H-pyrrol-2-yl]-2,4-dioxobutyric acid,
(62) 4-[5-(4-fluorobenzyl)-1-(4-fluorobenzyl)-1H-pyrrol-2-yl]-2,4-dioxobutyric acid,
(63) 4-[5-(3-chlorobenzyl)-1-(4-fluorobenzyl)-1H-pyrrol-2-yl]-2,4-dioxobutyric acid,
(64) 4-[5-(benzyl)-1-(4-fluorobenzyl)-1H-pyrrol-2,4-dioxobutyric acid,
(65) 4-[5-(3-chlorobenzyl)-1-(4-fluorobenzyl)-1H-pyrrol-2-yl]-2,4-dioxobutyric acid,
(66) 4-[5-(4-fluorobenzyl)-1-methyl-1H-pyrrol-3-yl]-2,4-dioxobutyric acid,
(67) 4-[5-(3-chlorobenzyl)-1-methyl-1H-pyrrol-3-yl]-2,4-dioxobutyric acid,
(68) 4-[5-(benzyl)-1-methyl-1H-pyrrol-3-yl]-2,4-dioxobutyric acid,
(69) 4-[5-(3-fluorobenzyl)-1-methyl-1H-pyrrol-3-yl]-2,4-dioxobutyric acid,
(70) 4-(5-benzyl-1H-pyrrol-3-yl)-2,4-dioxobutyric acid,
(71) 4-[2,5-bis-(3-chlorobenzyl)-1-H-pyrrol-3-yl]-2,4-dioxobutyric acid,
(72) 4-[1-(4-Fluorobenzyl)-5-phenyl-1H-pyrrol-2-yl]-2,4-dioxobutyric acid ethyl ester,
(73) 4-[1-(4-Fluorobenzyl)-5-phenyl-1H-pyrrol-2-yl]-2,4-dioxobutyric acid,
(74) 4-[4-Dimethylamino-1-(4-fluorobenzyl)-1H-pyrrol-2-yl]-2,4-dioxobutyric acid ethyl ester,
(75) 4-[4-Dimethylamino-1-(4-fluorobenzyl)-1H-pyrrol-2-yl]-2,4-dioxobutyric acid,
(76) 4-[1-(4-Fluorobenzyl)-4-nitro-1H-pyrrol-2-yl]-2,4-dioxobutyric acid,
(77) 4-[4-(Benzylamino)-1-(4-fluorobenzyl)-1H-pyrrol-2-yl]-2,4-dioxobutyric acid,
(78) 4-[5-Nitro-1-(4-fluorobenzyl)-1H-pyrrol-2-yl]-2,4-dioxobutyric
(79) 4-[1-benzyl-1H-pyrrol-3-yl]-2,4-dioxobutyric acid methyl ester,
(80) 4-[1-benzyl-1H-pyrrol-3-yl]-2,4-dioxobutyric acid,
(81) 4-[1-(4-fluorobenzyl)-1H-pyrrol-3-yl]-2,4-dioxobutyric acid,
(82) 4-[1-(3-bromobenzyl)-1H-pyrrol-3-yl]-2,4-dioxobutyric acid,
(83) 4-[1-(4-fluorobenzyl)-4-methyl-1H-pyrrol-3-yl]-2,4-dioxobutyric acid,
(84) 4-[2,4-dimethyl-1-(4-fluorobenzyl)-1H-pyrrol-3-yl]-2,4-dioxobutyric acid,
(85) 4-[1-(3,4-difluorobenzyl)-1H-pyrrol-3-yl]-2,4-dioxobutyric acid,
(86) 4-[1-(3-chlorobenzyl)-1H-pyrrol-3-yl]-2,4-dioxobutyric acid,
(87) 4-[1-(4-chlorobenzyl)-1H-pyrrol-3-yl]-2,4-dioxobutyric acid,
(88) 4-[1-(4-bromobenzyl)-1H-pyrrol-3-yl]-2,4-dioxobutyric acid,
(89) 4-[1-(3,4-dichlorobenzyl)-1H-pyrrol-3-yl]-2,4-dioxobutyric acid,
(90) 4-[1-(2-methylbenzyl)-1H-pyrrol-3-yl]-2,4-dioxobutyric acid,

(91) 4-[1-(3-chlorobenzyl)-4-methyl-1H-pyrrol-3-yl]-2,4-dioxobutyric acid,
(92) 4-[1-(3-trifluoromethylbenzyl)-1H-pyrrol-3-yl]-2,4-dioxobutyric acid,
(93) 4-[1-(4-methylbenzyl)-1H-pyrrol-3-yl]-2,4-dioxobutyric acid,
(94) 4-[1-(4-methoxybenzyl)-1H-pyrrol-3-yl]-2,4-dioxobutyric acid,
(95) 4-[1-(3-methylbenzyl)-1H-pyrrol-3-yl]-2,4-dioxobutyric acid,
(96) 4-{1-[3-(4-fluorophenyl)-propyl]-1H-pyrrol-3-yl}-2,4-dioxobutyric acid,
(97) 4-[1-(4-bromobenzyl)-1-H-pyrrol-3-yl]-2,4-dioxobutyric acid,
(98) 4-[1-(4-chlorobenzyl)-1-H-pyrrol-3-yl]-2,4-dioxobutyric acid,
(99) 4-[4-Benzylmethylamino-1-(4-fluorobenzyl)-1H-pyrrol-2-yl]-2,4-dioxobutyric, ethyl ester
(100) 4-[4-Benzylmethylamino-1-(4-fluorobenzyl)-1H-pyrrol-2-yl]-2,4-dioxobutyric acid,
(101) 4-[4-Phenyl-1-(4-fluorobenzyl)-1H-pyrrol-2-yl]-2,4-dioxobutyric acid ethyl ester,
(102) 4-[4-Phenyl-1-(4-fluorobenzyl)-1H-pyrrol-2-yl]-2,4-dioxobutyric acid,
(103) 4-[1-(4-fluorobenzyl)-4-methanesulfonylamino-1H-pyrrol-3-yl]-2,4-dioxo-butyric acid ethyl ester,
(104) 4-[1-(4-fluorobenzyl)-4-methanesulfonylamino-1H-pyrrol-3-yl]-2,4-dioxo-butyric acid,
(105) 4-[1-(4-Fluorobenzyl)-3-acetylamino-1H-pyrrol-2-yl]-2,4-dioxobutyric acid,
(106) 4-[4-acetylamino-1-(4-fluorobenzyl)-1H-pyrrol-2-yl]-2,4-dioxobutyric acid,
(108) 4-[4-(4-fluorobenzyl)-1H-pyrrol-3-yl]-2,4-dioxobutyric acid,
(109) 4-[1,4-bis-(4-fluorobenzyl)-1H-pyrrol-3-yl]-2,4-dioxobutyric acid,
(110) 4-[5-(3-ethoxycarbonyl-3-oxopropionyl)-1-(4-fluorobenzyl)-1H-pyrazol-3-yl]-2,4-dioxobutyric acid ethyl ester,
(111) 4-[1-(4-fluorobenzyl)-1H-pyrazol-4-yl]-2,4-dioxobutyric acid ethyl ester,
(112) 4-[1-(4-fluorobenzyl)-1H-pyrazol-4-yl]-2,4-dioxobutyric acid,
(113) 4-[4-Dimethylamino-1-(4-fluorobenzyl)-1H-pyrrol-3-yl]-2,4-dioxobutyric acid,
(114) 4-[1-(4-Fluorobenzyl)-5-methyl-1H-pyrazol-4-yl]-2-hydroxy-4-oxobut-2-enoic acid,
(115) 4-[2-(4-fluorobenzyl)-2H-pyrazol-3-yl]-2,4-dioxobutyric acid ethyl ester,
(116) 4-[2-(4-fluorobenzyl)-2H-pyrazol-3-yl]-2,4-dioxobutyric acid,
(117) 4-[2-(4-fluorobenzyl)-3-methyl-1H-pyrazol-4-yl]-2,4-dioxobutyric acid ethyl ester,
(118) 1-[1-(4-fluorobenzyl)-3-methyl-1H-pyrazol-4-yl]-2,4-dioxobutyric acid,
(119) 4-[3-methyl-1-(3-chlorobenzyl)-1H-pyrazol-4-yl]-2,4-dioxobutyric acid ethyl ester,
(120) 4-[3-methyl-1-(3-chlorobenzyl)-1H-pyrazol-4-yl]-2,4-dioxobutyric acid,
(121) 4-[5-methyl-1-(3-chlorobenzyl)-1H-pyrazol-4-yl]-2,4-dioxobutyric acid,
(122) 4-[5-methyl-1-(3-chlorobenzyl)-1H-pyrazol-4-yl]-2,4-dioxobutyric acid ethyl ester,
(123) 4-[5-methyl-1-(3-chlorobenzyl)-1H-pyrazol-4-yl]-2,4-dioxobutyric acid,
(124) 4-[1-(4-fluoro-benzyl)-1H-imidazol-2-yl]-2,4-dioxo-butyric acid,
(125) 4-[1-(4-fluorobenzyl)-1H-imidazol-2-yl]-2,4-dioxo-butyric acid ethyl ester,
(126) 4-[1-(4-fluorobenzyl)-1H-imidazol-2-yl]-2,4-dioxo-butylic acid,
(127) 4-(1-Benzyl-1H-imidazol-2-yl)-2,4-dioxobutyric acid,
(128) 4-[1-(4-fluorobenzyl)-1H-imidazol-4-yl]-2,4-dioxo-butyric acid ethyl ester,
(129) 4-[1-(4-fluorobenzyl)-1H-imidazol-4-yl]-2,4-dioxo-butyric acid,
(130) 4-[1-(4-fluorobenzyl)-1H-indol-2-yl]-2,4-dioxobutyric acid methyl ester,
(131) 4-[1-(4-fluorobenzyl)-1H-indol-2-yl]-2,4-dioxobutyric acid,
(132) 2-hydroxy-4-(1-methyl-1-H-indol-2-yl)-2,4-dioxobutyric acid,
(133) 4-[1-(4-fluorobenzyl)-1H-indol-3-yl]-2,4-dioxobutyric acid,
(134) 1-[1-(4-fluorobenzyl)-1H-indol-3-yl]-2,4-dioxobutyric acid ethyl ester,
(135) 1-[1-(4-fluorobenzyl)-1H-indol-3-yl]-2,4-dioxobutyric acid,
(136) 4-[1-fluorobenzyl)-1-H-pyrrol-3-yl]-2,4-dioxobutyric acid,
(137) 4-[4-(3-chlorobenzyl)-1-H-pyrrol-3-yl]-2,4-dioxobutylic acid,
(138) 4-[4-(4-fluorobenzyl)-1-methyl-1-H-pyrrol-3-yl]-2,4-dioxo-butyric acid,
(139) 4-[2,5-dimethyl-1-(4-fluorobenzyl)-1-H-pyrrol-3-yl]-2,4-dioxo-butyric acid,
(140) 4-[1-(3,5-dichlorobenzyl)-1-H-pyrrol-3-yl]-2,4-dioxobutyric acid,
(141) 4-[1-(3-thiophenemethyl)-1-H-pyrrol-3-yl]-2,4-dioxobutyric acid,
(142) 4-[1-2,4-dimethylbenzyl)-1-H-pyrrol-3-yl]-2,4-dioxobutyric acid,
(143) 4-[1-(3-chloro-5-methyl-benzyl)-1-H-pyrrol-3-yl]-2,4-dioxo-butyric acid,
(144) 4-[1-(1-naphthalenemethyl)-1-H-pyrrol-3-yl]-2,4-dioxobutyric acid,
(145) 4-[1-(2-thiophenemethyl)-1-H-pyrrole-3-yl]-2,4-dioxobutyric acid, and
(146) 4-[4-(3-chlorobenzyl)-1-methyl-1-H-pyrrol-3-yl]-2,4-dioxobutyric acid, or a tautomer or a pharmaceutically acceptable salt thereof.

21. The compound according to claim 1 selected from:
(1) 4-[1-(4-fluorobenzyl)-1H-pyrrol-2-yl]-2,4-dioxobutyric acid,
(2) 4-[1-(4-methylbenzyl)-1-H-pyrrol-2-yl]-2,4-dioxobutyric acid,
(3) 4-(1-benzyl-1H-pyrrol-2-yl)-2,4-dioxobutyric acid,
(4) 4-(1-naphthalen-2-ylmethyl-1H-pyrrol-2-yl)-2,4-dioxobutyric acid,
(5) 4-(1-biphenyl-4-ylmethyl-1H-pyrrol-2-yl)-2,4-dioxobutyric acid,
(6) 4-(1-naphthalen-1-ylmethyl-1H-pyrrol-2-yl)-2,4-dioxobutyric acid,
(7) 2,4-dioxo-4-[1-(4-phenylbutyl)-1H-pyrrol-2-yl]-butyric acid, (8) 4-[1-(4-chlorobenzyl)-1H-pyrrol-2-yl]-2,4-dioxobutyric acid,
(9) 2,4-dioxo-4-(1-phenethyl-1H-pyrrol-2-yl)-butyric acid,
(10) 4-[1-(2-methylbenzyl)-1H-pyrrol-2-yl]-2,4-dioxobutyric acid,
(11) 4-[1-(3,4-difluorobenzyl)-1H-pyrrol-2-yl]-2,4-dioxobutyric acid,
(12) 4-[1-(4-bromobenzyl)-1H-pyrrol-2-yl]-2,4-dioxobutyric acid,
(13) 4-[1-(2-bromobenzyl)-1H-pyrrol-2-yl]-2,4-dioxobutyric acid,
(14) 4-[1-(3-bromobenzyl)-1H-pyrrol-2-yl]-2,4-dioxobutyric acid,
(15) 4-[1-(3-chlorobenzyl)-1H-pyrrol-2-yl]-2,4-dioxobutyric acid,
(16) 4-[1-(3-methylbenzyl)-1H-pyrrol-2-yl]-2,4-dioxobutyric acid,
(17) 4-[4-(2-fluorobenzyl)-1H-pyrrol-2-yl]-2,4-dioxobutyric acid,
(18) 2,4-dioxo-4-(1-hexyl-1H-pyrrol-2-yl)-butyric acid,
(19) 4-(1-biphenyl-2-ylmethyl-1H-pyrrol-2-yl)-2,4-dioxobutyric acid,
(20) 2,4-dioxo-4-[1-(4-phenoxybutyl)-1H-pyrrol-2-yl]-butyric acid,
(21) 4-[1-(3-fluorobenzyl)-1H-pyrrol-2-yl]-2,4-dioxobutyric acid,
(22) 4-[1-(2-chlorobenzyl)-1H-pyrrol-2-yl]-2,4-dioxobutyric acid,
(23) 4-[1-(4-fluorobenzyl)-4-iodo-1H-pyrrol-2-yl]-2,4-dioxo-butyric acid,
(24) 4-[1-(4-methoxybenzyl)-1H-pyrrol-2-yl]-2,4-dioxobutyric acid,
(25) 4-[1-(2,4,5-trifluorobenzyl)-1H-pyrrol-2-yl]-2,4-dioxobutyric acid,
(26) 4-[1-(2,3-difluorobenzyl)-1H-pyrrol-2-yl]-2,4-dioxobutyric acid,
(27) 4-[1-(3,5-difluorobenzyl)-1H-pyrrol-2-yl]-2,4-dioxobutyric acid,
(28) 4-[1-(2,5-difluorobenzyl)-1H-pyrrol-2-yl]-2,4-dioxobutyric acid,
(29) 4-[1-(2,5,6-difluorobenzyl)-1H-pyrrol-2-yl]-2,4-dioxobutyric acid,
(30) 4-[1-(2-fluorobenzyl)-1H-pyrrol-2-yl]-2,4-dioxobutyric acid,
(31) 4-[1-(4-trifluoromethylbenzyl)-1H-pyrrol-2-yl]-2,4-dioxobutyric acid,
(32) 4-[1-(4-cyanobenzyl)-1H-pyrrol-2-yl]-2,4-dioxobutyric acid,
(33) 4-[1-(3-methoxybenzyl)-1H-pyrrol-2-yl]-2,4-dioxobutyric acid,
(34) 2-hydroxy-4-[1-(4-hydroxybenzyl)-1H-pyrrol-2-yl]-2,4-dioxobutyric acid,
(35) 4-(1-cyclopentylmethyl-1H-pyrrol-2-yl)-2,4-dioxobutyric acid,
(36) 4-{1-[3-(4-fluorophenyl)propyl]-1H-pyrrol-2-y}-2,4-dioxobutyric acid,
(37) 4-{1-[2-(4-fluorophenyl)ethyl]-1H-pyrrol-2-yl}-2,4-dioxobutyric acid,
(38) 4-[1-(3-phenylpropyl)-1H-pyrrol-2-yl]-2,4-dioxobutyric acid,
(39) 4-(1-ethyl-1H-pyrrol-2-yl)-2,4-dioxobutyric acid,
(40) 4-[1-(3-fluoro-benzyl)-1-H-pyrrol-2-yl]-2,4-dioxobutyric acid,
(41) 4-[1-(2-chloro-benzyl)-1-H-pyrrol-2-yl]-2,4-dioxobutyric acid,
(42) 4-[1-(3-benzoylaminopropyl)-1H-pyrrol-3-yl]-2,4-dioxobutyric acid,
(43) 4-{1-[3-(4-fluorophenoxy)benzyl]-1H-pyrrol-2-yl}]-2,4-dioxobutyric acid,
(44) 4-(1-cyclohexylmethyl-1-H-pyrrol-2-yl)-2,4-dioxo-butyric acid,
(45) 4-[1-(4-fluorobenzyl)-4-phenylethynyl-1H-pyrrol-2-yl]-2,4-dioxobutyric acid,
(46) 4-[1-(4-fluorobenzyl)-4-phenethyl-1H-pyrrol-2-yl]-2,4-dioxobutyric acid,
(47) 4-[5-(4-fluorobenzyl)-1-methyl-1H-pyrrol-2-yl]-2,4-dioxobutyric acid,
(48) 4-[5-(3-chlorobenzyl)-1-methyl-1H-pyrrol-2-yl]-2,4-dioxobutyric acid,
(49) 4-[5-(4-fluorobenzyl)-1H-pyrrol-2-yl]-2,4-dioxobutyric acid,
(50) 4-[5-(3-chlorobenzyl)-1H-pyrrol-2-yl]-2,4-dioxobutyric acid,
(51) 4-[5-(benzyl)-1H-pyrrol-2-yl]-2,4-dioxobutyric acid,
(52) 4-[5-(3-fluorobenzyl)-1H-pyrrol-2-yl]-2,4-dioxobutyric acid,
(53) 4-[5-(4-fluorobenzyl)-1-(4-fluorobenzyl)-1H-pyrrol-2-yl]-2,4-dioxobutyric acid,
(54) 4-[5-(3-chlorobenzyl)-1-(4-fluorobenzyl)-1H-pyrrol-2-yl]-2,4-dioxobutyric acid,
(55) 4-[5-(benzyl)-1-(4-fluorobenzyl)-1H-pyrrol-2-yl]-2,4-dioxobutyric acid,
(56) 4-[5-(3-chlorobenzyl)-1-(4-fluorobenzyl)-1H-pyrrol-2-yl]-2,4-dioxobutyric acid,
(57) 4-[5-(4-fluorobenzyl)-1-methyl-1H-pyrrol-3-yl]-2,4-dioxobutyric acid,
(58) 4-[5-(3-chlorobenzyl)-1-methyl-1H-pyrrol-3-yl]-2,4-dioxobutyric acid,
(59) 4-[5-(benzyl)-1-methyl-1H-pyrrol-3-yl]-2,4-dioxobutyric acid,
(60) 4-[5-(3-fluorobenzyl)-1-methyl-1H-pyrrol-3-yl]-2,4-dioxobutyric acid,
(61) 4-(5-benzyl-1H-pyrrol-3-yl)-2,4-dioxobutyric acid,
(62) 4-[2,5-bis-(3-chlorobenzyl)-1-H-pyrrol-3-yl]-2,4-dioxobutyric acid,
(63) 4-[1-(4-Fluorobenzyl)-5-phenyl-1H-pyrrol-2-yl]-2,4-dioxobutyric acid,
(64) 4-[4-Dimethylamino-1-(4-fluorobenzyl)-1H-pyrrol-2-yl]-2,4-dioxobutyric acid,
(65) 4-[1-(4-Fluorobenzyl)-4-nitro-1H-pyrrol-2-yl]-2,4-dioxobutyric acid,
(66) 4-[4-(Benzylamino)-1-(4-fluorobenzyl)-1H-pyrrol-2-yl]-2,4-dioxobutyric acid,
(67) 4-[5-Nitro-1-(4-fluorobenzyl)-1H-pyrrol-2-yl]-2,4-dioxobutyric
(68) 4-[1-benzyl-1H-pyrrol-3-yl]-2,4-dioxobutyric acid,
(69) 4-[1-(4-fluorobenzyl)-1H-pyrrol-3-yl]-2,4-dioxobutyric acid,
(70) 4-[1-(3-bromobenzyl)-1H-pyrrol-3-yl]-2,4-dioxobutyric acid,
(71) 4-[1-(4-fluorobenzyl)-4-methyl-1H-pyrrol-3-yl]-2,4-dioxobutyric acid,

(72) 4-[2,4-dimethyl-1-(4-fluorobenzyl)-1H-pyrrol-3-yl]-2,4-dioxobutyric acid,
(73) 4-[1-(3,4-difluorobenzyl)-1H-pyrrol-3-yl]-2,4-dioxobutyric acid,
(74) 4-[1-(3-chlorobenzyl)-1H-pyrrol-3-yl]-2,4-dioxobutyric acid,
(75) 4-[1-(4-chlorobenzyl)-1H-pyrrol-3-yl]-2,4-dioxobutyric acid,
(76) 4-[1-(4-bromobenzyl)-1H-pyrrol-3-yl]-2,4-dioxobutyric acid,
(77) 4-[1-(3,4-dichlorobenzyl)-1H-pyrrol-3-yl]-2,4-dioxobutyric acid,
(78) 4-[1-(2-methylbenzyl)-1H-pyrrol-3-yl]-2,4-dioxobutyric acid,
(79) 4-[1-(3-chlorobenzyl)-4-methyl-1H-pyrrol-3-yl]-2,4-dioxobutyric acid,
(80) 4-[1-(3-trifluoromethylbenzyl)-1H-pyrrol-3-yl]-2,4-dioxobutyric acid,
(81) 4-[1-(4-methylbenzyl)-1H-pyrrol-3-yl]-2,4-dioxobutyric acid,
(82) 4-[1-(4-methoxybenzyl)-1H-pyrrol-3-yl]-2,4-dioxobutyric acid,
(83) 4-[1-(3-methylbenzyl)-1H-pyrrol-3-yl]-2,4-dioxobutyric acid,
(84) 4-{1-[3-(4-fluorophenyl)-propyl]-1H-pyrrol-3-yl}-2,4-dioxobutyric acid,
(85) 4-[1-(4-bromobenzyl)-1-H-pyrrol-3-yl]-2,4-dioxobutyric acid,
(86) 4-[1-(4-chlorobenzyl)-1-H-pyrrol-3-yl]-2,4-dioxobutyric acid,
(87) 4-[4-Benzylmethylamino-1-(4-fluorobenzyl)-1H-pyrrol-2-yl]-2,4-dioxobutyric acid,
(88) 4-[4-Phenyl-1-(4-fluorobenzyl)-1H-pyrrol-2-yl]-2,4-dioxobutyric acid,
(89) 4-[1-(4-fluorobenzyl)-4-methanesulfonylamino-1H-pyrrol-3-yl]-2,4-dioxo-butyric acid,
(90) 4-[1-(4-Fluorobenzyl)-3-acetylamino-1H-pyrrol-2-yl]-2,4-dioxobutyric acid,
(91) 4-[4-acetylamino-1-(4-fluorobenzyl)-1H-pyrrol-2-yl]-2,4-dioxobutyric acid,
(93) 4-[4-(4-fluorobenzyl)-1H-pyrrol-3-yl]-2,4-dioxobutyric acid,
(94) 4-[1,4-bis-(4-fluorobenzyl)-1-H-pyrrol-3-yl]-2,4-dioxobutyric acid,
(95) 4-[1-(4-fluorobenzyl)-1H-pyrazol-4-yl]-2,4-dioxobutyric acid,
(96) 4-[4-Dimethylamino-1-(4-fluorobenzyl)-1H-pyrrol-3-yl]-2,4-dioxobutyric acid,
(97) 4-[1-(4-Fluorobenzyl)-5-methyl-1H-pyrazol-4-yl]-2-hydroxy-4-oxobut-2-enoic acid,
(98) 4-[2-(4-fluorobenzyl)-2H-pyrazol-3-yl]-2,4-dioxobutyric acid,
(99) 1-[1-(4-fluorobenzyl)-3-methyl-1H-pyrazol-4-yl]-2,4-dioxobutyric acid,
(100) 4-[3-methyl-1-(3-chlorobenzyl)-1H-pyrazol-4-yl]-2,4-dioxobutyric acid,
(101) 4-[5-methyl-1-(3-chlorobenzyl)-1H-pyrazol-4-yl]-2,4-dioxobutyric acid,
(102) 4-[5-methyl-1-(3-chlorobenzyl)-1H-pyrazol-4-yl]-2,4-dioxobutyric acid,
(103) 4-[1-(4-fluoro-benzyl)-1H-imidazol-2-yl]-2,4-dioxo-butyric acid,
(104) 4-[1-(4-fluorobenzyl)-1H-imidazol-2-yl]-2,4-dioxo-butyric acid,
(105) 4-(1-Benzyl-1H-imidazol-2-yl)-2,4-dioxobutyric acid,
(106) 4-[1-(4-fluorobenzyl)-1H-imidazol-4-yl]-2,4-dioxo-butyric acid,
(107) 4-[1-(4-fluorobenzyl)-1H-indol-2-yl]-2,4-dioxobutyric acid,
(108) 2-hydroxy-4-(1-methyl-1-H-indol-2-yl)-2,4-dioxobutyric acid,
(109) 4-[1-(4-fluorobenzyl)-1H-indol-3-yl]-2,4-dioxobutyric acid,
(110) 1-[1-(4-fluorobenzyl)-1H-indol-3-yl]-2,4-dioxobutyric acid, ethyl ester,
(111) 1-[1-(4-fluorobenzyl)-1H-indol-3-yl]-2,4-dioxobutyric acid,
(112) 4-[1-(3-fluorobenzyl)-1-H-pyrrol-3-yl]-2,4-dioxobutyric acid,
(113) 4-[4-(3-chlorobenzyl)-1-H-pyrrol-3-yl]-2,4-dioxobutyric acid,
(114) 4-[4-(4-fluorobenzyl)-1-methyl-1-H-pyrrol-3-yl]-2,4-dioxobutyric acid,
(115) 4-[2,5-dimethyl-1-(4-fluorobenzyl)-1-H-pyrrol-3-yl]-2,4-dioxobutyric acid,
(116) 4-[1-(3,5-dichlorobenzyl)-1-H-pyrrol-3-yl]-2,4-dioxobutyric acid,
(117) 4-[1-(3-thiophenemethyl)-1-H-pyrrol-3-yl]-2,4-dioxobutyric acid,
(118) 4-[1-2,4-dimethylbenzyl)-1-H-pyrrol-3-yl]-2,4-dioxobutyric acid,
(119) 4-[1-(3-chloro-5-methyl-benzyl)-1-H-pyrrol-3-yl]-2,4-dioxobutyric acid,
(120) 4-[1-(1-naphthalenemethyl)-1-H-pyrrol-3-yl]-2,4-dioxobutyric acid,
(121) 4-[1-(2-thiophenemethyl)-1-H-pyrrole-3-yl]-2,4-dioxobutyric acid, and
(122) 4-[4-(3-chlorobenzyl)-1-methyl-1-H-pyrrol-3-yl]-2,4-dioxobutyric acid, or a tautomer or a pharmaceutically acceptable salt thereof.

22. The compound according to claim 21 selected from:
(1) 4-[1-(2-thiophenemethyl)-1-H-pyrrole-3-yl]-2,4-dioxobutyric acid, and
(2) 4-[4-(3-chlorobenzyl)-1-methyl-1-H-pyrrol-3-yl]-2,4-dioxobutyric acid,
(3) 4-[1-(4-fluorobenzyl)-1H-pyrrol-2-yl]-2,4-dioxobutyric acid,
(4) 4-[5-(3-chlorobenzyl)-1-methyl-1H-pyrrol-2-yl]-2,4-dioxobutyric acid,
(5) 4-[5-(4-fluorobenzyl)-1H-pyrrol-2-yl]-2,4-dioxobutyric acid,
(6) 4-[5-(4-fluorobenzyl)-1-methyl-1H-pyrrol-3-yl]-2,4-dioxobutyric acid,
(7) 4-[5-(3-chlorobenzyl)-1-methyl-1H-pyrrol-3-yl]-2,4-dioxobutyric acid,
(8) 4-[5-(benzyl)-1-methyl-1H-pyrrol-3-yl]-2,4-dioxobutyric acid,
(9) 4-[5-(3-fluorobenzyl)-1-methyl-1H-pyrrol-3-yl]-2,4-dioxobutyric acid,
(10) 4-[4-Dimethylamino-1-(4-fluorobenzyl)-1H-pyrrol-2-yl]-2,4-dioxobutyric acid,
(11) 4-[1-benzyl-1H-pyrrol-3-yl]-2,4-dioxobutyric acid,
(12) 4-[1-(3-bromobenzyl)-1H-pyrrol-3-yl]-2,4-dioxobutyric acid,

(13) 4-[1-(4-fluorobenzyl)-4-methyl-1H-pyrrol-3-yl]-2,4-dioxobutyric acid,
(14) 4-[1-(3,4-difluorobenzyl)-1H-pyrrol-3-yl]-2,4-dioxobutyric acid,
(15) 4-[1-(3-chlorobenzyl)-1H-pyrrol-3-yl]-2,4-dioxobutyric acid,
(16) 4-[1-(2-methylbenzyl)-1H-pyrrol-3-yl]-2,4-dioxobutyric acid,
(17) 4-[1-(3-methylbenzyl)-1H-pyrrol-3-yl]-2,4-dioxobutyric acid,
(18) 4-[4-Benzylmethylamino-1-(4-fluorobenzyl)-1H-pyrrol-2-yl]-2,4-dioxobutyric acid,
(19) 4-[4-(4-fluorobenzyl)-1H-pyrrol-3-yl]-2,4-dioxobutyric acid,
(20) 4-[1,4-bis-(4-fluorobenzyl)-1H-pyrrol-3-yl]-2,4-dioxobutyric acid,
(21) 4-[1-(3-fluorobenzyl)-1-H-pyrrol-3-yl]-2,4-dioxobutyric acid,
(22) 4-[4-(3-chlorobenzyl)-1-H-pyrrol-3-yl]-2,4-dioxobutyric acid,
(23) 4-[4-(4-fluorobenzyl)-1-methyl-1-H-pyrrol-3-yl]-2,4-dioxobutyric acid,
(24) 4-[2,5-dimethyl-1-(4-fluorobenzyl)-1-H-pyrrol-3-yl]-2,4-dioxobutyric acid,
(25) 4-[1-(3,5-dichlorobenzyl)-1-H-pyrrol-3-yl]-2,4-dioxobutyric acid,
(26) 4-[1-(3-thiophenemethyl)-1-H-pyrrol-3-yl]-2,4-dioxobutyric acid,
(27) 4-[1-2,4-dimethylbenzyl)-1-H-pyrrol-3-yl]-2,4-dioxobutyric acid,
(28) 4-[1-(3-chloro-5-methyl-benzyl)-1-H-pyrrol-3-yl]-2,4-dioxobutyric acid, and
(29) 4-[1-(1-naphthalenemethyl)-1-H-pyrrol-3-yl]-2,4-dioxobutyric acid, or a tautomer or a pharmaceutically acceptable salt thereof.

23. A pharmaceutical composition useful for inhibiting HIV integrase, comprising an effective amount of a compound according to claim 1 and a pharmaceutically acceptable carrier.

24. The pharmaceutical composition of claim 23, useful for treating infection by HIV, or for treating AIDS or ARC.

25. A pharmaceutical composition comprising a therapeutically effective amount of a compound of claim 1 in combination with a therapeutically effective amount of an AIDS treatment agent selected from
   (1) an AIDS antiviral agent,
   (2) an anti-infective agent, and
   (3) an immunomodulator.

26. The composition of claim 25 wherein the antiviral agent is an HIV protease inhibitor.

27. The composition of claim 26 wherein the HIV protease inhibitor is N-(2(R)-hydroxy-1-(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide or a pharmaceutically acceptable salt thereof.

28. A pharmaceutical composition made by combining the compound of claim 1 and a pharmaceutically acceptable carrier.

29. A process for making a pharmaceutical composition comprising combining a compound of claim 1 and a pharmaceutically acceptable carrier.

30. A method of inhibiting HIV integrase, comprising the administration to a mammal in need of such treatment a therapeutically effective amount of a compound of claim 1.

31. A method of treating infection by HIV, or of treating AIDS or ARC, comprising the administration to a mammal in need of such treatment a therapeutically effective amount of a compound of claim 1.

* * * * *